US007855322B2

(12) United States Patent
Lanahan et al.

(10) Patent No.: US 7,855,322 B2
(45) Date of Patent: Dec. 21, 2010

(54) SELF PROCESSING PLANTS AND PLANT PARTS

(75) Inventors: Michael B. Lanahan, Cary, NC (US); Shib Sankar Basu, Apex, NC (US); Christopher J Batie, Durham, NC (US); Wen Chen, Cary, NC (US); Joyce Craig, Pittsboro, NC (US); Mark Kinkema, St. Lucia (AU)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/471,564

(22) Filed: May 26, 2009

(65) Prior Publication Data

US 2009/0288232 A1 Nov. 19, 2009

Related U.S. Application Data

(60) Continuation of application No. 11/415,818, filed on May 2, 2006, now Pat. No. 7,557,262, which is a division of application No. 10/228,063, filed on Aug. 27, 2002, now Pat. No. 7,102,057.

(60) Provisional application No. 60/315,281, filed on Aug. 27, 2001.

(51) Int. Cl.
*C12N 15/82* (2006.01)
*C12N 15/31* (2006.01)
*C12N 15/56* (2006.01)
*C12N 15/62* (2006.01)
*C12N 15/84* (2006.01)
*A01H 5/00* (2006.01)
*A01H 5/10* (2006.01)

(52) U.S. Cl. .................. 800/284; 800/287; 800/288; 800/320; 435/69.8; 435/202; 435/252.2; 435/419

(58) Field of Classification Search ........... None
See application file for complete search history.

(56) References Cited

U.S. PATENT DOCUMENTS

| | | | |
|---|---|---|---|
| 4,904,599 A | 2/1990 | Ozaki et al. | |
| 5,168,064 A | 12/1992 | Bennett et al. | |
| 5,366,883 A | 11/1994 | Asada | |
| 5,380,831 A | 1/1995 | Adang | |
| 5,393,670 A | 2/1995 | Knowles | |
| 5,457,046 A | 10/1995 | Wöldike | |
| 5,470,725 A | 11/1995 | Borriss et al. | |
| 5,475,101 A | 12/1995 | Ward | |
| 5,536,655 A | 7/1996 | Thomas et al. | |
| 5,543,576 A | 8/1996 | van Ooijen et al. | |
| 5,614,395 A | 3/1997 | Ryals et al. | |
| 5,705,375 A | 1/1998 | van Ooyen et al. | |
| 5,981,835 A | 11/1999 | Austin-Phillips et al. | |
| 6,013,860 A | 1/2000 | Himmel et al. | |
| 6,020,169 A * | 2/2000 | Lee et al. | 435/70.1 |
| 6,147,277 A | 11/2000 | Gausing et al. | |
| 6,344,600 B1 * | 2/2002 | Merot et al. | 800/288 |
| 6,489,540 B1 * | 12/2002 | Kavanagh et al. | 800/284 |
| 6,506,592 B1 | 1/2003 | Blum | |
| 6,639,126 B1 * | 10/2003 | Sewalt et al. | 800/284 |
| 6,737,563 B2 | 5/2004 | Yu et al. | |
| 7,049,485 B2 | 5/2006 | Sticklen et al. | |
| 2002/0062502 A1 | 5/2002 | Lebel et al. | |
| 2003/0125534 A1 | 7/2003 | Callen et al. | |
| 2003/0135885 A1 | 7/2003 | Lanahan | |
| 2004/0018607 A1 | 1/2004 | Callen et al. | |
| 2006/0026715 A1 | 2/2006 | Hood et al. | |

FOREIGN PATENT DOCUMENTS

| | | |
|---|---|---|
| EP | 0449376 | 2/1991 |
| EP | 0479359 | 8/1992 |
| FR | 2 778 412 | 11/1999 |
| WO | WO 9009436 | 8/1990 |
| WO | WO9201042 | 1/1992 |
| WO | WO 92/05259 | 4/1992 |
| WO | WO 97/32986 | 9/1997 |
| WO | WO 98/39461 | 9/1998 |
| WO | WO2004/091544 | 10/2004 |

OTHER PUBLICATIONS

GenBank Accession No. AF068255 [online], [retrieved on Sep. 23, 2004]. Retrieved from the Internet: <URL: http://www.ncbi.nlm.nih.gov>.

Jørgensen et al, Cloning, Sequencing, Characterization, and Expression of an Extracellular α-Amylase from the Hyperthermophilic Archaeon *Pyrococcus furiosus* in *Escherichia coli* and *Bacillus subtilis The Journal of Biological Chemistry*, vol. 272, No. 26, (Jun. 27, 1997) pp. 16335-16342.

Lévêque et al, Cloning and expression of an α-amylase encoding gene from the hyperthermophilic archaebacterium *Thermococcus hydrothermalis* and biochemical characterization of the recombinant enzyme *Federation of European Microbiological Societies*, vol. 186 (2000), pp. 67-71.

Swiss-Prot Accession No. O08452 [online], [retrieved on Sep. 23, 2004]. Retrieved from the Internet: <URL: http://au.expasy.org>.

Swiss-Prot Accession No. O33476 [online], [retrieved on Sep. 23, 2004]. Retrieved from the Internet: <URL: http://au.expasy.org>.

(Continued)

*Primary Examiner*—David T Fox
(74) *Attorney, Agent, or Firm*—Syngenta Biotechnology Inc.

(57) ABSTRACT

The invention provides polynucleotides, preferably synthetic polynucleotides, which encode processing enzymes that are optimized for expression in plants. The polynucleotides encode mesophilic, thermophilic, or hyperthermophilic processing enzymes, which are activated under suitable activating conditions to act upon the desired substrate. Also provided are "self-processing" transgenic plants, and plant parts, e.g., grain, which express one or more of these enzymes and have an altered composition that facilitates plant and grain processing. Methods for making and using these plants, e.g., to produce food products having improved taste and to produce fermentable substrates for the production of ethanol and fermented beverages are also provided.

23 Claims, 23 Drawing Sheets

OTHER PUBLICATIONS

Tachibana et al, Cloning and Expression of the α-Amylase Gene from the Hyperthermophilic Archaeon *Pyrococcus* sp. KOD1, and Characterization of the Enzyme *Journal of Fermentation and Bioengineering*, vol. 82, No. 3 (1996) pp. 224-232.

Taylor et al, Fermentation and Costs of Fuel Ethanol from Corn with Quick-Germ Process *Applied Biochemistry and Biotechnology*, vol. 94 (1) (Apr. 2001), pp. 41-50.

GenBank Accession No. AF504064 [online], [retrieved on Feb. 15, 2006]. Retrieved from the Internet: <URL: http://www.ncbi.nlm.nih.gov>.

GenBank Accession No. AF504065 [online], [retrieved on Feb. 15, 2006]. Retrieved from the Internet <URL: http://www.ncbi.nlm.nih.gov>.

GenBank Accession No. AY608688 [online], [retrieved on Feb. 15, 2006]. Retrieved from the Internet <URL: http://www.ncbi.nlm.nih.gov>.

GenBank Accession No. AF017454 [online], [retrieved on Feb. 15, 2006]. Retrieved from the Internet <URL: http://www.ncbi.nlm.nih.gov>.

GenBank Accession No. D83793 [online], [retrieved on Feb. 15, 2006]. Retrieved from the Internet <URL: http://www.ncbi.nlm.nih.gov>.

GenBank Accession No. AF504063 [online], [retrieved on Feb. 15, 2006]. Retrieved from the Internet <URL: http://www.ncbi.nlm.nih.gov>.

GenBank Accession No. AF504062 [online], [retrieved on Feb. 15, 2006]. Retrieved from the Internet <URL: http://www.ncbi.nlm.nih.gov>.

Dassa et al, EBI [online] *Escherichia coli periplasmic phosphoanhydride phosphohydrolase (AppA) gene, complete cds*; retrieved Jan. 14, 2005 from EMBL; accession No. M58708.

Rogers et al., Isolation and Sequence Analysis of a Barley Alpha-Amylase cDNA Clone, *The Journal of Biological Chemistry*. Jul. 1983, vol. 258, No. 13, pp. 8169-8174.

Syngenta Participations AG, International Publication No. WO2003/018766, *International Search Report*, (Mar. 6, 2003).

Syngenta Participations AG, International Publication No. WO2005/096804, *International Search Report*, (Oct. 20, 2005).

Pen, et al., Production of Active *Bacillus licheniformis* Alpha-Amylase in Tobacco and its Application *Bio/Technology*, vol. 10(3) (Mar. 1992) pp. 292-296.

Lashbrook et al., *Functional Analysis of Cx-Cellulase (Endo β-1-4-Glucanase) Gene Expression in Transgenic Tomato Fruit, Cellular and Molecular Aspects of the Plant Hormone Ethylene*, J.C. Pech et al. (eds.) (Kluwer Academic Publishers), (1993), pp. 123-128.

Koehler, et al., The Gene Promoter for a Bean Abscission Cellulase is Ethylene-Induced inTransgenic Tomato and Shows High Sequence Conservation with a Soybean Abscission Cellulase, *Plant Molecular Biology*, 31: 595-606, (1996).

Kawazu, et al., Expression of a *Ruminococcus albus* Cellulase Gene in Tobacco Suspension Cells, *Journal of Fermentation and Bioengineering* 82(3): 205-209, (1996).

Collmer, A. et al. Cloning and Expression of a *Thermomonospora* YX Endocellulase Gene in *E. coli Bio/Technology*, (Sep. 1983), pp. 594-601.

Ghangas, G.S et al., Cloning of the *Thermomonospora fusca* Endoglucanase E2 Gene in *Streptomyces lividans*: Affinity Purification and Functional Domains of the Cloned Gene Product *Applied and Environmental Microbiology*, vol. 54, No. 10 (Oct. 1988), pp. 2521-2526.

Jung et al, DNA Sequences and Expression in *Streptomyces lividans* of an Exoglucanase Gene and an Endoglucanase Gene from *Thermomonospora fusca Applied and Environmental Microbiology*, vol. 59, No. 9 (Sep. 1993), pp. 3032-3043.

Lao et al, DNA Sequences of Three β-1, 4-Endoglucanase Genes from *Thermomonospora fusca Journal of Bacteriology*, vol. 173, No. 11 (Jun. 1991), pp. 3397-3407.

Thomas et al, "Initial Approaches to Artificial Cellulase Systems for Conversion of Biomass to Ethanol", in Saddler, J.N.; Penner, M.H., eds. *Enzymatic Degradation of Insoluble Polysaccharides*, ACS Series 618, Washington, DC: American Chemical Society; pp. 208-236, (1996).

Wilson, D.B., Biochemistry and Genetics of Actinomycete Cellulases *Critical Reviews in Biotechnology*, vol. 12(1/2) (1992), pp. 45-63.

Lashbrook et al. Two Divergent Endo B-1, 4-glucanase Gene Exhibit Overlapping Expression in Ripening Fruit and Abscising Flowers, Oct. 1994, The Plant Cell, vol. 6, pp. 1485-1493.

Melchers et al. Extracellular Targeting of the Vacuolar Tobacco Proteins AP24, Chitinase and B-1, 3-glucanase in Transgenic Plants, 1993, Plant Molecular Biology, vol. 21, pp. 583-593.

Aspegren, et al., *Secretion of a heat stable fungal beta-glucanase from transgenic suspension-cultured barley cells* Molecular Breeding, vol. 1 (1995) pp. 91-99.

Dai et al., *Expression of Trichoderma reesei Exo-Cellobiohydrolase I in Transgenic Tobacco Leaves And Calli*, Applied Microbiology and Biotechnology,vol. 77-79 pp. 689-699 (1999).

Czihal et al., "Gene Farming in Plants: Expression of a Heatstable *Bacillus* Amylase in Transgenic Legume Seeds", J. Plant Physiol., vol. 155 (1999) pp. 183-189.

\* cited by examiner

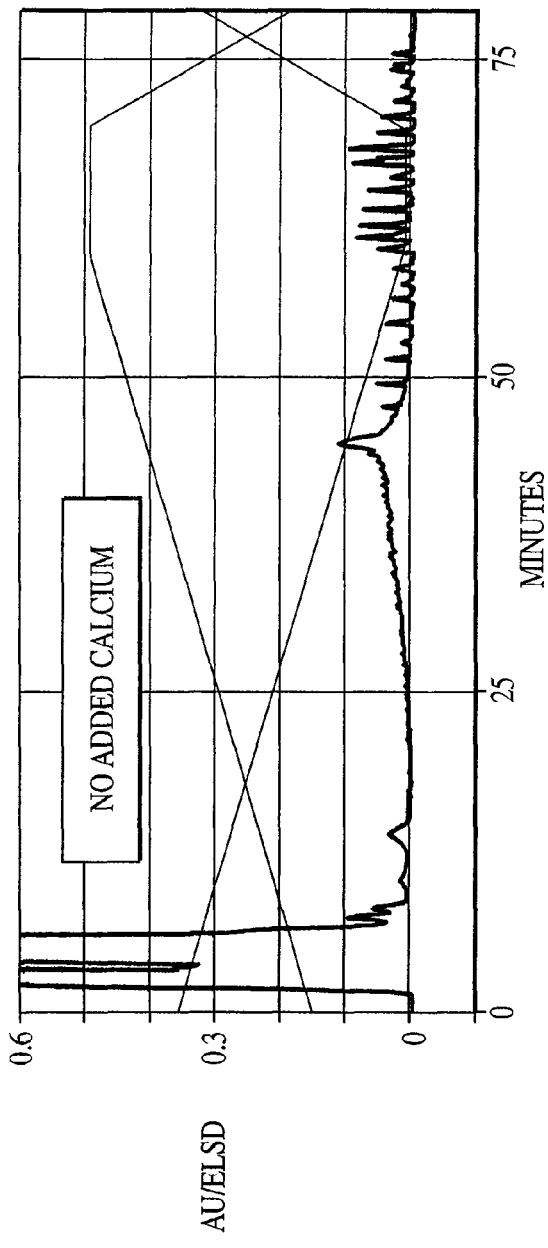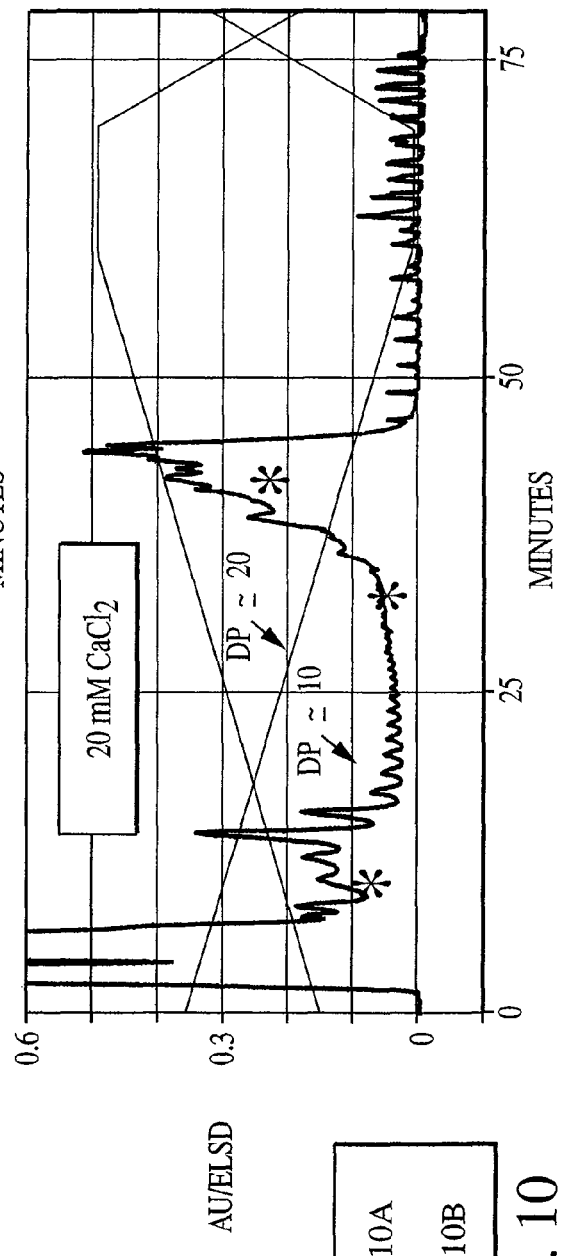
FIG. 10A
FIG. 10B
FIG. 10

SEQUENCE LISTING

```
<160> NUMBER OF SEQ ID NOS: 60

<210> SEQ ID NO 1
<211> LENGTH: 436
<212> TYPE: PRT
<213> ORGANISM: Artificial Sequence
<220> FEATURE:
<223> OTHER INFORMATION: synthetic

<400> SEQUENCE: 1

Met Ala Lys Tyr Leu Glu Leu Glu Glu Gly Gly Val Ile Met Gln Ala
 1               5                  10                  15

Phe Tyr Trp Asp Val Pro Ser Gly Gly Ile Trp Trp Asp Thr Ile Arg
                20                  25                  30

Gln Lys Ile Pro Glu Trp Tyr Asp Ala Gly Ile Ser Ala Ile Trp Ile
            35                  40                  45

Pro Pro Ala Ser Lys Gly Met Ser Gly Gly Tyr Ser Met Gly Tyr Asp
        50                  55                  60

Pro Tyr Asp Tyr Phe Asp Leu Gly Glu Tyr Tyr Gln Lys Gly Thr Val
    65                  70                  75                  80

Glu Thr Arg Phe Gly Ser Lys Gln Glu Leu Ile Asn Met Ile Asn Thr
```

```
                        85                  90                  95
Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
            130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
            195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
            355                 360                 365

Ile Asn Leu Gly Ser Ser Lys Val Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 2
<211> LENGTH: 1308
<212> TYPE: DNA
<213> ORGANISM: Artificial Sequence
<220> FEATURE:
<223> OTHER INFORMATION: synthetic

<400> SEQUENCE: 2
atggccaagt acctggagct ggaggagggc ggcgtgatca tgcaggcgtt ctactgggac    60
```

-continued

```
gtcccgagcg gaggcatctg gtgggacacc atccgccaga agatccccga gtggtacgac    120
gccggcatct ccgcgatctg gataccgcca gcttccaagg gcatgtccgg gggctactcg    180
atgggctacg acccgtacga ctacttcgac ctcggcgagt actaccagaa gggcacggtg    240
gagacgcgct tcgggtccaa gcaggagctc atcaacatga tcaacacggc gcacgcctac    300
ggcatcaagg tcatcgcgga catcgtgatc aaccacaggg ccggcggcga cctggagtgg    360
aacccgttcg tcggcgacta cacctggacg gacttctcca aggtcgcctc cggcaagtac    420
accgccaact acctcgactt ccaccccaac gagctgcacg cgggcgactc cggcacgttc    480
ggcggctacc cggacatctg ccacgacaag tcctgggacc agtactggct ctgggcctcg    540
caggagtcct acgcggccta cctgcgctcc atcggcatcg acgcgtggcg cttcgactac    600
gtcaagggct acggggcctg gtggtcaag gactggctca actggtgggg cggctgggcg    660
gtgggcgagt actgggacac caacgtcgac gcgctgctca ctgggcctac tcctccggc    720 gccaaggtgt tcgacttccc cctgtactac aagatggacg cggccttcga caacaagaac    780
atcccggcgc tcgtcgaggc cctgaagaac ggcggcacgg tggtctcccg cgacccgttc    840
aaggccgtga ccttcgtcgc caaccacgac acggacatca tctggaacaa gtacccggcg    900
tacgccttca tcctcaccta cgagggccag cccacgatct tctaccgcga ctacgaggag    960
tggctgaaca aggacaagct caagaacctg atctggattc acgacaacct cgcgggcggc   1020
tccactagta tcgtgtacta cgactccgac gagatgatct tcgtccgcaa cggctacggc   1080
tccaagcccg gcctgatcac gtacatcaac ctgggctcct ccaaggtggg ccgctggtg   1140 tacgtcccga gttcgccgg cgcgtgcatc cacgagtaca ccggcaacct cggcggctgg   1200
gtggacaagt acgtgtactc ctccggctgg gtctacctgg aggccccggc ctacgacccc   1260
gccaacggcc agtacggcta ctccgtgtgg tcctactgcg gcgtcggc                 1308
```

<210> SEQ ID NO 3
<211> LENGTH: 800
<212> TYPE: PRT
<213> ORGANISM: Artificial Sequence
<220> FEATURE:
<223> OTHER INFORMATION: synthetic

<400> SEQUENCE: 3

```
Met Gly His Trp Tyr Lys His Gln Arg Ala Tyr Gln Phe Thr Gly Glu
 1               5                  10                  15

Asp Asp Phe Gly Lys Val Ala Val Val Lys Leu Pro Met Asp Leu Thr
            20                  25                  30

Lys Val Gly Ile Ile Val Arg Leu Asn Glu Trp Gln Ala Lys Asp Val
        35                  40                  45

Ala Lys Asp Arg Phe Ile Glu Ile Lys Asp Gly Lys Ala Glu Val Trp
    50                  55                  60

Ile Leu Gln Gly Val Glu Glu Ile Phe Tyr Glu Lys Pro Asp Thr Ser
65                  70                  75                  80

Pro Arg Ile Phe Phe Ala Gln Ala Arg Ser Asn Lys Val Ile Glu Ala
                85                  90                  95

Phe Leu Thr Asn Pro Val Asp Thr Lys Lys Glu Leu Phe Lys Val
            100                 105                 110

Thr Val Asp Gly Lys Glu Ile Pro Val Ser Arg Val Glu Lys Ala Asp
        115                 120                 125

Pro Thr Asp Ile Asp Val Thr Asn Tyr Val Arg Ile Val Leu Ser Glu
    130                 135                 140
```

-continued

```
Ser Leu Lys Glu Glu Asp Leu Arg Lys Asp Val Glu Leu Ile Ile Glu
145                 150                 155                 160

Gly Tyr Lys Pro Ala Arg Val Ile Met Met Glu Ile Leu Asp Asp Tyr
                165                 170                 175

Tyr Tyr Asp Gly Glu Leu Gly Ala Val Tyr Ser Pro Glu Lys Thr Ile
            180                 185                 190

Phe Arg Val Trp Ser Pro Val Ser Lys Trp Val Lys Val Leu Leu Phe
        195                 200                 205

Lys Asn Gly Glu Asp Thr Glu Pro Tyr Gln Val Val Asn Met Glu Tyr
210                 215                 220

Lys Gly Asn Gly Val Trp Glu Ala Val Glu Gly Asp Leu Asp Gly
225                 230                 235                 240

Val Phe Tyr Leu Tyr Gln Leu Glu Asn Tyr Gly Lys Ile Arg Thr Thr
                245                 250                 255

Val Asp Pro Tyr Ser Lys Ala Val Tyr Ala Asn Asn Gln Glu Ser Ala
            260                 265                 270

Val Val Asn Leu Ala Arg Thr Asn Pro Glu Gly Trp Glu Asn Asp Arg
        275                 280                 285

Gly Pro Lys Ile Glu Gly Tyr Glu Asp Ala Ile Ile Tyr Glu Ile His
290                 295                 300

Ile Ala Asp Ile Thr Gly Leu Glu Asn Ser Gly Val Lys Asn Lys Gly
305                 310                 315                 320

Leu Tyr Leu Gly Leu Thr Glu Glu Asn Thr Lys Gly Pro Gly Gly Val
                325                 330                 335

Thr Thr Gly Leu Ser His Leu Val Glu Leu Gly Val Thr His Val His
            340                 345                 350

Ile Leu Pro Phe Phe Asp Phe Tyr Thr Gly Asp Glu Leu Asp Lys Asp
        355                 360                 365

Phe Glu Lys Tyr Tyr Asn Trp Gly Tyr Asp Pro Tyr Leu Phe Met Val
    370                 375                 380

Pro Glu Gly Arg Tyr Ser Thr Asp Pro Lys Asn Pro His Thr Arg Ile
385                 390                 395                 400

Arg Glu Val Lys Glu Met Val Lys Ala Leu His Lys His Gly Ile Gly
                405                 410                 415

Val Ile Met Asp Met Val Phe Pro His Thr Tyr Gly Ile Gly Glu Leu
            420                 425                 430

Ser Ala Phe Asp Gln Thr Val Pro Tyr Phe Tyr Arg Ile Asp Lys
        435                 440                 445

Thr Gly Ala Tyr Leu Asn Glu Ser Gly Cys Gly Asn Val Ile Ala Ser
    450                 455                 460

Glu Arg Pro Met Met Arg Lys Phe Ile Val Asp Thr Val Thr Tyr Trp
465                 470                 475                 480

Val Lys Glu Tyr His Ile Asp Gly Phe Arg Phe Asp Gln Met Gly Leu
                485                 490                 495

Ile Asp Lys Lys Thr Met Leu Glu Val Glu Arg Ala Leu His Lys Ile
            500                 505                 510

Asp Pro Thr Ile Ile Leu Tyr Gly Glu Pro Trp Gly Gly Trp Gly Ala
        515                 520                 525

Pro Ile Arg Phe Gly Lys Ser Asp Val Ala Gly Thr His Val Ala Ala
    530                 535                 540

Phe Asn Asp Glu Phe Arg Asp Ala Ile Arg Gly Ser Val Phe Asn Pro
545                 550                 555                 560
```

```
Ser Val Lys Gly Phe Val Met Gly Gly Tyr Gly Lys Glu Thr Lys Ile
                565                 570                 575

Lys Arg Gly Val Val Gly Ser Ile Asn Tyr Asp Gly Lys Leu Ile Lys
            580                 585                 590

Ser Phe Ala Leu Asp Pro Glu Glu Thr Ile Asn Tyr Ala Ala Cys His
        595                 600                 605

Asp Asn His Thr Leu Trp Asp Lys Asn Tyr Leu Ala Ala Lys Ala Asp
    610                 615                 620

Lys Lys Lys Glu Trp Thr Glu Glu Leu Lys Asn Ala Gln Lys Leu
625                 630                 635                 640

Ala Gly Ala Ile Leu Leu Thr Ser Gln Gly Val Pro Phe Leu His Gly
                645                 650                 655

Gly Gln Asp Phe Cys Arg Thr Thr Asn Phe Asn Asp Asn Ser Tyr Asn
            660                 665                 670

Ala Pro Ile Ser Ile Asn Gly Phe Asp Tyr Glu Arg Lys Leu Gln Phe
        675                 680                 685

Ile Asp Val Phe Asn Tyr His Lys Gly Leu Ile Lys Leu Arg Lys Glu
    690                 695                 700

His Pro Ala Phe Arg Leu Lys Asn Ala Glu Glu Ile Lys Lys His Leu
705                 710                 715                 720

Glu Phe Leu Pro Gly Gly Arg Arg Ile Val Ala Phe Met Leu Lys Asp
                725                 730                 735

His Ala Gly Gly Asp Pro Trp Lys Asp Ile Val Val Ile Tyr Asn Gly
            740                 745                 750

Asn Leu Glu Lys Thr Thr Tyr Lys Leu Pro Glu Gly Lys Trp Asn Val
        755                 760                 765

Val Val Asn Ser Gln Lys Ala Gly Thr Glu Val Ile Glu Thr Val Glu
    770                 775                 780

Gly Thr Ile Glu Leu Asp Pro Leu Ser Ala Tyr Val Leu Tyr Arg Glu
785                 790                 795                 800

<210> SEQ ID NO 4
<211> LENGTH: 2400
<212> TYPE: DNA
<213> ORGANISM: Artificial Sequence
<220> FEATURE:
<223> OTHER INFORMATION: synthetic

<400> SEQUENCE: 4
atgggccact ggtacaagca ccagcgcgcc taccagttca ccggcgagga cgacttcggg    60
aaggtggccg tggtgaagct cccgatggac ctcaccaagg tgggcatcat cgtgcgcctc   120
aacgagtggc aggcgaagga cgtggccaag accgcttca tcgagatcaa ggacggcaag    180
gccgaggtgt ggatactcca gggcgtggag gagatcttct acgagaagcc ggacacctcc   240
ccgcgcatct tcttcgccca ggcccgctcc aacaaggtga tcgaggcctt cctcaccaac   300
ccggtggaca ccaagaagaa ggagctgttc aaggtgaccg tcgacggcaa ggagatcccg   360
gtgtcccgcg tggagaaggc cgaccccgacc gacatcgacg tgaccaacta cgtgcgcatc   420
gtgctctccg agtccctcaa ggaggaggac ctccgcaagg acgtggagct gatcatcgag   480
ggctacaagc cggcccgcgt gatcatgatg gagatcctcg acgactacta ctacgacggc   540
gagctggggg cggtgtactc cccggagaag accatcttcc gcgtgtggtc cccggtgtcc   600
aagtgggtga aggtgctcct cttcaagaac ggcgaggaca ccgagccgta ccaggtggtg   660
aacatggagt acaagggcaa cggcgtgtgg gaggccgtgg tggagggcga cctcgacggc   720
```

```
gtgttctacc tctaccagct ggagaactac ggcaagatcc gcaccaccgt ggacccgtac      780
tccaaggccg tgtacgccaa caaccaggag tctgcagtgg tgaacctcgc cgcaccaac      840 ccggagggct gggagaacga ccgcggcccg aagatcgagg gctacgagga cgccatcatc      900
tacgagatcc acatcgccga catcaccggc ctggagaact ccggcgtgaa gaacaagggc      960
ctctacctcg gcctcaccga ggagaacacc aaggccccgg cggcgtgac caccggcctc     1020 tcccacctcg tggagctggg cgtgacccac gtgcacatcc tcccgttctt cgacttctac     1080
accggcgacg agctggacaa ggacttcgag aagtactaca actggggcta cgacccgtac     1140
ctcttcatgt gccggagggc cgctactcc accgacccga gaacccgca cacccgaatt     1200 cgcgaggtga aggagatggt gaaggccctc cacaagcacg gcatcggcgt gatcatggac     1260
atggtgttcc gcacacccta cggcatcggc gagctgtccg ccttcgacca gaccgtgccg     1320
tactacttct accgcatcga caagaccggc gcctacctca cgagtccgg ctgcggcaac      1380 gtgatcgcct ccgagcgccc gatgatgcgc aagttcatcg tggacaccgt gacctactgg     1440
gtgaaggagt accacatcga cggcttccgc ttcgaccaga tgggcctcat cgacaagaag     1500
accatgctgg aggtggagcg cgccctccac aagatcgacc cgaccatcat cctctacggc     1560
gagccgtggg gcggctgggg ggccccgatc cgcttcggca agtccgacgt ggccggcacc     1620
cacgtggccc ccttcaacga cgagttccgc gacgccatcc gcggctccgt gttcaacccg     1680
tccgtgaagg gcttcgtgat gggcggctac ggcaaggaga ccaagatcaa gcgcggcgtg     1740
gtgggctcca tcaactacga cggcaagctc atcaagtcct tcgccctcga cccggaggag     1800
accatcaact acgccgcctg ccacgacaac cacaccctct gggacaagaa ctacctcgcc     1860
gccaaggccg acaagaagaa ggagtggacc gaggaggagc tgaagaacgc ccagaagctc     1920
gccggcgcca tcctcctcac tagtcaggc gtgccgttcc tccacggcgg ccaggacttc     1980
tgccgcacca ccaacttcaa cgacaactcc tacaacgccc cgatctccat caacggcttc     2040
gactacgagc gcaagctcca gttcatcgac gtgttcaact accacaaggg cctcatcaag     2100
ctccgcaagg agcaccccgg cttccgcctc aagaacgccg aggagatcaa gaagcacctg     2160
gagttcctcc cgggcgggcg ccgcatcgtg gccttcatgc tcaaggacca cgccggcggc     2220
gacccgtgga aggacatcgt ggtgatctac aacggcaacc tggagaagac cacctacaag     2280 ctccccggagg gcaagtggaa cgtggtggtg aactcccaga aggccggcac cgaggtgatc     2340
gagaccgtgg agggcaccat cgagctggac ccgctctccg cctacgtgct ctaccgcgag     2400
```

<210> SEQ ID NO 5
<211> LENGTH: 693
<212> TYPE: PRT
<213> ORGANISM: Sulfolobus solfataricus

<400> SEQUENCE: 5

```
Met Glu Thr Ile Lys Ile Tyr Glu Asn Lys Gly Val Tyr Lys Val Val
 1               5                  10                  15

Ile Gly Glu Pro Phe Pro Pro Ile Glu Phe Pro Leu Glu Gln Lys Ile
            20                  25                  30

Ser Ser Asn Lys Ser Leu Ser Glu Leu Gly Leu Thr Ile Val Gln Gln
        35                  40                  45

Gly Asn Lys Val Ile Val Glu Lys Ser Leu Asp Leu Lys Glu His Ile
    50                  55                  60

Ile Gly Leu Gly Glu Lys Ala Phe Glu Leu Asp Arg Lys Arg Lys Arg
65                  70                  75                  80
```

-continued

```
Tyr Val Met Tyr Asn Val Asp Ala Gly Ala Tyr Lys Lys Tyr Gln Asp
             85                  90                  95

Pro Leu Tyr Val Ser Ile Pro Leu Phe Ile Ser Val Lys Asp Gly Val
            100                 105                 110

Ala Thr Gly Tyr Phe Phe Asn Ser Ala Ser Lys Val Ile Phe Asp Val
        115                 120                 125

Gly Leu Glu Glu Tyr Asp Lys Val Ile Val Thr Ile Pro Glu Asp Ser
    130                 135                 140

Val Glu Phe Tyr Val Ile Glu Gly Pro Arg Ile Glu Asp Val Leu Glu
145                 150                 155                 160

Lys Tyr Thr Glu Leu Thr Gly Lys Pro Phe Leu Pro Pro Met Trp Ala
                165                 170                 175

Phe Gly Tyr Met Ile Ser Arg Tyr Ser Tyr Pro Gln Asp Lys Val
            180                 185                 190

Val Glu Leu Val Asp Ile Met Gln Lys Glu Gly Phe Arg Val Ala Gly
        195                 200                 205

Val Phe Leu Asp Ile His Tyr Met Asp Ser Tyr Lys Leu Phe Thr Trp
    210                 215                 220

His Pro Tyr Arg Phe Pro Glu Pro Lys Lys Leu Ile Asp Glu Leu His
225                 230                 235                 240

Lys Arg Asn Val Lys Leu Ile Thr Ile Val Asp His Gly Ile Arg Val
                245                 250                 255

Asp Gln Asn Tyr Ser Pro Phe Leu Ser Gly Met Gly Lys Phe Cys Glu
            260                 265                 270

Ile Glu Ser Gly Glu Leu Phe Val Gly Lys Met Trp Pro Gly Thr Thr
        275                 280                 285

Val Tyr Pro Asp Phe Phe Arg Glu Asp Thr Arg Glu Trp Trp Ala Gly
    290                 295                 300

Leu Ile Ser Glu Trp Leu Ser Gln Gly Val Asp Gly Ile Trp Leu Asp
305                 310                 315                 320

Met Asn Glu Pro Thr Asp Phe Ser Arg Ala Ile Glu Ile Arg Asp Val
                325                 330                 335

Leu Ser Ser Leu Pro Val Gln Phe Arg Asp Asp Arg Leu Val Thr Thr
            340                 345                 350

Phe Pro Asp Asn Val Val His Tyr Leu Arg Gly Lys Arg Val Lys His
        355                 360                 365

Glu Lys Val Arg Asn Ala Tyr Pro Leu Tyr Glu Ala Met Ala Thr Phe
    370                 375                 380

Lys Gly Phe Arg Thr Ser His Arg Asn Glu Ile Phe Ile Leu Ser Arg
385                 390                 395                 400

Ala Gly Tyr Ala Gly Ile Gln Arg Tyr Ala Phe Ile Trp Thr Gly Asp
                405                 410                 415

Asn Thr Pro Ser Trp Asp Asp Leu Lys Leu Gln Leu Gln Leu Val Leu
            420                 425                 430

Gly Leu Ser Ile Ser Gly Val Pro Phe Val Gly Cys Asp Ile Gly Gly
        435                 440                 445

Phe Gln Gly Arg Asn Phe Ala Glu Ile Asp Asn Ser Met Asp Leu Leu
    450                 455                 460

Val Lys Tyr Tyr Ala Leu Ala Leu Phe Phe Pro Phe Tyr Arg Ser His
465                 470                 475                 480

Lys Ala Thr Asp Gly Ile Asp Thr Glu Pro Val Phe Leu Pro Asp Tyr
                485                 490                 495

Tyr Lys Glu Lys Val Lys Glu Ile Val Glu Leu Arg Tyr Lys Phe Leu
```

```
                500             505             510
Pro Tyr Ile Tyr Ser Leu Ala Leu Glu Ala Ser Glu Lys Gly His Pro
            515                 520                 525

Val Ile Arg Pro Leu Phe Tyr Glu Phe Gln Asp Asp Asp Met Tyr
        530                 535                 540

Arg Ile Glu Asp Glu Tyr Met Val Gly Lys Tyr Leu Leu Tyr Ala Pro
545                 550                 555                 560

Ile Val Ser Lys Glu Glu Ser Arg Leu Val Thr Leu Pro Arg Gly Lys
                565                 570                 575

Trp Tyr Asn Tyr Trp Asn Gly Glu Ile Ile Asn Gly Lys Ser Val Val
            580                 585                 590

Lys Ser Thr His Glu Leu Pro Ile Tyr Leu Arg Glu Gly Ser Ile Ile
            595                 600                 605

Pro Leu Glu Gly Asp Glu Leu Ile Val Tyr Gly Glu Thr Ser Phe Lys
        610                 615                 620

Arg Tyr Asp Asn Ala Glu Ile Thr Ser Ser Asn Glu Ile Lys Phe
625                 630                 635                 640

Ser Arg Glu Ile Tyr Val Ser Lys Leu Thr Ile Thr Ser Glu Lys Pro
                645                 650                 655

Val Ser Lys Ile Ile Val Asp Asp Ser Lys Glu Ile Gln Val Glu Lys
            660                 665                 670

Thr Met Gln Asn Thr Tyr Val Ala Lys Ile Asn Gln Lys Ile Arg Gly
            675                 680                 685

Lys Ile Asn Leu Glu
    690

<210> SEQ ID NO 6
<211> LENGTH: 2082
<212> TYPE: DNA
<213> ORGANISM: Sulfolobus solfataricus

<400> SEQUENCE: 6
atggagacca tcaagatcta cgagaacaag ggcgtgtaca aggtggtgat cggcgagccg      60
ttcccgccga tcgagttccc gctcgagcag aagatctcct ccaacaagtc cctctccgag     120
ctgggcctca ccatcgtgca gcagggcaac aaggtgatcg tggagaagtc cctcgacctc     180
aaggagcaca tcatcggcct cggcgagaag gccttcgagc tggaccgcaa gcgcaagcgc     240
tacgtgatgt acaacgtgga cgccggcgcc tacaagaagt accaggaccc gctctacgtg     300
tccatcccgc tcttcatctc cgtgaaggac ggcgtggcca ccggctactt cttcaactcc     360
gcctccaagg tgatcttcga cgtgggcctc gaggagtacg acaaggtgat cgtgaccatc     420
ccggaggact ccgtggagtt ctacgtgatc gagggcccgc gcatcgagga cgtgctcgag     480
aagtacaccg agctgaccgg caagccgttc ctcccgccga tgtgggcctt cggctacatg     540
atctcccgct actcctacta cccgcaggac aaggtggtgg agctggtgga catcatgcag     600
aaggagggct ccgcgtggc cggcgtgttc ctcgacatcc actacatgga ctcctacaag     660
ctcttcacct ggcacccgta ccgcttcccg gagccgaaga gctcatcga cgagctgcac     720 aagcgcaacg tgaagctcat caccatcgtg gaccacggca tccgcgtgga ccagaactac     780
tccccgttcc tctccggcat gggcaagttc tgcgagatcg agtccggcga gctgttcgtg     840
ggcaagatgt ggccgggcac accgtgtac ccggacttct tccgcgagga cacccgcgag     900
tggtgggccg gctcatctc cgagtggctc tccagggcg tggacggcat ctggctcgac     960
atgaacgagc cgaccgactt ctcccgcgcc atcgagatcc gcgacgtgct ctcctccctc    1020
```

```
ccggtgcagt tccgcgacga ccgcctcgtg accaccttcc cggacaacgt ggtgcactac    1080
ctccgcggca agcgcgtgaa gcacgagaag gtgcgcaacg cctacccgct ctacgaggcg    1140
atggccacct tcaagggctt ccgcacctcc caccgcaacg agatcttcat cctctcccgc    1200
gccggctacg ccggcatcca gcgctacgcc ttcatctgga ccggcgacaa caccccgtcc    1260
tgggacgacc tcaagctcca gctccagctc gtgctcggcc tctccatctc cggcgtgccg    1320
ttcgtgggct gcgacatcgg cggcttccag gccgcaact tcgccgagat cgacaactcg     1380
atggacctcc tcgtgaagta ctacgccctc gccctcttct cccgttcta ccgctcccac     1440 aaggccaccg acggcatcga caccgagccg tgttcctcc ggactacta caaggagaag      1500 gtgaaggaga tcgtggagct cgctacaag ttcctcccgt acatctactc cctcgccctc    1560
gaggcctccg agaagggcca cccggtgatc cgcccgctct tctacgagtt ccaggacgac    1620
gacgacatgt accgcatcga ggacgagtac atggtgggca agtacctcct ctacgccccg    1680
atcgtgtcca aggaggagtc ccgcctcgtg accctcccgc gcggcaagtg gtacaactac    1740
tggaacggcg agatcatcaa cggcaagtcc gtggtgaagt ccacccacga gctgccgatc    1800
tacctccgcg agggctccat catcccgctc gagggcgacg agctgatcgt gtacggcgag    1860
acctccttca gcgctacga caacgccgag atcacctcct cctccaacga gatcaagttc     1920
tcccgcgaga tctacgtgtc caagctcacc atcacctccg agaagccggt gtccaagatc     1980
atcgtggacg actccaagga gatccaggtg gagaagacca tgcagaacac ctacgtggcc    2040
aagatcaacc agaagatccg cggcaagatc aacctcgagt ga                      2082

<210> SEQ ID NO 7
<211> LENGTH: 1818
<212> TYPE: DNA
<213> ORGANISM: Artificial Sequence
<220> FEATURE:
<223> OTHER INFORMATION: synthetic

<400> SEQUENCE: 7
atggcggctc tggccacgtc gcagctcgtc gcaacgcgcg ccggcctggg cgtcccggac     60
gcgtccacgt tccgccgcgg cgccgcgcag ggcctgaggg gggcccgggc gtcggcggcg    120
gcggacacgc tcagcatgcg gaccagcgcg cgcgcggcgc ccaggcacca gcaccagcag    180
gcgcgccgcg gggccaggtt cccgtcgctc gtcgtgtgcg ccagcgccgg catgaacgtc    240
gtcttcgtcg gcgccgagat ggcgccgtgg agcaagaccg gaggcctcgg cgacgtcctc    300
ggcggcctgc cgccggccat ggccgcgaac gggcaccgtg tcatggtcgt ctctccccgc    360
tacgaccagt acaaggacgc ctgggacacc agcgtcgtgt ccgagatcaa gatgggagac    420
gggtacgaga cggtcaggtt cttccactgc tacaagcgcg gagtggaccg cgtgttcgtt    480
gaccacccac tgttcctgga gagggtttgg ggaaagaccg aggagaagat ctacgggcct    540
gtcgctggaa cggactacag ggacaaccag ctgcggttca gcctgctatg ccaggcagca    600
cttgaagctc caaggatcct gagcctcaac aacaacccat acttctccgg accatacggg    660
gaggacgtcg tgttcgtctg caacgactgg cacaccggcc ctctctcgtg ctacctcaag    720
agcaactacc agtcccacgg catctacagg gacgcaaaga ccgctttctg catccacaac    780
atctcctacc agggccggtt cgccttctcc gactaccgg agctgaacct ccccgagaga    840
ttcaagtcgt ccttcgattt catcgacggc tacgagaagc ccgtggaagg ccggaagatc    900
aactggatga aggccgggat cctcgaggcc gacagggtcc tcaccgtcag cccctactac    960
```

```
gccgaggagc tcatctccgg catcgccagg ggctgcgagc tcgacaacat catgcgcctc    1020
accggcatca ccggcatcgt caacggcatg gacgtcagcg agtgggaccc cagcagggac    1080
aagtacatcg ccgtgaagta cgacgtgtcg acggccgtgg aggccaaggc gctgaacaag    1140
gaggcgctgc aggcggaggt cgggctcccg gtggaccgga acatcccgct ggtggcgttc    1200
atcggcaggc tggaagagca gaagggcccc gacgtcatgg cggccgccat cccgcagctc    1260
atggagatgg tggaggacgt gcagatcgtt ctgctgggca cgggcaagaa gaagttcgag    1320
cgcatgctca tgagcgccga ggagaagttc ccaggcaagg tgcgcgccgt ggtcaagttc    1380
aacgcggcgc tggcgcacca catcatggcc ggcgccgacg tgctcgccgt caccagccgc    1440
ttcgagccct gcggcctcat ccagctgcag gggatgcgat acggaacgcc ctgcgcctgc    1500
gcgtccaccg gtggactcgt cgacaccatc atcgaaggca agaccgggtt ccacatgggc    1560
cgcctcagcg tcgactgcaa cgtcgtggag ccggcggacg tcaagaaggt ggccaccacc    1620
ttgcagcgcg ccatcaaggt ggtcggcacg ccggcgtacg aggagatggt gaggaactgc    1680
atgatccagg atctctcctg gaagggcccc gccaagaact gggagaacgt gctgctcagc    1740
ctcggggtcg ccggcggcga gccaggggtt gaaggcgagg agatcgcgcc gctcgccaag    1800
gagaacgtgg ccgcgccc                                                  1818

<210> SEQ ID NO 8
<211> LENGTH: 606
<212> TYPE: PRT
<213> ORGANISM: Artificial Sequence
<220> FEATURE:
<223> OTHER INFORMATION: synthetic

<400> SEQUENCE: 8

Met Ala Ala Leu Ala Thr Ser Gln Leu Val Ala Thr Arg Ala Gly Leu
 1               5                  10                  15

Gly Val Pro Asp Ala Ser Thr Phe Arg Arg Gly Ala Ala Gln Gly Leu
                20                  25                  30

Arg Gly Ala Arg Ala Ser Ala Ala Ala Asp Thr Leu Ser Met Arg Thr
            35                  40                  45

Ser Ala Arg Ala Ala Pro Arg His Gln His Gln Gln Ala Arg Arg Gly
        50                  55                  60

Ala Arg Phe Pro Ser Leu Val Val Cys Ala Ser Ala Gly Met Asn Val
 65                  70                  75                  80

Val Phe Val Gly Ala Glu Met Ala Pro Trp Ser Lys Thr Gly Gly Leu
                85                  90                  95

Gly Asp Val Leu Gly Gly Leu Pro Pro Ala Met Ala Ala Asn Gly His
                100                 105                 110

Arg Val Met Val Val Ser Pro Arg Tyr Asp Gln Tyr Lys Asp Ala Trp
            115                 120                 125

Asp Thr Ser Val Val Ser Glu Ile Lys Met Gly Asp Gly Tyr Glu Thr
        130                 135                 140

Val Arg Phe Phe His Cys Tyr Lys Arg Gly Val Asp Arg Val Phe Val
145                 150                 155                 160

Asp His Pro Leu Phe Leu Glu Arg Val Trp Gly Lys Thr Glu Glu Lys
                165                 170                 175

Ile Tyr Gly Pro Val Ala Gly Thr Asp Tyr Arg Asp Asn Gln Leu Arg
            180                 185                 190

Phe Ser Leu Leu Cys Gln Ala Ala Leu Glu Ala Pro Arg Ile Leu Ser
        195                 200                 205
```

```
Leu Asn Asn Asn Pro Tyr Phe Ser Gly Pro Tyr Gly Glu Asp Val Val
    210                 215                 220

Phe Val Cys Asn Asp Trp His Thr Gly Pro Leu Ser Cys Tyr Leu Lys
225                 230                 235                 240

Ser Asn Tyr Gln Ser His Gly Ile Tyr Arg Asp Ala Lys Thr Ala Phe
                245                 250                 255

Cys Ile His Asn Ile Ser Tyr Gln Gly Arg Phe Ala Phe Ser Asp Tyr
            260                 265                 270

Pro Glu Leu Asn Leu Pro Glu Arg Phe Lys Ser Ser Phe Asp Phe Ile
        275                 280                 285

Asp Gly Tyr Glu Lys Pro Val Glu Gly Arg Lys Ile Asn Trp Met Lys
290                 295                 300

Ala Gly Ile Leu Glu Ala Asp Arg Val Leu Thr Val Ser Pro Tyr Tyr
305                 310                 315                 320

Ala Glu Glu Leu Ile Ser Gly Ile Ala Arg Gly Cys Glu Leu Asp Asn
                325                 330                 335

Ile Met Arg Leu Thr Gly Ile Thr Gly Ile Val Asn Gly Met Asp Val
            340                 345                 350

Ser Glu Trp Asp Pro Ser Arg Asp Lys Tyr Ile Ala Val Lys Tyr Asp
        355                 360                 365

Val Ser Thr Ala Val Glu Ala Lys Ala Leu Asn Lys Glu Ala Leu Gln
370                 375                 380

Ala Glu Val Gly Leu Pro Val Asp Arg Asn Ile Pro Leu Val Ala Phe
385                 390                 395                 400

Ile Gly Arg Leu Glu Glu Gln Lys Gly Pro Asp Val Met Ala Ala Ala
                405                 410                 415

Ile Pro Gln Leu Met Glu Met Val Glu Asp Val Gln Ile Val Leu Leu
            420                 425                 430

Gly Thr Gly Lys Lys Lys Phe Glu Arg Met Leu Met Ser Ala Glu Glu
        435                 440                 445

Lys Phe Pro Gly Lys Val Arg Ala Val Val Lys Phe Asn Ala Ala Leu
450                 455                 460

Ala His His Ile Met Ala Gly Ala Asp Val Leu Ala Val Thr Ser Arg
465                 470                 475                 480

Phe Glu Pro Cys Gly Leu Ile Gln Leu Gln Gly Met Arg Tyr Gly Thr
                485                 490                 495

Pro Cys Ala Cys Ala Ser Thr Gly Gly Leu Val Asp Thr Ile Ile Glu
            500                 505                 510

Gly Lys Thr Gly Phe His Met Gly Arg Leu Ser Val Asp Cys Asn Val
        515                 520                 525

Val Glu Pro Ala Asp Val Lys Lys Val Ala Thr Thr Leu Gln Arg Ala
530                 535                 540

Ile Lys Val Val Gly Thr Pro Ala Tyr Glu Glu Met Val Arg Asn Cys
545                 550                 555                 560

Met Ile Gln Asp Leu Ser Trp Lys Gly Pro Ala Lys Asn Trp Glu Asn
                565                 570                 575

Val Leu Leu Ser Leu Gly Val Ala Gly Gly Glu Pro Gly Val Glu Gly
            580                 585                 590

Glu Glu Ile Ala Pro Leu Ala Lys Glu Asn Val Ala Ala Pro
        595                 600                 605

<210> SEQ ID NO 9
<211> LENGTH: 2223
<212> TYPE: DNA
```

<213> ORGANISM: Artificial Sequence
<220> FEATURE:
<223> OTHER INFORMATION: synthetic

<400> SEQUENCE: 9

| | | | | | |
|---|---|---|---|---|---|
| atggccaagt | acctggagct | ggaggagggc | ggcgtgatca | tgcaggcgtt | ctactgggac | 60 |
| gtcccgagcg | gaggcatctg | gtgggacacc | atccgccaga | agatccccga | gtggtacgac | 120 |
| gccggcatct | ccgcgatctg | gataccgcca | gcttccaagg | gcatgtccgg | gggctactcg | 180 |
| atgggctacg | acccgtacga | ctacttcgac | ctcggcgagt | actaccagaa | gggcacggtg | 240 |
| gagacgcgct | tcgggtccaa | gcaggagctc | atcaacatga | tcaacacggc | gcacgcctac | 300 |
| ggcatcaagg | tcatcgcgga | catcgtgatc | aaccacaggg | ccggcggcga | cctggagtgg | 360 |
| aacccgttcg | tcggcgacta | cacctggacg | gacttctcca | aggtcgcctc | cggcaagtac | 420 |
| accgccaact | acctcgactt | ccaccccaac | gagctgcacg | cgggcgactc | cggcacgttc | 480 |
| ggcggctacc | cggacatctg | ccacgacaag | tcctgggacc | agtactggct | ctgggcctcg | 540 |
| caggagtcct | acgcggccta | cctgcgctcc | atcggcatcg | acgcgtggcg | cttcgactac | 600 |
| gtcaagggct | acggggcctg | ggtggtcaag | gactggctca | actggtgggg | cggctgggcg | 660 |
| gtgggcgagt | actgggacac | caacgtcgac | gcgctgctca | actgggccta | ctcctccggc | 720 |
| gccaaggtgt | tcgacttccc | cctgtactac | aagatggacg | cggccttcga | caacaagaac | 780 |
| atcccggcgc | tcgtcgaggc | cctgaagaac | ggcggcacgg | tggtctcccg | cgacccgttc | 840 |
| aaggccgtga | ccttcgtcgc | caaccacgac | acggacatca | tctggaacaa | gtacccggcg | 900 |
| tacgccttca | tcctcaccta | cgagggccag | cccacgatct | tctaccgcga | ctacgaggag | 960 |
| tggctgaaca | aggacaagct | caagaacctg | atctggattc | acgacaacct | cgcgggcggc | 1020 |
| tccactagta | tcgtgtacta | cgactccgac | gagatgatct | tcgtccgcaa | cggctacggc | 1080 |
| tccaagcccg | gcctgatcac | gtacatcaac | ctgggctcct | ccaaggtggg | ccgctgggtg | 1140 |
| tacgtcccga | agttcgccgg | cgcgtgcatc | cacgagtaca | ccggcaacct | cggcggctgg | 1200 |
| gtggacaagt | acgtgtactc | ctccggctgg | gtctacctgg | aggccccggc | ctacgacccc | 1260 |
| gccaacggcc | agtacggcta | ctccgtgtgg | tcctactgcg | gcgtcggcac | atcgattgct | 1320 |
| ggcatcctcg | aggccgacag | ggtcctcacc | gtcagcccct | actacgccga | ggagctcatc | 1380 |
| tccggcatcg | ccaggggctg | cgagctcgac | aacatcatgc | gcctcaccgg | catcaccggc | 1440 |
| atcgtcaacg | gcatggacgt | cagcgagtgg | gaccccagca | gggacaagta | catcgccgtg | 1500 |
| aagtacgacg | tgtcgacggc | cgtggaggcc | aaggcgctga | acaaggaggc | gctgcaggcg | 1560 |
| gaggtcgggc | tcccggtgga | ccggaacatc | ccgctggtgg | cgttcatcgg | caggctggaa | 1620 |
| gagcagaagg | gccccgacgt | catggcggcc | gccatcccgc | agctcatgga | gatggtggag | 1680 |
| gacgtgcaga | tcgttctgct | gggcacgggc | aagaagaagt | tcgagcgcat | gctcatgagc | 1740 |
| gccgaggaga | agttcccagg | caaggtgcgc | gccgtggtca | agttcaacgc | ggcgctggcg | 1800 |
| caccacatca | tggccggcgc | cgacgtgctc | gccgtcacca | gccgcttcga | gccctgcggc | 1860 |
| ctcatccagc | tgcaggggat | gcgatacgga | acgcccgtgcg | cctgcgcgtc | caccggtgga | 1920 |
| ctcgtcgaca | ccatcatcga | aggcaagacc | gggttccaca | tgggccgcct | cagcgtcgac | 1980 |
| tgcaacgtcg | tggagccggc | ggacgtcaag | aaggtggcca | ccaccttgca | gcgcgccatc | 2040 |
| aaggtggtcg | gcacgccggc | gtacgaggag | atggtgagga | actgcatgat | ccaggatctc | 2100 |
| tcctggaagg | gccctgccaa | gaactgggag | aacgtgctgc | tcagcctcgg | ggtcgccggc | 2160 |
| ggcgagccag | gggttgaagg | cgaggagatc | gcgccgctcg | ccaaggagaa | cgtggccgcg | 2220 | ccc                                                                                          2223

<210> SEQ ID NO 10
<211> LENGTH: 741
<212> TYPE: PRT
<213> ORGANISM: Artificial Sequence
<220> FEATURE:
<223> OTHER INFORMATION: synthetic

<400> SEQUENCE: 10

```
Met Ala Lys Tyr Leu Glu Leu Glu Gly Gly Val Ile Met Gln Ala
 1               5                  10                  15

Phe Tyr Trp Asp Val Pro Ser Gly Gly Ile Trp Trp Asp Thr Ile Arg
                20                  25                  30

Gln Lys Ile Pro Glu Trp Tyr Asp Ala Gly Ile Ser Ala Ile Trp Ile
                35                  40                  45

Pro Pro Ala Ser Lys Gly Met Ser Gly Gly Tyr Ser Met Gly Tyr Asp
 50                  55                  60

Pro Tyr Asp Tyr Phe Asp Leu Gly Glu Tyr Tyr Gln Lys Gly Thr Val
 65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Gly Asp Tyr Thr
                115                 120                 125

Trp Thr Asp Phe Ser Lys Val Ala Ser Gly Lys Tyr Thr Ala Asn Tyr
 130                 135                 140

Leu Asp Phe His Pro Asn Glu Leu His Ala Gly Asp Ser Gly Thr Phe
 145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
                180                 185                 190

Ile Asp Ala Trp Arg Phe Asp Tyr Val Lys Gly Tyr Gly Ala Trp Val
                195                 200                 205

Val Lys Asp Trp Leu Asn Trp Trp Gly Gly Trp Ala Val Gly Glu Tyr
 210                 215                 220

Trp Asp Thr Asn Val Asp Ala Leu Leu Asn Trp Ala Tyr Ser Ser Gly
 225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
                260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
 290                 295                 300

Leu Thr Tyr Glu Gly Gln Pro Thr Ile Phe Tyr Arg Asp Tyr Glu Glu
 305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
                340                 345                 350
```

```
Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
        370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly Thr Ser Ile Ala Gly Ile Leu Glu Ala Asp Arg Val
        435                 440                 445

Leu Thr Val Ser Pro Tyr Tyr Ala Glu Glu Leu Ile Ser Gly Ile Ala
        450                 455                 460

Arg Gly Cys Glu Leu Asp Asn Ile Met Arg Leu Thr Gly Ile Thr Gly
465                 470                 475                 480

Ile Val Asn Gly Met Asp Val Ser Glu Trp Asp Pro Ser Arg Asp Lys
                485                 490                 495

Tyr Ile Ala Val Lys Tyr Asp Val Ser Thr Ala Val Glu Ala Lys Ala
                500                 505                 510

Leu Asn Lys Glu Ala Leu Gln Ala Glu Val Gly Leu Pro Val Asp Arg
        515                 520                 525

Asn Ile Pro Leu Val Ala Phe Ile Gly Arg Leu Glu Glu Gln Lys Gly
        530                 535                 540

Pro Asp Val Met Ala Ala Ile Pro Gln Leu Met Glu Met Val Glu
545                 550                 555                 560

Asp Val Gln Ile Val Leu Leu Gly Thr Gly Lys Lys Lys Phe Glu Arg
                565                 570                 575

Met Leu Met Ser Ala Glu Glu Lys Phe Pro Gly Lys Val Arg Ala Val
                580                 585                 590

Val Lys Phe Asn Ala Ala Leu Ala His His Ile Met Ala Gly Ala Asp
        595                 600                 605

Val Leu Ala Val Thr Ser Arg Phe Glu Pro Cys Gly Leu Ile Gln Leu
        610                 615                 620

Gln Gly Met Arg Tyr Gly Thr Pro Cys Ala Cys Ala Ser Thr Gly Gly
625                 630                 635                 640

Leu Val Asp Thr Ile Ile Glu Gly Lys Thr Gly Phe His Met Gly Arg
                645                 650                 655

Leu Ser Val Asp Cys Asn Val Val Glu Pro Ala Asp Val Lys Lys Val
                660                 665                 670

Ala Thr Thr Leu Gln Arg Ala Ile Lys Val Val Gly Thr Pro Ala Tyr
        675                 680                 685

Glu Glu Met Val Arg Asn Cys Met Ile Gln Asp Leu Ser Trp Lys Gly
        690                 695                 700

Pro Ala Lys Asn Trp Glu Asn Val Leu Leu Ser Leu Gly Val Ala Gly
705                 710                 715                 720

Gly Glu Pro Gly Val Glu Gly Glu Glu Ile Ala Pro Leu Ala Lys Glu
                725                 730                 735

Asn Val Ala Ala Pro
                740

<210> SEQ ID NO 11
<211> LENGTH: 1515
<212> TYPE: DNA
```

<213> ORGANISM: Zea mays

<400> SEQUENCE: 11

```
ggagagctat gagacgtatg tcctcaaagc cactttgcat tgtgtgaaac caatatcgat      60
ctttgttact tcatcatgca tgaacatttg tggaaactac tagcttacaa gcattagtga     120
cagctcagaa aaaagttatc tatgaaaggt ttcatgtgta ccgtgggaaa tgagaaatgt     180
tgccaactca aacaccttca atatgttgtt tgcaggcaaa ctcttctgga agaaaggtgt     240
ctaaaactat gaacgggtta cagaaaggta taaaccacgg ctgtgcattt tggaagtatc     300
atctatagat gtctgttgag gggaaagccg tacgccaacg ttatttactc agaaacagct     360
tcaacacaca gttgtctgct ttatgatggc atctccaccc aggcacccac catcacctat     420
ctctcgtgcc tgtttatttt cttgcccttt ctgatcataa aaaaacatta agagtttgca     480
aacatgcata ggcatatcaa tatgctcatt tattaatttg ctagcagatc atcttcctac     540
tctttacttt atttattgtt tgaaaaatat gtcctgcacc tagggagctc gtatacagta     600
ccaatgcatc ttcattaaat gtgaatttca gaaaggaagt aggaacctat gagagtattt     660
ttcaaaatta attagcggct tctattatgt ttatagcaaa ggccaagggc aaaattggaa     720
cactaatgat ggttggttgc atgagtctgt cgattacttg caagaaatgt gaacctttgt     780
ttctgtgcgt gggcataaaa caaacagctt ctagcctctt ttacggtact tgcacttgca     840
agaaatgtga actccttttc atttctgtat gtggacataa tgccaaagca tccaggcttt     900
ttcatggttg ttgatgtctt tacacagttc atctccacca gtatgccctc ctcatactct     960
atataaacac atcaacagca tcgcaattag ccacaagatc acttcgggag gcaagtgcga    1020
tttcgatctc gcagccacct tttttgttc tgttgtaagt ataccttccc ttaccatctt    1080
tatctgttag tttaatttgt aattgggaag tattagtgga aagaggatga gatgctatca    1140
tctatgtact ctgcaaatgc atctgacgtt atatgggctg cttcatataa tttgaattgc    1200
tccattcttg ccgacaatat attgcaaggt atatgcctag ttccatcaaa agttctgttt    1260
tttcattcta aaagcatttt agtggcacac aattttttgtc catgagggaa aggaaatctg    1320
ttttggttac tttgcttgag gtgcattctt catatgtcca gttttatgga agtaataaac    1380
ttcagtttgg tcataagatg tcatattaaa gggcaaacat atattcaatg ttcaattcat    1440
cgtaaatgtt ccctttttgt aaaagattgc atactcattt atttgagttg caggtgtatc    1500
tagtagttgg aggag                                                     1515
```

<210> SEQ ID NO 12
<211> LENGTH: 673
<212> TYPE: DNA
<213> ORGANISM: Zea mays

<400> SEQUENCE: 12

```
gatcatccag gtgcaaccgt ataagtccta aagtggtgag gaacacgaaa caaccatgca      60
ttggcatgta aagctccaag aatttgttgt atccttaaca actcacagaa catcaaccaa     120
aattgcacgt caagggtatt gggtaagaaa caatcaaaca aatcctctct gtgtgcaaag     180
aaacacggtg agtcatgccg agatcatact catctgatat acatgcttac agctcacaag     240
acattcaaaa caactcatat tgcattacaa agatcgtttc atgaaaaata aaataggccg     300
gacaggacaa aaatccttga cgtgtaaagt aaatttacaa caaaaaaaaa gccatatgtc     360
aagctaaatc taattcgttt tacgtagatc aacaacctgt agaaggcaac aaaactgagc     420
cacgcagaag tacagaatga ttccagatga accatcgacg tgctacgtaa agagagtgac     480
```

-continued

```
gagtcatata catttggcaa gaaaccatga agctgcctac agccgtctcg gtggcataag    540
aacacaagaa attgtgttaa ttaatcaaag ctataaataa cgctcgcatg cctgtgcact    600
tctccatcac caccactggg tcttcagacc attagcttta tctactccag agcgcagaag    660
aacccgatcg aca                                                       673
```

<210> SEQ ID NO 13
<211> LENGTH: 454
<212> TYPE: PRT
<213> ORGANISM: Artificial Sequence
<220> FEATURE:
<223> OTHER INFORMATION: synthetic

<400> SEQUENCE: 13

```
Met Arg Val Leu Leu Val Ala Leu Ala Leu Ala Leu Ala Ala Ser
 1               5                  10                  15

Ala Thr Ser Ala Lys Tyr Leu Glu Leu Glu Glu Gly Gly Val Ile Met
                20                  25                  30

Gln Ala Phe Tyr Trp Asp Val Pro Ser Gly Gly Ile Trp Trp Asp Thr
            35                  40                  45

Ile Arg Gln Lys Ile Pro Glu Trp Tyr Asp Ala Gly Ile Ser Ala Ile
50                  55                  60

Trp Ile Pro Pro Ala Ser Lys Gly Met Ser Gly Gly Tyr Ser Met Gly
65                  70                  75                  80

Tyr Asp Pro Tyr Asp Tyr Phe Asp Leu Gly Glu Tyr Tyr Gln Lys Gly
                85                  90                  95

Thr Val Glu Thr Arg Phe Gly Ser Lys Gln Glu Leu Ile Asn Met Ile
            100                 105                 110

Asn Thr Ala His Ala Tyr Gly Ile Lys Val Ile Ala Asp Ile Val Ile
        115                 120                 125

Asn His Arg Ala Gly Gly Asp Leu Glu Trp Asn Pro Phe Val Gly Asp
    130                 135                 140

Tyr Thr Trp Thr Asp Phe Ser Lys Val Ala Ser Gly Lys Tyr Thr Ala
145                 150                 155                 160

Asn Tyr Leu Asp Phe His Pro Asn Glu Leu His Ala Gly Asp Ser Gly
                165                 170                 175

Thr Phe Gly Gly Tyr Pro Asp Ile Cys His Asp Lys Ser Trp Asp Gln
            180                 185                 190

Tyr Trp Leu Trp Ala Ser Gln Glu Ser Tyr Ala Ala Tyr Leu Arg Ser
        195                 200                 205

Ile Gly Ile Asp Ala Trp Arg Phe Asp Tyr Val Lys Gly Tyr Gly Ala
    210                 215                 220

Trp Val Val Lys Asp Trp Leu Asn Trp Trp Gly Gly Trp Ala Val Gly
225                 230                 235                 240

Glu Tyr Trp Asp Thr Asn Val Asp Ala Leu Leu Asn Trp Ala Tyr Ser
                245                 250                 255

Ser Gly Ala Lys Val Phe Asp Phe Pro Leu Tyr Tyr Lys Met Asp Ala
            260                 265                 270

Ala Phe Asp Asn Lys Asn Ile Pro Ala Leu Val Glu Ala Leu Lys Asn
        275                 280                 285

Gly Gly Thr Val Val Ser Arg Asp Pro Phe Lys Ala Val Thr Phe Val
    290                 295                 300

Ala Asn His Asp Thr Asp Ile Ile Trp Asn Lys Tyr Pro Ala Tyr Ala
305                 310                 315                 320
```

```
Phe Ile Leu Thr Tyr Glu Gly Gln Pro Thr Ile Phe Tyr Arg Asp Tyr
                325                 330                 335

Glu Glu Trp Leu Asn Lys Asp Lys Leu Lys Asn Leu Ile Trp Ile His
            340                 345                 350

Asp Asn Leu Ala Gly Gly Ser Thr Ser Ile Val Tyr Tyr Asp Ser Asp
                355                 360                 365

Glu Met Ile Phe Val Arg Asn Gly Tyr Gly Ser Lys Pro Gly Leu Ile
            370                 375                 380

Thr Tyr Ile Asn Leu Gly Ser Ser Lys Val Gly Arg Trp Val Tyr Val
385                 390                 395                 400

Pro Lys Phe Ala Gly Ala Cys Ile His Glu Tyr Thr Gly Asn Leu Gly
                405                 410                 415

Gly Trp Val Asp Lys Tyr Val Tyr Ser Ser Gly Trp Val Tyr Leu Glu
            420                 425                 430

Ala Pro Ala Tyr Asp Pro Ala Asn Gly Gln Tyr Gly Tyr Ser Val Trp
                435                 440                 445

Ser Tyr Cys Gly Val Gly
            450

<210> SEQ ID NO 14
<211> LENGTH: 460
<212> TYPE: PRT
<213> ORGANISM: Artificial Sequence
<220> FEATURE:
<223> OTHER INFORMATION: synthetic

<400> SEQUENCE: 14

Met Arg Val Leu Leu Val Ala Leu Ala Leu Leu Ala Leu Ala Ala Ser
1               5                   10                  15

Ala Thr Ser Ala Lys Tyr Leu Glu Leu Glu Glu Gly Gly Val Ile Met
                20                  25                  30

Gln Ala Phe Tyr Trp Asp Val Pro Ser Gly Gly Ile Trp Trp Asp Thr
            35                  40                  45

Ile Arg Gln Lys Ile Pro Glu Trp Tyr Asp Ala Gly Ile Ser Ala Ile
        50                  55                  60

Trp Ile Pro Pro Ala Ser Lys Gly Met Ser Gly Gly Tyr Ser Met Gly
65                  70                  75                  80

Tyr Asp Pro Tyr Asp Tyr Phe Asp Leu Gly Glu Tyr Tyr Gln Lys Gly
                85                  90                  95

Thr Val Glu Thr Arg Phe Gly Ser Lys Gln Glu Leu Ile Asn Met Ile
            100                 105                 110

Asn Thr Ala His Ala Tyr Gly Ile Lys Val Ile Ala Asp Ile Val Ile
        115                 120                 125

Asn His Arg Ala Gly Gly Asp Leu Glu Trp Asn Pro Phe Val Gly Asp
    130                 135                 140

Tyr Thr Trp Thr Asp Phe Ser Lys Val Ala Ser Gly Lys Tyr Thr Ala
145                 150                 155                 160

Asn Tyr Leu Asp Phe His Pro Asn Glu Leu His Ala Gly Asp Ser Gly
                165                 170                 175

Thr Phe Gly Gly Tyr Pro Asp Ile Cys His Asp Lys Ser Trp Asp Gln
            180                 185                 190

Tyr Trp Leu Trp Ala Ser Gln Glu Ser Tyr Ala Ala Tyr Leu Arg Ser
        195                 200                 205

Ile Gly Ile Asp Ala Trp Arg Phe Asp Tyr Val Lys Gly Tyr Gly Ala
    210                 215                 220
```

```
Trp Val Val Lys Asp Trp Leu Asn Trp Trp Gly Gly Trp Ala Val Gly
225                 230                 235                 240

Glu Tyr Trp Asp Thr Asn Val Asp Ala Leu Leu Asn Trp Ala Tyr Ser
            245                 250                 255

Ser Gly Ala Lys Val Phe Asp Phe Pro Leu Tyr Tyr Lys Met Asp Ala
        260                 265                 270

Ala Phe Asp Asn Lys Asn Ile Pro Ala Leu Val Glu Ala Leu Lys Asn
    275                 280                 285

Gly Gly Thr Val Val Ser Arg Asp Pro Phe Lys Ala Val Thr Phe Val
290                 295                 300

Ala Asn His Asp Thr Asp Ile Ile Trp Asn Lys Tyr Pro Ala Tyr Ala
305                 310                 315                 320

Phe Ile Leu Thr Tyr Glu Gly Gln Pro Thr Ile Phe Tyr Arg Asp Tyr
                325                 330                 335

Glu Glu Trp Leu Asn Lys Asp Lys Leu Lys Asn Leu Ile Trp Ile His
            340                 345                 350

Asp Asn Leu Ala Gly Gly Ser Thr Ser Ile Val Tyr Tyr Asp Ser Asp
        355                 360                 365

Glu Met Ile Phe Val Arg Asn Gly Tyr Gly Ser Lys Pro Gly Leu Ile
370                 375                 380

Thr Tyr Ile Asn Leu Gly Ser Ser Lys Val Gly Arg Trp Val Tyr Val
385                 390                 395                 400

Pro Lys Phe Ala Gly Ala Cys Ile His Glu Tyr Thr Gly Asn Leu Gly
                405                 410                 415

Gly Trp Val Asp Lys Tyr Val Tyr Ser Ser Gly Trp Val Tyr Leu Glu
            420                 425                 430

Ala Pro Ala Tyr Asp Pro Ala Asn Gly Gln Tyr Gly Tyr Ser Val Trp
        435                 440                 445

Ser Tyr Cys Gly Val Gly Ser Glu Lys Asp Glu Leu
    450                 455                 460

<210> SEQ ID NO 15
<211> LENGTH: 518
<212> TYPE: PRT
<213> ORGANISM: Artificial Sequence
<220> FEATURE:
<223> OTHER INFORMATION: synthetic

<400> SEQUENCE: 15

Met Leu Ala Ala Leu Ala Thr Ser Gln Leu Val Ala Thr Arg Ala Gly
1               5                   10                  15

Leu Gly Val Pro Asp Ala Ser Thr Phe Arg Arg Gly Ala Ala Gln Gly
            20                  25                  30

Leu Arg Gly Ala Arg Ala Ser Ala Ala Ala Asp Thr Leu Ser Met Arg
        35                  40                  45

Thr Ser Ala Arg Ala Ala Pro Arg His Gln His Gln Ala Arg Arg
    50                  55                  60

Gly Ala Arg Phe Pro Ser Leu Val Val Cys Ala Ser Ala Gly Ala Met
65                  70                  75                  80

Ala Lys Tyr Leu Glu Leu Glu Glu Gly Gly Val Ile Met Gln Ala Phe
                85                  90                  95

Tyr Trp Asp Val Pro Ser Gly Gly Ile Trp Trp Asp Thr Ile Arg Gln
            100                 105                 110

Lys Ile Pro Glu Trp Tyr Asp Ala Gly Ile Ser Ala Ile Trp Ile Pro
        115                 120                 125
```

Pro Ala Ser Lys Gly Met Ser Gly Gly Tyr Ser Met Gly Tyr Asp Pro
    130                 135                 140

Tyr Asp Tyr Phe Asp Leu Gly Glu Tyr Tyr Gln Lys Gly Thr Val Glu
145                 150                 155                 160

Thr Arg Phe Gly Ser Lys Gln Glu Leu Ile Asn Met Ile Asn Thr Ala
                165                 170                 175

His Ala Tyr Gly Ile Lys Val Ile Ala Asp Ile Val Ile Asn His Arg
            180                 185                 190

Ala Gly Gly Asp Leu Glu Trp Asn Pro Phe Val Gly Asp Tyr Thr Trp
        195                 200                 205

Thr Asp Phe Ser Lys Val Ala Ser Gly Lys Tyr Thr Ala Asn Tyr Leu
    210                 215                 220

Asp Phe His Pro Asn Glu Leu His Ala Gly Asp Ser Gly Thr Phe Gly
225                 230                 235                 240

Gly Tyr Pro Asp Ile Cys His Asp Lys Ser Trp Asp Gln Tyr Trp Leu
                245                 250                 255

Trp Ala Ser Gln Glu Ser Tyr Ala Ala Tyr Leu Arg Ser Ile Gly Ile
            260                 265                 270

Asp Ala Trp Arg Phe Asp Tyr Val Lys Gly Tyr Gly Ala Trp Val Val
        275                 280                 285

Lys Asp Trp Leu Asn Trp Trp Gly Gly Trp Ala Val Gly Glu Tyr Trp
    290                 295                 300

Asp Thr Asn Val Asp Ala Leu Leu Asn Trp Ala Tyr Ser Ser Gly Ala
305                 310                 315                 320

Lys Val Phe Asp Phe Pro Leu Tyr Tyr Lys Met Asp Ala Ala Phe Asp
                325                 330                 335

Asn Lys Asn Ile Pro Ala Leu Val Glu Ala Leu Lys Asn Gly Gly Thr
            340                 345                 350

Val Val Ser Arg Asp Pro Phe Lys Ala Val Thr Phe Val Ala Asn His
        355                 360                 365

Asp Thr Asp Ile Ile Trp Asn Lys Tyr Pro Ala Tyr Ala Phe Ile Leu
    370                 375                 380

Thr Tyr Glu Gly Gln Pro Thr Ile Phe Tyr Arg Asp Tyr Glu Glu Trp
385                 390                 395                 400

Leu Asn Lys Asp Lys Leu Lys Asn Leu Ile Trp Ile His Asp Asn Leu
                405                 410                 415

Ala Gly Gly Ser Thr Ser Ile Val Tyr Tyr Asp Ser Asp Glu Met Ile
            420                 425                 430

Phe Val Arg Asn Gly Tyr Gly Ser Lys Pro Gly Leu Ile Thr Tyr Ile
        435                 440                 445

Asn Leu Gly Ser Ser Lys Val Gly Arg Trp Val Tyr Val Pro Lys Phe
    450                 455                 460

Ala Gly Ala Cys Ile His Glu Tyr Thr Gly Asn Leu Gly Gly Trp Val
465                 470                 475                 480

Asp Lys Tyr Val Tyr Ser Ser Gly Trp Val Tyr Leu Glu Ala Pro Ala
                485                 490                 495

Tyr Asp Pro Ala Asn Gly Gln Tyr Gly Tyr Ser Val Trp Ser Tyr Cys
            500                 505                 510

Gly Val Gly Thr Ser Ile
            515

<210> SEQ ID NO 16
<211> LENGTH: 820
<212> TYPE: PRT

<213> ORGANISM: Artificial Sequence
<220> FEATURE:
<223> OTHER INFORMATION: synthetic

<400> SEQUENCE: 16

```
Met Leu Ala Ala Leu Ala Thr Ser Gln Leu Val Ala Thr Arg Ala Gly
  1               5                  10                  15

Leu Gly Val Pro Asp Ala Ser Thr Phe Arg Arg Gly Ala Ala Gln Gly
             20                  25                  30

Leu Arg Gly Ala Arg Ala Ser Ala Ala Asp Thr Leu Ser Met Arg
         35                  40                  45

Thr Ser Ala Arg Ala Ala Pro Arg His Gln His Gln Gln Ala Arg Arg
     50                  55                  60

Gly Ala Arg Phe Pro Ser Leu Val Val Cys Ala Ser Ala Gly Ala Met
 65                  70                  75                  80

Ala Lys Tyr Leu Glu Leu Glu Glu Gly Gly Val Ile Met Gln Ala Phe
                 85                  90                  95

Tyr Trp Asp Val Pro Ser Gly Gly Ile Trp Trp Asp Thr Ile Arg Gln
            100                 105                 110

Lys Ile Pro Glu Trp Tyr Asp Ala Gly Ile Ser Ala Ile Trp Ile Pro
        115                 120                 125

Pro Ala Ser Lys Gly Met Ser Gly Gly Tyr Ser Met Gly Tyr Asp Pro
130                 135                 140

Tyr Asp Tyr Phe Asp Leu Gly Glu Tyr Tyr Gln Lys Gly Thr Val Glu
145                 150                 155                 160

Thr Arg Phe Gly Ser Lys Gln Glu Leu Ile Asn Met Ile Asn Thr Ala
                165                 170                 175

His Ala Tyr Gly Ile Lys Val Ile Ala Asp Ile Val Ile Asn His Arg
            180                 185                 190

Ala Gly Gly Asp Leu Glu Trp Asn Pro Phe Val Gly Asp Tyr Thr Trp
        195                 200                 205

Thr Asp Phe Ser Lys Val Ala Ser Gly Lys Tyr Thr Ala Asn Tyr Leu
210                 215                 220

Asp Phe His Pro Asn Glu Leu His Ala Gly Asp Ser Gly Thr Phe Gly
225                 230                 235                 240

Gly Tyr Pro Asp Ile Cys His Asp Lys Ser Trp Asp Gln Tyr Trp Leu
                245                 250                 255

Trp Ala Ser Gln Glu Ser Tyr Ala Ala Tyr Leu Arg Ser Ile Gly Ile
            260                 265                 270

Asp Ala Trp Arg Phe Asp Tyr Val Lys Gly Tyr Gly Ala Trp Val Val
        275                 280                 285

Lys Asp Trp Leu Asn Trp Trp Gly Gly Trp Ala Val Gly Glu Tyr Trp
290                 295                 300

Asp Thr Asn Val Asp Ala Leu Leu Asn Trp Ala Tyr Ser Ser Gly Ala
305                 310                 315                 320

Lys Val Phe Asp Phe Pro Leu Tyr Tyr Lys Met Asp Ala Ala Phe Asp
                325                 330                 335

Asn Lys Asn Ile Pro Ala Leu Val Glu Ala Leu Lys Asn Gly Gly Thr
            340                 345                 350

Val Val Ser Arg Asp Pro Phe Lys Ala Val Thr Phe Val Ala Asn His
        355                 360                 365

Asp Thr Asp Ile Ile Trp Asn Lys Tyr Pro Ala Tyr Ala Phe Ile Leu
370                 375                 380

Thr Tyr Glu Gly Gln Pro Thr Ile Phe Tyr Arg Asp Tyr Glu Glu Trp
```

-continued

```
            385                 390                 395                 400
Leu Asn Lys Asp Lys Leu Lys Asn Leu Ile Trp Ile His Asp Asn Leu
            405                 410                 415
Ala Gly Gly Ser Thr Ser Ile Val Tyr Tyr Asp Ser Asp Glu Met Ile
            420                 425                 430
Phe Val Arg Asn Gly Tyr Gly Ser Lys Pro Gly Leu Ile Thr Tyr Ile
            435                 440                 445
Asn Leu Gly Ser Ser Lys Val Gly Arg Trp Val Tyr Val Pro Lys Phe
            450                 455                 460
Ala Gly Ala Cys Ile His Glu Tyr Thr Gly Asn Leu Gly Gly Trp Val
465                 470                 475                 480
Asp Lys Tyr Val Tyr Ser Ser Gly Trp Val Tyr Leu Glu Ala Pro Ala
            485                 490                 495
Tyr Asp Pro Ala Asn Gly Gln Tyr Gly Tyr Ser Val Trp Ser Tyr Cys
            500                 505                 510
Gly Val Gly Thr Ser Ile Ala Gly Ile Leu Glu Ala Asp Arg Val Leu
            515                 520                 525
Thr Val Ser Pro Tyr Tyr Ala Glu Leu Ile Ser Gly Ile Ala Arg
            530                 535                 540
Gly Cys Glu Leu Asp Asn Ile Met Arg Leu Thr Gly Ile Thr Gly Ile
545                 550                 555                 560
Val Asn Gly Met Asp Val Ser Glu Trp Asp Pro Ser Arg Asp Lys Tyr
            565                 570                 575
Ile Ala Val Lys Tyr Asp Val Ser Thr Ala Val Glu Ala Lys Ala Leu
            580                 585                 590
Asn Lys Glu Ala Leu Gln Ala Glu Val Gly Leu Pro Val Asp Arg Asn
            595                 600                 605
Ile Pro Leu Val Ala Phe Ile Gly Arg Leu Glu Glu Gln Lys Gly Pro
            610                 615                 620
Asp Val Met Ala Ala Ala Ile Pro Gln Leu Met Glu Met Val Glu Asp
625                 630                 635                 640
Val Gln Ile Val Leu Leu Gly Thr Gly Lys Lys Lys Phe Glu Arg Met
            645                 650                 655
Leu Met Ser Ala Glu Glu Lys Phe Pro Gly Lys Val Arg Ala Val Val
            660                 665                 670
Lys Phe Asn Ala Ala Leu Ala His His Ile Met Ala Gly Ala Asp Val
            675                 680                 685
Leu Ala Val Thr Ser Arg Phe Glu Pro Cys Gly Leu Ile Gln Leu Gln
            690                 695                 700
Gly Met Arg Tyr Gly Thr Pro Cys Ala Cys Ala Ser Thr Gly Gly Leu
705                 710                 715                 720
Val Asp Thr Ile Ile Glu Gly Lys Thr Gly Phe His Met Gly Arg Leu
            725                 730                 735
Ser Val Asp Cys Asn Val Val Glu Pro Ala Asp Val Lys Lys Val Ala
            740                 745                 750
Thr Thr Leu Gln Arg Ala Ile Lys Val Val Gly Thr Pro Ala Tyr Glu
            755                 760                 765
Glu Met Val Arg Asn Cys Met Ile Gln Asp Leu Ser Trp Lys Gly Pro
            770                 775                 780
Ala Lys Asn Trp Glu Asn Val Leu Leu Ser Leu Gly Val Ala Gly Gly
785                 790                 795                 800
Glu Pro Gly Val Glu Gly Glu Glu Ile Ala Pro Leu Ala Lys Glu Asn
            805                 810                 815
```

```
Val Ala Ala Pro
         820

<210> SEQ ID NO 17
<211> LENGTH: 19
<212> TYPE: PRT
<213> ORGANISM: Artificial Sequence
<220> FEATURE:
<223> OTHER INFORMATION: synthetic

<400> SEQUENCE: 17

Met Arg Val Leu Leu Val Ala Leu Ala Leu Ala Leu Ala Ala Ser
 1               5                  10                  15

Ala Thr Ser

<210> SEQ ID NO 18
<211> LENGTH: 444
<212> TYPE: PRT
<213> ORGANISM: Thermotoga maritima

<400> SEQUENCE: 18

Met Ala Glu Phe Phe Pro Glu Ile Pro Lys Ile Gln Phe Glu Gly Lys
 1               5                  10                  15

Glu Ser Thr Asn Pro Leu Ala Phe Arg Phe Tyr Asp Pro Asn Glu Val
             20                  25                  30

Ile Asp Gly Lys Pro Leu Lys Asp His Leu Lys Phe Ser Val Ala Phe
         35                  40                  45

Trp His Thr Phe Val Asn Glu Gly Arg Asp Pro Phe Gly Asp Pro Thr
     50                  55                  60

Ala Glu Arg Pro Trp Asn Arg Phe Ser Asp Pro Met Asp Lys Ala Phe
65                  70                  75                  80

Ala Arg Val Asp Ala Leu Phe Glu Phe Cys Glu Lys Leu Asn Ile Glu
                 85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Tyr Ala Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Leu Glu Leu Glu Asn
        195                 200                 205

Leu Ala Arg Phe Leu Arg Met Ala Val Glu Tyr Ala Lys Lys Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Asn
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
```

```
                275                 280                 285
Leu Gly Lys Leu Gly Ser Ile Asp Ala Asn Gln Gly Asp Leu Leu Leu
        290                 295                 300
Gly Trp Asp Thr Asp Gln Phe Pro Thr Asn Ile Tyr Asp Thr Thr Leu
305                 310                 315                 320
Ala Met Tyr Glu Val Ile Lys Ala Gly Gly Phe Thr Lys Gly Gly Leu
                325                 330                 335
Asn Phe Asp Ala Lys Val Arg Arg Ala Ser Tyr Lys Val Glu Asp Leu
            340                 345                 350
Phe Ile Gly His Ile Ala Gly Met Asp Thr Phe Ala Leu Gly Phe Lys
        355                 360                 365
Ile Ala Tyr Lys Leu Ala Lys Asp Gly Val Phe Asp Lys Phe Ile Glu
    370                 375                 380
Glu Lys Tyr Arg Ser Phe Lys Glu Gly Ile Gly Lys Glu Ile Val Glu
385                 390                 395                 400
Gly Lys Thr Asp Phe Glu Lys Leu Glu Glu Tyr Ile Ile Asp Lys Glu
                405                 410                 415
Asp Ile Glu Leu Pro Ser Gly Lys Gln Glu Tyr Leu Glu Ser Leu Leu
            420                 425                 430
Asn Ser Tyr Ile Val Lys Thr Ile Ala Glu Leu Arg
        435                 440

<210> SEQ ID NO 19
<211> LENGTH: 1335
<212> TYPE: DNA
<213> ORGANISM: Thermotoga maritima

<400> SEQUENCE: 19
atggccgagt tcttcccgga gatcccgaag atccagttcg agggcaagga gtccaccaac        60
ccgctcgcct ccgcttcta cgaccccgaac gaggtgatcg acggcaagcc gctcaaggac       120
cacctcaagt tctccgtggc cttctggcac accttcgtga acgagggccg cgacccgttc       180
ggcgacccga ccgccgagcg cccgtggaac cgcttctccg accgatgga caaggccttc       240 gcccgcgtgg acgccctctt cgagttctgc gagaagctca catcgagta cttctgcttc       300 cacgaccgcg acatcgcccc ggagggcaag accctccgcg agaccaacaa gatcctcgac       360
aaggtggtgg agcgcatcaa ggagcgcatg aaggactcca acgtgaagct cctctggggc       420
accgccaacc tcttctccca cccgcgctac atgcacggcg ccgccaccac ctgctccgcc       480
gacgtgttcg cctacgccgc cgcccaggtg aagaaggccc tggagatcac caaggagctg       540
ggcggcgagg gctacgtgtt ctggggcggc gcgagggct acgagaccct cctcaacacc       600
gacctcggcc tggagctgga gaacctcgcc cgcttcctcc gcatggccgt ggagtacgcc       660
aagaagatcg gcttcaccgg ccagttcctc atcgagccga agccgaagga gccgaccaag       720
caccagtacg acttcgacgt ggccaccgcc tacgccttcc tcaagaacca cggcctcgac       780
gagtacttca gttcaacat cgaggccaac acgccaccc tcgccggcca caccttccag       840
cacgagctgc gcatggcccg catcctcggc aagctcggct ccatcgacgc caaccagggc       900
gacctcctcc tcggctggga caccgaccag ttcccgacca acatctacga caccaccctc       960
gccatgtacg aggtgatcaa ggccggcggc ttcaccaagg cggcctcaa cttcgacgcc      1020 aaggtgcgcc gcgcctccta caaggtggag gacctcttca tcggccacat cgccggcatg      1080
gacaccttcg ccctcggctt caagatcgcc tacaagctcg ccaaggacgg cgtgttcgac      1140
aagttcatcg aggagaagta ccgctccttc aaggagggca tcggcaagga gatcgtggag      1200
```

-continued

```
ggcaagaccg acttcgagaa gctggaggag tacatcatcg acaaggagga catcgagctg    1260
ccgtccggca agcaggagta cctggagtcc ctcctcaact cctacatcgt gaagaccatc    1320
gccgagctgc gctga                                                      1335
```

<210> SEQ ID NO 20
<211> LENGTH: 444
<212> TYPE: PRT
<213> ORGANISM: Thermotoga neapolitana

<400> SEQUENCE: 20

```
Met Ala Glu Phe Phe Pro Glu Ile Pro Lys Val Gln Phe Glu Gly Lys
1               5                   10                  15

Glu Ser Thr Asn Pro Leu Ala Phe Lys Phe Tyr Asp Pro Glu Glu Ile
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Tyr Ala Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Phe Glu Leu Glu Asn
        195                 200                 205

Leu Ala Arg Phe Leu Arg Met Ala Val Asp Tyr Ala Lys Arg Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
        275                 280                 285

Leu Gly Lys Leu Gly Ser Ile Asp Ala Asn Gln Gly Asp Leu Leu Leu
    290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
```

```
                    340                 345                 350
Phe Ile Gly His Ile Ala Gly Met Asp Thr Phe Ala Leu Gly Phe Lys
            355                 360                 365
Val Ala Tyr Lys Leu Val Lys Asp Gly Val Leu Asp Lys Phe Ile Glu
        370                 375                 380
Glu Lys Tyr Arg Ser Phe Arg Glu Gly Ile Gly Arg Asp Ile Val Glu
385                 390                 395                 400
Gly Lys Val Asp Phe Glu Lys Leu Glu Glu Tyr Ile Ile Asp Lys Glu
                405                 410                 415
Thr Ile Glu Leu Pro Ser Gly Lys Gln Glu Tyr Leu Glu Ser Leu Ile
            420                 425                 430
Asn Ser Tyr Ile Val Lys Thr Ile Leu Glu Leu Arg
        435                 440

<210> SEQ ID NO 21
<211> LENGTH: 1335
<212> TYPE: DNA
<213> ORGANISM: Thermotoga neapolitana

<400> SEQUENCE: 21
atggccgagt tcttcccgga gatcccgaag gtgcagttcg agggcaagga gtccaccaac      60
ccgctcgcct tcaagttcta cgacccggag gagatcatcg acggcaagcc gctcaaggac     120
cacctcaagt tctccgtggc cttctggcac accttcgtga acgagggccg cgacccgttc     180
ggcgacccga ccgccgaccg cccgtggaac cgctacaccg accgatgga caaggccttc     240 gcccgcgtgg acgccctctt cgagttctgc gagaagctca acatcgagta cttctgcttc     300
cacgaccgcg acatcgcccc ggagggcaag accctccgcg agaccaacaa gatcctcgac     360
aaggtggtgg agcgcatcaa ggagcgcatg aaggactcca acgtgaagct cctctggggc     420
accgccaacc tcttctccca cccgcgctac atgcacggcg ccgccaccac ctgctccgcc     480
gacgtgttcg cctacgccgc cgcccaggtg aagaaggccc tggagatcac caaggagctg     540
ggcggcgagg gctacgtgtt ctggggcggc cgcgagggct acgagaccct cctcaacacc     600
gacctcggct cgagctgga gaacctcgcc cgcttcctcc gcatggccgt ggactacgcc     660
aagcgcatcg gcttcaccgg ccagttcctc atcgagccga agccgaagga gccgaccaag     720
caccagtacg acttcgacgt ggccaccgcc tacgccttcc tcaagtccca cggcctcgac     780
gagtacttca gttcaacat cgaggccaac cacgccaccc tcgccggcca caccttccag     840
cacgagctgc gcatggcccg catcctcggc aagctcggct ccatcgacgc caaccagggc     900
gacctcctcc tcggctggga caccgaccag ttcccgacca acgtgtacga caccaccctc     960
gccatgtacg aggtgatcaa ggccggcggc ttcaccaagg cggcctcaa cttcgacgcc    1020 aaggtgcgcc gcgcctccta caaggtggag gacctcttca tcggccacat cgccggcatg    1080
gacaccttcg ccctcggctt caaggtggcc tacaagctcg tgaaggacgg cgtgctcgac    1140
aagttcatcg aggagaagta ccgctccttc gcgagggca tcggccgcga catcgtggag    1200
ggcaaggtgg acttcgagaa gctggaggag tacatcatcg acaaggagac catcgagctg    1260
ccgtccggca agcaggagta cctggagtcc ctcatcaact cctacatcgt gaagaccatc    1320
ctggagctgc gctga                                                   1335

<210> SEQ ID NO 22
<211> LENGTH: 28
<212> TYPE: DNA
<213> ORGANISM: Artificial Sequence
```

<220> FEATURE:
<223> OTHER INFORMATION: synthetic

<400> SEQUENCE: 22
agcgaattca tggcggctct ggccacgt                                               28

<210> SEQ ID NO 23
<211> LENGTH: 29
<212> TYPE: DNA
<213> ORGANISM: Artificial Sequence
<220> FEATURE:
<223> OTHER INFORMATION: synthetic

<400> SEQUENCE: 23
agctaagctt cagggcgcgg ccacgttct                                              29

<210> SEQ ID NO 24
<211> LENGTH: 825
<212> TYPE: PRT
<213> ORGANISM: Artificial Sequence
<220> FEATURE:
<223> OTHER INFORMATION: synthetic

<400> SEQUENCE: 24

```
Met Arg Val Leu Leu Val Ala Leu Ala Leu Ala Leu Ala Ala Ser
 1               5                  10                  15

Ala Thr Ser Ala Gly His Trp Tyr Lys His Gln Arg Ala Tyr Gln Phe
             20                  25                  30

Thr Gly Glu Asp Asp Phe Gly Lys Val Ala Val Val Lys Leu Pro Met
         35                  40                  45

Asp Leu Thr Lys Val Gly Ile Ile Val Arg Leu Asn Glu Trp Gln Ala
     50                  55                  60

Lys Asp Val Ala Lys Asp Arg Phe Ile Glu Ile Lys Asp Gly Lys Ala
 65                  70                  75                  80

Glu Val Trp Ile Leu Gln Gly Val Glu Glu Ile Phe Tyr Glu Lys Pro
                 85                  90                  95

Asp Thr Ser Pro Arg Ile Phe Phe Ala Gln Ala Arg Ser Asn Lys Val
            100                 105                 110

Ile Glu Ala Phe Leu Thr Asn Pro Val Asp Thr Lys Lys Lys Glu Leu
        115                 120                 125

Phe Lys Val Thr Val Asp Gly Lys Glu Ile Pro Val Ser Arg Val Glu
    130                 135                 140

Lys Ala Asp Pro Thr Asp Ile Asp Val Thr Asn Tyr Val Arg Ile Val
145                 150                 155                 160

Leu Ser Glu Ser Leu Lys Glu Glu Asp Leu Arg Lys Asp Val Glu Leu
                165                 170                 175

Ile Ile Glu Gly Tyr Lys Pro Ala Arg Val Ile Met Met Glu Ile Leu
            180                 185                 190

Asp Asp Tyr Tyr Asp Gly Glu Leu Gly Ala Val Tyr Ser Pro Glu
        195                 200                 205

Lys Thr Ile Phe Arg Val Trp Ser Pro Val Ser Lys Trp Val Lys Val
    210                 215                 220

Leu Leu Phe Lys Asn Gly Glu Asp Thr Glu Pro Tyr Gln Val Val Asn
225                 230                 235                 240

Met Glu Tyr Lys Gly Asn Gly Val Trp Glu Ala Val Val Glu Gly Asp
                245                 250                 255

Leu Asp Gly Val Phe Tyr Leu Tyr Gln Leu Glu Asn Tyr Gly Lys Ile
            260                 265                 270
```

```
Arg Thr Thr Val Asp Pro Tyr Ser Lys Ala Val Tyr Ala Asn Asn Gln
        275                 280                 285

Glu Ser Ala Val Val Asn Leu Ala Arg Thr Asn Pro Glu Gly Trp Glu
    290                 295                 300

Asn Asp Arg Gly Pro Lys Ile Glu Gly Tyr Glu Asp Ala Ile Ile Tyr
305                 310                 315                 320

Glu Ile His Ile Ala Asp Ile Thr Gly Leu Glu Asn Ser Gly Val Lys
                325                 330                 335

Asn Lys Gly Leu Tyr Leu Gly Leu Thr Glu Glu Asn Thr Lys Ala Pro
            340                 345                 350

Gly Gly Val Thr Thr Gly Leu Ser His Leu Val Glu Leu Gly Val Thr
        355                 360                 365

His Val His Ile Leu Pro Phe Phe Asp Phe Tyr Thr Gly Asp Glu Leu
    370                 375                 380

Asp Lys Asp Phe Glu Lys Tyr Tyr Asn Trp Gly Tyr Asp Pro Tyr Leu
385                 390                 395                 400

Phe Met Val Pro Glu Gly Arg Tyr Ser Thr Asp Pro Lys Asn Pro His
                405                 410                 415

Thr Arg Ile Arg Glu Val Lys Glu Met Val Lys Ala Leu His Lys His
            420                 425                 430

Gly Ile Gly Val Ile Met Asp Met Val Phe Pro His Thr Tyr Gly Ile
        435                 440                 445

Gly Glu Leu Ser Ala Phe Asp Gln Thr Val Pro Tyr Tyr Phe Tyr Arg
    450                 455                 460

Ile Asp Lys Thr Gly Ala Tyr Leu Asn Glu Ser Gly Cys Gly Asn Val
465                 470                 475                 480

Ile Ala Ser Glu Arg Pro Met Met Arg Lys Phe Ile Val Asp Thr Val
                485                 490                 495

Thr Tyr Trp Val Lys Glu Tyr His Ile Asp Gly Phe Arg Phe Asp Gln
            500                 505                 510

Met Gly Leu Ile Asp Lys Lys Thr Met Leu Glu Val Glu Arg Ala Leu
        515                 520                 525

His Lys Ile Asp Pro Thr Ile Ile Leu Tyr Gly Glu Pro Trp Gly Gly
    530                 535                 540

Trp Gly Ala Pro Ile Arg Phe Gly Lys Ser Asp Val Ala Gly Thr His
545                 550                 555                 560

Val Ala Ala Phe Asn Asp Glu Phe Arg Asp Ala Ile Arg Gly Ser Val
                565                 570                 575

Phe Asn Pro Ser Val Lys Gly Phe Val Met Gly Gly Tyr Gly Lys Glu
            580                 585                 590

Thr Lys Ile Lys Arg Gly Val Val Gly Ser Ile Asn Tyr Asp Gly Lys
        595                 600                 605

Leu Ile Lys Ser Phe Ala Leu Asp Pro Glu Glu Thr Ile Asn Tyr Ala
    610                 615                 620

Ala Cys His Asp Asn His Thr Leu Trp Asp Lys Asn Tyr Leu Ala Ala
625                 630                 635                 640

Lys Ala Asp Lys Lys Lys Glu Trp Thr Glu Glu Leu Lys Asn Ala
                645                 650                 655

Gln Lys Leu Ala Gly Ala Ile Leu Leu Thr Ser Gln Gly Val Pro Phe
            660                 665                 670

Leu His Gly Gly Gln Asp Phe Cys Arg Thr Thr Asn Phe Asn Asp Asn
    675                 680                 685
```

```
Ser Tyr Asn Ala Pro Ile Ser Ile Asn Gly Phe Asp Tyr Glu Arg Lys
        690                 695                 700

Leu Gln Phe Ile Asp Val Phe Asn Tyr His Lys Gly Leu Ile Lys Leu
705                 710                 715                 720

Arg Lys Glu His Pro Ala Phe Arg Leu Lys Asn Ala Glu Glu Ile Lys
                725                 730                 735

Lys His Leu Glu Phe Leu Pro Gly Gly Arg Arg Ile Val Ala Phe Met
            740                 745                 750

Leu Lys Asp His Ala Gly Gly Asp Pro Trp Lys Asp Ile Val Val Ile
        755                 760                 765

Tyr Asn Gly Asn Leu Glu Lys Thr Thr Tyr Lys Leu Pro Glu Gly Lys
    770                 775                 780

Trp Asn Val Val Val Asn Ser Gln Lys Ala Gly Thr Glu Val Ile Glu
785                 790                 795                 800

Thr Val Glu Gly Thr Ile Glu Leu Asp Pro Leu Ser Ala Tyr Val Leu
                805                 810                 815

Tyr Arg Glu Ser Glu Lys Asp Glu Leu
                820                 825

<210> SEQ ID NO 25
<211> LENGTH: 2478
<212> TYPE: DNA
<213> ORGANISM: Artificial Sequence
<220> FEATURE:
<223> OTHER INFORMATION: synthetic

<400> SEQUENCE: 25
atgagggtgt tgctcgttgc cctcgctctc ctggctctcg ctgcgagcgc caccagcgct      60
ggccactggt acaagcacca gcgcgcctac cagttcaccg cgcgaggacga cttcgggaag    120
gtggccgtgg tgaagctccc gatggacctc accaaggtgg gcatcatcgt gcgcctcaac    180
gagtggcagg cgaaggacgt ggccaaggac cgcttcatcg agatcaagga cggcaaggcc    240
gaggtgtgga tactccaggg cgtggaggag atcttctacg agaagccgga cacctccccg    300
cgcatcttct tcgcccaggc ccgctccaac aaggtgatcg aggccttcct caccaacccg    360
gtggacacca agaagaagga gctgttcaag gtgaccgtcg acggcaagga gatcccggtg    420
tcccgcgtgg agaaggccga cccgaccgac atcgacgtga ccaactacgt cgcatcgtg    480
ctctccgagt ccctcaagga ggaggacctc cgcaaggacg tggagctgat catcgagggc    540
tacaagccgg cccgcgtgat catgatggag atcctcgacg actactacta cgacggcgag    600
ctggggggcgg tgtactcccc ggagaagacc atcttccgcg tgtggtcccc ggtgtccaag    660
tgggtgaagg tgctcctctt caagaacggc gaggacaccg agccgtacca ggtggtgaac    720
atggagtaca agggcaacgg cgtgtgggag gccgtggtgg agggcgacct cgacggcgtg    780
ttctacctct accagctgga gaactacggc aagatccgca ccaccgtgga cccgtactcc    840
aaggccgtgt acgccaacaa ccaggagtct gcagtggtga acctcgcccg caccaacccg    900
gagggctggg agaacgaccg cggcccgaag atcgagggct acgaggacgc catcatctac    960
gagatccaca tcgccgacat caccggcctg gagaactccg gcgtgaagaa caagggcctc   1020
tacctcggcc tcaccgagga gaacaccaag gccccgggcg gcgtgaccac cggcctctcc   1080
cacctcgtgg agctgggcgt gacccacgtg cacatcctcc gttcttcga cttctacacc   1140
ggcgacgagc tggacaagga cttcgagaag tactacaact ggggctacga cccgtacctc   1200
ttcatggtgc cggagggccg ctactccacc gacccgaaga cccgcacac ccgaattcgc    1260
```

-continued

```
gaggtgaagg agatggtgaa ggccctccac aagcacggca tcggcgtgat catggacatg    1320
gtgttcccgc acacctacgg catcggcgag ctgtccgcct cgaccagac cgtgccgtac    1380 tacttctacc gcatcgacaa gaccggcgcc tacctcaacg agtccggctg cggcaacgtg    1440
atcgcctccg agcgcccgat gatgcgcaag ttcatcgtgg acaccgtgac ctactgggtg    1500
aaggagtacc acatcgacgg cttccgcttc gaccagatgg gcctcatcga caagaagacc    1560
atgctggagg tggagcgcgc cctccacaag atcgacccga ccatcatcct ctacggcgag    1620
ccgtggggcg gctgggggc cccgatccgc ttcggcaagt ccgacgtggc cggcacccac    1680
gtggccgcct tcaacgacga gttccgcgac gccatccgcg ctccgtgtt caacccgtcc    1740 gtgaagggct tcgtgatggg cggctacggc aaggagacca agatcaagcg cggcgtggtg    1800
ggctccatca actacgacgg caagctcatc aagtccttcg ccctcgaccc ggaggagacc    1860
atcaactacg ccgcctgcca cgacaaccac accctctggg acaagaacta cctcgccgcc    1920
aaggccgaca gaagaagga gtggaccgag gaggagctga agaacgccca gaagctcgcc    1980
ggcgccatcc tcctcactag tcagggcgtg ccgttcctcc acggcggcca ggacttctgc    2040
cgcaccacca acttcaacga caactcctac aacgccccga tctccatcaa cggcttcgac    2100
tacgagcgca agctccagtt catcgacgtg ttcaactacc acaagggcct catcaagctc    2160
cgcaaggagc acccggcctt ccgcctcaag aacgccgagg agatcaagaa gcacctggag    2220
ttcctcccgg gcgggcgccg catcgtggcc ttcatgctca aggaccacgc cggcggcgac    2280
ccgtggaagg acatcgtggt gatctacaac ggcaacctgg agaagaccac ctacaagctc    2340
ccggagggca gtggaacgt ggtggtgaac tcccagaagg ccggcaccga ggtgatcgag    2400
accgtggagg gcaccatcga gctggacccg ctctccgcct acgtgctcta ccgcgagtcc    2460
gagaaggacg agctgtga                                                  2478
```

<210> SEQ ID NO 26
<211> LENGTH: 718
<212> TYPE: PRT
<213> ORGANISM: Artificial Sequence
<220> FEATURE:
<223> OTHER INFORMATION: synthetic

<400> SEQUENCE: 26

```
Met Arg Val Leu Leu Val Ala Leu Ala Leu Ala Leu Ala Ala Ser
  1               5                  10                  15

Ala Thr Ser Met Glu Thr Ile Lys Ile Tyr Glu Asn Lys Gly Val Tyr
             20                  25                  30

Lys Val Val Ile Gly Glu Pro Phe Pro Ile Glu Phe Pro Leu Glu
         35                  40                  45

Gln Lys Ile Ser Ser Asn Lys Ser Leu Ser Glu Leu Gly Leu Thr Ile
     50                  55                  60

Val Gln Gln Gly Asn Lys Val Ile Val Glu Lys Ser Leu Asp Leu Lys
 65                  70                  75                  80

Glu His Ile Ile Gly Leu Gly Glu Lys Ala Phe Glu Leu Asp Arg Lys
                 85                  90                  95

Arg Lys Arg Tyr Val Met Tyr Asn Val Asp Ala Gly Ala Tyr Lys Lys
                100                 105                 110

Tyr Gln Asp Pro Leu Tyr Val Ser Ile Pro Leu Phe Ile Ser Val Lys
            115                 120                 125

Asp Gly Val Ala Thr Gly Tyr Phe Phe Asn Ser Ala Ser Lys Val Ile
        130                 135                 140
```

-continued

```
Phe Asp Val Gly Leu Glu Glu Tyr Asp Lys Val Ile Val Thr Ile Pro
145                 150                 155                 160

Glu Asp Ser Val Glu Phe Tyr Val Ile Glu Gly Pro Arg Ile Glu Asp
            165                 170                 175

Val Leu Glu Lys Tyr Thr Glu Leu Thr Gly Lys Pro Phe Leu Pro Pro
        180                 185                 190

Met Trp Ala Phe Gly Tyr Met Ile Ser Arg Tyr Ser Tyr Tyr Pro Gln
    195                 200                 205

Asp Lys Val Val Glu Leu Val Asp Ile Met Gln Lys Glu Gly Phe Arg
210                 215                 220

Val Ala Gly Val Phe Leu Asp Ile His Tyr Met Asp Ser Tyr Lys Leu
225                 230                 235                 240

Phe Thr Trp His Pro Tyr Arg Phe Pro Glu Pro Lys Lys Leu Ile Asp
                245                 250                 255

Glu Leu His Lys Arg Asn Val Lys Leu Ile Thr Ile Val Asp His Gly
            260                 265                 270

Ile Arg Val Asp Gln Asn Tyr Ser Pro Phe Leu Ser Gly Met Gly Lys
        275                 280                 285

Phe Cys Glu Ile Glu Ser Gly Glu Leu Phe Val Gly Lys Met Trp Pro
290                 295                 300

Gly Thr Thr Val Tyr Pro Asp Phe Phe Arg Glu Asp Thr Arg Glu Trp
305                 310                 315                 320

Trp Ala Gly Leu Ile Ser Glu Trp Leu Ser Gln Gly Val Asp Gly Ile
                325                 330                 335

Trp Leu Asp Met Asn Glu Pro Thr Asp Phe Ser Arg Ala Ile Glu Ile
            340                 345                 350

Arg Asp Val Leu Ser Ser Leu Pro Val Gln Phe Arg Asp Asp Arg Leu
        355                 360                 365

Val Thr Thr Phe Pro Asp Asn Val Val His Tyr Leu Arg Gly Lys Arg
370                 375                 380

Val Lys His Glu Lys Val Arg Asn Ala Tyr Pro Leu Tyr Glu Ala Met
385                 390                 395                 400

Ala Thr Phe Lys Gly Phe Arg Thr Ser His Arg Asn Glu Ile Phe Ile
                405                 410                 415

Leu Ser Arg Ala Gly Tyr Ala Gly Ile Gln Arg Tyr Ala Phe Ile Trp
            420                 425                 430

Thr Gly Asp Asn Thr Pro Ser Trp Asp Asp Leu Lys Leu Gln Leu Gln
        435                 440                 445

Leu Val Leu Gly Leu Ser Ile Ser Gly Val Pro Phe Val Gly Cys Asp
450                 455                 460

Ile Gly Gly Phe Gln Gly Arg Asn Phe Ala Glu Ile Asp Asn Ser Met
465                 470                 475                 480

Asp Leu Leu Val Lys Tyr Tyr Ala Leu Ala Leu Phe Phe Pro Phe Tyr
                485                 490                 495

Arg Ser His Lys Ala Thr Asp Gly Ile Asp Thr Glu Pro Val Phe Leu
            500                 505                 510

Pro Asp Tyr Tyr Lys Glu Lys Val Lys Glu Ile Val Glu Leu Arg Tyr
        515                 520                 525

Lys Phe Leu Pro Tyr Ile Tyr Ser Leu Ala Leu Glu Ala Ser Glu Lys
530                 535                 540

Gly His Pro Val Ile Arg Pro Leu Phe Tyr Glu Phe Gln Asp Asp Asp
545                 550                 555                 560

Asp Met Tyr Arg Ile Glu Asp Glu Tyr Met Val Gly Lys Tyr Leu Leu
```

```
                    565                 570                 575
Tyr Ala Pro Ile Val Ser Lys Glu Glu Ser Arg Leu Val Thr Leu Pro
                580                 585                 590

Arg Gly Lys Trp Tyr Asn Tyr Trp Asn Gly Glu Ile Ile Asn Gly Lys
            595                 600                 605

Ser Val Val Lys Ser Thr His Glu Leu Pro Ile Tyr Leu Arg Glu Gly
        610                 615                 620

Ser Ile Ile Pro Leu Glu Gly Asp Glu Leu Ile Val Tyr Gly Glu Thr
625                 630                 635                 640

Ser Phe Lys Arg Tyr Asp Asn Ala Glu Ile Thr Ser Ser Ser Asn Glu
                645                 650                 655

Ile Lys Phe Ser Arg Glu Ile Tyr Val Ser Lys Leu Thr Ile Thr Ser
            660                 665                 670

Glu Lys Pro Val Ser Lys Ile Ile Val Asp Asp Ser Lys Glu Ile Gln
        675                 680                 685

Val Glu Lys Thr Met Gln Asn Thr Tyr Val Ala Lys Ile Asn Gln Lys
    690                 695                 700

Ile Arg Gly Lys Ile Asn Leu Glu Ser Glu Lys Asp Glu Leu
705                 710                 715

<210> SEQ ID NO 27
<211> LENGTH: 712
<212> TYPE: PRT
<213> ORGANISM: Artificial Sequence
<220> FEATURE:
<223> OTHER INFORMATION: synthetic

<400> SEQUENCE: 27

Met Arg Val Leu Leu Val Ala Leu Ala Leu Leu Ala Leu Ala Ala Ser
1               5                   10                  15

Ala Thr Ser Met Glu Thr Ile Lys Ile Tyr Glu Asn Lys Gly Val Tyr
            20                  25                  30

Lys Val Val Ile Gly Glu Pro Phe Pro Ile Glu Phe Pro Leu Glu
        35                  40                  45

Gln Lys Ile Ser Ser Asn Lys Ser Leu Ser Glu Leu Gly Leu Thr Ile
    50                  55                  60

Val Gln Gln Gly Asn Lys Val Ile Val Glu Lys Ser Leu Asp Leu Lys
65                  70                  75                  80

Glu His Ile Ile Gly Leu Gly Glu Lys Ala Phe Glu Leu Asp Arg Lys
                85                  90                  95

Arg Lys Arg Tyr Val Met Tyr Asn Val Asp Ala Gly Ala Tyr Lys Lys
            100                 105                 110

Tyr Gln Asp Pro Leu Tyr Val Ser Ile Pro Leu Phe Ile Ser Val Lys
        115                 120                 125

Asp Gly Val Ala Thr Gly Tyr Phe Phe Asn Ser Ala Ser Lys Val Ile
    130                 135                 140

Phe Asp Val Gly Leu Glu Glu Tyr Asp Lys Val Ile Val Thr Ile Pro
145                 150                 155                 160

Glu Asp Ser Val Glu Phe Tyr Val Ile Glu Gly Pro Arg Ile Glu Asp
                165                 170                 175

Val Leu Glu Lys Tyr Thr Glu Leu Thr Gly Lys Pro Phe Leu Pro Pro
            180                 185                 190

Met Trp Ala Phe Gly Tyr Met Ile Ser Arg Tyr Ser Tyr Tyr Pro Gln
        195                 200                 205

Asp Lys Val Val Glu Leu Val Asp Ile Met Gln Lys Glu Gly Phe Arg
```

-continued

```
            210                 215                 220
Val Ala Gly Val Phe Leu Asp Ile His Tyr Met Asp Ser Tyr Lys Leu
225                 230                 235                 240

Phe Thr Trp His Pro Tyr Arg Phe Pro Glu Pro Lys Lys Leu Ile Asp
                245                 250                 255

Glu Leu His Lys Arg Asn Val Lys Leu Ile Thr Ile Val Asp His Gly
                260                 265                 270

Ile Arg Val Asp Gln Asn Tyr Ser Pro Phe Leu Ser Gly Met Gly Lys
                275                 280                 285

Phe Cys Glu Ile Glu Ser Gly Glu Leu Phe Val Gly Lys Met Trp Pro
290                 295                 300

Gly Thr Thr Val Tyr Pro Asp Phe Phe Arg Glu Asp Thr Arg Glu Trp
305                 310                 315                 320

Trp Ala Gly Leu Ile Ser Glu Trp Leu Ser Gln Gly Val Asp Gly Ile
                325                 330                 335

Trp Leu Asp Met Asn Glu Pro Thr Asp Phe Ser Arg Ala Ile Glu Ile
                340                 345                 350

Arg Asp Val Leu Ser Ser Leu Pro Val Gln Phe Arg Asp Asp Arg Leu
                355                 360                 365

Val Thr Thr Phe Pro Asp Asn Val Val His Tyr Leu Arg Gly Lys Arg
                370                 375                 380

Val Lys His Glu Lys Val Arg Asn Ala Tyr Pro Leu Tyr Glu Ala Met
385                 390                 395                 400

Ala Thr Phe Lys Gly Phe Arg Thr Ser His Arg Asn Glu Ile Phe Ile
                405                 410                 415

Leu Ser Arg Ala Gly Tyr Ala Gly Ile Gln Arg Tyr Ala Phe Ile Trp
                420                 425                 430

Thr Gly Asp Asn Thr Pro Ser Trp Asp Asp Leu Lys Leu Gln Leu Gln
                435                 440                 445

Leu Val Leu Gly Leu Ser Ile Ser Gly Val Pro Phe Val Gly Cys Asp
                450                 455                 460

Ile Gly Gly Phe Gln Gly Arg Asn Phe Ala Glu Ile Asp Asn Ser Met
465                 470                 475                 480

Asp Leu Leu Val Lys Tyr Tyr Ala Leu Ala Leu Phe Phe Pro Phe Tyr
                485                 490                 495

Arg Ser His Lys Ala Thr Asp Gly Ile Asp Thr Glu Pro Val Phe Leu
                500                 505                 510

Pro Asp Tyr Tyr Lys Glu Lys Val Lys Glu Ile Val Glu Leu Arg Tyr
                515                 520                 525

Lys Phe Leu Pro Tyr Ile Tyr Ser Leu Ala Leu Glu Ala Ser Glu Lys
530                 535                 540

Gly His Pro Val Ile Arg Pro Leu Phe Tyr Glu Phe Gln Asp Asp Asp
545                 550                 555                 560

Asp Met Tyr Arg Ile Glu Asp Glu Tyr Met Val Gly Lys Tyr Leu Leu
                565                 570                 575

Tyr Ala Pro Ile Val Ser Lys Glu Glu Ser Arg Leu Val Thr Leu Pro
                580                 585                 590

Arg Gly Lys Trp Tyr Asn Tyr Trp Asn Gly Glu Ile Ile Asn Gly Lys
                595                 600                 605

Ser Val Val Lys Ser Thr His Glu Leu Pro Ile Tyr Leu Arg Glu Gly
                610                 615                 620

Ser Ile Ile Pro Leu Glu Gly Asp Glu Leu Ile Val Tyr Gly Glu Thr
625                 630                 635                 640
```

```
Ser Phe Lys Arg Tyr Asp Asn Ala Glu Ile Thr Ser Ser Ser Asn Glu
            645                 650                 655

Ile Lys Phe Ser Arg Glu Ile Tyr Val Ser Lys Leu Thr Ile Thr Ser
            660                 665                 670

Glu Lys Pro Val Ser Lys Ile Val Asp Asp Ser Lys Glu Ile Gln
            675                 680                 685

Val Glu Lys Thr Met Gln Asn Thr Tyr Val Ala Lys Ile Asn Gln Lys
            690                 695                 700

Ile Arg Gly Lys Ile Asn Leu Glu
705                 710

<210> SEQ ID NO 28
<211> LENGTH: 469
<212> TYPE: PRT
<213> ORGANISM: Artificial Sequence
<220> FEATURE:
<223> OTHER INFORMATION: synthetic

<400> SEQUENCE: 28

Met Arg Val Leu Leu Val Ala Leu Ala Leu Leu Ala Leu Ala Ala Ser
1               5                   10                  15

Ala Thr Ser Met Ala Glu Phe Phe Pro Glu Ile Pro Lys Ile Gln Phe
            20                  25                  30

Glu Gly Lys Glu Ser Thr Asn Pro Leu Ala Phe Arg Phe Tyr Asp Pro
        35                  40                  45

Asn Glu Val Ile Asp Gly Lys Pro Leu Lys Asp His Leu Lys Phe Ser
50                  55                  60

Val Ala Phe Trp His Thr Phe Val Asn Glu Gly Arg Asp Pro Phe Gly
65                  70                  75                  80

Asp Pro Thr Ala Glu Arg Pro Trp Asn Arg Phe Ser Asp Pro Met Asp
                85                  90                  95

Lys Ala Phe Ala Arg Val Asp Ala Leu Phe Glu Phe Cys Glu Lys Leu
            100                 105                 110

Asn Ile Glu Tyr Phe Cys Phe His Asp Arg Asp Ile Ala Pro Glu Gly
            115                 120                 125

Lys Thr Leu Arg Glu Thr Asn Lys Ile Leu Asp Lys Val Val Glu Arg
        130                 135                 140

Ile Lys Glu Arg Met Lys Asp Ser Asn Val Lys Leu Leu Trp Gly Thr
145                 150                 155                 160

Ala Asn Leu Phe Ser His Pro Arg Tyr Met His Gly Ala Ala Thr Thr
                165                 170                 175

Cys Ser Ala Asp Val Phe Ala Tyr Ala Ala Gln Val Lys Lys Ala
            180                 185                 190

Leu Glu Ile Thr Lys Glu Leu Gly Gly Glu Gly Tyr Val Phe Trp Gly
            195                 200                 205

Gly Arg Glu Gly Tyr Glu Thr Leu Leu Asn Thr Asp Leu Gly Leu Glu
        210                 215                 220

Leu Glu Asn Leu Ala Arg Phe Leu Arg Met Ala Val Glu Tyr Ala Lys
225                 230                 235                 240

Lys Ile Gly Phe Thr Gly Gln Phe Leu Ile Glu Pro Lys Pro Lys Glu
                245                 250                 255

Pro Thr Lys His Gln Tyr Asp Phe Asp Val Ala Thr Ala Tyr Ala Phe
            260                 265                 270

Leu Lys Asn His Gly Leu Asp Glu Tyr Phe Lys Phe Asn Ile Glu Ala
            275                 280                 285
```

```
Asn His Ala Thr Leu Ala Gly His Thr Phe Gln His Glu Leu Arg Met
            290                 295                 300

Ala Arg Ile Leu Gly Lys Leu Gly Ser Ile Asp Ala Asn Gln Gly Asp
305                 310                 315                 320

Leu Leu Leu Gly Trp Asp Thr Asp Gln Phe Pro Thr Asn Ile Tyr Asp
                325                 330                 335

Thr Thr Leu Ala Met Tyr Glu Val Ile Lys Ala Gly Gly Phe Thr Lys
                340                 345                 350

Gly Gly Leu Asn Phe Asp Ala Lys Val Arg Arg Ala Ser Tyr Lys Val
                355                 360                 365

Glu Asp Leu Phe Ile Gly His Ile Ala Gly Met Asp Thr Phe Ala Leu
370                 375                 380

Gly Phe Lys Ile Ala Tyr Lys Leu Ala Lys Asp Gly Val Phe Asp Lys
385                 390                 395                 400

Phe Ile Glu Glu Lys Tyr Arg Ser Phe Lys Glu Gly Ile Gly Lys Glu
                405                 410                 415

Ile Val Glu Gly Lys Thr Asp Phe Glu Lys Leu Glu Glu Tyr Ile Ile
                420                 425                 430

Asp Lys Glu Asp Ile Glu Leu Pro Ser Gly Lys Gln Glu Tyr Leu Glu
                435                 440                 445

Ser Leu Leu Asn Ser Tyr Ile Val Lys Thr Ile Ala Glu Leu Arg Ser
            450                 455                 460

Glu Lys Asp Glu Leu
465

<210> SEQ ID NO 29
<211> LENGTH: 469
<212> TYPE: PRT
<213> ORGANISM: Artificial Sequence
<220> FEATURE:
<223> OTHER INFORMATION: synthetic

<400> SEQUENCE: 29

Met Arg Val Leu Leu Val Ala Leu Ala Leu Leu Ala Leu Ala Ala Ser
1               5                   10                  15

Ala Thr Ser Met Ala Glu Phe Phe Pro Glu Ile Pro Lys Val Gln Phe
                20                  25                  30

Glu Gly Lys Glu Ser Thr Asn Pro Leu Ala Phe Lys Phe Tyr Asp Pro
            35                  40                  45

Glu Glu Ile Ile Asp Gly Lys Pro Leu Lys Asp His Leu Lys Phe Ser
        50                  55                  60

Val Ala Phe Trp His Thr Phe Val Asn Glu Gly Arg Asp Pro Phe Gly
65                  70                  75                  80

Asp Pro Thr Ala Asp Arg Pro Trp Asn Arg Tyr Thr Asp Pro Met Asp
                85                  90                  95

Lys Ala Phe Ala Arg Val Asp Ala Leu Phe Glu Phe Cys Glu Lys Leu
            100                 105                 110

Asn Ile Glu Tyr Phe Cys Phe His Asp Arg Asp Ile Ala Pro Glu Gly
        115                 120                 125

Lys Thr Leu Arg Glu Thr Asn Lys Ile Leu Asp Lys Val Val Glu Arg
    130                 135                 140

Ile Lys Glu Arg Met Lys Asp Ser Asn Val Lys Leu Leu Trp Gly Thr
145                 150                 155                 160

Ala Asn Leu Phe Ser His Pro Arg Tyr Met His Gly Ala Ala Thr Thr
                165                 170                 175
```

```
Cys Ser Ala Asp Val Phe Ala Tyr Ala Ala Gln Val Lys Lys Ala
            180                 185                 190

Leu Glu Ile Thr Lys Glu Leu Gly Gly Glu Gly Tyr Val Phe Trp Gly
            195                 200                 205

Gly Arg Glu Gly Tyr Glu Thr Leu Leu Asn Thr Asp Leu Gly Phe Glu
            210                 215                 220

Leu Glu Asn Leu Ala Arg Phe Leu Arg Met Ala Val Asp Tyr Ala Lys
225                 230                 235                 240

Arg Ile Gly Phe Thr Gly Gln Phe Leu Ile Glu Pro Lys Pro Lys Glu
                245                 250                 255

Pro Thr Lys His Gln Tyr Asp Phe Asp Val Ala Thr Ala Tyr Ala Phe
            260                 265                 270

Leu Lys Ser His Gly Leu Asp Glu Tyr Phe Lys Phe Asn Ile Glu Ala
            275                 280                 285

Asn His Ala Thr Leu Ala Gly His Thr Phe Gln His Glu Leu Arg Met
            290                 295                 300

Ala Arg Ile Leu Gly Lys Leu Gly Ser Ile Asp Ala Asn Gln Gly Asp
305                 310                 315                 320

Leu Leu Leu Gly Trp Asp Thr Asp Gln Phe Pro Thr Asn Val Tyr Asp
                325                 330                 335

Thr Thr Leu Ala Met Tyr Glu Val Ile Lys Ala Gly Gly Phe Thr Lys
            340                 345                 350

Gly Gly Leu Asn Phe Asp Ala Lys Val Arg Arg Ala Ser Tyr Lys Val
            355                 360                 365

Glu Asp Leu Phe Ile Gly His Ile Ala Gly Met Asp Thr Phe Ala Leu
370                 375                 380

Gly Phe Lys Val Ala Tyr Lys Leu Val Lys Asp Gly Val Leu Asp Lys
385                 390                 395                 400

Phe Ile Glu Glu Lys Tyr Arg Ser Phe Arg Glu Gly Ile Gly Arg Asp
                405                 410                 415

Ile Val Glu Gly Lys Val Asp Phe Glu Lys Leu Glu Glu Tyr Ile Ile
            420                 425                 430

Asp Lys Glu Thr Ile Glu Leu Pro Ser Gly Lys Gln Glu Tyr Leu Glu
            435                 440                 445

Ser Leu Ile Asn Ser Tyr Ile Val Lys Thr Ile Leu Glu Leu Arg Ser
            450                 455                 460

Glu Lys Asp Glu Leu
465

<210> SEQ ID NO 30
<211> LENGTH: 463
<212> TYPE: PRT
<213> ORGANISM: Artificial Sequence
<220> FEATURE:
<223> OTHER INFORMATION: synthetic

<400> SEQUENCE: 30

Met Arg Val Leu Leu Val Ala Leu Ala Leu Leu Ala Leu Ala Ala Ser
  1               5                  10                  15

Ala Thr Ser Met Ala Glu Phe Phe Pro Glu Ile Pro Lys Val Gln Phe
             20                  25                  30

Glu Gly Lys Glu Ser Thr Asn Pro Leu Ala Phe Lys Phe Tyr Asp Pro
         35                  40                  45

Glu Glu Ile Ile Asp Gly Lys Pro Leu Lys Asp His Leu Lys Phe Ser
     50                  55                  60
```

```
Val Ala Phe Trp His Thr Phe Val Asn Glu Gly Arg Asp Pro Phe Gly
 65                  70                  75                  80

Asp Pro Thr Ala Asp Arg Pro Trp Asn Arg Tyr Thr Asp Pro Met Asp
                 85                  90                  95

Lys Ala Phe Ala Arg Val Asp Ala Leu Phe Glu Phe Cys Glu Lys Leu
            100                 105                 110

Asn Ile Glu Tyr Phe Cys Phe His Asp Arg Asp Ile Ala Pro Glu Gly
        115                 120                 125

Lys Thr Leu Arg Glu Thr Asn Lys Ile Leu Asp Lys Val Val Glu Arg
    130                 135                 140

Ile Lys Glu Arg Met Lys Asp Ser Asn Val Lys Leu Leu Trp Gly Thr
145                 150                 155                 160

Ala Asn Leu Phe Ser His Pro Arg Tyr Met His Gly Ala Ala Thr Thr
                165                 170                 175

Cys Ser Ala Asp Val Phe Ala Tyr Ala Ala Gln Val Lys Lys Ala
            180                 185                 190

Leu Glu Ile Thr Lys Glu Leu Gly Gly Glu Gly Tyr Val Phe Trp Gly
        195                 200                 205

Gly Arg Glu Gly Tyr Glu Thr Leu Leu Asn Thr Asp Leu Gly Phe Glu
    210                 215                 220

Leu Glu Asn Leu Ala Arg Phe Leu Arg Met Ala Val Asp Tyr Ala Lys
225                 230                 235                 240

Arg Ile Gly Phe Thr Gly Gln Phe Leu Ile Glu Pro Lys Pro Lys Glu
                245                 250                 255

Pro Thr Lys His Gln Tyr Asp Phe Asp Val Ala Thr Ala Tyr Ala Phe
            260                 265                 270

Leu Lys Ser His Gly Leu Asp Glu Tyr Phe Lys Phe Asn Ile Glu Ala
        275                 280                 285

Asn His Ala Thr Leu Ala Gly His Thr Phe Gln His Glu Leu Arg Met
    290                 295                 300

Ala Arg Ile Leu Gly Lys Leu Gly Ser Ile Asp Ala Asn Gln Gly Asp
305                 310                 315                 320

Leu Leu Leu Gly Trp Asp Thr Asp Gln Phe Pro Thr Asn Val Tyr Asp
                325                 330                 335

Thr Thr Leu Ala Met Tyr Glu Val Ile Lys Ala Gly Gly Phe Thr Lys
            340                 345                 350

Gly Gly Leu Asn Phe Asp Ala Lys Val Arg Arg Ala Ser Tyr Lys Val
        355                 360                 365

Glu Asp Leu Phe Ile Gly His Ile Ala Gly Met Asp Thr Phe Ala Leu
    370                 375                 380

Gly Phe Lys Val Ala Tyr Lys Leu Val Lys Asp Gly Val Leu Asp Lys
385                 390                 395                 400

Phe Ile Glu Glu Lys Tyr Arg Ser Phe Arg Glu Gly Ile Gly Arg Asp
                405                 410                 415

Ile Val Glu Gly Lys Val Asp Phe Glu Lys Leu Glu Glu Tyr Ile Ile
            420                 425                 430

Asp Lys Glu Thr Ile Glu Leu Pro Ser Gly Lys Gln Glu Tyr Leu Glu
        435                 440                 445

Ser Leu Ile Asn Ser Tyr Ile Val Lys Thr Ile Leu Glu Leu Arg
    450                 455                 460

<210> SEQ ID NO 31
<211> LENGTH: 25
```

```
<212> TYPE: PRT
<213> ORGANISM: Artificial Sequence
<220> FEATURE:
<223> OTHER INFORMATION: synthetic

<400> SEQUENCE: 31

Met Gly Lys Asn Gly Asn Leu Cys Cys Phe Ser Leu Leu Leu Leu Leu
1               5                   10                  15

Leu Ala Gly Leu Ala Ser Gly His Gln
            20                  25

<210> SEQ ID NO 32
<211> LENGTH: 30
<212> TYPE: PRT
<213> ORGANISM: Artificial Sequence
<220> FEATURE:
<223> OTHER INFORMATION: synthetic

<400> SEQUENCE: 32

Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala
            20                  25                  30

<210> SEQ ID NO 33
<211> LENGTH: 460
<212> TYPE: PRT
<213> ORGANISM: Artificial Sequence
<220> FEATURE:
<223> OTHER INFORMATION: synthetic

<400> SEQUENCE: 33

Met Arg Val Leu Leu Val Ala Leu Ala Leu Leu Ala Leu Ala Ala Ser
1               5                   10                  15

Ala Thr Ser Ala Lys Tyr Leu Glu Leu Glu Glu Gly Gly Val Ile Met
            20                  25                  30

Gln Ala Phe Tyr Trp Asp Val Pro Ser Gly Gly Ile Trp Trp Asp Thr
        35                  40                  45

Ile Arg Gln Lys Ile Pro Glu Trp Tyr Asp Ala Gly Ile Ser Ala Ile
    50                  55                  60

Trp Ile Pro Pro Ala Ser Lys Gly Met Ser Gly Gly Tyr Ser Met Gly
65                  70                  75                  80

Tyr Asp Pro Tyr Asp Tyr Phe Asp Leu Gly Glu Tyr Tyr Gln Lys Gly
                85                  90                  95

Thr Val Glu Thr Arg Phe Gly Ser Lys Gln Glu Leu Ile Asn Met Ile
            100                 105                 110

Asn Thr Ala His Ala Tyr Gly Ile Lys Val Ile Ala Asp Ile Val Ile
        115                 120                 125

Asn His Arg Ala Gly Gly Asp Leu Glu Trp Asn Pro Phe Val Gly Asp
    130                 135                 140

Tyr Thr Trp Thr Asp Phe Ser Lys Val Ala Ser Gly Lys Tyr Thr Ala
145                 150                 155                 160

Asn Tyr Leu Asp Phe His Pro Asn Glu Leu His Ala Gly Asp Ser Gly
                165                 170                 175

Thr Phe Gly Gly Tyr Pro Asp Ile Cys His Asp Lys Ser Trp Asp Gln
            180                 185                 190

Tyr Trp Leu Trp Ala Ser Gln Glu Ser Tyr Ala Ala Tyr Leu Arg Ser
        195                 200                 205

Ile Gly Ile Asp Ala Trp Arg Phe Asp Tyr Val Lys Gly Tyr Gly Ala
```

```
              210                 215                 220
Trp Val Val Lys Asp Trp Leu Asn Trp Trp Gly Gly Trp Ala Val Gly
225                 230                 235                 240

Glu Tyr Trp Asp Thr Asn Val Asp Ala Leu Leu Asn Trp Ala Tyr Ser
                245                 250                 255

Ser Gly Ala Lys Val Phe Asp Phe Pro Leu Tyr Tyr Lys Met Asp Ala
            260                 265                 270

Ala Phe Asp Asn Lys Asn Ile Pro Ala Leu Val Glu Ala Leu Lys Asn
            275                 280                 285

Gly Gly Thr Val Val Ser Arg Asp Pro Phe Lys Ala Val Thr Phe Val
290                 295                 300

Ala Asn His Asp Thr Asp Ile Ile Trp Asn Lys Tyr Pro Ala Tyr Ala
305                 310                 315                 320

Phe Ile Leu Thr Tyr Glu Gly Gln Pro Thr Ile Phe Tyr Arg Asp Tyr
                325                 330                 335

Glu Glu Trp Leu Asn Lys Asp Lys Leu Lys Asn Leu Ile Trp Ile His
                340                 345                 350

Asp Asn Leu Ala Gly Gly Ser Thr Ser Ile Val Tyr Tyr Asp Ser Asp
            355                 360                 365

Glu Met Ile Phe Val Arg Asn Gly Tyr Gly Ser Lys Pro Gly Leu Ile
370                 375                 380

Thr Tyr Ile Asn Leu Gly Ser Ser Lys Val Gly Arg Trp Val Tyr Val
385                 390                 395                 400

Pro Lys Phe Ala Gly Ala Cys Ile His Glu Tyr Thr Gly Asn Leu Gly
                405                 410                 415

Gly Trp Val Asp Lys Tyr Val Tyr Ser Ser Gly Trp Val Tyr Leu Glu
            420                 425                 430

Ala Pro Ala Tyr Asp Pro Ala Asn Gly Gln Tyr Gly Tyr Ser Val Trp
            435                 440                 445

Ser Tyr Cys Gly Val Gly Ser Glu Lys Asp Glu Leu
        450                 455                 460

<210> SEQ ID NO 34
<211> LENGTH: 825
<212> TYPE: PRT
<213> ORGANISM: Artificial Sequence
<220> FEATURE:
<223> OTHER INFORMATION: synthetic

<400> SEQUENCE: 34

Met Arg Val Leu Leu Val Ala Leu Ala Leu Leu Ala Leu Ala Ala Ser
1               5                   10                  15

Ala Thr Ser Ala Gly His Trp Tyr Lys His Gln Arg Ala Tyr Gln Phe
            20                  25                  30

Thr Gly Glu Asp Asp Phe Gly Lys Val Ala Val Val Lys Leu Pro Met
        35                  40                  45

Asp Leu Thr Lys Val Gly Ile Ile Val Arg Leu Asn Glu Trp Gln Ala
    50                  55                  60

Lys Asp Val Ala Lys Asp Arg Phe Ile Glu Ile Lys Asp Gly Lys Ala
65                  70                  75                  80

Glu Val Trp Ile Leu Gln Gly Val Glu Glu Ile Phe Tyr Glu Lys Pro
                85                  90                  95

Asp Thr Ser Pro Arg Ile Phe Phe Ala Gln Ala Arg Ser Asn Lys Val
            100                 105                 110

Ile Glu Ala Phe Leu Thr Asn Pro Val Asp Thr Lys Lys Lys Glu Leu
```

```
                115                 120                 125
Phe Lys Val Thr Val Asp Gly Lys Glu Ile Pro Val Ser Arg Val Glu
130                 135                 140

Lys Ala Asp Pro Thr Asp Ile Asp Val Thr Asn Tyr Val Arg Ile Val
145                 150                 155                 160

Leu Ser Glu Ser Leu Lys Glu Asp Leu Arg Lys Asp Val Glu Leu
                165                 170                 175

Ile Ile Glu Gly Tyr Lys Pro Ala Arg Val Ile Met Met Glu Ile Leu
                180                 185                 190

Asp Asp Tyr Tyr Asp Gly Glu Leu Gly Ala Val Tyr Ser Pro Glu
            195                 200                 205

Lys Thr Ile Phe Arg Val Trp Ser Pro Val Ser Lys Trp Val Lys Val
210                 215                 220

Leu Leu Phe Lys Asn Gly Glu Asp Thr Glu Pro Tyr Gln Val Val Asn
225                 230                 235                 240

Met Glu Tyr Lys Gly Asn Gly Val Trp Glu Ala Val Val Glu Gly Asp
                245                 250                 255

Leu Asp Gly Val Phe Tyr Leu Tyr Gln Leu Glu Asn Tyr Gly Lys Ile
                260                 265                 270

Arg Thr Thr Val Asp Pro Tyr Ser Lys Ala Val Tyr Ala Asn Asn Gln
            275                 280                 285

Glu Ser Ala Val Val Asn Leu Ala Arg Thr Asn Pro Glu Gly Trp Glu
            290                 295                 300

Asn Asp Arg Gly Pro Lys Ile Glu Gly Tyr Glu Asp Ala Ile Ile Tyr
305                 310                 315                 320

Glu Ile His Ile Ala Asp Ile Thr Gly Leu Glu Asn Ser Gly Val Lys
                325                 330                 335

Asn Lys Gly Leu Tyr Leu Gly Leu Thr Glu Glu Asn Thr Lys Ala Pro
                340                 345                 350

Gly Gly Val Thr Thr Gly Leu Ser His Leu Val Glu Leu Gly Val Thr
            355                 360                 365

His Val His Ile Leu Pro Phe Phe Asp Phe Tyr Thr Gly Asp Glu Leu
            370                 375                 380

Asp Lys Asp Phe Glu Lys Tyr Tyr Asn Trp Gly Tyr Asp Pro Tyr Leu
385                 390                 395                 400

Phe Met Val Pro Glu Gly Arg Tyr Ser Thr Asp Pro Lys Asn Pro His
                405                 410                 415

Thr Arg Ile Arg Glu Val Lys Glu Met Val Lys Ala Leu His Lys His
                420                 425                 430

Gly Ile Gly Val Ile Met Asp Met Val Phe Pro His Thr Tyr Gly Ile
            435                 440                 445

Gly Glu Leu Ser Ala Phe Asp Gln Thr Val Pro Tyr Tyr Phe Tyr Arg
            450                 455                 460

Ile Asp Lys Thr Gly Ala Tyr Leu Asn Glu Ser Gly Cys Gly Asn Val
465                 470                 475                 480

Ile Ala Ser Glu Arg Pro Met Met Arg Lys Phe Ile Val Asp Thr Val
                485                 490                 495

Thr Tyr Trp Val Lys Glu Tyr His Ile Asp Gly Phe Arg Phe Asp Gln
            500                 505                 510

Met Gly Leu Ile Asp Lys Lys Thr Met Leu Glu Val Glu Arg Ala Leu
            515                 520                 525

His Lys Ile Asp Pro Thr Ile Ile Leu Tyr Gly Glu Pro Trp Gly Gly
530                 535                 540
```

Trp Gly Ala Pro Ile Arg Phe Gly Lys Ser Asp Val Ala Gly Thr His
545                 550                 555                 560

Val Ala Ala Phe Asn Asp Glu Phe Arg Asp Ala Ile Arg Gly Ser Val
                565                 570                 575

Phe Asn Pro Ser Val Lys Gly Phe Val Met Gly Gly Tyr Gly Lys Glu
            580                 585                 590

Thr Lys Ile Lys Arg Gly Val Val Gly Ser Ile Asn Tyr Asp Gly Lys
        595                 600                 605

Leu Ile Lys Ser Phe Ala Leu Asp Pro Glu Glu Thr Ile Asn Tyr Ala
    610                 615                 620

Ala Cys His Asp Asn His Thr Leu Trp Asp Lys Asn Tyr Leu Ala Ala
625                 630                 635                 640

Lys Ala Asp Lys Lys Glu Trp Thr Glu Glu Leu Lys Asn Ala
                645                 650                 655

Gln Lys Leu Ala Gly Ala Ile Leu Leu Thr Ser Gln Gly Val Pro Phe
            660                 665                 670

Leu His Gly Gly Gln Asp Phe Cys Arg Thr Thr Asn Phe Asn Asp Asn
    675                 680                 685

Ser Tyr Asn Ala Pro Ile Ser Ile Asn Gly Phe Asp Tyr Glu Arg Lys
690                 695                 700

Leu Gln Phe Ile Asp Val Phe Asn Tyr His Lys Gly Leu Ile Lys Leu
705                 710                 715                 720

Arg Lys Glu His Pro Ala Phe Arg Leu Lys Asn Ala Glu Glu Ile Lys
                725                 730                 735

Lys His Leu Glu Phe Leu Pro Gly Gly Arg Arg Ile Val Ala Phe Met
            740                 745                 750

Leu Lys Asp His Ala Gly Gly Asp Pro Trp Lys Asp Ile Val Val Ile
        755                 760                 765

Tyr Asn Gly Asn Leu Glu Lys Thr Thr Tyr Lys Leu Pro Glu Gly Lys
    770                 775                 780

Trp Asn Val Val Val Asn Ser Gln Lys Ala Gly Thr Glu Val Ile Glu
785                 790                 795                 800

Thr Val Glu Gly Thr Ile Glu Leu Asp Pro Leu Ser Ala Tyr Val Leu
                805                 810                 815

Tyr Arg Glu Ser Glu Lys Asp Glu Leu
            820                 825

<210> SEQ ID NO 35
<211> LENGTH: 460
<212> TYPE: PRT
<213> ORGANISM: Artificial Sequence
<220> FEATURE:
<223> OTHER INFORMATION: synthetic

<400> SEQUENCE: 35

Met Arg Val Leu Leu Val Ala Leu Ala Leu Leu Ala Leu Ala Ala Ser
1               5                   10                  15

Ala Thr Ser Ala Lys Tyr Leu Glu Leu Glu Glu Gly Gly Val Ile Met
            20                  25                  30

Gln Ala Phe Tyr Trp Asp Val Pro Ser Gly Gly Ile Trp Trp Asp Thr
        35                  40                  45

Ile Arg Gln Lys Ile Pro Glu Trp Tyr Asp Ala Gly Ile Ser Ala Ile
    50                  55                  60

Trp Ile Pro Pro Ala Ser Lys Gly Met Ser Gly Gly Tyr Ser Met Gly
65                  70                  75                  80

-continued

```
Tyr Asp Pro Tyr Asp Tyr Phe Asp Leu Gly Glu Tyr Tyr Gln Lys Gly
                 85                  90                  95

Thr Val Glu Thr Arg Phe Gly Ser Lys Gln Glu Leu Ile Asn Met Ile
            100                 105                 110

Asn Thr Ala His Ala Tyr Gly Ile Lys Val Ile Ala Asp Ile Val Ile
        115                 120                 125

Asn His Arg Ala Gly Gly Asp Leu Glu Trp Asn Pro Phe Val Gly Asp
    130                 135                 140

Tyr Thr Trp Thr Asp Phe Ser Lys Val Ala Ser Gly Lys Tyr Thr Ala
145                 150                 155                 160

Asn Tyr Leu Asp Phe His Pro Asn Glu Leu His Ala Gly Asp Ser Gly
                165                 170                 175

Thr Phe Gly Gly Tyr Pro Asp Ile Cys His Asp Lys Ser Trp Asp Gln
            180                 185                 190

Tyr Trp Leu Trp Ala Ser Gln Glu Ser Tyr Ala Ala Tyr Leu Arg Ser
        195                 200                 205

Ile Gly Ile Asp Ala Trp Arg Phe Asp Tyr Val Lys Gly Tyr Gly Ala
    210                 215                 220

Trp Val Val Lys Asp Trp Leu Asn Trp Trp Gly Gly Trp Ala Val Gly
225                 230                 235                 240

Glu Tyr Trp Asp Thr Asn Val Asp Ala Leu Leu Asn Trp Ala Tyr Ser
                245                 250                 255

Ser Gly Ala Lys Val Phe Asp Phe Pro Leu Tyr Tyr Lys Met Asp Ala
            260                 265                 270

Ala Phe Asp Asn Lys Asn Ile Pro Ala Leu Val Glu Ala Leu Lys Asn
        275                 280                 285

Gly Gly Thr Val Val Ser Arg Asp Pro Phe Lys Ala Val Thr Phe Val
    290                 295                 300

Ala Asn His Asp Thr Asp Ile Ile Trp Asn Lys Tyr Pro Ala Tyr Ala
305                 310                 315                 320

Phe Ile Leu Thr Tyr Glu Gly Gln Pro Thr Ile Phe Tyr Arg Asp Tyr
                325                 330                 335

Glu Glu Trp Leu Asn Lys Asp Lys Leu Lys Asn Leu Ile Trp Ile His
            340                 345                 350

Asp Asn Leu Ala Gly Gly Ser Thr Ser Ile Val Tyr Tyr Asp Ser Asp
        355                 360                 365

Glu Met Ile Phe Val Arg Asn Gly Tyr Gly Ser Lys Pro Gly Leu Ile
    370                 375                 380

Thr Tyr Ile Asn Leu Gly Ser Ser Lys Val Gly Arg Trp Val Tyr Val
385                 390                 395                 400

Pro Lys Phe Ala Gly Ala Cys Ile His Glu Tyr Thr Gly Asn Leu Gly
                405                 410                 415

Gly Trp Val Asp Lys Tyr Val Tyr Ser Ser Gly Trp Val Tyr Leu Glu
            420                 425                 430

Ala Pro Ala Tyr Asp Pro Ala Asn Gly Gln Tyr Gly Tyr Ser Val Trp
        435                 440                 445

Ser Tyr Cys Gly Val Gly Ser Glu Lys Asp Glu Leu
    450                 455                 460

<210> SEQ ID NO 36
<211> LENGTH: 718
<212> TYPE: PRT
<213> ORGANISM: Artificial Sequence
<220> FEATURE:
```

<223> OTHER INFORMATION: synthetic

<400> SEQUENCE: 36

```
Met Arg Val Leu Leu Val Ala Leu Ala Leu Ala Leu Ala Ala Ser
 1               5                  10                  15

Ala Thr Ser Met Glu Thr Ile Lys Ile Tyr Glu Asn Lys Gly Val Tyr
             20                  25                  30

Lys Val Val Ile Gly Glu Pro Phe Pro Pro Ile Glu Phe Pro Leu Glu
         35                  40                  45

Gln Lys Ile Ser Ser Asn Lys Ser Leu Ser Glu Leu Gly Leu Thr Ile
     50                  55                  60

Val Gln Gln Gly Asn Lys Val Ile Val Glu Lys Ser Leu Asp Leu Lys
 65                  70                  75                  80

Glu His Ile Ile Gly Leu Gly Glu Lys Ala Phe Glu Leu Asp Arg Lys
                 85                  90                  95

Arg Lys Arg Tyr Val Met Tyr Asn Val Asp Ala Gly Ala Tyr Lys Lys
            100                 105                 110

Tyr Gln Asp Pro Leu Tyr Val Ser Ile Pro Leu Phe Ile Ser Val Lys
        115                 120                 125

Asp Gly Val Ala Thr Gly Tyr Phe Phe Asn Ser Ala Ser Lys Val Ile
    130                 135                 140

Phe Asp Val Gly Leu Glu Glu Tyr Asp Lys Val Ile Val Thr Ile Pro
145                 150                 155                 160

Glu Asp Ser Val Glu Phe Tyr Val Ile Glu Gly Pro Arg Ile Glu Asp
                165                 170                 175

Val Leu Glu Lys Tyr Thr Glu Leu Thr Gly Lys Pro Phe Leu Pro Pro
            180                 185                 190

Met Trp Ala Phe Gly Tyr Met Ile Ser Arg Tyr Ser Tyr Tyr Pro Gln
        195                 200                 205

Asp Lys Val Val Glu Leu Val Asp Ile Met Gln Lys Glu Gly Phe Arg
    210                 215                 220

Val Ala Gly Val Phe Leu Asp Ile His Tyr Met Asp Ser Tyr Lys Leu
225                 230                 235                 240

Phe Thr Trp His Pro Tyr Arg Phe Pro Glu Pro Lys Lys Leu Ile Asp
                245                 250                 255

Glu Leu His Lys Arg Asn Val Lys Leu Ile Thr Ile Val Asp His Gly
            260                 265                 270

Ile Arg Val Asp Gln Asn Tyr Ser Pro Phe Leu Ser Gly Met Gly Lys
        275                 280                 285

Phe Cys Glu Ile Glu Ser Gly Glu Leu Phe Val Gly Lys Met Trp Pro
    290                 295                 300

Gly Thr Thr Val Tyr Pro Asp Phe Phe Arg Glu Asp Thr Arg Glu Trp
305                 310                 315                 320

Trp Ala Gly Leu Ile Ser Glu Trp Leu Ser Gln Gly Val Asp Gly Ile
                325                 330                 335

Trp Leu Asp Met Asn Glu Pro Thr Asp Phe Ser Arg Ala Ile Glu Ile
            340                 345                 350

Arg Asp Val Leu Ser Ser Leu Pro Val Gln Phe Arg Asp Asp Arg Leu
        355                 360                 365

Val Thr Thr Phe Pro Asp Asn Val Val His Tyr Leu Arg Gly Lys Arg
    370                 375                 380

Val Lys His Glu Lys Val Arg Asn Ala Tyr Pro Leu Tyr Glu Ala Met
385                 390                 395                 400
```

-continued

```
Ala Thr Phe Lys Gly Phe Arg Thr Ser His Arg Asn Glu Ile Phe Ile
            405                 410                 415
Leu Ser Arg Ala Gly Tyr Ala Gly Ile Gln Arg Tyr Ala Phe Ile Trp
        420                 425                 430
Thr Gly Asp Asn Thr Pro Ser Trp Asp Leu Lys Leu Gln Leu Gln
    435                 440                 445
Leu Val Leu Gly Leu Ser Ile Ser Gly Val Pro Phe Val Gly Cys Asp
450                 455                 460
Ile Gly Gly Phe Gln Gly Arg Asn Phe Ala Glu Ile Asp Asn Ser Met
465                 470                 475                 480
Asp Leu Leu Val Lys Tyr Tyr Ala Leu Ala Leu Phe Phe Pro Phe Tyr
                485                 490                 495
Arg Ser His Lys Ala Thr Asp Gly Ile Asp Thr Glu Pro Val Phe Leu
            500                 505                 510
Pro Asp Tyr Tyr Lys Glu Lys Val Lys Glu Ile Val Glu Leu Arg Tyr
        515                 520                 525
Lys Phe Leu Pro Tyr Ile Tyr Ser Leu Ala Leu Glu Ala Ser Glu Lys
    530                 535                 540
Gly His Pro Val Ile Arg Pro Leu Phe Tyr Phe Gln Asp Asp Asp
545                 550                 555                 560
Asp Met Tyr Arg Ile Glu Asp Glu Tyr Met Val Gly Lys Tyr Leu Leu
                565                 570                 575
Tyr Ala Pro Ile Val Ser Lys Glu Glu Ser Arg Leu Val Thr Leu Pro
            580                 585                 590
Arg Gly Lys Trp Tyr Asn Tyr Trp Asn Gly Glu Ile Ile Asn Gly Lys
        595                 600                 605
Ser Val Val Lys Ser Thr His Glu Leu Pro Ile Tyr Leu Arg Glu Gly
    610                 615                 620
Ser Ile Ile Pro Leu Glu Gly Asp Glu Leu Ile Val Tyr Gly Glu Thr
625                 630                 635                 640
Ser Phe Lys Arg Tyr Asp Asn Ala Glu Ile Thr Ser Ser Ser Asn Glu
                645                 650                 655
Ile Lys Phe Ser Arg Glu Ile Tyr Val Ser Lys Leu Thr Ile Thr Ser
            660                 665                 670
Glu Lys Pro Val Ser Lys Ile Ile Val Asp Asp Ser Lys Glu Ile Gln
        675                 680                 685
Val Glu Lys Thr Met Gln Asn Thr Tyr Val Ala Lys Ile Asn Gln Lys
    690                 695                 700
Ile Arg Gly Lys Ile Asn Leu Glu Ser Glu Lys Asp Glu Leu
705                 710                 715
```

<210> SEQ ID NO 37
<211> LENGTH: 1434
<212> TYPE: DNA
<213> ORGANISM: Thermotoga maritima

<400> SEQUENCE: 37

```
atgaaagaaa ccgctgctgc taaattcgaa cgccagcaca tggacagccc agatctgggt      60
accctggtgc cacgcggttc catggccgag ttcttcccgg agatcccgaa gatccagttc     120
gagggcaagg agtccaccaa cccgctcgcc ttccgcttct acgacccgaa cgaggtgatc     180
gacggcaagc cgctcaagga ccacctcaag ttctccgtgg ccttctggca caccttcgtg     240
aacgagggcc gcgacccgtt cggcgacccg accgccgagc gccgtggaa ccgcttctcc     300
gacccgatgg acaaggcctt cgcccgcgtg acgcccctct tcgagttctg cgagaagctc     360
```

-continued

```
aacatcgagt acttctgctt ccacgaccgc gacatcgccc cggagggcaa gaccctccgc    420
gagaccaaca agatcctcga caaggtggtg gagcgcatca aggagcgcat gaaggactcc    480
aacgtgaagc tcctctgggg caccgccaac ctcttctccc acccgcgcta catgcacggc    540
gccgccacca cctgctccgc cgacgtgttc gcctacgccg ccgcccaggt gaagaaggcc    600
ctggagatca ccaaggagct gggcggcgag ggctacgtgt tctggggcgg ccgcgagggc    660
tacgagaccc tcctcaacac cgacctcggc ctggagctgg agaacctcgc ccgcttcctc    720
cgcatggccg tggagtacgc caagaagatc ggcttcaccg ccagttcct catcgagccg    780 aagccgaagg agccgaccaa gcaccagtac gacttcgacg tggccaccgc ctacgccttc    840
ctcaagaacc acggcctcga cgagtacttc aagttcaaca tcgaggccaa ccacgccacc    900
ctcgccggcc acaccttcca gcacgagctg cgcatggccc gcatcctcgg caagctcggc    960
tccatcgacg ccaaccaggg cgacctcctc ctcggctggg acaccgacca gttcccgacc   1020
aacatctacg acaccaccct cgccatgtac gaggtgatca aggccggcgg cttcaccaag   1080
ggcggcctca acttcgacgc caaggtgcgc gcgcctcct acaaggtgga ggacctcttc   1140
atcggccaca tcgccggcat ggacaccttc gccctcggct tcaagatcgc ctacaagctc   1200
gccaaggacg gcgtgttcga caagttcatc gaggagaagt accgctcctt caaggagggc   1260
atcggcaagg agatcgtgga gggcaagacc gacttcgaga agctggagga gtacatcatc   1320
gacaaggagg acatcgagct gccgtccggc aagcaggagt acctggagtc cctcctcaac   1380
tcctacatcg tgaagaccat cgccgagctg cgctccgaga aggacgagct gtga          1434
```

<210> SEQ ID NO 38
<211> LENGTH: 477
<212> TYPE: PRT
<213> ORGANISM: Thermotoga maritima

<400> SEQUENCE: 38

```
Met Lys Glu Thr Ala Ala Ala Lys Phe Glu Arg Gln His Met Asp Ser
 1               5                  10                  15

Pro Asp Leu Gly Thr Leu Val Pro Arg Gly Ser Met Ala Glu Phe Phe
            20                  25                  30

Pro Glu Ile Pro Lys Ile Gln Phe Glu Gly Lys Glu Ser Thr Asn Pro
        35                  40                  45

Leu Ala Phe Arg Phe Tyr Asp Pro Asn Glu Val Ile Asp Gly Lys Pro
    50                  55                  60

Leu Lys Asp His Leu Lys Phe Ser Val Ala Phe Trp His Thr Phe Val
65                  70                  75                  80

Asn Glu Gly Arg Asp Pro Phe Gly Asp Pro Thr Ala Glu Arg Pro Trp
                85                  90                  95

Asn Arg Phe Ser Asp Pro Met Asp Lys Ala Phe Ala Arg Val Asp Ala
            100                 105                 110

Leu Phe Glu Phe Cys Glu Lys Leu Asn Ile Glu Tyr Phe Cys Phe His
        115                 120                 125

Asp Arg Asp Ile Ala Pro Glu Gly Lys Thr Leu Arg Glu Thr Asn Lys
    130                 135                 140

Ile Leu Asp Lys Val Val Glu Arg Ile Lys Glu Arg Met Lys Asp Ser
145                 150                 155                 160

Asn Val Lys Leu Leu Trp Gly Thr Ala Asn Leu Phe Ser His Pro Arg
                165                 170                 175

Tyr Met His Gly Ala Ala Thr Thr Cys Ser Ala Asp Val Phe Ala Tyr
```

```
                    180                 185                 190
Ala Ala Ala Gln Val Lys Lys Ala Leu Glu Ile Thr Lys Glu Leu Gly
            195                 200                 205

Gly Glu Gly Tyr Val Phe Trp Gly Gly Arg Glu Gly Tyr Glu Thr Leu
210                 215                 220

Leu Asn Thr Asp Leu Gly Leu Glu Leu Glu Asn Leu Ala Arg Phe Leu
225                 230                 235                 240

Arg Met Ala Val Glu Tyr Ala Lys Lys Ile Gly Phe Thr Gly Gln Phe
                245                 250                 255

Leu Ile Glu Pro Lys Pro Lys Glu Pro Thr Lys His Gln Tyr Asp Phe
            260                 265                 270

Asp Val Ala Thr Ala Tyr Ala Phe Leu Lys Asn His Gly Leu Asp Glu
        275                 280                 285

Tyr Phe Lys Phe Asn Ile Glu Ala Asn His Ala Thr Leu Ala Gly His
    290                 295                 300

Thr Phe Gln His Glu Leu Arg Met Ala Arg Ile Leu Gly Lys Leu Gly
305                 310                 315                 320

Ser Ile Asp Ala Asn Gln Gly Asp Leu Leu Leu Gly Trp Asp Thr Asp
                325                 330                 335

Gln Phe Pro Thr Asn Ile Tyr Asp Thr Thr Leu Ala Met Tyr Glu Val
            340                 345                 350

Ile Lys Ala Gly Gly Phe Thr Lys Gly Gly Leu Asn Phe Asp Ala Lys
        355                 360                 365

Val Arg Arg Ala Ser Tyr Lys Val Glu Asp Leu Phe Ile Gly His Ile
    370                 375                 380

Ala Gly Met Asp Thr Phe Ala Leu Gly Phe Lys Ile Ala Tyr Lys Leu
385                 390                 395                 400

Ala Lys Asp Gly Val Phe Asp Lys Phe Ile Glu Glu Lys Tyr Arg Ser
                405                 410                 415

Phe Lys Glu Gly Ile Gly Lys Glu Ile Val Glu Gly Lys Thr Asp Phe
            420                 425                 430

Glu Lys Leu Glu Glu Tyr Ile Ile Asp Lys Glu Asp Ile Glu Leu Pro
        435                 440                 445

Ser Gly Lys Gln Glu Tyr Leu Glu Ser Leu Leu Asn Ser Tyr Ile Val
    450                 455                 460

Lys Thr Ile Ala Glu Leu Arg Ser Glu Lys Asp Glu Leu
465                 470                 475

<210> SEQ ID NO 39
<211> LENGTH: 1434
<212> TYPE: DNA
<213> ORGANISM: Thermotoga neapolitana

<400> SEQUENCE: 39
atgaaagaaa ccgctgctgc taaattcgaa cgccagcaca tggacagccc agatctgggt      60
accctggtgc acgcgggttc catggccgag ttcttcccgg agatcccgaa ggtgcagttc     120
gagggcaagg agtccaccaa cccgctcgcc ttcaagttct cgaccccgga ggagatcatc     180
gacggcaagc cgctcaagga ccacctcaag ttctccgtgg ccttctggca caccttcgtg     240
aacgagggcc gcgacccgtt cggcgacccg accgccgacc gccgtgaa ccgctacacc       300 gacccgatgg acaaggcctt cgcccgcgtg acgccctct tcgagttctg cgagaagctc       360
aacatcgagt acttctgctt ccacgaccgc gacatcgccc cggagggcaa gaccctccgc     420
gagaccaaca gatcctcga caaggtggtg gagcgcatca aggagcgcat gaaggactcc      480
```

```
aacgtgaagc tcctctgggg caccgccaac ctcttctccc acccgcgcta catgcacggc    540
gccgccacca cctgctccgc cgacgtgttc gcctacgccg ccgcccaggt gaagaaggcc    600
ctggagatca ccaaggagct gggcggcgag ggctacgtgt tctggggcgg ccgcgagggc    660
tacgagaccc tcctcaacac cgacctcggc ttcgagctgg agaacctcgc ccgcttcctc    720
cgcatggccg tggactacgc caagcgcatc ggcttcaccg ccagttcct catcgagccg    780
aagccgaagg agccgaccaa gcaccagtac gacttcgacg tggccaccgc ctacgccttc    840
ctcaagtccc acggcctcga cgagtacttc aagttcaaca tcgaggccaa ccacgccacc    900
ctcgccggcc acaccttcca gcacgagctg cgcatggccc gcatcctcgg caagctcggc    960
tccatcgacg ccaaccaggg cgacctcctc ctcggctggg acaccgacca gttcccgacc   1020
aacgtgtacg acaccaccct cgccatgtac gaggtgatca aggccggcgg cttcaccaag   1080
ggcggcctca acttcgacgc caaggtgcgc gcgcctcct acaaggtgga ggacctcttc   1140
atcggccaca tcgccggcat ggacaccttc gccctcggct tcaaggtggc ctacaagctc   1200
gtgaaggacg gcgtgctcga caagttcatc gaggagaagt accgctcctt ccgcgagggc   1260
atcggccgcg acatcgtgga gggcaaggtg gacttcgaga gctggagga gtacatcatc   1320
gacaaggaga ccatcgagct gccgtccggc aagcaggagt acctggagtc cctcatcaac   1380
tcctacatcg tgaagaccat cctggagctg cgctccgaga aggacgagct gtga          1434
```

<210> SEQ ID NO 40
<211> LENGTH: 477
<212> TYPE: PRT
<213> ORGANISM: Thermotoga neapolitana

<400> SEQUENCE: 40

```
Met Lys Glu Thr Ala Ala Ala Lys Phe Glu Arg Gln His Met Asp Ser
 1               5                  10                  15

Pro Asp Leu Gly Thr Leu Val Pro Arg Gly Ser Met Ala Glu Phe Phe
            20                  25                  30

Pro Glu Ile Pro Lys Val Gln Phe Glu Gly Lys Glu Ser Thr Asn Pro
        35                  40                  45

Leu Ala Phe Lys Phe Tyr Asp Pro Glu Glu Ile Ile Asp Gly Lys Pro
    50                  55                  60

Leu Lys Asp His Leu Lys Phe Ser Val Ala Phe Trp His Thr Phe Val
65                  70                  75                  80

Asn Glu Gly Arg Asp Pro Phe Gly Asp Pro Thr Ala Asp Arg Pro Trp
                85                  90                  95

Asn Arg Tyr Thr Asp Pro Met Asp Lys Ala Phe Ala Arg Val Asp Ala
            100                 105                 110

Leu Phe Glu Phe Cys Glu Lys Leu Asn Ile Glu Tyr Phe Cys Phe His
        115                 120                 125

Asp Arg Asp Ile Ala Pro Glu Gly Lys Thr Leu Arg Glu Thr Asn Lys
    130                 135                 140

Ile Leu Asp Lys Val Val Glu Arg Ile Lys Glu Arg Met Lys Asp Ser
145                 150                 155                 160

Asn Val Lys Leu Leu Trp Gly Thr Ala Asn Leu Phe Ser His Pro Arg
                165                 170                 175

Tyr Met His Gly Ala Ala Thr Thr Cys Ser Ala Asp Val Phe Ala Tyr
            180                 185                 190

Ala Ala Ala Gln Val Lys Lys Ala Leu Glu Ile Thr Lys Glu Leu Gly
        195                 200                 205
```

Gly Glu Gly Tyr Val Phe Trp Gly Gly Arg Glu Gly Tyr Glu Thr Leu
210                215                 220

Leu Asn Thr Asp Leu Gly Phe Glu Leu Glu Asn Leu Ala Arg Phe Leu
225                 230                235                 240

Arg Met Ala Val Asp Tyr Ala Lys Arg Ile Gly Phe Thr Gly Gln Phe
                245                 250                 255

Leu Ile Glu Pro Lys Pro Lys Gly Pro Thr Lys His Gln Tyr Asp Phe
            260                 265                 270

Asp Val Ala Thr Ala Tyr Ala Phe Leu Lys Ser His Gly Leu Asp Glu
            275                 280                 285

Tyr Phe Lys Phe Asn Ile Glu Ala Asn His Ala Thr Leu Ala Gly His
            290                 295                 300

Thr Phe Gln His Glu Leu Arg Met Ala Arg Ile Leu Gly Lys Leu Gly
305                 310                 315                 320

Ser Ile Asp Ala Asn Gln Gly Asp Leu Leu Gly Trp Asp Thr Asp
                325                 330                 335

Gln Phe Pro Thr Asn Val Tyr Asp Thr Thr Leu Ala Met Tyr Glu Val
                340                 345                 350

Ile Lys Ala Gly Gly Phe Thr Lys Gly Gly Leu Asn Phe Asp Ala Lys
            355                 360                 365

Val Arg Arg Ala Ser Tyr Lys Val Glu Asp Leu Phe Ile Gly His Ile
            370                 375                 380

Ala Gly Met Asp Thr Phe Ala Leu Gly Phe Lys Val Ala Tyr Lys Leu
385                 390                 395                 400

Val Lys Asp Gly Val Leu Asp Lys Phe Ile Glu Glu Lys Tyr Arg Ser
                405                 410                 415

Phe Arg Glu Gly Ile Gly Arg Asp Ile Val Glu Gly Lys Val Asp Phe
            420                 425                 430

Glu Lys Leu Glu Glu Tyr Ile Ile Asp Lys Glu Thr Ile Glu Leu Pro
            435                 440                 445

Ser Gly Lys Gln Glu Tyr Leu Glu Ser Leu Ile Asn Ser Tyr Ile Val
450                 455                 460

Lys Thr Ile Leu Glu Leu Arg Ser Glu Lys Asp Glu Leu
465                 470                 475

<210> SEQ ID NO 41
<211> LENGTH: 1435
<212> TYPE: DNA
<213> ORGANISM: Thermotoga maritima

<400> SEQUENCE: 41
atgggcagca gccatcatca tcatcatcac agcagcggcc tggtgccgcg cggcagccat      60
atggctagca tgactggtgg acagcaaatg ggtcggatcc ccatggccga gttcttcccg     120
gagatcccga agatccagtt cgagggcaag gagtccacca cccgctcgc cttccgcttc     180 tacgacccga acgaggtgat cgacggcaag ccgctcaagg accacctcaa gttctccgtg     240
gccttctggc acaccttcgt gaacgagggc cgcgacccgt cggcgaccc gaccgccgag     300 cgcccgtgga accgcttctc cgacccgatg acaaggcct cgcccgcgt ggacgccctc      360 ttcgagttct gcgagaagct caacatcgag tacttctgct ccacgaccg cgacatcccc     420 cggagggcaa gaccctccgc gagaccaaca agatcctcga caaggtggtg agcgcatca     480 aggagcgcat gaaggactcc aacgtgaagc tcctctgggg caccgccaac ctcttctccc     540
acccgcgcta catgcacggc gccgccacca cctgctccgc cgacgtgttc gcctacgccg     600

```
ccgcccaggt gaagaaggcc ctggagatca ccaaggagct gggcggcgag ggctacgtgt    660
tctggggcgg ccgcgagggc tacgagaccc tcctcaacac cgacctcggc ctggagctgg    720
agaacctcgc cgcttcctc cgcatggccg tggagtacgc caagaagatc ggcttcaccg    780
gccagttcct catcgagccg aagccgaagg agccgaccaa gcaccagtac gcttcgacgt    840
ggccaccgcc tacgccttcc tcaagaacca cggcctcgac gagtacttca agttcaacat    900
cgaggccaac cacgccaccc tcgccggcca caccttccag cacgagctgc gcatggcccg    960
catcctcggc aagctcggct ccatcgacgc caaccagggc gacctcctcc tcggctggga   1020
caccgaccag ttcccgacca acatctacga caccaccctc gccatgtacg aggtgatcaa   1080
ggccggcggc ttcaccaagg gcggcctcaa cttcgacgcc aaggtgcgcc gcgcctccta   1140
caaggtggag gacctcttca tcggccacat cgccggcatg gacaccttcg ccctcggctt   1200
caagatcgcc tacaagctcg ccaaggacg cgtgttcgac aagttcatcg aggagaagta   1260
ccgctccttc aaggagggca tcggcaagga gatcgtggag ggcaagaccg acttcgagaa   1320
gctggaggag tacatcatcg acaaggagga catcgagctg ccgtccggca agcaggagta   1380
cctggagtcc ctcctcaact cctacatcgt gaagaccatc gccgagctgc gctga         1435
```

<210> SEQ ID NO 42
<211> LENGTH: 478
<212> TYPE: PRT
<213> ORGANISM: Thermotoga maritima

<400> SEQUENCE: 42

```
Met Gly Ser Ser His His His His His His Ser Ser Gly Leu Val Pro
  1               5                  10                  15

Arg Gly Ser His Met Ala Ser Met Thr Gly Gly Gln Gln Met Gly Arg
             20                  25                  30

Ile Pro Met Ala Glu Phe Phe Pro Glu Ile Pro Lys Ile Gln Phe Glu
         35                  40                  45

Gly Lys Glu Ser Thr Asn Pro Leu Ala Phe Arg Phe Tyr Asp Pro Asn
     50                  55                  60

Glu Val Ile Asp Gly Lys Pro Leu Lys Asp His Leu Lys Phe Ser Val
 65                  70                  75                  80

Ala Phe Trp His Thr Phe Val Asn Glu Gly Arg Asp Pro Phe Gly Asp
                 85                  90                  95

Pro Thr Ala Glu Arg Pro Trp Asn Arg Phe Ser Asp Pro Met Asp Lys
            100                 105                 110

Ala Phe Ala Arg Val Asp Ala Leu Phe Glu Phe Cys Glu Lys Leu Asn
        115                 120                 125

Ile Glu Tyr Phe Cys Phe His Asp Arg Asp Ile Ala Pro Glu Gly Lys
    130                 135                 140

Thr Leu Arg Glu Thr Asn Lys Ile Leu Asp Lys Val Glu Arg Ile
145                 150                 155                 160

Lys Glu Arg Met Lys Asp Ser Asn Val Lys Leu Leu Trp Gly Thr Ala
                165                 170                 175

Asn Leu Phe Ser His Pro Arg Tyr Met His Gly Ala Ala Thr Thr Cys
            180                 185                 190

Ser Ala Asp Val Phe Ala Tyr Ala Ala Gln Val Lys Lys Ala Leu
        195                 200                 205

Glu Ile Thr Lys Glu Leu Gly Gly Glu Gly Tyr Val Phe Trp Gly Gly
    210                 215                 220
```

```
Arg Glu Gly Tyr Glu Thr Leu Leu Asn Thr Asp Leu Gly Leu Glu Leu
225                 230                 235                 240

Glu Asn Leu Ala Arg Phe Leu Arg Met Ala Val Glu Tyr Ala Lys Lys
                245                 250                 255

Ile Gly Phe Thr Gly Gln Phe Leu Ile Glu Pro Lys Pro Lys Glu Pro
            260                 265                 270

Thr Lys His Gln Tyr Asp Phe Asp Val Ala Thr Ala Tyr Ala Phe Leu
        275                 280                 285

Lys Asn His Gly Leu Asp Glu Tyr Phe Lys Phe Asn Ile Glu Ala Asn
    290                 295                 300

His Ala Thr Leu Ala Gly His Thr Phe Gln His Glu Leu Arg Met Ala
305                 310                 315                 320

Arg Ile Leu Gly Lys Leu Gly Ser Ile Asp Ala Asn Gln Gly Asp Leu
                325                 330                 335

Leu Leu Gly Trp Asp Thr Asp Gln Phe Pro Thr Asn Ile Tyr Asp Thr
            340                 345                 350

Thr Leu Ala Met Tyr Glu Val Ile Lys Ala Gly Gly Phe Thr Lys Gly
        355                 360                 365

Gly Leu Asn Phe Asp Ala Lys Val Arg Arg Ala Ser Tyr Lys Val Glu
    370                 375                 380

Asp Leu Phe Ile Gly His Ile Ala Gly Met Asp Thr Phe Ala Leu Gly
385                 390                 395                 400

Phe Lys Ile Ala Tyr Lys Leu Ala Lys Asp Gly Val Phe Asp Lys Phe
                405                 410                 415

Ile Glu Glu Lys Tyr Arg Ser Phe Lys Glu Gly Ile Gly Lys Glu Ile
            420                 425                 430

Val Glu Gly Lys Thr Asp Phe Glu Lys Leu Glu Tyr Ile Ile Asp
        435                 440                 445

Lys Glu Asp Ile Glu Leu Pro Ser Gly Lys Gln Glu Tyr Leu Glu Ser
    450                 455                 460

Leu Leu Asn Ser Tyr Ile Val Lys Thr Ile Ala Glu Leu Arg
465                 470                 475

<210> SEQ ID NO 43
<211> LENGTH: 1436
<212> TYPE: DNA
<213> ORGANISM: Thermotoga neapolitana

<400> SEQUENCE: 43
atgggcagca gccatcatca tcatcatcac agcagcggcc tggtgccgcg cggcagccat      60
atggctagca tgactggtgg acagcaaatg ggtcggatcc ccatggccga gttcttcccg     120
gagatcccga aggtgcagtt cgagggcaag gagtccacca cccgctcgc cttcaagttc      180 tacgacccgg aggagatcat cgacggcaag ccgctcaagg accacctcaa gttctccgtg     240
gccttctggc acaccttcgt gaacgagggc gcgacccgt cggcgaccc gaccgccgac       300 cgcccgtgga accgctacac cgacccgatg acaaggcct cgcccgcgt ggacgccctc       360 ttcgagttct gcgagaagct caacatcgag tacttctgct ccacgaccg cgacatcccc     420 cggagggcaa gaccctccgc gagaccaaca agatcctcga caaggtggtg agcgcatca      480 aggagcgcat gaaggactcc aacgtgaagc tcctctgggg gaccgccaac ctcttctccc     540
acccgcgcta catgcacggc gccgccacca cctgctccgc cgacgtgttc gcctacgccg     600
ccgcccaggt gaagaaggcc ctggagatca ccaaggagct gggcggcgag ggctacgtgt     660 tctgggggcgg ccgcgagggc tacgagaccc tcctcaacac cgacctcggc ttcgagctgg   720
```

```
agaacctcgc ccgcttcctc cgcatggccg tggactacgc caagcgcatc ggcttcaccg    780
gccagttcct catcgagccg aagccgaagg agccgaccaa gcaccagtac gacttcgacg    840
tggccaccgc ctacgccttc ctcaagtccc acggcctcga cgagtacttc aagttcaaca    900
tcgaggccaa ccacgccacc ctcgccggcc acaccttcca gcacgagctg cgcatggccc    960
gcatcctcgg caagctcggc tccatcgacg ccaaccaggg cgacctcctc ctcggctggg   1020
acaccgacca gttcccgacc aacgtgtacg acaccaccct cgccatgtac gaggtgatca   1080
aggccggcgg cttcaccaag gcggcctca acttcgacgc caaggtgcgc cgcgcctcct   1140
acaaggtgga ggacctcttc atcggccaca tcgccggcat ggacaccttc gccctcggct   1200
tcaaggtggc ctacaagctc gtgaaggacg gcgtgctcga caagttcatc gaggagaagt   1260
accgctcctt ccgcgagggc atcggccgcg acatcgtgga gggcaaggtg gacttcgaga   1320
agctggagga gtacatcatc gacaaggaga ccatcgagct gccgtccggc aagcaggagt   1380
acctggagtc cctcatcaac tcctacatcg tgaagaccat cctggagctg cgctga        1436
```

<210> SEQ ID NO 44
<211> LENGTH: 478
<212> TYPE: PRT
<213> ORGANISM: Thermotoga neapolitana

<400> SEQUENCE: 44

```
Met Gly Ser Ser His His His His His Ser Ser Gly Leu Val Pro
 1               5                  10                  15

Arg Gly Ser His Met Ala Ser Met Thr Gly Gly Gln Gln Met Gly Arg
                20                  25                  30

Ile Pro Met Ala Glu Phe Phe Pro Glu Ile Pro Lys Val Gln Phe Glu
            35                  40                  45

Gly Lys Glu Ser Thr Asn Pro Leu Ala Phe Lys Phe Tyr Asp Pro Glu
        50                  55                  60

Glu Ile Ile Asp Gly Lys Pro Leu Lys Asp His Leu Lys Phe Ser Val
65                  70                  75                  80

Ala Phe Trp His Thr Phe Val Asn Glu Gly Arg Asp Pro Phe Gly Asp
                85                  90                  95

Pro Thr Ala Asp Arg Pro Trp Asn Arg Tyr Thr Asp Pro Met Asp Lys
            100                 105                 110

Ala Phe Ala Arg Val Asp Ala Leu Phe Glu Phe Cys Glu Lys Leu Asn
        115                 120                 125

Ile Glu Tyr Phe Cys Phe His Asp Arg Asp Ile Ala Pro Glu Gly Lys
    130                 135                 140

Thr Leu Arg Glu Thr Asn Lys Ile Leu Asp Lys Val Val Glu Arg Ile
145                 150                 155                 160

Lys Glu Arg Met Lys Asp Ser Asn Val Lys Leu Leu Trp Gly Thr Ala
                165                 170                 175

Asn Leu Phe Ser His Pro Arg Tyr Met His Gly Ala Ala Thr Thr Cys
            180                 185                 190

Ser Ala Asp Val Phe Ala Tyr Ala Ala Ala Gln Val Lys Lys Ala Leu
        195                 200                 205

Glu Ile Thr Lys Glu Leu Gly Gly Glu Gly Tyr Val Phe Trp Gly Gly
    210                 215                 220

Arg Glu Gly Tyr Glu Thr Leu Leu Asn Thr Asp Leu Gly Phe Glu Leu
225                 230                 235                 240

Glu Asn Leu Ala Arg Phe Leu Arg Met Ala Val Asp Tyr Ala Lys Arg
```

```
                245                 250                 255
Ile Gly Phe Thr Gly Gln Phe Leu Ile Glu Pro Lys Pro Lys Glu Pro
        260                 265                 270

Thr Lys His Gln Tyr Asp Phe Asp Val Ala Thr Ala Tyr Ala Phe Leu
            275                 280                 285

Lys Ser His Gly Leu Asp Glu Tyr Phe Lys Phe Asn Ile Glu Ala Asn
        290                 295                 300

His Ala Thr Leu Ala Gly His Thr Phe Gln His Glu Leu Arg Met Ala
305                 310                 315                 320

Arg Ile Leu Gly Lys Leu Gly Ser Ile Asp Ala Asn Gln Gly Asp Leu
                325                 330                 335

Leu Leu Gly Trp Asp Thr Asp Gln Phe Pro Thr Asn Val Tyr Asp Thr
            340                 345                 350

Thr Leu Ala Met Tyr Glu Val Ile Lys Ala Gly Gly Phe Thr Lys Gly
        355                 360                 365

Gly Leu Asn Phe Asp Ala Lys Val Arg Arg Ala Ser Tyr Lys Val Glu
    370                 375                 380

Asp Leu Phe Ile Gly His Ile Ala Gly Met Asp Thr Phe Ala Leu Gly
385                 390                 395                 400

Phe Lys Val Ala Tyr Lys Leu Val Lys Asp Gly Val Leu Asp Lys Phe
                405                 410                 415

Ile Glu Glu Lys Tyr Arg Ser Phe Arg Glu Gly Ile Gly Arg Asp Ile
            420                 425                 430

Val Glu Gly Lys Val Asp Phe Glu Lys Leu Glu Tyr Ile Ile Asp
        435                 440                 445

Lys Glu Thr Ile Glu Leu Pro Ser Gly Lys Gln Glu Tyr Leu Glu Ser
    450                 455                 460

Leu Ile Asn Ser Tyr Ile Val Lys Thr Ile Leu Glu Leu Arg
465                 470                 475

<210> SEQ ID NO 45
<211> LENGTH: 1095
<212> TYPE: PRT
<213> ORGANISM: Aspergillus shirousami

<400> SEQUENCE: 45

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140
```

-continued

```
Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
            165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
            195                 200                 205

Lys His Val Gln Lys Asp Phe Trp Pro Gly Tyr Asn Lys Ala Ala Gly
210                 215                 220

Val Tyr Cys Ile Gly Glu Val Leu Asp Val Asp Pro Ala Tyr Thr Cys
225                 230                 235                 240

Pro Tyr Gln Asn Val Met Asp Gly Val Leu Asn Tyr Pro Ile Tyr Tyr
            245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
            275                 280                 285

Leu Gly Thr Phe Val Glu Asn His Asp Asn Pro Arg Phe Ala Ser Tyr
            290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
            325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
            355                 360                 365

Arg Asn Tyr Ala Ile Ser Lys Asp Thr Gly Phe Val Thr Tyr Lys Asn
370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
            405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Gly Ser Asp
            435                 440                 445

Gly Asn Val Pro Val Pro Met Ala Gly Gly Leu Pro Arg Val Leu Tyr
450                 455                 460

Pro Thr Glu Lys Leu Ala Gly Ser Lys Ile Cys Ser Ser Ser Lys Pro
465                 470                 475                 480

Ala Thr Leu Asp Ser Trp Leu Ser Asn Glu Ala Thr Val Ala Arg Thr
            485                 490                 495

Ala Ile Leu Asn Asn Ile Gly Ala Asp Gly Ala Trp Val Ser Gly Ala
            500                 505                 510

Asp Ser Gly Ile Val Val Ala Ser Pro Ser Thr Asp Asn Pro Asp Tyr
            515                 520                 525

Phe Tyr Thr Trp Thr Arg Asp Ser Gly Ile Val Leu Lys Thr Leu Val
            530                 535                 540

Asp Leu Phe Arg Asn Gly Asp Thr Asp Leu Leu Ser Thr Ile Glu His
545                 550                 555                 560

Tyr Ile Ser Ser Gln Ala Ile Ile Gln Gly Val Ser Asn Pro Ser Gly
```

-continued

```
                  565                 570                 575
Asp Leu Ser Ser Gly Gly Leu Gly Glu Pro Lys Phe Asn Val Asp Glu
              580                 585                 590

Thr Ala Tyr Ala Gly Ser Trp Gly Arg Pro Gln Arg Asp Gly Pro Ala
              595                 600                 605

Leu Arg Ala Thr Ala Met Ile Gly Phe Gly Gln Trp Leu Leu Asp Asn
              610                 615                 620

Gly Tyr Thr Ser Ala Ala Thr Glu Ile Val Trp Pro Leu Val Arg Asn
625                 630                 635                 640

Asp Leu Ser Tyr Val Ala Gln Tyr Trp Asn Gln Thr Gly Tyr Asp Leu
                  645                 650                 655

Trp Glu Glu Val Asn Gly Ser Ser Phe Phe Thr Ile Ala Val Gln His
              660                 665                 670

Arg Ala Leu Val Glu Gly Ser Ala Phe Ala Thr Ala Val Gly Ser Ser
              675                 680                 685

Cys Ser Trp Cys Asp Ser Gln Ala Pro Gln Ile Leu Cys Tyr Leu Gln
              690                 695                 700

Ser Phe Trp Thr Gly Ser Tyr Ile Leu Ala Asn Phe Asp Ser Ser Arg
705                 710                 715                 720

Ser Gly Lys Asp Thr Asn Thr Leu Leu Gly Ser Ile His Thr Phe Asp
                  725                 730                 735

Pro Glu Ala Gly Cys Asp Asp Ser Thr Phe Gln Pro Cys Ser Pro Arg
              740                 745                 750

Ala Leu Ala Asn His Lys Glu Val Val Asp Ser Phe Arg Ser Ile Tyr
              755                 760                 765

Thr Leu Asn Asp Gly Leu Ser Asp Ser Glu Ala Val Ala Val Gly Arg
              770                 775                 780

Tyr Pro Glu Asp Ser Tyr Tyr Asn Gly Asn Pro Trp Phe Leu Cys Thr
785                 790                 795                 800

Leu Ala Ala Ala Glu Gln Leu Tyr Asp Ala Leu Tyr Gln Trp Asp Lys
                  805                 810                 815

Gln Gly Ser Leu Glu Ile Thr Asp Val Ser Leu Asp Phe Phe Lys Ala
              820                 825                 830

Leu Tyr Ser Gly Ala Ala Thr Gly Thr Tyr Ser Ser Ser Ser Ser Thr
              835                 840                 845

Tyr Ser Ser Ile Val Ser Ala Val Lys Thr Phe Ala Asp Gly Phe Val
              850                 855                 860

Ser Ile Val Glu Thr His Ala Ala Ser Asn Gly Ser Leu Ser Glu Gln
865                 870                 875                 880

Phe Asp Lys Ser Asp Gly Asp Glu Leu Ser Ala Arg Asp Leu Thr Trp
                  885                 890                 895

Ser Tyr Ala Ala Leu Leu Thr Ala Asn Asn Arg Arg Asn Ser Val Val
              900                 905                 910

Pro Pro Ser Trp Gly Glu Thr Ser Ala Ser Ser Val Pro Gly Thr Cys
              915                 920                 925

Ala Ala Thr Ser Ala Ser Gly Thr Tyr Ser Ser Val Thr Val Thr Ser
              930                 935                 940

Trp Pro Ser Ile Val Ala Thr Gly Gly Thr Thr Thr Ala Thr Thr
945                 950                 955                 960

Thr Gly Ser Gly Gly Val Thr Ser Thr Ser Lys Thr Thr Thr Ala
                  965                 970                 975

Ser Lys Thr Ser Thr Thr Thr Ser Ser Thr Ser Cys Thr Thr Pro Thr
              980                 985                 990
```

```
Ala Val Ala Val Thr Phe Asp Leu Thr Ala Thr Thr Tyr Gly Glu
        995                 1000                1005

Asn Ile Tyr Leu Val Gly Ser Ile Ser Gln Leu Gly Asp Trp Glu Thr
    1010                1015                1020

Ser Asp Gly Ile Ala Leu Ser Ala Asp Lys Tyr Thr Ser Ser Asn Pro
1025                1030                1035                1040

Pro Trp Tyr Val Thr Val Thr Leu Pro Ala Gly Glu Ser Phe Glu Tyr
                1045                1050                1055

Lys Phe Ile Arg Val Glu Ser Asp Asp Ser Val Glu Trp Glu Ser Asp
                1060                1065                1070

Pro Asn Arg Glu Tyr Thr Val Pro Gln Ala Cys Gly Glu Ser Thr Ala
        1075                1080                1085

Thr Val Thr Asp Thr Trp Arg
    1090                1095
```

<210> SEQ ID NO 46
<211> LENGTH: 3285
<212> TYPE: DNA
<213> ORGANISM: Aspergillus shirousami

<400> SEQUENCE: 46

```
gccaccccgg ccgactggcg ctcccagtcc atctacttcc tcctcaccga ccgcttcgcc      60
cgcaccgacg gctccaccac cgccacctgc aacaccgccg accagaagta ctgcggcggc     120
acctggcagg gcatcatcga caagctcgac tacatccagg gcatgggctt caccgccatc     180
tggatcaccc cggtgaccgc ccagctcccg cagaccaccg cctacggcga cgcctaccac     240
ggctactggc agcaggacat ctactccctc aacgagaact acggcaccgc cgacgacctc     300
aaggccctct cctccgccct ccacgagcgc ggcatgtacc tcatggtgga cgtggtggcc     360
aaccacatgg gctacgacgg cgccggctcc tccgtggact actccgtgtt caagccgttc     420
tcctcccagg actacttcca cccgttctgc ttcatccaga actacgagga ccagacccag     480
gtggaggact gctggctcgg cgacaacacc gtgtccctcc cggacctcga caccaccaag     540
gacgtggtga agaacgagtg gtacgactgg gtgggctccc tcgtgtccaa ctactccatc     600
gacggcctcc gcatcgacac cgtgaagcac gtgcagaagg acttctggcc gggctacaac     660
aaggccgccg gcgtgtactg catcggcgag gtgctcgacg tggacccggc ctacacctgc     720
ccgtaccaga acgtgatgga cggcgtgctc aactacccga tctactaccc gctcctcaac     780
gccttcaagt ccacctccgg ctcgatggac gacctctaca catgatcaa caccgtgaag     840
tccgactgcc cggactccac cctcctcggc accttcgtgg agaaccacga caacccgcgc     900
ttcgcctcct acaccaacga catcgccctc gccaagaact ggccgccctt catcatcctc     960
aacgacggca tcccgatcat ctacgccggc caggagcagc actacgccgg cggcaacgac    1020
ccggccaacc gcgaggccac ctggctctcc ggctacccga ccgactccga gctgtacaag    1080
ctcatcgcct ccgccaacgc catccgcaac tacgccatct ccaaggacac cggcttcgtg    1140
acctacaaga actggccgat ctacaaggac gacaccacca tcgccatgcg caagggcacc    1200
gacggctccc agatcgtgac catcctctcc aacaagggcg cctccggcga ctcctacacc    1260
ctctccctct ccggcgccgg ctacaccgcc ggcagcagc tcaccgaggt gatcggctgc    1320
accaccgtga ccgtgggctc cgacggcaac gtgccggtgc cgatggccgg cggcctcccg    1380
cgcgtgctct acccgaccga gaagctcgcc ggctccaaga tatgctcctc ctccaagccg    1440
gccacctcg actcctggct ctccaacgag gccaccgtgg ccgcaccgc catcctcaac    1500
```

```
aacatcggcg ccgacggcgc ctgggtgtcc ggcgccgact ccggcatcgt ggtggcctcc    1560
ccgtccaccg acaacccgga ctacttctac acctggaccc gcgactccgg catcgtgctc    1620
aagaccctcg tggacctctt ccgcaacggg gacaccgacc tcctctccac catcgagcac    1680
tacatctcct cccaggccat catccagggc gtgtccaacc cgtccggcga cctctcctcc    1740
ggcggcctcg cgagccgaa gttcaacgtg gacgagaccg cctacgccgg ctcctggggc     1800
cgcccgcagc gcgacggccc ggccctccgc gccaccgcca tgatcggctt cggccagtgg    1860
ctcctcgaca acggctacac ctccgccgcc accgagatcg tgtggccgct cgtgcgcaac    1920
gacctctcct acgtggccca gtactggaac cagaccggct acgacctctg ggaggaggtg    1980
aacggctcct ccttcttcac catcgccgtg cagcaccgcg ccctcgtgga gggctccgcc    2040
ttcgccaccg ccgtgggctc ctcctgctcc tggtgcgact cccaggcccc gcagatcctc    2100
tgctacctcc agtccttctg gaccggctcc tacatcctcg ccaacttcga ctcctcccgc    2160
tccggcaagg acaccaacac cctcctcggc tccatccaca ccttcgaccc ggaggccggc    2220
tgcgacgact ccaccttcca gccgtgctcc ccgcgcgccc tcgccaacca caaggaggtg    2280
gtggactcct tccgctccat ctacaccctc aacgacggc tctccgactc cgaggccgtg     2340
gccgtgggcc gctacccgga ggactcctac tacaacggca acccgtggtt cctctgcacc    2400
ctcgccgccg ccgagcagct ctacgacgcc ctctaccagt gggacaagca gggctccctg    2460
gagatcaccg acgtgtccct cgacttcttc aaggccctct actccggcgc cgccaccggc    2520
acctactcct cctcctcctc cacctactcc tccatcgtgt ccgccgtgaa gaccttcgcc    2580
gacggcttcg tgtccatcgt ggagacccac gccgcctcca acggctccct ctccgagcag    2640
ttcgacaagt ccgacggcga cgagctgtcc gcccgcgacc tcacctggtc ctacgccgcc    2700
ctcctcaccg ccaacaaccg ccgcaactcc gtggtgccgc cgtcctgggg cgagacctcc    2760
gcctcctccg tgccgggcac ctgcgccgcc acctccgcct ccggcaccta tcctccgtg    2820 accgtgacct cctggccgtc catcgtggcc accggcggca ccaccaccac cgccaccacc    2880
accggctccg gcggcgtgac ctccacctcc aagaccacca ccaccgcctc caagacctcc    2940
accaccacct cctccaccctc ctgcaccacc ccgaccgccg tggccgtgac cttcgacctc    3000
accgccacca ccacctacgg cgagaacatc tacctcgtgg gctccatctc ccagctcggc    3060
gactgggaga cctccgacgg catcgccctc tccgccgaca gtacacctc ctccaacccg     3120 ccgtggtacg tgaccgtgac cctcccggcc ggcgagtcct tcgagtacaa gttcatccgc    3180
gtggagtccg acgactccgt ggagtgggag tccgacccga accgcgagta caccgtgccg    3240
caggcctgcg cgagtccac cgccaccgtg accgacacct ggcgc                     3285
```

<210> SEQ ID NO 47
<211> LENGTH: 679
<212> TYPE: PRT
<213> ORGANISM: Thermoanaerobacterium thermosaccharolyticum

<400> SEQUENCE: 47

```
Val Leu Ser Gly Cys Ser Asn Asn Val Ser Ser Ile Lys Ile Asp Arg
 1               5                  10                  15

Phe Asn Asn Ile Ser Ala Val Asn Gly Pro Gly Glu Glu Asp Thr Trp
            20                  25                  30

Ala Ser Ala Gln Lys Gln Gly Val Gly Thr Ala Asn Asn Tyr Val Ser
        35                  40                  45

Arg Val Trp Phe Thr Leu Ala Asn Gly Ala Ile Ser Glu Val Tyr Tyr
```

```
                50                    55                    60
Pro Thr Ile Asp Thr Ala Asp Val Lys Glu Ile Lys Phe Ile Val Thr
 65                      70                      75                      80

Asp Gly Lys Ser Phe Val Ser Asp Glu Thr Lys Asp Ala Ile Ser Lys
                         85                      90                      95

Val Glu Lys Phe Thr Asp Lys Ser Leu Gly Tyr Lys Leu Val Asn Thr
                        100                     105                     110

Asp Lys Lys Gly Arg Tyr Arg Ile Thr Lys Glu Ile Phe Thr Asp Val
                115                     120                     125

Lys Arg Asn Ser Leu Ile Met Lys Ala Lys Phe Glu Ala Leu Glu Gly
130                     135                     140

Ser Ile His Asp Tyr Lys Leu Tyr Leu Ala Tyr Asp Pro His Ile Lys
145                     150                     155                     160

Asn Gln Gly Ser Tyr Asn Gly Tyr Val Ile Lys Ala Asn Asn Asn
                        165                     170                     175

Glu Met Leu Met Ala Lys Arg Asp Asn Val Tyr Thr Ala Leu Ser Ser
                180                     185                     190

Asn Ile Gly Trp Lys Gly Tyr Ser Ile Gly Tyr Tyr Lys Val Asn Asp
                195                     200                     205

Ile Met Thr Asp Leu Asp Glu Asn Lys Gln Met Thr Lys His Tyr Asp
                210                     215                     220

Ser Ala Arg Gly Asn Ile Ile Glu Gly Ala Glu Ile Asp Leu Thr Lys
225                     230                     235                     240

Asn Ser Glu Phe Glu Ile Val Leu Ser Phe Gly Gly Ser Asp Ser Glu
                        245                     250                     255

Ala Ala Lys Thr Ala Leu Glu Thr Leu Gly Glu Asp Tyr Asn Asn Leu
                260                     265                     270

Lys Asn Asn Tyr Ile Asp Glu Trp Thr Lys Tyr Cys Asn Thr Leu Asn
                275                     280                     285

Asn Phe Asn Gly Lys Ala Asn Ser Leu Tyr Tyr Asn Ser Met Met Ile
                290                     295                     300

Leu Lys Ala Ser Glu Asp Lys Thr Asn Lys Gly Ala Tyr Ile Ala Ser
305                     310                     315                     320

Leu Ser Ile Pro Trp Gly Asp Gly Gln Arg Asp Asp Asn Thr Gly Gly
                        325                     330                     335

Tyr His Leu Val Trp Ser Arg Asp Leu Tyr His Val Ala Asn Ala Phe
                340                     345                     350

Ile Ala Ala Gly Asp Val Asp Ser Ala Asn Arg Ser Leu Asp Tyr Leu
                355                     360                     365

Ala Lys Val Val Lys Asp Asn Gly Met Ile Pro Gln Asn Thr Trp Ile
                370                     375                     380

Ser Gly Lys Pro Tyr Trp Thr Ser Ile Gln Leu Asp Glu Gln Ala Asp
385                     390                     395                     400

Pro Ile Ile Leu Ser Tyr Arg Leu Lys Arg Tyr Asp Leu Tyr Asp Ser
                        405                     410                     415

Leu Val Lys Pro Leu Ala Asp Phe Ile Ile Lys Ile Gly Pro Lys Thr
                420                     425                     430

Gly Gln Glu Arg Trp Glu Glu Ile Gly Gly Tyr Ser Pro Ala Thr Met
                435                     440                     445

Ala Ala Glu Val Ala Gly Leu Thr Cys Ala Ala Tyr Ile Ala Glu Gln
                450                     455                     460

Asn Lys Asp Tyr Glu Ser Ala Gln Lys Tyr Gln Glu Lys Ala Asp Asn
465                     470                     475                     480
```

```
Trp Gln Lys Leu Ile Asp Asn Leu Thr Tyr Thr Glu Asn Gly Pro Leu
                485                 490                 495
Gly Asn Gly Gln Tyr Tyr Ile Arg Ile Ala Gly Leu Ser Asp Pro Asn
            500                 505                 510
Ala Asp Phe Met Ile Asn Ile Ala Asn Gly Gly Val Tyr Asp Gln
        515                 520                 525
Lys Glu Ile Val Asp Pro Ser Phe Leu Glu Leu Val Arg Leu Gly Val
    530                 535                 540
Lys Ser Ala Asp Pro Lys Ile Leu Asn Thr Leu Lys Val Val Asp
545                 550                 555                 560
Ser Thr Ile Lys Val Asp Thr Pro Lys Gly Pro Ser Trp Tyr Arg Tyr
                565                 570                 575
Asn His Asp Gly Tyr Gly Glu Pro Ser Lys Thr Glu Leu Tyr His Gly
            580                 585                 590
Ala Gly Lys Gly Arg Leu Trp Pro Leu Leu Thr Gly Glu Arg Gly Met
        595                 600                 605
Tyr Glu Ile Ala Ala Gly Lys Asp Ala Thr Pro Tyr Val Lys Ala Met
    610                 615                 620
Glu Lys Phe Ala Asn Glu Gly Gly Ile Ile Ser Glu Gln Val Trp Glu
625                 630                 635                 640
Asp Thr Gly Leu Pro Thr Asp Ser Ala Ser Pro Leu Asn Trp Ala His
                645                 650                 655
Ala Glu Tyr Val Ile Leu Phe Ala Ser Asn Ile Glu His Lys Val Leu
            660                 665                 670
Asp Met Pro Asp Ile Val Tyr
        675

<210> SEQ ID NO 48
<211> LENGTH: 2037
<212> TYPE: DNA
<213> ORGANISM: Thermoanaerobacterium thermosaccharolyticum
<220> FEATURE:
<223> OTHER INFORMATION: synthetic

<400> SEQUENCE: 48
gtgctctccg ctgctccaa caacgtgtcc tccatcaaga tcgaccgctt caacaacatc      60
tccgccgtga acggcccggg cgaggaggac acctgggcct ccgcccagaa gcagggcgtg     120
ggcaccgcca caactacgt gtcccgcgtg tggttcaccc tcgccaacgg cgccatctcc     180
gaggtgtact acccgaccat cgacaccgcc gacgtgaagg agatcaagtt catcgtgacc     240
gacggcaagt ccttcgtgtc cgacgagacc aaggacgcca tctccaaggt ggagaagttc     300
accgacaagt ccctcggcta caagctcgtg aacaccgaca agaagggccg ctaccgcatc     360
accaaggaaa tcttcaccga cgtgaagcgc aactccctca tcatgaaggc caagttcgag     420
gccctcgagg gctccatcca cgactacaag ctctacctcg cctacgaccc gcacatcaag     480
aaccagggct cctacaacga gggctacgtg atcaaggcca acaacga tgctcatg     540 gccaagcgcg acaacgtgta caccgccctc tcctccaaca tcggctggaa gggctactcc     600
atcggctact acaaggtgaa cgacatcatg accgacctcg acgagaacaa gcagatgacc     660
aagcactacg actccgcccg cggcaacatc atcgagggcg ccgagatcga cctcaccaag     720
aactccgagt tcgagatcgt gctctccttc ggcggctccg actccgaggc cgccaagacc     780
gccctcgaga ccctcggcga ggactacaac aacctcaaga caactacat cgacgagtgg     840 accaagtact gcaacacccct caacaacttc aacggcaagg ccaactccct ctactacaac     900
```

-continued

```
tccatgatga tcctcaaggc ctccgaggac aagaccaaca agggcgccta catcgcctcc    960
ctctccatcc cgtggggcga cggccagcgc gacgacaaca ccggcggcta ccacctcgtg   1020
tggtcccgcg acctctacca cgtggccaac gccttcatcg ccgccggcga cgtggactcc   1080
gccaaccgct ccctcgacta cctcgccaag gtggtgaagg acaacggcat gatcccgcag   1140
aacacctgga tctccggcaa gccgtactgg acctccatcc agctcgacga gcaggccgac   1200
ccgatcatcc tctcctaccg cctcaagcgc tacgacctct acgactccct cgtgaagccg   1260
ctcgccgact tcatcatcaa gatcggcccg aagaccggcc aggagcgctg ggaggagatc   1320
ggcggctact ccccggccac gatggccgcc gaggtggccg gcctcacctg cgccgcctac   1380
atcgccgagc agaacaagga ctacgagtcc gcccagaagt accaggagaa ggccgacaac   1440
tggcagaagc tcatcgacaa cctcacctac accgagaacg cccgctcgg caacggccag   1500
tactacatcc gcatcgccgg cctctccgac ccgaacgccg acttcatgat caacatcgcc   1560
aacggcggcg gcgtgtacga ccagaaggag atcgtggacc cgtccttcct cgagctggtg   1620
cgcctcggcg tgaagtccgc cgacgacccg aagatcctca acaccctcaa ggtggtggac   1680
tccaccatca aggtggacac cccgaagggc ccgtcctggt atcgctacaa ccacgacggc   1740
tacggcgagc cgtccaagac cgagctgtac cacggcgccg gcaagggccg cctctggccg   1800
ctcctcaccg gcgagcgcgg catgtacgag atcgccgccg gcaaggacgc cacccccgtac   1860
gtgaaggcga tggagaagtt cgccaacgag ggcggcatca tctccgagca ggtgtgggag   1920
gacaccggcc tcccgaccga ctccgcctcc ccgctcaact gggcccacgc cgagtacgtg   1980
atcctcttcg cctccaacat cgagcacaag gtgctcgaca tgccggacat cgtgtac     2037
```

<210> SEQ ID NO 49
<211> LENGTH: 579
<212> TYPE: PRT
<213> ORGANISM: Rhizopus oryzae

<400> SEQUENCE: 49

```
Ala Ser Ile Pro Ser Ser Ala Ser Val Gln Leu Asp Ser Tyr Asn Tyr
 1               5                  10                  15

Asp Gly Ser Thr Phe Ser Gly Lys Ile Tyr Val Lys Asn Ile Ala Tyr
            20                  25                  30

Ser Lys Lys Val Thr Val Ile Tyr Ala Asp Gly Ser Asp Asn Trp Asn
        35                  40                  45

Asn Asn Gly Asn Thr Ile Ala Ala Ser Tyr Ser Ala Pro Ile Ser Gly
    50                  55                  60

Ser Asn Tyr Glu Tyr Trp Thr Phe Ser Ala Ser Ile Asn Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser Lys Pro Thr Thr Thr
            100                 105                 110

Thr Ala Thr Ala Thr Thr Thr Thr Ala Pro Ser Thr Ser Thr Thr Thr
        115                 120                 125

Pro Pro Ser Arg Ser Glu Pro Ala Thr Phe Pro Thr Gly Asn Ser Thr
    130                 135                 140

Ile Ser Ser Trp Ile Lys Lys Gln Glu Gly Ile Ser Arg Phe Ala Met
145                 150                 155                 160

Leu Arg Asn Ile Asn Pro Pro Gly Ser Ala Thr Gly Phe Ile Ala Ala
                165                 170                 175
```

```
Ser Leu Ser Thr Ala Gly Pro Asp Tyr Tyr Tyr Ala Trp Thr Arg Asp
            180                 185                 190
Ala Ala Leu Thr Ser Asn Val Ile Val Tyr Glu Tyr Asn Thr Thr Leu
        195                 200                 205
Ser Gly Asn Lys Thr Ile Leu Asn Val Leu Lys Asp Tyr Val Thr Phe
        210                 215                 220
Ser Val Lys Thr Gln Ser Thr Ser Thr Val Cys Asn Cys Leu Gly Glu
225                 230                 235                 240
Pro Lys Phe Asn Pro Asp Ala Ser Gly Tyr Thr Gly Ala Trp Gly Arg
                245                 250                 255
Pro Gln Asn Asp Gly Pro Ala Glu Arg Ala Thr Thr Phe Ile Leu Phe
                260                 265                 270
Ala Asp Ser Tyr Leu Thr Gln Thr Lys Asp Ala Ser Tyr Val Thr Gly
            275                 280                 285
Thr Leu Lys Pro Ala Ile Phe Lys Asp Leu Asp Tyr Val Val Asn Val
        290                 295                 300
Trp Ser Asn Gly Cys Phe Asp Leu Trp Glu Glu Val Asn Gly Val His
305                 310                 315                 320
Phe Tyr Thr Leu Met Val Met Arg Lys Gly Leu Leu Leu Gly Ala Asp
                325                 330                 335
Phe Ala Lys Arg Asn Gly Asp Ser Thr Arg Ala Ser Tyr Ser Ser
                340                 345                 350
Thr Ala Ser Thr Ile Ala Asn Lys Ile Ser Ser Phe Trp Val Ser Ser
            355                 360                 365
Asn Asn Trp Ile Gln Val Ser Gln Ser Val Thr Gly Gly Val Ser Lys
        370                 375                 380
Lys Gly Leu Asp Val Ser Thr Leu Leu Ala Ala Asn Leu Gly Ser Val
385                 390                 395                 400
Asp Asp Gly Phe Phe Thr Pro Gly Ser Glu Lys Ile Leu Ala Thr Ala
                405                 410                 415
Val Ala Val Glu Asp Ser Phe Ala Ser Leu Tyr Pro Ile Asn Lys Asn
            420                 425                 430
Leu Pro Ser Tyr Leu Gly Asn Ser Ile Gly Arg Tyr Pro Glu Asp Thr
        435                 440                 445
Tyr Asn Gly Asn Gly Asn Ser Gln Gly Asn Ser Trp Phe Leu Ala Val
        450                 455                 460
Thr Gly Tyr Ala Glu Leu Tyr Tyr Arg Ala Ile Lys Glu Trp Ile Gly
465                 470                 475                 480
Asn Gly Gly Val Thr Val Ser Ser Ile Ser Leu Pro Phe Phe Lys Lys
                485                 490                 495
Phe Asp Ser Ser Ala Thr Ser Gly Lys Lys Tyr Thr Val Gly Thr Ser
            500                 505                 510
Asp Phe Asn Asn Leu Ala Gln Asn Ile Ala Leu Ala Ala Asp Arg Phe
        515                 520                 525
Leu Ser Thr Val Gln Leu His Ala His Asn Asn Gly Ser Leu Ala Glu
        530                 535                 540
Glu Phe Asp Arg Thr Thr Gly Leu Ser Thr Gly Ala Arg Asp Leu Thr
545                 550                 555                 560
Trp Ser His Ala Ser Leu Ile Thr Ala Ser Tyr Ala Lys Ala Gly Ala
                565                 570                 575
Pro Ala Ala
```

<210> SEQ ID NO 50
<211> LENGTH: 1737
<212> TYPE: DNA
<213> ORGANISM: Rhizopus oryzae

<400> SEQUENCE: 50

| | | | | | |
|---|---|---|---|---|---|
| gcctccatcc | cgtcctccgc | ctccgtgcag | ctcgactcct | acaactacga | cggctccacc | 60 |
| ttctccggca | aaatctacgt | gaagaacatc | gcctactcca | agaaggtgac | cgtgatctac | 120 |
| gccgacggct | ccgacaactg | gaacaacaac | ggcaacacca | tcgccgcctc | ctactccgcc | 180 |
| ccgatctccg | gctccaacta | cgagtactgg | accttctccg | cctccatcaa | cggcatcaag | 240 |
| gagttctaca | tcaagtacga | ggtgtccggc | aagacctact | acgacaacaa | caactccgcc | 300 |
| aactaccagg | tgtccaccct | caagccgacc | accaccaccg | ccaccgccac | caccaccacc | 360 |
| gccccgtcca | cctccaccac | caccccgccg | tcccgctccg | agccggccac | cttcccgacc | 420 |
| ggcaactcca | ccatctcctc | ctggatcaag | aagcaggagg | catctcccg | cttcgccatg | 480 |
| ctccgcaaca | tcaacccgcc | gggctccgcc | accggcttca | tcgccgcctc | cctctccacc | 540 |
| gccggcccgg | actactacta | cgcctggacc | cgcgacgccg | ccctcacctc | caacgtgatc | 600 |
| gtgtacgagt | acaacaccac | cctctccggc | aacaagacca | tcctcaacgt | gctcaaggac | 660 |
| tacgtgacct | tctccgtgaa | gacccagtcc | acctccaccg | tgtgcaactg | cctcggcgag | 720 |
| ccgaagttca | acccggacgc | ctccggctac | accggcgcct | ggggccgccc | gcagaacgac | 780 |
| ggcccggccg | agcgcgccac | caccttcatc | ctcttcgccg | actcctacct | cacccagacc | 840 |
| aaggacgcct | cctacgtgac | cggcaccctc | aagccggcca | tcttcaagga | cctcgactac | 900 |
| gtggtgaacg | tgtggtccaa | cggctgcttc | gacctctggg | aggaggtgaa | cggcgtgcac | 960 |
| ttctacaccc | tcatggtgat | gcgcaagggc | ctcctcctcg | cgccgacttt | cgccaagcgc | 1020 |
| aacggcgact | ccacccgcgc | ctccacctac | tcctccaccg | cctccaccat | cgccaacaaa | 1080 |
| atctcctcct | tctgggtgtc | ctccaacaac | tggatacagg | tgtcccagtc | cgtgaccggc | 1140 |
| ggcgtgtcca | agaagggcct | cgacgtgtcc | accctcctcg | ccgccaacct | cggctccgtg | 1200 |
| gacgacggct | tcttcacccc | gggctccgag | aagatcctcg | ccaccgccgt | ggccgtggag | 1260 |
| gactccttcg | cctccctcta | cccgatcaac | aagaacctcc | cgtcctacct | cggcaactcc | 1320 |
| atcggccgct | acccggagga | cacctacaac | ggcaacggca | actcccaggg | caactcctgg | 1380 |
| ttcctcgccg | tgaccggcta | cgccgagctg | tactaccgcg | ccatcaagga | gtggatcggc | 1440 |
| aacgccggcg | tgaccgtgtc | ctccatctcc | ctcccgttct | tcaagaagtt | cgactcctcc | 1500 |
| gccacctccg | gcaagaagta | caccgtgggc | acctccgact | caacaacct | cgcccagaac | 1560 |
| atcgccctcg | ccgccgaccg | cttcctctcc | accgtgcagc | tccacgccca | caacaacggc | 1620 |
| tccctcgccg | aggagttcga | ccgcaccacc | ggcctctcca | ccggcgcccg | cgacctcacc | 1680 |
| tggtcccacg | cctccctcat | caccgcctcc | tacgccaagg | ccggcgcccc | ggccgcc | 1737 |

<210> SEQ ID NO 51
<211> LENGTH: 439
<212> TYPE: PRT
<213> ORGANISM: Artificial Sequence
<220> FEATURE:
<223> OTHER INFORMATION: synthetic

<400> SEQUENCE: 51

Met Ala Lys His Leu Ala Ala Met Cys Trp Cys Ser Leu Leu Val Leu
1               5                   10                  15

Val Leu Leu Cys Leu Gly Ser Gln Leu Ala Gln Ser Gln Val Leu Phe

-continued

```
                 20                  25                  30
Gln Gly Phe Asn Trp Glu Ser Trp Lys Lys Gln Gly Gly Trp Tyr Asn
            35                  40                  45
Tyr Leu Leu Gly Arg Val Asp Asp Ile Ala Ala Thr Gly Ala Thr His
        50                  55                  60
Val Trp Leu Pro Gln Pro Ser His Ser Val Ala Pro Gln Gly Tyr Met
65                  70                  75                  80
Pro Gly Arg Leu Tyr Asp Leu Asp Ala Ser Lys Tyr Gly Thr His Ala
                85                  90                  95
Glu Leu Lys Ser Leu Thr Ala Ala Phe His Ala Lys Gly Val Gln Cys
            100                 105                 110
Val Ala Asp Val Val Ile Asn His Arg Cys Ala Asp Tyr Lys Asp Gly
        115                 120                 125
Arg Gly Ile Tyr Cys Val Phe Glu Gly Gly Thr Pro Asp Ser Arg Leu
    130                 135                 140
Asp Trp Gly Pro Asp Met Ile Cys Ser Asp Asp Thr Gln Tyr Ser Asn
145                 150                 155                 160
Gly Arg Gly His Arg Asp Thr Gly Ala Asp Phe Ala Ala Ala Pro Asp
                165                 170                 175
Ile Asp His Leu Asn Pro Arg Val Gln Gln Glu Leu Ser Asp Trp Leu
            180                 185                 190
Asn Trp Leu Lys Ser Asp Leu Gly Phe Asp Gly Trp Arg Leu Asp Phe
        195                 200                 205
Ala Lys Gly Tyr Ser Ala Ala Val Ala Lys Val Tyr Val Asp Ser Thr
    210                 215                 220
Ala Pro Thr Phe Val Val Ala Glu Ile Trp Ser Ser Leu His Tyr Asp
225                 230                 235                 240
Gly Asn Gly Glu Pro Ser Ser Asn Gln Asp Ala Asp Arg Gln Glu Leu
                245                 250                 255
Val Asn Trp Ala Gln Ala Val Gly Gly Pro Ala Ala Ala Phe Asp Phe
            260                 265                 270
Thr Thr Lys Gly Val Leu Gln Ala Ala Val Gln Gly Glu Leu Trp Arg
        275                 280                 285
Met Lys Asp Gly Asn Gly Lys Ala Pro Gly Met Ile Gly Trp Leu Pro
    290                 295                 300
Glu Lys Ala Val Thr Phe Val Asp Asn His Asp Thr Gly Ser Thr Gln
305                 310                 315                 320
Asn Ser Trp Pro Phe Pro Ser Asp Lys Val Met Gln Gly Tyr Ala Tyr
                325                 330                 335
Ile Leu Thr His Pro Gly Thr Pro Cys Ile Phe Tyr Asp His Val Phe
            340                 345                 350
Asp Trp Asn Leu Lys Gln Glu Ile Ser Ala Leu Ser Ala Val Arg Ser
        355                 360                 365
Arg Asn Gly Ile His Pro Gly Ser Glu Leu Asn Ile Leu Ala Ala Asp
    370                 375                 380
Gly Asp Leu Tyr Val Ala Lys Ile Asp Lys Val Ile Val Lys Ile
385                 390                 395                 400
Gly Ser Arg Tyr Asp Val Gly Asn Leu Ile Pro Ser Asp Phe His Ala
                405                 410                 415
Val Ala His Gly Asn Asn Tyr Cys Val Trp Glu Lys His Gly Leu Arg
            420                 425                 430
Val Pro Ala Gly Arg His His
        435
```

<210> SEQ ID NO 52
<211> LENGTH: 1320
<212> TYPE: DNA
<213> ORGANISM: Artificial Sequence
<220> FEATURE:
<223> OTHER INFORMATION: synthetic

<400> SEQUENCE: 52

```
atggcgaagc acttggctgc catgtgctgg tgcagcctcc tagtgcttgt actgctctgc      60
ttgggctccc agctggccca atcccaggtc ctcttccagg ggttcaactg ggagtcgtgg     120
aagaagcaag gtgggtggta caactacctc ctggggcggg tggacgacat cgccgcgacg     180
ggggccacgc acgtctggct cccgcagccg tcgcactcgg tggcgccgca ggggtacatg     240
cccggccggc tctacgacct ggacgcgtcc aagtacggca cccacgcgga gctcaagtcg     300
ctcaccgcgg cgttccacgc caagggcgtc cagtgcgtcg ccgacgtcgt gatcaaccac     360
cgctgcgccg actacaagga cggccgcggc atctactgcg tcttcgaggg cggcacgccc     420
gacagccgcc tcgactgggg ccccgacatg atctgcagcg acgacacgca gtactccaac     480
gggcgcgggc accgcgacac gggggccgac ttcgccgccg cgcccgacat cgaccacctc     540
aacccgcgcg tgcagcagga gctctcggac tggctcaact ggctcaagtc cgacctcggc     600
ttcgacggct ggcgcctcga cttcgccaag ggctactccg ccgccgtcgc caaggtgtac     660
gtcgacagca ccgcccccac cttcgtcgtc gccgagatat ggagctccct ccactacgac     720
ggcaacggcg agccgtccag caaccaggac gccgacaggc aggagctggt caactgggcg     780
caggcggtgg gcggccccgc cgcggcgttc gacttcacca ccaagggcgt gctgcaggcg     840
gccgtccagg gcgagctgtg gcgcatgaag acggcaacg gcaaggcgcc cgggatgatc     900
ggctggctgc cggagaaggc cgtcacgttc gtcgacaacc acgacaccgg ctccacgcag     960
aactcgtggc cattccccte cgacaaggtc atgcagggct acgcctatat cctcacgcac    1020
ccaggaactc catgcatctt ctacgaccac gttttcgact ggaacctgaa gcaggagatc    1080
agcgcgctgt ctgcggtgag gtcaagaaac gggatccacc cggggagcga gctgaacatc    1140
ctcgccgccg acggggatct ctacgtcgcc aagattgacg acaaggtcat cgtgaagatc    1200
gggtcacggt acgacgtcgg gaacctgatc ccctcagact ccacgccgt tgcccctggc     1260
aacaactact gcgtttggga agcacggt ctgagagttc agcggggcg gcaccactag     1320
```

<210> SEQ ID NO 53
<211> LENGTH: 45
<212> TYPE: PRT
<213> ORGANISM: Artificial Sequence
<220> FEATURE:
<223> OTHER INFORMATION: synthetic

<400> SEQUENCE: 53

Ala Thr Gly Gly Thr Thr Thr Thr Ala Thr Thr Gly Ser Gly Gly
 1               5                  10                  15

Val Thr Ser Thr Ser Lys Thr Thr Thr Ala Ser Lys Thr Ser Thr
             20                  25                  30

Thr Thr Ser Ser Thr Ser Cys Thr Thr Pro Thr Ala Val
         35                  40                  45

<210> SEQ ID NO 54
<211> LENGTH: 137
<212> TYPE: DNA
<213> ORGANISM: Artificial Sequence

```
<220> FEATURE:
<223> OTHER INFORMATION: synthetic

<400> SEQUENCE: 54
gccaccggcg gcaccaccac caccgccacc accaccggct ccggcggcgt gacctccacc      60
tccaagacca ccaccaccgc ctccaagacc tccaccacca cctcctccac ctcctgcacc     120
accccgaccg ccgtgtc                                                    137

<210> SEQ ID NO 55
<211> LENGTH: 300
<212> TYPE: PRT
<213> ORGANISM: Pyrococcus furiosus

<400> SEQUENCE: 55

Ile Tyr Phe Val Glu Lys Tyr His Thr Ser Glu Asp Lys Ser Thr Ser
  1               5                  10                  15

Asn Thr Ser Ser Thr Pro Pro Gln Thr Thr Leu Ser Thr Thr Lys Val
             20                  25                  30

Leu Lys Ile Arg Tyr Pro Asp Asp Gly Glu Trp Pro Gly Ala Pro Ile
         35                  40                  45

Asp Lys Asp Gly Asp Gly Asn Pro Glu Phe Tyr Ile Glu Ile Asn Leu
     50                  55                  60

Trp Asn Ile Leu Asn Ala Thr Gly Phe Ala Glu Met Thr Tyr Asn Leu
 65                  70                  75                  80

Thr Ser Gly Val Leu His Tyr Val Gln Gln Leu Asp Asn Ile Val Leu
                 85                  90                  95

Arg Asp Arg Ser Asn Trp Val His Gly Tyr Pro Glu Ile Phe Tyr Gly
            100                 105                 110

Asn Lys Pro Trp Asn Ala Asn Tyr Ala Thr Asp Gly Pro Ile Pro Leu
        115                 120                 125

Pro Ser Lys Val Ser Asn Leu Thr Asp Phe Tyr Leu Thr Ile Ser Tyr
    130                 135                 140

Lys Leu Glu Pro Lys Asn Gly Leu Pro Ile Asn Phe Ala Ile Glu Ser
145                 150                 155                 160

Trp Leu Thr Arg Glu Ala Trp Arg Thr Thr Gly Ile Asn Ser Asp Glu
                165                 170                 175

Gln Glu Val Met Ile Trp Ile Tyr Tyr Asp Gly Leu Gln Pro Ala Gly
            180                 185                 190

Ser Lys Val Lys Glu Ile Val Val Pro Ile Ile Val Asn Gly Thr Pro
        195                 200                 205

Val Asn Ala Thr Phe Glu Val Trp Lys Ala Asn Ile Gly Trp Glu Tyr
    210                 215                 220

Val Ala Phe Arg Ile Lys Thr Pro Ile Lys Glu Gly Thr Val Thr Ile
225                 230                 235                 240

Pro Tyr Gly Ala Phe Ile Ser Val Ala Ala Asn Ile Ser Ser Leu Pro
                245                 250                 255

Asn Tyr Thr Glu Leu Tyr Leu Glu Asp Val Glu Ile Gly Thr Glu Phe
            260                 265                 270

Gly Thr Pro Ser Thr Thr Ser Ala His Leu Glu Trp Trp Ile Thr Asn
        275                 280                 285

Ile Thr Leu Thr Pro Leu Asp Arg Pro Leu Ile Ser
    290                 295                 300

<210> SEQ ID NO 56
<211> LENGTH: 903
```

```
<212> TYPE: DNA
<213> ORGANISM: Pyrococcus furiosus

<400> SEQUENCE: 56
atctacttcg tggagaagta ccacacctcc gaggacaagt ccacctccaa cacctcctcc      60
accccgccgc agaccaccct ctccaccacc aaggtgctca agatccgcta cccggacgac     120
ggcgagtggc ccggcgcccc gatcgacaag gacggcgacg gcaacccgga gttctacatc     180
gagatcaacc tctggaacat cctcaacgcc accggcttcg ccgagatgac ctacaacctc     240
actagtggcg tgctccacta cgtgcagcag ctcgacaaca tcgtgctccg cgaccgctcc     300
aactgggtgc acggctaccc ggaaatcttc tacggcaaca agccgtggaa cgccaactac     360
gccaccgacg cccgatcccc gctcccgtcc aaggtgtcca acctcaccga cttctacctc     420
accatctcct acaagctcga gccgaagaac ggtctcccga tcaacttcgc catcgagtcc     480
tggctcaccc gcgaggcctg cgcaccacc ggcatcaact ccgacgagca ggaggtgatg     540
atctggatct actacgacgg cctccagccc gcgggctcca aggtgaagga gatcgtggtg     600
ccgatcatcg tgaacggcac cccggtgaac gccaccttcg aggtgtggaa ggccaacatc     660
ggctgggagt acgtggcctt ccgcatcaag accccgatca aggagggcac cgtgaccatc     720
ccgtacggcg ccttcatctc cgtggccgcc aacatctcct ccctcccgaa ctacaccgag     780
aagtacctcg aggacgtgga gatcggcacc gagttcggca cccgtccac cacctccgcc     840
cacctcgagt ggtggatcac caacatcacc ctcaccccgc tcgaccgccc gctcatctcc     900
tag                                                                    903

<210> SEQ ID NO 57
<211> LENGTH: 387
<212> TYPE: PRT
<213> ORGANISM: Thermus flavus

<400> SEQUENCE: 57

Met Tyr Glu Pro Lys Pro Glu His Arg Phe Thr Phe Gly Leu Trp Thr
 1               5                  10                  15

Val Asp Asn Val Asp Arg Asp Pro Phe Gly Asp Thr Val Arg Glu Arg
            20                  25                  30

Leu Asp Pro Val Tyr Val Val His Lys Leu Ala Glu Leu Gly Ala Tyr
        35                  40                  45

Gly Val Asn Leu His Asp Glu Asp Leu Ile Pro Arg Gly Thr Pro Pro
    50                  55                  60

Gln Glu Arg Asp Gln Ile Val Arg Arg Phe Lys Lys Ala Leu Asp Glu
65                  70                  75                  80

Thr Val Leu Lys Val Pro Met Val Thr Ala Asn Leu Phe Ser Glu Pro
                85                  90                  95

Ala Phe Arg Asp Gly Ala Ser Thr Thr Arg Asp Pro Trp Val Trp Ala
           100                 105                 110

Tyr Ala Leu Arg Lys Ser Leu Glu Thr Met Asp Leu Gly Ala Glu Leu
       115                 120                 125

Gly Ala Glu Ile Tyr Met Phe Trp Met Val Arg Arg Ser Glu Val
   130                 135                 140

Glu Ser Thr Asp Lys Thr Arg Lys Val Trp Asp Trp Val Arg Glu Thr
145                 150                 155                 160

Leu Asn Phe Met Thr Ala Tyr Thr Glu Asp Gln Gly Tyr Gly Tyr Arg
                165                 170                 175

Phe Ser Val Glu Pro Lys Pro Asn Glu Pro Arg Gly Asp Ile Tyr Phe
```

```
                    180                 185                 190
Thr Thr Val Gly Ser Met Leu Ala Leu Ile His Thr Leu Asp Arg Pro
            195                 200                 205
Glu Arg Phe Gly Leu Asn Pro Glu Phe Ala His Glu Thr Met Ala Gly
        210                 215                 220
Leu Asn Phe Asp His Ala Val Ala Gln Ala Val Asp Ala Gly Lys Leu
225                 230                 235                 240
Phe His Ile Asp Leu Asn Asp Gln Arg Met Ser Arg Phe Asp Gln Asp
                245                 250                 255
Leu Arg Phe Gly Ser Glu Asn Leu Lys Ala Gly Phe Phe Leu Val Asp
            260                 265                 270
Leu Leu Glu Ser Ser Gly Tyr Gln Gly Pro Arg His Phe Glu Ala His
        275                 280                 285
Ala Leu Arg Thr Glu Asp Glu Glu Gly Val Trp Thr Phe Val Arg Val
        290                 295                 300
Cys Met Arg Thr Tyr Leu Ile Ile Lys Val Arg Ala Glu Thr Phe Arg
305                 310                 315                 320
Glu Asp Pro Glu Val Lys Glu Leu Leu Ala Ala Tyr Tyr Gln Glu Asp
                325                 330                 335
Pro Ala Thr Leu Ala Leu Leu Asp Pro Tyr Ser Arg Glu Lys Ala Glu
            340                 345                 350
Ala Leu Lys Arg Ala Glu Leu Pro Leu Glu Thr Lys Arg Arg Arg Gly
        355                 360                 365
Tyr Ala Leu Glu Arg Leu Asp Gln Leu Ala Val Glu Tyr Leu Leu Gly
        370                 375                 380
Val Arg Gly
385

<210> SEQ ID NO 58
<211> LENGTH: 978
<212> TYPE: DNA
<213> ORGANISM: Artificial Sequence
<220> FEATURE:
<223> OTHER INFORMATION: synthetic

<400> SEQUENCE: 58
atggggaaga acggcaacct gtgctgcttc tctctgctgc tgcttcttct cgccgggttg    60
gcgtccggcc atcaaatcta cttcgtggag aagtaccaca cctccgagga caagtccacc   120
tccaacacct cctccacccc gccgcagacc accctctcca ccaccaaggt gctcaagatc   180
cgctacccgg acgacggtga gtggcccggc gccccgatcg acaaggacgg cgacggcaac   240
ccggagttct acatcgagat caacctctgg aacatcctca cgccaccgg cttcgccgag   300 atgacctaca acctcactag tggcgtgctc cactacgtgc agcagctcga caacatcgtg   360
ctccgcgacc gctccaactg ggtgcacggc tacccggaaa tcttctacgg caacaagccg   420
tggaacgcca actacgccac cgacggcccg atcccgctcc cgtccaaggt gtccaacctc   480
accgacttct acctcaccat ctcctacaag ctcgagccga gaacggtct cccgatcaac   540 ttcgccatcg agtcctggct caccgcgag gcctggcgca ccaccggcat caactccgac   600
gagcaggagg tgatgatctg gatctactac gacggcctcc agcccgcggg ctccaaggtg   660
aaggagatcg tggtgccgat catcgtgaac ggcaccccgg tgaacgccac cttcgaggtg   720
tggaaggcca acatcggctg ggagtacgtg gccttccgca tcaagacccc gatcaaggag   780
ggcaccgtga ccatcccgta cggcgccttc atctccgtgg ccgccaacat ctcctccctc   840
```

```
ccgaactaca ccgagaagta cctcgaggac gtggagatcg gcaccgagtt cggcaccccg      900
tccaccacct ccgcccacct cgagtggtgg atcaccaaca tcaccctcac cccgctcgac      960
cgcccgctca tctcctag                                                    978
```

<210> SEQ ID NO 59
<211> LENGTH: 1920
<212> TYPE: DNA
<213> ORGANISM: Aspergillus niger

<400> SEQUENCE: 59

```
atgtccttcc gctccctcct cgccctctcc ggcctcgtgt gcaccggcct cgccaacgtg       60
atctccaagc gcgccaccct cgactcctgg ctctccaacg aggccaccgt ggcccgcacc      120
gccatcctca caacatcgg cgccgacggc gcctgggtgt ccggcgccga ctccggcatc      180
gtggtggcct ccccgtccac cgacaacccg gactacttct acacctggac ccgcgactcc      240
ggcctcgtgc tcaagaccct cgtggacctc ttccgcaacg gcgacacctc cctcctctcc      300
accatcgaga actacatctc cgcccaggcc atcgtgcagg gcatctccaa cccgtccggc      360
gacctctcct ccgcgccgg cctcggcgag ccgaagttca acgtggacga gaccgcctac      420
accggctcct ggggccgccc gcagcgcgac ggcccggccc tccgcgccac cgccatgatc      480
ggcttcggcc agtggctcct cgacaacggc tacacctcca ccgccaccga catcgtgtgg      540
ccgctcgtgc gcaacgacct ctcctacgtg gcccagtact ggaaccagac cggctacgac      600
ctctgggagg aggtgaacgg ctcctccttc ttcaccatcg ccgtgcagca ccgcgccctc      660
gtggagggct ccgccttcgc caccgccgtg ggctcctcct gctcctggtg cgactcccag      720
gccccggaga tcctctgcta cctccagtcc ttctggaccg gctccttcat cctcgccaac      780
ttcgactcct cccgctccgg caaggacgcc aacaccctcc tcggctccat ccacaccttc      840
gacccggagg ccgcctgcga cgactccacc ttccagccgt gctccccgcg cgccctcgcc      900
aaccacaagg aggtggtgga ctccttccgc tccatctaca ccctcaacga cggcctctcc      960
gactccgagg ccgtggccgt gggccgctac ccggaggaca cctactacaa cggcaacccg     1020
tggttcctct gcaccctcgc cgccgccgag cagctctacg acgccctcta ccagtgggac     1080
aagcagggct ccctcgaggt gaccgacgtg tccctcgact tcttcaaggc cctctactcc     1140
gacgccgcca ccggcaccta tcctcctcc tcctccacct actcctccat cgtggacgcc     1200
gtgaagacct tcgccgacgg cttcgtgtcc atcgtggaga cccacgccgc ctccaacggc     1260
tccatgtccg agcagtacga caagtccgac ggcgagcagc tctccgcccg cgacctcacc     1320
tggtcctacg ccgccctcct caccgccaac aaccgccgca actccgtggt gccggcctcc     1380
tggggcgaga cctccgcctc ctccgtgccg ggcacctgcg ccgccacctc cgccatcggc     1440
acctactcct ccgtgaccgt gacctcctgg ccgtccatcg tggccaccgg cggcaccacc     1500
accaccgcca cccgaccgg ctcggctcc gtgacctcca cctccaagac caccgccacc     1560
gcctccaaga cctccacctc cacctcctcc acctcctgca ccaccccgac cgccgtggcc     1620
gtgaccttcg acctcaccgc caccaccacc tacggcgaga catctaccct cgtgggctcc     1680
atctcccagc tcggcgactg ggagacctcc gacggcatcg ccctctccgc cgacaagtac     1740
acctcctccg acccgctctg gtacgtgacc gtgaccctcc cggccggcga gtccttcgag     1800
tacaagttca tccgcatcga gtccgacgac tccgtggagt gggagtccga cccgaaccgc     1860
gagtacaccg tgccgcaggc ctgcggcacc tccaccgcca ccgtgaccga cacctggcgc     1920
```

```
<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Ser Glu Lys Asp Glu Leu
 1               5
```

SELF PROCESSING PLANTS AND PLANT PARTS

RELATED APPLICATIONS

This application is a continuation of application Ser. No. 11/415,818 filed May 2, 2006, now U.S. Pat. No. 7,557,262, which is a divisional of application Ser. No. 10/228,063 filed Aug. 27, 2002, now U.S. Pat. No. 7,102,057, which claims priority to provisional application No. 60/315,281 filed Aug. 27, 2001.

FIELD OF THE INVENTION

The present invention generally relates to the field of plant molecular biology, and more specifically, to the creation of plants that express a processing enzyme which provides a desired characteristic to the plant or products thereof.

BACKGROUND OF THE INVENTION

Enzymes are used to process a variety of agricultural products such as wood, fruits and vegetables, starches, juices, and the like. Typically, processing enzymes are produced and recovered on an industrial scale from various sources, such as microbial fermentation (*Bacillus* α-amylase), or isolation from plants (coffee β-galactosidase or papain from plant parts). Enzyme preparations are used in different processing applications by mixing the enzyme and the substrate under the appropriate conditions of moisture, temperature, time, and mechanical mixing such that the enzymatic reaction is achieved in a commercially viable manner. The methods involve separate steps of enzyme production, manufacture of an enzyme preparation, mixing the enzyme and substrate, and subjecting the mixture to the appropriate conditions to facilitate the enzymatic reaction. A method that reduces or eliminates the time, energy, mixing, capital expenses, and/or enzyme production costs, or results in improved or novel products, would be useful and beneficial. One example of where such improvements are needed is in the area of corn milling.

Today corn is milled to obtain cornstarch and other corn-milling co-products such as corn gluten feed, corn gluten meal, and corn oil. The starch obtained from the process is often further processed into other products such as derivatized starches and sugars, or fermented to make a variety of products including alcohols or lactic acid. Processing of cornstarch often involves the use of enzymes, in particular, enzymes that hydrolyze and convert starch into fermentable sugars or fructose (α- and gluco-amylase, α-glucosidase, glucose isomerase, and the like). The process used commercially today is capital intensive as construction of very large mills is required to process corn on scales required for reasonable cost-effectiveness. In addition the process requires the separate manufacture of starch-hydrolyzing or modifying enzymes and then the machinery to mix the enzyme and substrate to produce the hydrolyzed starch products.

The process of starch recovery from corn grain is well known and involves a wet-milling process. Corn wet-milling includes the steps of steeping the corn kernel, grinding the corn kernel and separating the components of the kernel. The kernels are steeped in a steep tank with a countercurrent flow of water at about 120° F. and the kernels remain in the steep tank for 24 to 48 hours. This steepwater typically contains sulfur dioxide at a concentration of about 0.2% by weight. Sulfur dioxide is employed in the process to help reduce microbial growth and also to reduce disulfide bonds in endosperm proteins to facilitate more efficient starch-protein separation. Normally, about 0.59 gallons of steepwater is used per bushel of corn. The steepwater is considered waste and often contains undesirable levels of residual sulfur dioxide.

The steeped kernels are then dewatered and subjected to sets of attrition type mills. The first set of attrition type mills rupture the kernels releasing the germ from the rest of the kernel. A commercial attrition type mill suitable for the wet milling business is sold under the brand name Bauer. Centrifugation is used to separate the germ from the rest of the kernel. A typical commercial centrifugation separator is the Merco centrifugal separator. Attrition mills and centrifugal separators are large expensive items that use energy to operate.

In the next step of the process, the remaining kernel components including the starch, hull, fiber, and gluten are subjected to another set of attrition mills and passed through a set of wash screens to separate the fiber components from the starch and gluten (endosperm protein). The starch and gluten pass through the screens while the fiber does not. Centrifugation or a third grind followed by centrifugation is used to separate the starch from the endosperm protein. Centrifugation produces a starch slurry which is dewatered, then washed with fresh water and dried to about 12% moisture. The substantially pure starch is typically further processed by the use of enzymes.

The separation of starch from the other components of the grain is performed because removing the seed coat, embryo and endosperm proteins allows one to efficiently contact the starch with processing enzymes, and the resulting hydrolysis products are relatively free from contaminants from the other kernel components. Separation also ensures that other components of the grain are effectively recovered and can be subsequently sold as co-products to increase the revenues from the mill.

After the starch is recovered from the wet-milling process it typically undergoes the processing steps of gelatinization, liquefaction and dextrinization for maltodextrin production, and subsequent steps of saccharification, isomerization and refining for the production of glucose, maltose and fructose.

Gelatinization is employed in the hydrolysis of starch because currently available enzymes cannot rapidly hydrolyze crystalline starch. To make the starch available to the hydrolytic enzymes, the starch is typically made into a slurry with water (20-40% dry solids) and heated at the appropriate gelling temperature. For cornstarch this temperature is between 105-110° C. The gelatinized starch is typically very viscous and is therefore thinned in the next step called liquefaction. Liquefaction breaks some of the bonds between the glucose molecules of the starch and is accomplished enzymatically or through the use of acid. Heat-stable endo α-amylase enzymes are used in this step, and in the subsequent step of dextrinization. The extent of hydrolysis is controlled in the dextrinization step to yield hydrolysis products of the desired percentage of dextrose.

Further hydrolysis of the dextrin products from the liquefaction step is carried out by a number of different exo-amylases and debranching enzymes, depending on the products that are desired. And finally if fructose is desired then immobilized glucose isomerase enzyme is typically employed to convert glucose into fructose.

Dry-mill processes of making fermentable sugars (and then ethanol, for example) from cornstarch facilitate efficient contacting of exogenous enzymes with starch. These processes are less capital intensive than wet-milling but significant cost advantages are still desirable, as often the co-products derived from these processes are not as valuable as those derived from wet-milling. For example, in dry milling corn, the kernel is ground into a powder to facilitate efficient contact of starch by degrading enzymes. After enzyme hydrolysis of the corn flour the residual solids have some feed value as they contain proteins and some other components. Eckhoff recently described the potential for improvements and the relevant issues related to dry milling in a paper entitled "Fermentation and costs of fuel ethanol from corn with quick-germ process" (*Appl. Biochem. Biotechnol.,* 94: 41 (2001)). The "quick germ" method allows for the separation of the oil-rich germ from the starch using a reduced steeping time.

One example where the regulation and/or level of endogenous processing enzymes in a plant can result in a desirable product is sweet corn. Typical sweet corn varieties are distinguished from field corn varieties by the fact that sweet corn is not capable of normal levels of starch biosynthesis. Genetic mutations in the genes encoding enzymes involved in starch biosynthesis are typically employed in sweet corn varieties to limit starch biosynthesis. Such mutations are in the genes encoding starch synthases and ADP-glucose pyrophosphorylases (such as the sugary and super-sweet mutations). Fructose, glucose and sucrose, which are the simple sugars necessary for producing the palatable sweetness that consumers of edible fresh corn desire, accumulate in the developing endosperm of such mutants. However, if the level of starch accumulation is too high, such as when the corn is left to mature for too long (late harvest) or the corn is stored for an excessive period before it is consumed, the product loses sweetness and takes on a starchy taste and mouthfeel. The harvest window for sweet corn is therefore quite narrow, and shelf-life is limited.

Another significant drawback to the farmer who plants sweet corn varieties is that the usefulness of these varieties is limited exclusively to edible food. If a farmer wanted to forego harvesting his sweet corn for use as edible food during seed development, the crop would be essentially a loss. The grain yield and quality of sweet corn is poor for two fundamental reasons. The first reason is that mutations in the starch biosynthesis pathway cripple the starch biosynthetic machinery and the grains do not fill out completely, causing the yield and quality to be compromised. Secondly, due to the high levels of sugars present in the grain and the inability to sequester these sugars as starch, the overall sink strength of the seed is reduced, which exacerbates the reduction of nutrient storage in the grain. The endosperms of sweet corn variety seeds are shrunken and collapsed, do not undergo proper desiccation, and are susceptible to diseases. The poor quality of the sweet corn grain has further agronomic implications; as poor seed viability, poor germination, seedling disease susceptibility, and poor early seedling vigor result from the combination of factors caused by inadequate starch accumulation. Thus, the poor quality issues of sweet corn impact the consumer, farmer/grower, distributor, and seed producer.

Thus, for dry-milling, there is a need for a method which improves the efficiency of the process and/or increases the value of the co-products. For wet-milling, there is a need for a method of processing starch that does not require the equipment necessary for prolonged steeping, grinding, milling, and/or separating the components of the kernel. For example, there is a need to modify or eliminate the steeping step in wet milling as this would reduce the amount of waste water requiring disposal, thereby saving energy and time, and increasing mill capacity (kernels would spend less time in steep tanks). There is also a need to eliminate or improve the process of separating the starch-containing endosperm from the embryo.

SUMMARY OF THE INVENTION

The present invention is directed to self-processing plants and plant parts and methods of using the same. The self-processing plant and plant parts of the present invention are capable of expressing and activating enzyme(s) (mesophilic, thermophilic, and/or hyperthermophilic). Upon activation of the enzyme(s) (mesophilic, thermophilic, or hyperthermophilic) the plant or plant part is capable of self-processing the substrate upon which it acts to obtain the desired result.

The present invention is directed to an isolated polynucleotide a) comprising SEQ ID NO: 2, 4, 6, 9, 19, 21, 25, 37, 39, 41, 43, 46, 48, 50, 52, or 59 or the complement thereof, or a polynucleotide which hybridizes to the complement of any one of SEQ ID NO: 2, 4, 6, 9, 19, 21, 25, 37, 39, 41, 43, 46, 48, 50, 52, or 59 under low stringency hybridization conditions and encodes a polypeptide having α-amylase, pullulanase, α-glucosidase, glucose isomerase, or glucoamylase activity or b) encoding a polypeptide comprising SEQ ID NO: 10, 13, 14, 15, 16, 18, 20 24, 26, 27, 28, 29, 30, 33, 34, 35, 36, 38, 40, 42, 44, 45, 47, 49, or 51 or an enzymatically active fragment thereof. Preferably, the isolated polynucleotide encodes a fusion polypeptide comprising a first polypeptide and a second peptide, wherein said first polypeptide has α-amylase, pullulanase, α-glucosidase, glucose isomerase, or glucoamylase activity. Most preferably, the second peptide comprises a signal sequence peptide, which may target the first polypeptide to a vacuole, endoplasmic reticulum, chloroplast, starch granule, seed or cell wall of a plant. For example, the signal sequence may be an N-terminal signal sequence from waxy, an N-terminal signal sequence from γ-zein, a starch binding domain, or a C-terminal starch binding domain. Polynucleotides that hybridize to the complement of any one of SEQ ID NO: 2, 9, or 52 under low stringency hybridization conditions and encodes a polypeptide having α-amylase activity; to the complement of SEQ ID NO: 4 or 25 under low stringency hybridization conditions and encodes a polypeptide having pullulanase activity; to the complement of SEQ ID NO:6 and encodes a polypeptide having α-glucosidase activity; to the complement of any one of SEQ ID NO: 19, 21, 37, 39, 41, or 43 under low stringency hybridization conditions and encodes a polypeptide having glucose isomerase activity; to the complement of any one of SEQ ID NO: 46, 48, 50, or 59 under low stringency hybridization conditions and encodes a polypeptide having glucoamylase activity are further encompassed.

Moreover, an expression cassette comprising a polynucleotide a) having SEQ ID NO: 2, 4, 6, 9, 19, 21, 25, 37, 39, 41, 43, 46, 48, 50, 52, or 59 or the complement thereof, or a polynucleotide which hybridizes to the complement of any one of SEQ ID NO: 2, 4, 6, 9, 19, 21, 25, 37, 39, 41, 43, 46, 48, 50, 52, or 59 or under low stringency hybridization conditions and encodes an polypeptide having α-amylase, pullulanase, α-glucosidase, glucose isomerase, or glucoamylase activity or b) encoding a polypeptide comprising SEQ ID NO: 10, 13, 14, 15, 16, 18, 20, 24, 26, 27, 28, 29, 30, 33, 34, 35, 36, 38, 40, 42, 44, 45, 47, 49, or 51, or an enzymatically active fragment thereof. Preferably, the expression cassette further comprises a promoter operably linked to the polynucleotide, such as an inducible promoter, tissue-specific promoter, or preferably an endosperm-specific promoter. Preferably, the endosperm-specific promoter is a maize γ-zein promoter or a maize ADP-gpp promoter. In a preferred embodiment, the promoter comprises SEQ ID NO: 11 or SEQ ID NO: 12. Moreover, in another preferred embodiment the polynucleotide is oriented in sense orientation relative to the promoter. The expression cassette of the present invention may further encode a signal sequence which is operably linked to the polypeptide encoded by the polynucleotide. The signal sequence preferably targets the operably linked polypeptide to a vacuole, endoplasmic reticulum, chloroplast, starch granule, seed or cell wall of a plant. Preferably signal sequences include an N-terminal signal sequence from waxy, an N-terminal signal sequence from γ-zein, or a starch binding domain.

The present invention is further directed to a vector or cell comprising the expression cassettes of the present invention. The cell may be selected from the group consisting of an *Agrobacterium*, a monocot cell, a dicot cell, a Liliopsida cell, a Panicoideae cell, a maize cell, and a cereal cell. Preferably, the cell is a maize cell.

Moreover, the present invention encompasses a plant stably transformed with the vectors of the present invention. A plant stably transformed with a vector comprising an α-amylase having an amino acid sequence of any of SEQ ID NO: 1, 10, 13, 14, 15, 16, 33, or 35, or encoded by a polynucleotide comprising any of SEQ ID NO: 2 or 9 is provided. Preferably, the α-amylase is hyperthermophilic.

In another embodiment, a plant stably transformed with a vector comprising a pullulanase having an amino acid sequence of any of SEQ ID NO:24 or 34, or encoded by a polynucleotide comprising any of SEQ ID NO:4 or 25 is provided. A plant stably transformed with a vector comprising an α-glucosidase having an amino acid sequence of any of SEQ ID NO:26 or 27, or encoded by a polynucleotide comprising SEQ ID NO:6 is further provided. Preferably, the α-glucosidase is hyperthermophilic. A plant stably transformed with a vector comprising an glucose isomerase having an amino acid sequence of any of SEQ ID NO: 18, 20, 28, 29, 30, 38, 40, 42, pr 44, or encoded by a polynucleotide comprising any of SEQ ID NO: 19, 21, 37, 39, 41, or 43 is further described herein. Preferably, the glucose isomerase is hyperthermophilic. In another embodiment, a plant stably transformed with a vector comprising a glucose amylase having an amino acid sequence of any of SEQ ID NO:45, 47, or 49, or encoded by a polynucleotide comprising any of SEQ ID NO:46, 48, 50, or 59 is described. Preferably, the glucose amylase is hyperthermophilic.

Plant products, such as seed, fruit or grain from the stably transformed plants of the present invention are further provided.

In another embodiment, the invention is directed to a transformed plant, the genome of which is augmented with a recombinant polynucleotide encoding at least one processing enzyme operably linked to a promoter sequence, the sequence of which polynucleotide is optimized for expression in the plant. The plant may be a monocot, such as maize, or a dicot. Preferably, the plant is a cereal plant or a commercially grown plant. The processing enzyme is selected from the group consisting of an α-amylase, glucoamylase, glucose isomerase, glucanase, β-amylase, α-glucosidase, isoamylase, pullulanase, neo-pullulanase, iso-pullulanase, amylopullulanase, cellulase, exo-1,4-β-cellobiohydrolase, exo-1,3-β-D-glucanase, β-glucosidase, endoglucanase, L-arabinase, α-arabinosidase, galactanase, galactosidase, mannanase, mannosidase, xylanase, xylosidase, protease, glucanase, xylanase, esterase, phytase, and lipase. Preferably, the processing enzyme is a starch-processing enzyme selected from the group consisting of α-amylase, glucoamylase, glucose isomerase, β-amylase, α-glucosidase, isoamylase, pullulanase, neo-pullulanase, iso-pullulanase, and amylopullulanase. More preferably, the enzyme is selected from α-amylase, glucoamylase, glucose isomerase, glucose isomerase, α-glucosidase, and pullulanase. The processing enzyme is further preferably hyperthermophilic. In accordance with this aspect of the invention, the enzyme may be a non-starch degrading enzyme selected from the group consisting of protease, glucanase, xylanase, esterase, phytase, and lipase. Such enzymes may further be hyperthermophilic. In a preferred embodiment, the enzyme accumulates in the vacuole, endoplasmic reticulum, chloroplast, starch granule, seed or cell wall of a plant. Moreover, in another embodiment, the genome of plant may be further augmented with a second recombinant polynucleotide comprising a non-hyperthermophilic enzyme.

In another aspect of the invention, provided is a transformed plant, the genome of which is augmented with a recombinant polynucleotide encoding at least one processing enzyme selected from the group consisting of α-amylase, glucoamylase, glucose isomerase, α-glucosidase, and pullulanase, operably linked to a promoter sequence, the sequence of which polynucleotide is optimized for expression in the plant. Preferably, the processing enzyme is hyperthermophilic and maize.

Another embodiment is directed to a transformed maize plant, the genome of which is augmented with a recombinant polynucleotide encoding at least one processing enzyme selected from the group consisting of α-amylase, glucoamylase, glucose isomerase, α-glucosidase, and pullulanase, operably linked to a promoter sequence, the sequence of which polynucleotide is optimized for expression in the maize plant. Preferably, the processing enzyme is hyperthermophilic.

A transformed plant, the genome of which is augmented with a recombinant polynucleotide having the SEQ ID NO: 2, 9, or 52, operably linked to a promoter and to a signal sequence is provided. Additionally, a transformed plant, the genome of which is augmented with a recombinant polynucleotide having the SEQ ID NO: 4 or 25, operably linked to a promoter and to a signal sequence is described. In another embodiment, a transformed plant, the genome of which is augmented with a recombinant polynucleotide having the SEQ ID NO: 6, operably linked to a promoter and to a signal sequence. Moreover, a transformed plant, the genome of which is augmented with a recombinant polynucleotide having the SEQ ID NO: 19, 21, 37, 35, 41, or 43 is described. A transformed plant, the genome of which is augmented with a recombinant polynucleotide having the SEQ ID NO: 46, 48, 50, or 59.

Products of the transformed plants are further envisioned herein. The product, for example, include seed, fruit, or grain. The product may alternatively be the processing enzyme, starch or sugar.

A plant obtained from the stably transformed plants of the present invention are further described. In this aspect, the plant may be a hybrid plant or an inbred plant.

A starch composition is a further embodiment of the invention comprising at least one processing enzyme which is a protease, glucanase, or esterase. Preferably, the enzyme is hyperthermophilic.

Grain is another embodiment of the invention comprising at least one processing enzyme, which is an α-amylase, pullulanase, α-glucosidase, glucoamylase, or glucose isomerase. Preferably, the enzyme is hyperthermophilic.

In another embodiment, a method of preparing starch granules, comprising; treating grain which comprises at least one non-starch processing enzyme under conditions which activate the at least one enzyme, yielding a mixture comprising starch granules and non-starch degradation products, wherein the grain is obtained from a transformed plant, the genome of which is augmented with an expression cassette encoding the at least one enzyme; and separating starch granules from the mixture is provided. Therein, the enzyme is preferably a protease, glucanase, xylanase, phytase, or esterase. Moreover, the enzyme is preferably hyperthermophilic. The grain may be cracked grain and/or may be treated under low or high moisture conditions. Alternatively, the grain may treated with sulfur dioxide. The present invention may preferably further comprise separating non-starch products from the mixture. The starch products and non-starch products obtained by this method are further described.

In yet another embodiment, a method to produce hypersweet corn comprising treating transformed corn or a part thereof, the genome of which is augmented with and expresses in the endosperm an expression cassette encoding at least one starch-degrading or starch-isomerizing enzyme, under conditions which activate the at least one enzyme so as to convert polysaccharides in the corn into sugar, yielding hypersweet corn is provided. The expression cassette preferably further comprises a promoter operably linked to the polynucleotide encoding the enzyme. The promoter may be a constitutive promoter, seed-specific promoter, or endosperm-specific promoter, for example. Preferably, the enzyme is a hyperthermophilic. More preferably, the enzyme is α-amylase. The expression cassette used herein may further comprise a polynucleotide which encodes a signal sequence operably linked to the at least one enzyme. The signal sequence may direct the hyperthermophilic enzyme to the apoplast or the endoplasmic reticulum, for example. Preferably, the enzyme comprises any one of SEQ ID NO: 13, 14, 15, 16, 33, or 35.

In a most preferred embodiment, a method of producing hypersweet corn comprising treating transformed corn or a part thereof, the genome of which is augmented with and expresses in the endosperm an expression cassette encoding an α-amylase, under conditions which activate the at least one enzyme so as to convert polysaccharides in the corn into sugar, yielding hypersweet corn is described. Preferably, the enzyme is hyperthermophilic and the hyperthermophilic α-amylase comprises the amino acid sequence of any of SEQ ID NO: 10, 13, 14, 15, 16, 33, or 35, or an enzymatically active fragment thereof having α-amylase activity.

A method to prepare a solution of hydrolyzed starch product comprising; treating a plant part comprising starch granules and at least one processing enzyme under conditions which activate the at least one enzyme thereby processing the starch granules to form an aqueous solution comprising hydrolyzed starch product, wherein the plant part is obtained from a transformed plant, the genome of which is augmented with an expression cassette encoding the at least one starch processing enzyme; and collecting the aqueous solution comprising the hydrolyzed starch product is described herein. The hydrolyzed starch product may comprise a dextrin, maltooligosaccharide, glucose and/or mixtures thereof. Preferably, the enzyme is α-amylase, α-glucosidase, glucoamylase, pullulanase, amylopullulanase, glucose isomerase, or any combination thereof. Moreover, preferably, the enzyme is hyperthermophilic. In another aspect, the genome of the plant part may be further augmented with an expression cassette encoding a non-hyperthermophilic starch processing enzyme. The non-hyperthermophilic starch processing enzyme may be selected from the group consisting of amylase, glucoamylase, α-glucosidase, pullulanase, glucose-isomerase, or a combination thereof. In yet another aspect, the processing enzyme is preferably expressed in the endosperm. Preferably, the plant part is grain, and is from corn, wheat, barley, rye, oat, sugar cane or rice. Preferably, the at least one processing enzyme is operably linked to a promoter and to a signal sequence that targets the enzyme to the starch granule or the endoplasmic reticulum, or to the cell wall. The method may further comprise isolating the hydrolyzed starch product and/or fermenting the hydrolyzed starch product.

In another aspect of the invention, a method of preparing hydrolyzed starch product comprising treating a plant part comprising starch granules and at least one starch processing enzyme under conditions which activate the at least one enzyme thereby processing the starch granules to form an aqueous solution comprising a hydrolyzed starch product, wherein the plant part is obtained from a transformed plant, the genome of which is augmented with an expression cassette encoding at least one α-amylase; and collecting the aqueous solution comprising hydrolyzed starch product is described. Preferably, the α-amylase is hyperthermophilic and more preferably, the hyperthermophilic α-amylase comprises the amino acid sequence of any of SEQ ID NO: 1, 10, 13, 14, 15, 16, 33, or 35, or an active fragment thereof having α-amylase activity. Preferably, the expression cassette comprises a polynucleotide selected from any of SEQ ID NO: 2, 9, 46, or 52, a complement thereof, or a polynucleotide that hybridizes to any of SEQ ID NO: 2, 9, 46, or 52 under low stringency hybridization conditions and encodes a polypeptide having α-amylase activity. Moreover, the invention further provides for the genome of the transformed plant further comprising a polynucleotide encoding a non-thermophilic starch-processing enzyme. Alternatively, the plant part may be treated with a non-hyperthermophilic starch-processing enzyme.

The present invention is further directed to a transformed plant part comprising at least one starch-processing enzyme present in the cells of the plant, wherein the plant part is obtained from a transformed plant, the genome of which is augmented with an expression cassette encoding the at least one starch processing enzyme. Preferably, the enzyme is a starch-processing enzyme selected from the group consisting of α-amylase, glucoamylase, glucose isomerase, β-amylase, α-glucosidase, isoamylase, pullulanase, neo-pullulanase, iso-pullulanase, and amylopullulanase. Moreover, the enzyme is preferably hyperthermophilic. The plant may be any plant, but is preferably corn.

Another embodiment of the invention is a transformed plant part comprising at least one non-starch processing enzyme present in the cell wall or the cells of the plant, wherein the plant part is obtained from a transformed plant, the genome of which is augmented with an expression cassette encoding the at least one non-starch processing enzyme or at least one non-starch polysaccharide processing enzyme. Preferably, the enzyme is hyperthermophilic. Moreover, the non-starch processing enzyme is preferably selected from the group consisting of protease, glucanase, xylanase, esterase, phytase, and lipase. The plant part can be any plant part, but preferably is an ear, seed, fruit, grain, stover, chaff, or bagasse.

The present invention is also directed to transformed plant parts. For example, a transformed plant part comprising an α-amylase having an amino acid sequence of any of SEQ ID NO: 1, 10, 13, 14, 15, 16, 33, or 35, or encoded by a polynucleotide comprising any of SEQ ID NO: 2, 9, 46, or 52, a transformed plant part comprising an α-glucosidase having an amino acid sequence of any of SEQ ID NO: 5, 26 or 27, or encoded by a polynucleotide comprising SEQ ID NO:6, a transformed plant part comprising a glucose isomerase having the amino acid sequence of any one of SEQ ID NO: 28, 29, 30, 38, 40, 42, or 44, or encoded by a polynucleotide comprising any one of SEQ ID NO: 19, 21, 37, 39, 41, or 43, a transformed plant part comprising a glucoamylase having the amino acid sequence of SEQ ID NO:45 or SEQ ID NO:47, or SEQ ID NO:49, or encoded by a polynucleotide comprising any of SEQ ID NO: 46, 48, 50, or 59, and a transformed plant part comprising a pullulanase encoded by a polynucleotide comprising any of SEQ ID NO: 4 or 25 are described.

Another embodiment is a method of converting starch in the transformed plant part comprising activating the starch processing enzyme contained therein. The starch, dextrin, maltooligosaccharide or sugar produced according to this method is further described.

The present invention further describes a method of using a transformed plant part comprising at least one non-starch processing enzyme in the cell wall or the cell of the plant part, comprising treating a transformed plant part comprising at least one non-starch polysaccharide processing enzyme under conditions so as to activate the at least one enzyme thereby digesting non-starch polysaccharide to form an aqueous solution comprising oligosaccharide and/or sugars, wherein the plant part is obtained from a transformed plant, the genome of which is augmented with an expression cassette encoding the at least one non-starch polysaccharide processing enzyme; and collecting the aqueous solution comprising the oligosaccharides and/or sugars. Preferably, the non-starch polysaccharide processing enzyme is hyperthermophilic.

A method of using transformed seeds comprising at least one processing enzyme, comprising treating transformed seeds which comprise at least one protease or lipase under conditions so as the activate the at least one enzyme yielding an aqueous mixture comprising amino acids and fatty acids, wherein the seed is obtained from a transformed plant, the genome of which is augmented with an expression cassette encoding the at least one enzyme; and collecting the aqueous mixture. The amino acids, fatty acids or both are preferably isolated. Preferably, the at least one protease or lipase is hyperthermophilic.

A method to prepare ethanol comprising treating a plant part comprising at least one polysaccharide processing enzyme under conditions to activate the at least one enzyme thereby digesting polysaccharide to form oligosaccharide or fermentable sugar, wherein the plant part is obtained from a transformed plant, the genome of which is augmented with an expression cassette encoding the at least one polysaccharide processing enzyme; and incubating the fermentable sugar under conditions that promote the conversion of the fermentable sugar or oligosaccharide into ethanol. Preferably, the plant part is a grain, fruit, seed, stalks, wood, vegetable or root. Preferably, the plant part is obtained from a plant selected from the group consisting of oats, barley, wheat, berry, grapes, rye, corn, rice, potato, sugar beet, sugar cane, pineapple, grasses and trees. In another preferred embodiment, the polysaccharide processing enzyme is α-amylase, glucoamylase, α-glucosidase, glucose isomerase, pullulanase, or a combination thereof.

A method to prepare ethanol comprising treating a plant part comprising at least one enzyme selected from the group consisting of α-amylase, glucoamylase, α-glucosidase, glucose isomerase, or pullulanase, or a combination thereof, with heat for an amount of time and under conditions to activate the at least one enzyme thereby digesting polysaccharide to form fermentable sugar, wherein the plant part is obtained from a transformed plant, the genome of which is augmented with an expression cassette encoding the at least one enzyme; and incubating the fermentable sugar under conditions that promote the conversion of the fermentable sugar into ethanol is provided. Preferably, the at least one enzyme is hyperthermophilic or mesophilic.

In another embodiment, a method to prepare ethanol comprising treating a plant part comprising at least one non-starch processing enzyme under conditions to activate the at least one enzyme thereby digesting non-starch polysaccharide to oligosaccharide and fermentable sugar, wherein the plant part is obtained from a transformed plant, the genome of which is augmented with an expression cassette encoding the at least one enzyme; and incubating the fermentable sugar under conditions that promote the conversion of the fermentable sugar into ethanol is provided. Preferably, the non-starch processing enzyme is a glucanase, xylanase or cellulase.

A method to prepare ethanol comprising treating a plant part comprising at least one enzyme selected from the group consisting of α-amylase, glucoamylase, α-glucosidase, glucose isomerase, or pullulanase, or a combination thereof, under conditions to activate the at least one enzyme thereby digesting polysaccharide to form fermentable sugar, wherein the plant part is obtained from a transformed plant, the genome of which is augmented with an expression cassette encoding the at least one enzyme; and incubating the fermentable sugar under conditions that promote the conversion of the fermentable sugar into ethanol is further provided. Preferably, the enzyme is hyperthermophilic.

Moreover, a method to produce a sweetened farinaceous food product without adding additional sweetener comprising treating a plant part comprising at least one starch processing enzyme under conditions which activate the at least one enzyme, thereby processing starch granules in the plant part to sugars so as to form a sweetened product, wherein the plant part is obtained from a transformed plant, the genome of which is augmented with an expression cassette encoding the at least one enzyme; and processing the sweetened product into a farinaceous food product is described. The farinaceous food product may be formed from the sweetened product and water. Moreover, the farinaceous food product may contain malt, flavorings, vitamins, minerals, coloring agents or any combination thereof. Preferably, the at least one enzyme is hyperthermophilic. The enzyme may be selected from α-amylase, α-glucosidase, glucoamylase, pullulanase, glucose isomerase, or any combination thereof. The plant may further be selected from the group consisting of soybean, rye, oats, barley, wheat, corn, rice and sugar cane. Preferably, the farinaceous food product is a cereal food, a breakfast food, a ready to eat food, or a baked food. The processing may include baking, boiling, heating, steaming, electrical discharge or any combination thereof.

The present invention is further directed to a method to sweeten a starch-containing product without adding sweetener comprising treating starch comprising at least one starch processing enzyme under conditions to activate the at least one enzyme thereby digesting the starch to form a sugar to form sweetened starch, wherein the starch is obtained from a transformed plant, the genome of which is augmented with an expression cassette encoding the at least one enzyme; and adding the sweetened starch to a product to produce a sweetened starch containing product. Preferably, the transformed plant is selected from the group consisting of corn, soybean, rye, oats, barley, wheat, rice and sugar cane. Preferably, the at least one enzyme is hyperthermophilic. More preferably, the at least one enzyme is α-amylase, α-glucosidase, glucoamylase, pullulanase, glucose isomerase, or any combination thereof.

A farinaceous food product and sweetened starch containing product is provided for herein.

The invention is also directed to a method to sweeten a polysaccharide-containing fruit or vegetable comprising treating a fruit or vegetable comprising at least one polysaccharide processing enzyme under conditions which activate the at least one enzyme, thereby processing the polysaccharide in the fruit or vegetable to form sugar, yielding a sweetened fruit or vegetable, wherein the fruit or vegetable is obtained from a transformed plant, the genome of which is augmented with an expression cassette encoding the at least one polysaccharide processing enzyme. The fruit or vegetable is selected from the group consisting of potato, tomato, banana, squash, peas, and beans. Preferably, the at least one enzyme is hyperthermophilic.

The present invention is further directed to a method of preparing an aqueous solution comprising sugar comprising treating starch granules obtained from the plant part under conditions which activate the at least one enzyme, thereby yielding an aqueous solution comprising sugar.

Another embodiment is directed to a method of preparing starch derived products from grain that does not involve wet or dry milling grain prior to recovery of starch-derived products comprising treating a plant part comprising starch granules and at least one starch processing enzyme under conditions which activate the at least one enzyme thereby processing the starch granules to form an aqueous solution comprising dextrins or sugars, wherein the plant part is obtained from a transformed plant, the genome of which is augmented with an expression cassette encoding the at least one starch processing enzyme; and collecting the aqueous solution comprising the starch derived product. Preferably, the at least one starch processing enzyme is hyperthermophilic.

A method of isolating an α-amylase, glucoamylase, glucose isomerase, α-glucosidase, and pullulanase comprising culturing the transformed plant and isolating the α-amylase, glucoamylase, glucose isomerase, α-glucosidase, and pullulanase therefrom is further provided. Preferably, the enzyme is hyperthermophilic.

A method of preparing maltodextrin comprising mixing transgenic grain with water, heating said mixture, separating solid from the dextrin syrup generated, and collecting the maltodextrin. Preferably, the transgenic grain comprises at least one starch processing enzyme. Preferably, the starch processing enzyme is α-amylase, glucoamylase, α-glucosidase, and glucose isomerase. Moreover, maltodextrin produced by the method is provided as well as composition produced by this method.

A method of preparing dextrins, or sugars from grain that does not involve mechanical disruption of the grain prior to recovery of starch-derived comprising: treating a plant part comprising starch granules and at least one starch processing enzyme under conditions which activate the at least one enzyme thereby processing the starch granules to form an aqueous solution comprising dextrins or sugars, wherein the plant part is obtained from a transformed plant, the genome of which is augmented with an expression cassette-encoding the at least one processing enzyme; and collecting the aqueous solution comprising sugar and/or dextrins is provided.

The present invention is further directed to a method of producing fermentable sugar comprising treating a plant part comprising starch granules and at least one starch processing enzyme under conditions which activate the at least one enzyme thereby processing the starch granules to form an aqueous solution comprising dextrins or sugars, wherein the plant part is obtained from a transformed plant, the genome of which is augmented with an expression cassette encoding the at least one enzyme; and collecting the aqueous solution comprising the fermentable sugar.

Moreover, a maize plant stably transformed with a vector comprising a hyperthermophlic α-amylase is provided herein. For example, preferably, a maize plant stably transformed with a vector comprising a polynucleotide sequence that encodes α-amylase that is greater than 60% identical to SEQ ID NO: 1 or SEQ ID NO: 51 is encompassed.

BRIEF DESCRIPTION OF THE FIGURES

FIGS. 10A and 10B show the results of the HPLC analysis of the hydrolytic products generated by expressed pullulanase from starch in the transgenic corn flour. Incubation of the flour of pullulanase expressing corn in reaction buffer at 75° C. for 30 minutes results in production of medium chain oligosaccharides (degree of polymerization (DP) ~10-30) and short amylose chains (DP ~100-200) from cornstarch. FIGS. 10A and 10B also show the effect of added calcium ions on the activity of the pullulanase.

DETAILED DESCRIPTION OF THE INVENTION

Figure 1A:
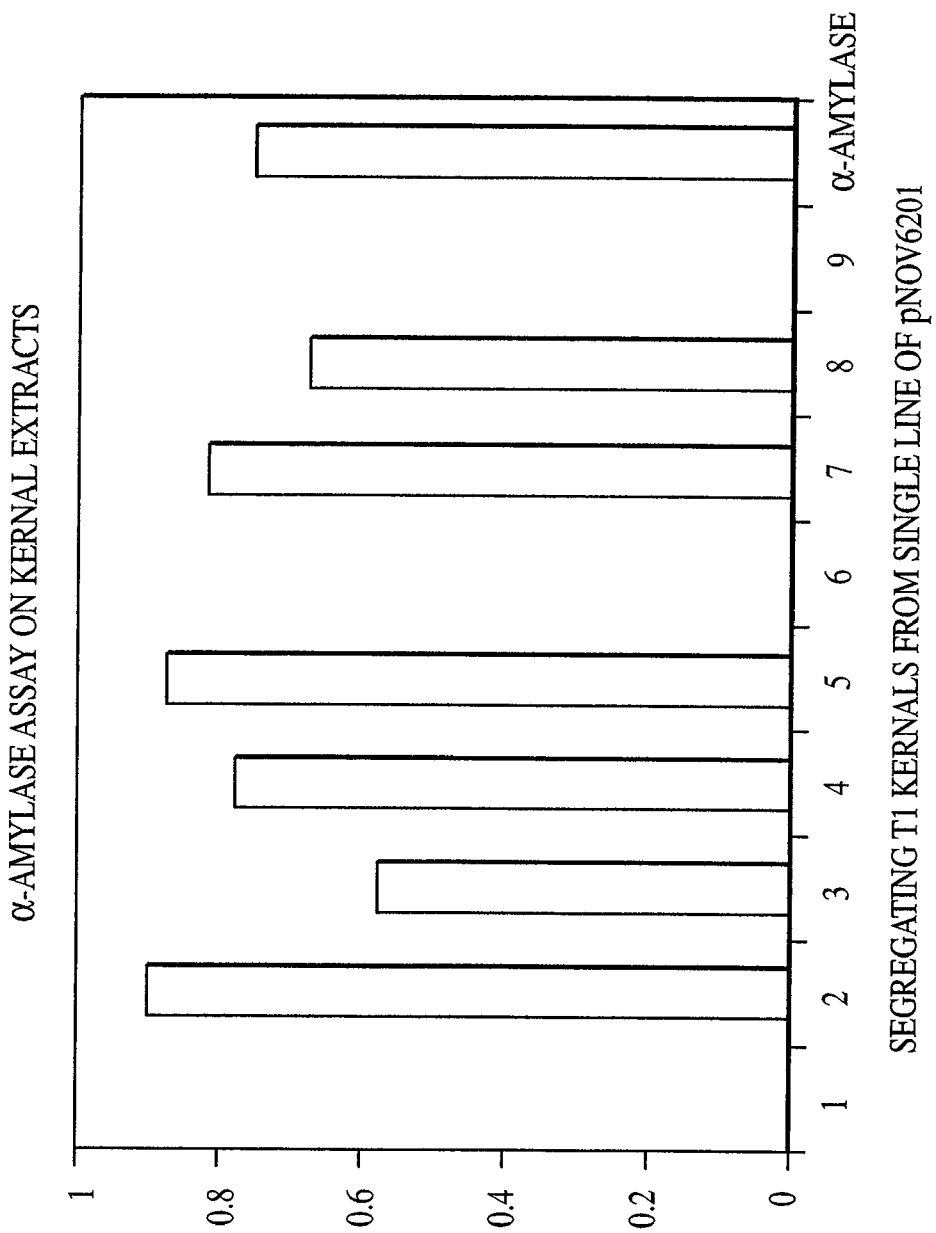
FIGS. 1A and 1B illustrate the activity of α-amylase expressed in corn kernels and in the endosperm from segregating T1 kernels from pNOV6201 plants and from six pNOV6200 lines.

In accordance with the present invention, a "self-processing" plant or plant part has incorporated therein an isolated polynucleotide encoding a processing enzyme capable of processing, e.g., modifying, starches, polysaccharides, lipids, proteins, and the like in plants, wherein the processing enzyme can be mesophilic, thermophilic or hyperthermophilic, and may be activated by grinding, addition of water, heating, or otherwise providing favorable conditions for function of the enzyme. The isolated polynucleotide encoding the processing enzyme is integrated into a plant or plant part for expression therein. Upon expression and activation of the processing enzyme, the plant or plant part of the present invention processes the substrate upon which the processing enzyme acts. Therefore, the plant or plant parts of the present invention are capable of self-processing the substrate of the enzyme upon activation of the processing enzyme contained therein in the absence of or with reduced external sources normally required for processing these substrates. As such, the transformed plants, transformed plant cells, and transformed plant parts have "built-in" processing capabilities to process desired substrates via the enzymes incorporated therein according to this invention. Preferably, the processing enzyme-encoding polynucleotide are "genetically stable," i.e., the polynucleotide is stably maintained in the transformed plant or plant parts of the present invention and stably inherited by progeny through successive generations.

In accordance with the present invention, methods which employ such plants and plant parts can eliminate the need to mill or otherwise physically disrupt the integrity of plant parts prior to recovery of starch-derived products. For example, the invention provides improved methods for processing corn and other grain to recover starch-derived products. The invention also provides a method which allows for the recovery of starch granules that contain levels of starch degrading enzymes, in or on the granules, that are adequate for the hydrolysis of specific bonds within the starch without the requirement for adding exogenously produced starch hydrolyzing enzymes. The invention also provides improved products from the self-processing plant or plant parts obtained by the methods of the invention.

In addition, the "self-processing" transformed plant part, e.g., grain, and transformed plant avoid major problems with existing technology, i.e., processing enzymes are typically produced by fermentation of microbes, which requires isolating the enzymes from the culture supernatants, which costs money; the isolated enzyme needs to be formulated for the particular application, and processes and machinery for adding, mixing and reacting the enzyme with its substrate must be developed. The transformed plant of the invention or a part thereof is also a source of the processing enzyme itself as well as substrates and products of that enzyme, such as sugars, amino acids, fatty acids and starch and non-starch polysaccharides. The plant of the invention may also be employed to prepare progeny plants such as hybrids and inbreds.

Processing Enzymes and Polynucleotides Encoding Them

A polynucleotide encoding a processing enzyme (mesophilic, thermophilic, or hyperthermophilic) is introduced into a plant or plant part. The processing enzyme is selected based on the desired substrate upon which it acts as found in plants or transgenic plants and/or the desired end product. For example, the processing enzyme may be a starch-processing enzyme, such as a starch-degrading or starch-isomerizing enzyme, or a non-starch processing enzyme. Suitable processing enzymes include, but are not limited to, starch degrading or isomerizing enzymes including, for example, α-amylase, endo or exo-1,4, or 1,6-α-D, glucoamylase, glucose isomerase, β-amylases, α-glucosidases, and other exo-amylases; and starch debranching enzymes, such as isoamylase, pullulanase, neo-pullulanase, iso-pullulanase, amylopullulanase and the like, glycosyl transferases such as cyclodextrin glycosyltransferase and the like, cellulases such as exo-1,4-β-cellobiohydrolase, exo-1,3-β-D-glucanase, hemicellulase, β-glucosidase and the like; endoglucanases such as endo-1,3-β-glucanase and endo-1,4-β-glucanase and the like; L-arabinases, such as endo-1,5-α-L-arabinase, α-arabinosidases and the like; galactanases such as endo-1, 4-β-D-galactanase, endo-1,3-β-D-galactanase, β-galactosidase, α-galactosidase and the like; mannanases, such as endo-1,4-β-D-mannanase, β-mannosidase, α-mannosidase and the like; xylanases, such as endo-1,4-β-xylanase, β-D-xylosidase, 1,3-β-D-xylanase, and the like; and pectinases; and non-starch processing enzymes, including protease, glucanase, xylanase, thioredoxin/thioredoxin reductase, esterase, phytase, and lipase.

In one embodiment, the processing enzyme is a starch-degrading enzyme selected from the group of α-amylase, pullulanase, α-glucosidase, glucoamylase, amylopullulanase, glucose isomerase, or combinations thereof. According to this embodiment, the starch-degrading enzyme is able to allow the self-processing plant or plant part to degrade starch upon activation of the enzyme contained in the plant or plant part, as will be further described herein. The starch-degrading enzyme(s) is selected based on the desired end-products. For example, a glucose-isomerase may be selected to convert the glucose (hexose) into fructose. Alternatively, the enzyme may be selected based on the desired starch-derived end product with various chain length based on, e.g., a function of the extent of processing or with various branching patterns desired. For example, an α-amylase, glucoamylase, or amylopullulanase can be used under short incubation times to produce dextrin products and under longer incubation times to produce shorter chain products or sugars. A pullulanase can be used to specifically hydrolyze branch points in the starch yielding a high-amylose starch, or a neopullulanase can be used to produce starch with stretches of α1,4 linkages with interspersed α1,6 linkages. Glucosidases could be used to produce limit dextrins, or a combination of different enzymes to make other starch derivatives.

In another embodiment, the processing enzyme is a non-starch processing enzyme selected from protease, glucanase, xylanase, and esterase. These non-starch degrading enzymes allow the self-processing plant or plant part of the present invention to incorporate in a targeted area of the plant and, upon activation, disrupt the plant while leaving the starch granule therein intact. For example, in a preferred embodiment, the non-starch degrading enzymes target the endosperm matrix of the plant cell and, upon activation, disrupt the endosperm matrix while leaving the starch granule therein intact and more readily recoverable from the resulting material.

Combinations of processing enzymes are further envisioned by the present invention. For example, starch-processing and non-starch processing enzymes may be used in combination. Combinations of processing enzymes may be obtained by employing the use of multiple gene constructs encoding each of the enzymes. Alternatively, the individual transgenic plants stably transformed with the enzymes may be crossed by known methods to obtain a plant containing both enzymes. Another method includes the use of exogenous enzyme(s) with the transgenic plant.

The processing enzymes may be isolated or derived from any source and the polynucleotides corresponding thereto may be ascertained by one having skill in the art. For example, the processing enzyme, preferably α-amylase, is derived from the *Pyrococcus* (e.g., *Pyrococcus furiosus*), *Thermus*, *Thermococcus* (e.g., *Thermococcus hydrothermalis*), *Sulfolobus* (e.g., *Sulfolobus solfataricus*) *Thermotoga* (e.g., *Thermotoga maritima* and *Thermotoga neapolitana*), *Thermoanaerobacterium* (e.g. *Thermoanaerobacter tengcongensis*), *Aspergillus* (e.g., *Aspergillus shirousami* and *Aspergillus niger*), *Rhizopus* (eg., *Rhizopus oryzae*), Thermoproteales, *Desulfurococcus* (e.g. *Desulfurococcus amylolyticus*), *Methanobacterium thermoautotrophicum, Methanococcus jannaschii, Methanopyrus kandleri, Thermosynechococcus elongatus, The rnoplasma acidophilum, Thermoplasma volcanium, Aeropyrum pernix* and plants such as corn, barley, and rice.

The processing enzymes of the present invention are capable of being activated after being introduced and expressed in the genome of a plant. Conditions for activating the enzyme are determined for each individual enzyme and may include varying conditions such as temperature, pH, hydration, presence of metals, activating compounds, inactivating compounds, etc. For example, temperature-dependent enzymes may include mesophilic, thermophilic, and hyper-thermophilic enzymes. Mesophilic enzymes typically have maximal activity at temperatures between 20°-65° C. and are inactivated at temperatures greater than 70° C. Mesophilic enzymes have significant activity at 30 to 37° C., the activity at 30° C. is preferably at least 10% of maximal activity, more preferably at least 20% of maximal activity.

Thermophilic enzymes have a maximal activity at temperatures of between 50 and 80° C. and are inactivated at temperatures greater than 80° C. A thermophilic enzyme will preferably have less than 20% of maximal activity at 30° C., more preferably less than 10% of maximal activity.

A "hyperthermophilic" enzyme has activity at even higher temperatures. Hyperthermophilic enzymes have a maximal activity at temperatures greater than 80° C. and retain activity at temperatures at least 80° C., more preferably retain activity at temperatures of at least 90° C. and most preferably retain activity at temperatures of at least 95° C. Hyperthermophilic enzymes also have reduced activity at low temperatures. A hyperthermophilic enzyme may have activity at 30° C. that is less than 10% of maximal activity, and preferably less than 5% of maximal activity.

The polynucleotide encoding the processing enzyme is preferably modified to include codons that are optimized for expression in a selected organism such as a plant (see, e.g., Wada et al., *Nucl. Acids Res.*, 18:2367 (1990), Murray et al., *Nucl. Acids Res.*, 17:477 (1989), U.S. Pat. Nos. 5,096,825, 5,625,136, 5,670,356 and 5,874,304). Codon optimized sequences are synthetic sequences, i.e., they do not occur in nature, and preferably encode the identical polypeptide (or an enzymatically active fragment of a full length polypeptide which has substantially the same activity as the full length polypeptide) encoded by the non-codon optimized parent polynucleotide which encodes a processing enzyme. It is preferred that the polypeptide is biochemically distinct or improved, e.g., via recursive mutagenesis of DNA encoding a particular processing enzyme, from the parent source polypeptide such that its performance in the process application is improved. Preferred polynucleotides are optimized for expression in a target host plant and encode a processing enzyme. Methods to prepare these enzymes include mutagenesis, e.g., recursive mutagenesis and selection. Methods for mutagenesis and nucleotide sequence alterations are well-known in the art. See, for example, Kunkel, *Proc. Natl. Acad. Sci. USA,* 82:488, (1985); Kunkel et al., *Methods in Enzymol.,* 154:367 (1987); U.S. Pat. No. 4,873,192; Walker and Gaastra, eds. (1983) *Techniques in Molecular Biology* (MacMillan Publishing Company, New York) and the references cited therein and Arnold et al., *Chem. Eng. Sci.,* 51:5091 (1996)). Methods to optimize the expression of a nucleic acid segment in a target plant or organism are well-known in the art. Briefly, a codon usage table indicating the optimal codons used by the target organism is obtained and optimal codons are selected to replace those in the target polynucleotide and the optimized sequence is then chemically synthesized. Preferred codons for maize are described in U.S. Pat. No. 5,625,136.

Complementary nucleic acids of the polynucleotides of the present invention are further envisioned. An example of low stringency conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60° C. to 65° C. Exemplary low stringency conditions include hybridization with a buffer solution of 30 to 35% form amide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Moreover, polynucleotides encoding an "enzymatically active" fragment of the processing enzymes are further envisioned. As used herein, "enzymatically active" means a polypeptide fragment of the processing enzyme that has substantially the same biological activity as the processing enzyme to modify the substrate upon which the processing enzyme normally acts under appropriate conditions.

In a preferred embodiment, the polynucleotide of the present invention is a maize-optimized polynucleotide encoding α-amylase, such as provided in SEQ ID NOs:2, 9, 46, and 52. In another preferred embodiment, the polynucleotide is a maize-optimized polynucleotide encoding pullulanase, such as provided in SEQ ID NOs: 4 and 25. In yet another preferred embodiment, the polynucleotide is a maize-optimized polynucleotide encoding α-glucosidase as provided in SEQ ID NO:6. Another preferred polynucleotide is the maize-optimized polynucleotide encoding glucose isomerase having SEQ ID NO: 19, 21, 37, 39, 41, or 43. In another embodiment, the maize-optimized polynucleotide encoding glucoamylase as set forth in SEQ ID NO: 46, 48, or 50 is preferred. Moreover, a maize-optimized polynucleotide for glucanase/mannanase fusion polypeptide is provided in SEQ ID NO: 57. The invention further provides for complements of such polynucleotides, which hybridize under moderate, or preferably under low stringency, hybridization conditions and which encodes a polypeptide having α-amylase, pullulanase, α-glucosidase, glucose isomerase, glucoamylase, glucanase, or mannanase activity, as the case may be.

The polynucleotide may be used interchangeably with "nucleic acid" or "polynucleic acid" and refers to deoxyribonucleotides or ribonucleotides and polymers thereof in either single- or double-stranded form, composed of monomers (nucleotides) containing a sugar, phosphate and a base, which is either a purine or pyrimidine. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

"Variants" or substantially similar sequences are further encompassed herein. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR), hybridization techniques, and ligation reassembly techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, preferably 70%, more preferably 80%, even more preferably 90%, most preferably 99%, and single unit percentage identity to the native nucleotide sequence based on these classes. For example, 71%, 72%, 73% and the like, up to at least the 90% class. Variants may also include a full-length gene corresponding to an identified gene fragment.

Regulatory Sequences: Promoters/Signal Sequences/Selectable Markers

The polynucleotide sequences encoding the processing enzyme of the present invention may be operably linked to polynucleotide sequences encoding localization signals or signal sequence (at the N- or C-terminus of a polypeptide), e.g., to target the hyperthermophilic enzyme to a particular compartment within a plant. Examples of such targets include, but are not limited to, the vacuole, endoplasmic reticulum, chloroplast, amyloplast, starch granule, or cell wall, or to a particular tissue, e.g., seed. The expression of a polynucleotide encoding a processing enzyme having a signal sequence in a plant, in particular, in conjunction with the use of a tissue-specific or inducible promoter, can yield high levels of localized processing enzyme in the plant. Numerous signal sequences are known to influence the expression or targeting of a polynucleotide to a particular compartment or outside a particular compartment. Suitable signal sequences and targeting promoters are known in the art and include, but are not limited to, those provided herein.

For example, where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A number of plant promoters have been described with various expression characteristics. Examples of some constitutive promoters which have been described include the rice actin 1 (Wang et al., *Mol. Cell. Biol.*, 12:3399 (1992); U.S. Pat. No. 5,641,876), CaMV 35S (Odell et al., *Nature,* 313:810 (1985)), CaMV 19S (Lawton et al., 1987), nos (Ebert et al., 1987), Adh (Walker et al., 1987), sucrose synthase (Yang & Russell, 1990), and the ubiquitin promoters.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an α-tubulin gene that directs expression in roots and promoters derived from zein storage protein genes which direct expression in endosperm.

Tissue specific expression may be functionally accomplished by introducing a constitutively expressed gene (all tissues) in combination with an antisense gene that is expressed only in those tissues where the gene product is not desired. For example, a gene coding for a lipase may be introduced such that it is expressed in all tissues using the 35S promoter from Cauliflower Mosaic Virus. Expression of an antisense transcript of the lipase gene in a maize kernel, using for example a zein promoter, would prevent accumulation of the lipase protein in seed. Hence the protein encoded by the introduced gene would be present in all tissues except the kernel.

Moreover, several tissue-specific regulated genes and/or promoters have been reported in plants. Some reported tissue-specific genes include the genes encoding the seed storage proteins (such as napin, cruciferin, beta-conglycinin, and phaseolin) zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et al., *Seed Science Research,* 1:209 (1991)). Examples of tissue-specific promoters, which have been described include the lectin (Vodkin, *Prog. Clin. Biol. Res.,* 138; 87 (1983); Lindstrom et al., *Der. Genet.,* 11:160 (1990)), corn alcohol dehydrogenase 1 (Vogel et al., 1989; Dennis et al., *Nucleic Acids Res.,* 12:3983 (1984)), corn light harvesting complex (Simpson, 1986; Bansal et al., *Proc. Natl. Acad. Sci. USA,* 89:3654 (1992)), corn heat shock protein (Odell et al., 1985; Rochester et al., 1986), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (vanTunen et al., *EMBO J.,* 7; 1257 (1988)), bean glycine rich protein 1 (Keller et al., *Genes Dev.,* 3:1639 (1989)), truncated CaMV 35s (Odell et al., *Nature,* 313:810 (1985)), potato patatin (Wenzler et al., *Plant Mol. Biol.,* 13:347 (1989)), root cell (Yamamoto et al., *Nucleic Acids Res.,* 18:7449 (1990)), maize zein (Reina et al., *Nucleic Acids Res.,* 18:6425 (1990); Kriz et al., *Mol. Gen. Genet.,* 207:90 (1987); Wandelt et al., *Nucleic Acids Res.,* 17:2354 (1989); Langridge et al., *Cell,* 34:1015 (1983); Reina et al., *Nucleic Acids Res.,* 18:7449 (1990)), globulin-1 (Belanger et al., *Genetics,* 129:863 (1991)), α-tubulin, cab (Sullivan et al., *Mol. Gen. Genet.,* 215:431 (1989)), PEPCase (Hudspeth & Grula, 1989), R gene complex-associated promoters (Chandler et al., *Plant Cell,* 1:1175 (1989)), and chalcone synthase promoters (Franken et al., *EMBO J.,* 10:2605 (1991)). Particularly useful for seed-specific expression is the pea vicilin promoter (Czako et al., *Mol. Gen. Genet.,* 235:33 (1992). (See also U.S. Pat. No. 5,625,136, herein incorporated by reference). Other useful promoters for expression in mature leaves are those that are switched on at the onset of senescence, such as the SAG promoter from *Arabidopsis* (Gan et al., *Science,* 270: 1986 (1995).

A class of fruit-specific promoters expressed at or during anthesis through fruit development, at least until the beginning of ripening, is discussed in U.S. Pat. No. 4,943,674, the disclosure of which is hereby incorporated by reference. cDNA clones that are preferentially expressed in cotton fiber have been isolated (John et al., *Proc. Natl. Acad. Sci. USA,* 89:5769 (1992). cDNA clones from tomato displaying differential expression during fruit development have been isolated and characterized (Mansson et al., *Gen. Genet.,* 200:356 (1985), Slater et al., *Plant Mol. Biol.,* 5:137 (1985)). The promoter for polygalacturonase gene is active in fruit ripening. The polygalacturonase gene is described in U.S. Pat. No. 4,535,060, U.S. Pat. No. 4,769,061, U.S. Pat. No. 4,801,590, and U.S. Pat. No. 5,107,065, which disclosures are incorporated herein by reference.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., *Proc. Natl. Acad. Sci. USA,* 89:5769 (1992). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., *Plant Cell,* 9:1527 (1997)). Other tissue-specific promoters can be isolated by one skilled in the art (see U.S. Pat. No. 5,589,379).

In one embodiment, the direction of the product from a polysaccharide hydrolysis gene, such as α-amylase, may be targeted to a particular organelle such as the apoplast rather than to the cytoplasm. This is exemplified by the use of the maize γ-zein N-terminal signal sequence (SEQ ID NO:17), which confers apoplast-specific targeting of proteins. Directing the protein or enzyme to a specific compartment will allow the enzyme to be localized in a manner that it will not come into contact with the substrate. In this manner the enzymatic action of the enzyme will not occur until the enzyme contacts its substrate. The enzyme can be contacted with its substrate by the process of milling (physical disruption of the cell integrity), or heating the cells or plant tissues to disrupt the physical integrity of the plant cells or organs that contain the enzyme. For example a mesophilic starch-hydrolyzing enzyme can be targeted to the apoplast or to the endoplasmic reticulum and so as not to come into contact with starch granules in the amyloplast. Milling of the grain will disrupt the integrity of the grain and the starch hydrolyzing enzyme will then contact the starch granules. In this manner the potential negative effects of co-localization of an enzyme and its substrate can be circumvented.

In another embodiment, a tissue-specific promoter includes the endosperm-specific promoters such as the maize γ-zein promoter (exemplified by SEQ ID NO:12) or the maize ADP-gpp promoter (exemplified by SEQ ID NO:11, which includes a 5' untranslated and an intron sequence). Thus, the present invention includes an isolated polynucleotide comprising a promoter comprising SEQ ID NO:11 or 12, a polynucleotide which hybridizes to the complement thereof under low stringency hybridization conditions, or a fragment thereof which has promoter activity, e.g., at least 10%, and preferably at least 50%, the activity of a promoter having SEQ ID NO:11 or 12.

In another embodiment of the invention, the polynucleotide encodes a hyperthermophilic processing enzyme that is operably linked to a chloroplast (amyloplast) transit peptide (CTP) and a starch binding domain, e.g., from the waxy gene. An exemplary polynucleotide in this embodiment encodes SEQ ID NO:10 (α-amylase linked to the starch binding domain from waxy). Other exemplary polynucleotides encode a hyperthermophilic processing enzyme linked to a signal sequence that targets the enzyme to the endoplasmic reticulum and secretion to the apoplast (exemplified by a polynucleotide encoding SEQ ID NO:13, 27, or 30, which comprises the N-terminal sequence from maize γ-zein operably linked to α-amylase, α-glucosidase, glucose isomerase, respectively), a hyperthermophilic processing enzyme linked to a signal sequence which retains the enzyme in the endoplasmic reticulum (exemplified by a polynucleotide encoding SEQ ID NO:14, 26, 28, 29, 33, 34, 35, or 36, which comprises the N-terminal sequence from maize γ-zein operably linked to the hyperthermophilic enzyme, which is operably linked to SEKDEL, wherein the enzyme is α-amylase, malA α-glucosidase, T. maritima glucose isomerase, T. neapolitana glucose isomerase), a hyperthermophilic processing enzyme linked to an N-terminal sequence that targets the enzyme to the amyloplast (exemplified by a polynucleotide encoding SEQ ID NO:15, which comprises the N-terminal amyloplast targeting sequence from waxy operably linked to α-amylase), a hyperthermophilic fusion polypeptide which targets the enzyme to starch granules (exemplified by a polynucleotide encoding SEQ ID NO:16, which comprises the N-terminal amyloplast targeting sequence from waxy operably linked to an α-amylase/waxy fusion polypeptide comprising the waxy starch binding domain), a hyperthermophilic processing enzyme linked to an ER retention signal (exemplified by a polynucleotide encoding SEQ ID NO:38 and 39). Moreover, a hyperthermophilic processing enzyme may be linked to a raw-starch binding site having the amino acid sequence (SEQ ID NO:53), wherein the polynucleotide encoding the processing enzyme is linked to the maize-optimized nucleic acid sequence (SEQ ID NO:54) encoding this binding site.

Several inducible promoters have been reported. Many are described in a review by Gatz, in *Current Opinion in Biotechnology*, 7:168 (1996) and Gatz, C., *Annu. Rev. Plant Physiol. Plant Mol. Biol.*, 48:89 (1997). Examples include tetracycline repressor system, Lac repressor system, copper-inducible systems, salicylate-inducible systems (such as the PR1a system), glucocorticoid-inducible (Aoyama T. et al., *N-H Plant Journal*, 11:605 (1997)) and ecdysone-inducible systems. Other inducible promoters include ABA- and turgor-inducible promoters, the promoter of the auxin-binding protein gene (Schwob et al., *Plant J.*, 4:423 (1993)), the UDP glucose flavonoid glycosyl-transferase gene promoter (Ralston et al., *Genetics*, 119:185 (1988)), the MPI proteinase inhibitor promoter (Cordero et al., *Plant J.*, 6:141 (1994)), and the glyceraldehyde-3-phosphate dehydrogenase gene promoter (Kohler et al., *Plant Mol. Biol.*, 29; 1293 (1995); Quigley et al., *J. Mol. Evol.*, 29:412 (1989); Martinez et al., *J. Mol. Biol.*, 208:551 (1989)). Also included are the benzene sulphonamide-inducible (U.S. Pat. No. 5,364,780) and alcohol-inducible (WO 97/06269 and WO 97/06268) systems and glutathione S-transferase promoters.

Other studies have focused on genes inducibly regulated in response to environmental stress or stimuli such as increased salinity, drought, pathogen and wounding. (Graham et al., *J. Biol. Chem.*, 260:6555 (1985); Graham et al., *J. Biol. Chem.*, 260:6561 (1985), Smith et al., *Planta*, 168:94 (1986)). Accumulation of metallocarboxypeptidase-inhibitor protein has been reported in leaves of wounded potato plants (Graham et al., *Biochem. Biophys. Res. Comm.*, 101:1164 (1981)). Other plant genes have been reported to be induced by methyl jasmonate, elicitors, heat-shock, anaerobic stress, or herbicide safeners.

Regulated expression of a chimeric transacting viral replication protein can be further regulated by other genetic strategies, such as, for example, Cre-mediated gene activation (Odell et al. *Mol. Gen. Genet.*, 113:369 (1990)). Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon (Ulmasov et al. *Plant Mol. Biol.*, 35:417 (1997)). Again, either the chimeric tRNA suppressor gene, the chimeric transacting replication gene, or both can be under the control of tissue- and developmental-specific or inducible promoters.

Preferably, in the case of a multicellular organism, the promoter can also be specific to a particular tissue, organ or stage of development. Examples of such promoters include, but are not limited to, the *Zea mays* ADP-gpp and the *Zea mays* γ-zein promoter and the *Zea mays* globulin promoter.

Expression of a gene in a transgenic plant may be desired only in a certain time period during the development of the plant. Developmental timing is frequently correlated with tissue specific gene expression. For example, expression of zein storage proteins is initiated in the endosperm about 15 days after pollination.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A signal sequence such as the maize γ-zein N-terminal signal sequence for targeting to the endoplasmic reticulum and secretion into the apoplast may be operably linked to a polynucleotide encoding a hyperthermophilic processing enzyme in accordance with the present invention (Torrent et al., 1997). For example, SEQ ID NOs:13, 27, and 30 provides for a polynucleotide encoding a hyperthermophilic enzyme operably linked to the N-terminal sequence from maize γ-zein protein. Another signal sequence is the amino acid sequence SEKDEL for retaining polypeptides in the endoplasmic reticulum (Munro and Pelham, 1987). For example, a polynucleotide encoding SEQ ID NOS:14, 26, 28, 29, 33, 34, 35, or 36, which comprises the N-terminal sequence from maize γ-zein operably linked to a processing enzyme which is operably linked to SEKDEL. A polypeptide may also be targeted to the amyloplast by fusion to the waxy amyloplast targeting peptide (Klosgen et al., 1986) or to a starch granule. For example, the polynucleotide encoding a hyperthermophilic processing enzyme may be operably linked to a chloroplast (amyloplast) transit peptide (CTP) and a starch binding domain, e.g., from the waxy gene. SEQ ID NO:10 exemplifies α-amylase linked to the starch binding domain from waxy. SEQ ID NO:15 exemplifies the N-terminal sequence amyloplast targeting sequence from waxy operably linked to α-amylase. Moreover, the polynucleotide encoding the processing enzyme may be fused to target starch granules using the waxy starch binding domain. For example, SEQ ID NO:16 exemplifies a fusion polypeptide comprising the N-terminal amyloplast targeting sequence from waxy operably linked to an α-amylase/waxy fusion polypeptide comprising the waxy starch binding domain.

The polynucleotides of the present invention, in addition to processing signals, may further include other regulatory sequences, as is known in the art. "Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences, which may be a combination of synthetic and natural sequences.

Selectable markers may also be used in the present invention to allow for the selection of transformed plants and plant tissue, as is well-known in the art. One may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can select for by chemical means, i.e., through the use of a selective agent (e.g., a herbicide, antibiotic, or the like), or whether it is simply a trait that one can identify through observation or testing, i.e., by screening (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel et al., *The Plant Cell*, 2:785 (1990)) molecule is well characterized in terms of molecular biology, expression and protein structure. However, any one of a variety of extensins and/or glycine-rich wall proteins (Keller et al., *EMBO Journal*, 8:1309 (1989)) could be modified by the addition of an antigenic site to create a screenable marker.

a. Selectable Markers

Possible selectable markers for use in connection with the present invention include, but are not limited to, a neo or nptII gene (Potrykus et al., *Mol. Gen. Genet.*, 199:183 (1985)) which codes for kanamycin resistance and can be selected for using kanamycin, G418, and the like; a bar gene which confers resistance to the herbicide phosphinothricin; a gene which encodes an altered EPSP synthase protein (Hinchee et al., *Biotech.*, 6:915 (1988)) thus conferring glyphosate resistance; a nitrilase gene such as bxn from *Klebsiella ozaenae* which confers resistance to bromoxynil (Stalker et al., *Science*, 242:419 (1988)); a mutant acetolactate synthase gene (ALS) which confers resistance to imidazolinone, sulfonylurea or other ALS-inhibiting chemicals (European Patent Application 154, 204, 1985); a methotrexate-resistant DHFR gene (Thillet et al., *J. Biol. Chem.*, 263:12500 (1988)); a dalapon dehalogenase gene that confers resistance to the herbicide dalapon; a phosphomannose isomerase (PMI) gene; a mutated anthranilate synthase gene that confers resistance to 5-methyl tryptophan; the hph gene which confers resistance to the antibiotic hygromycin; or the mannose-6-phosphate isomerase gene (also referred to herein as the phosphomannose isomerase gene), which provides the ability to metabolize mannose (U.S. Pat. Nos. 5,767,378 and 5,994,629). One skilled in the art is capable of selecting a suitable selectable marker gene for use in the present invention. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants are the genes that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.*, 205:42 (1986); Twell et al., *Plant Physiol.*, 91:1270 (1989)) causing rapid accumulation of ammonia and cell death. The success in using this selective system in conjunction with monocots was particularly surprising because of the major difficulties which have been reported in transformation of cereals (Potrykus, *Trends Biotech.*, 7:269 (1989)).

Where one desires to employ a bialaphos resistance gene in the practice of the invention, a particularly useful gene for this purpose is the bar or pat genes obtainable from species of *Streptomyces* (e.g., ATCC No. 21,705). The cloning of the bar gene has been described (Murakami et al., *Mol. Gen. Genet.*, 205:42 (1986); Thompson et al., *EMBO Journal*, 6:2519 (1987)) as has the use of the bar gene in the context of plants other than monocots (De Block et al., *EMBO Journal*, 6:2513 (1987); De Block et al., *Plant Physiol.*, 91:694 (1989)).

b. Screenable Markers

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in *Chromosome Structure and Function*, pp. 263-282 (1988)); a β-lactamase gene (Sutcliffe, *PNAS USA*, 75:3737 (1978)), which encodes an enzyme for which various chromogenic substrates are known (e.g., PADAC, a chromogenic cephalosporin); a xylE gene (Zukowsky et al., *PNAS USA*, 80:1101 (1983)) which encodes a catechol dioxygenase that can convert chromogenic catechols; an α-amylase gene (Ikuta et al., *Biotech.*, 8:241 (1990)); a tyrosinase gene (Katz et al., *J. Gen. Microbiol.*, 129:2703 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science*, 234:856 (1986)), which allows for bioluminescence detection, or an aequorin gene (Prasher et al., *Biochem. Biophys. Res. Comm.*, 126:1259 (1985)), which may be employed in calcium-sensitive bioluminescence detection, or a green fluorescent protein gene (Niedz et al., *Plant Cell Reports*, 14: 403 (1995)).

Genes from the maize R gene complex are contemplated to be particularly useful as screenable markers. The R gene complex in maize encodes a protein that acts to regulate the production of anthocyanin pigments in most seed and plant tissue. A gene from the R gene complex is suitable for maize transformation, because the expression of this gene in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together. A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

The polynucleotides used to transform the plant may include, but is not limited to, DNA from plant genes and non-plant genes such as those from bacteria, yeasts, animals or viruses. The introduced DNA can include modified genes, portions of genes, or chimeric genes, including genes from the same or different maize genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of the untransformed plant.

Expression cassettes comprising the polynucleotide encoding a hyperthermophilic processing enzyme, and preferably a codon-optimized polynucleotide is further provided. It is preferred that the polynucleotide in the expression cassette (the first polynucleotide) is operably linked to regulatory sequences, such as a promoter, an enhancer, an intron, a termination sequence, or any combination thereof, and, optionally, to a second polynucleotide encoding a signal sequence (N- or C-terminal) which directs the enzyme encoded by the first polynucleotide to a particular cellular or subcellular location. Thus, a promoter and one or more signal sequences can provide for high levels of expression of the enzyme in particular locations in a plant, plant tissue or plant cell. Promoters can be constitutive promoters, inducible (conditional) promoters or tissue-specific promoters, e.g., endosperm-specific promoters such as the maize γ-zein promoter (exemplified by SEQ ID NO:12) or the maize ADP-gpp promoter (exemplified by SEQ ID NO:11, which includes a 5' untranslated and an intron sequence). The invention also provides an isolated polynucleotide comprising a promoter comprising SEQ ID NO:11 or 12, a polynucleotide which hybridizes to the complement thereof under low stringency hybridization conditions, or a fragment thereof which has promoter activity, e.g., at least 10%, and preferably at least 50%, the activity of a promoter having SEQ ID NO:11 or 12. Also provided are vectors which comprise the expression cassette or polynucleotide of the invention and transformed cells comprising the polynucleotide, expression cassette or vector of the invention. A vector of the invention can comprise a polynucleotide sequence which encodes more than one hyperthermophilic processing enzyme of the invention, which sequence can be in sense or antisense orientation, and a transformed cell may comprise one or more vectors of the invention. Preferred vectors are those useful to introduce nucleic acids into plant cells.

Transformation

The expression cassette, or a vector construct containing the expression cassette may be inserted into a cell. The expression cassette or vector construct may be carried episomally or integrated into the genome of the cell. The transformed cell may then be grown into a transgenic plant. Accordingly, the invention provides the products of the transgenic plant. Such products may include, but are not limited to, the seeds, fruit, progeny, and products of the progeny of the transgenic plant.

A variety of techniques are available and known to those skilled in the art for introduction of constructs into a cellular host. Transformation of bacteria and many eukaryotic cells may be accomplished through use of polyethylene glycol, calcium chloride, viral infection, phage infection, electroporation and other methods known in the art. Techniques for transforming plant cells or tissue include transformation with DNA employing *A. tumefaciens* or *A. rhizogenes* as the transforming agent, electroporation, DNA injection, microprojectile bombardment, particle acceleration, etc. (See, for example, EP 295959 and EP 138341).

In one embodiment, binary type vectors of Ti and Ri plasmids of *Agrobacterium* spp. Ti-derived vectors are used to transform a wide variety of higher plants, including monocotyledonous and dicotyledonous plants, such as soybean, cotton, rape, tobacco, and rice (Pacciotti et al. *Bio/Technology*, 3:241 (1985): Byrne et al. *Plant Cell Tissue and Organ Culture*, 8:3 (1987); Sukhapinda et al. *Plant Mol. Biol.*, 8:209 (1987); Lorz et al. *Mol. Gen. Genet.*, 199:178 (1985); Potrykus *Mol. Gen. Genet.*, 199:183 (1985); Park et al., *J. Plant Biol.*, 38:365 (1985): Hiei et al., *Plant J.*, 6:271 (1994)). The use of T-DNA to transform plant cells has received extensive study and is amply described (EP 120516; Hoekema, In: *The Binary Plant Vector System*. Offset-drukkerij Kanters B. V.; Alblasserdam (1985), Chapter V; Knauf, et al., Genetic Analysis of Host Range Expression by *Agrobacterium* In: *Molecular Genetics of the Bacteria-Plant Interaction*, Puhler, A. ed., Springer-Verlag, New York, 1983, p. 245; and An. et al., *EMBO J.*, 4:277 (1985)).

Other transformation methods are available to those skilled in the art, such as direct uptake of foreign DNA constructs (see EP 295959), techniques of electroporation (Fromm et al. *Nature (London)*, 319:791 (1986), or high velocity ballistic bombardment with metal particles coated with the nucleic acid constructs (Kline et al. *Nature (London)* 327:70 (1987), and U.S. Pat. No. 4,945,050). Once transformed, the cells can be regenerated by those skilled in the art. Of particular relevance are the recently described methods to transform foreign genes into commercially important crops, such as rapeseed (De Block et al., *Plant Physiol.* 91:694-701 (1989)), sunflower (Everett et al., *Bio/Technology*, 5:1201 (987)), soybean (McCabe et al., *Bio/Technology*, 6:923 (1988); Hinchee et al., *Bio/Technology*, 6:915 (1988); Chee et al., *Plant Physiol.*, 91:1212 (1989); Christou et al., *Proc. Natl. Acad. Sci. USA*, 86:7500 (1989) EP 301749), rice (Hiei et al., *Plant J.*, 6:271 (1994)), and corn (Gordon Kamm et al., *Plant Cell*, 2:603 (1990); Fromm et al., *Biotechnology*, 8:833, (1990)).

Expression vectors containing genomic or synthetic fragments can be introduced into protoplasts or into intact tissues or isolated cells. Preferably expression vectors are introduced into intact tissue. General methods of culturing plant tissues are provided, for example, by Maki et al. "Procedures for Introducing Foreign DNA into Plants" in Methods in Plant Molecular Biology & Biotechnology, Glich et al. (Eds.), pp. 67-88 CRC Press (1993); and by Phillips et al. "Cell-Tissue Culture and In-Vitro Manipulation" in Corn & Corn Improvement, 3rd Edition 10, Sprague et al. (Eds.) pp. 345-387, American Society of Agronomy Inc. (1988).

In one embodiment, expression vectors may be introduced into maize or other plant tissues using a direct gene transfer method such as microprojectile-mediated delivery, DNA injection, electroporation and the like. Expression vectors are introduced into plant tissues using the microprojectile media delivery with the biolistic device. See, for example, Tomes et al. "Direct DNA transfer into intact plant cells via microprojectile bombardment" in Gamborg and Phillips (Eds.) Plant Cell, Tissue and Organ Culture: Fundamental Methods, Springer Verlag, Berlin (1995). Nevertheless, the present invention contemplates the transformation of plants with a hyperthermophilic processing enzyme in accord with known transforming methods. Also see, Weissinger et al., *Annual Rev. Genet.*, 22:421 (1988); Sanford et al., *Particulate Science and Technology*, 5:27 (1987) (onion); Christou et al., *Plant Physiol.*, 87:671 (1988)(soybean); McCabe et al., *Bio/Technology*, 6:923 (1988) (soybean); Datta et al., *Bio/Technology*, 8:736 (1990) (rice); Klein et al., *Proc. Natl. Acad. Sci. USA*, 85:4305 (1988)(maize); Klein et al., *Bio/Technology*, 6:559 (1988)(maize); Klein et al., *Plant Physiol.*, 91:440 (1988)(maize); Fromm et al., *Bio/Technology*, 8:833 (1990) (maize); and Gordon-Kamm et al., *Plant Cell*, 2, 603 (1990) (maize); Svab et al., *Proc. Natl. Acad. Sci. USA*, 87:8526 (1990) (tobacco chloroplast); Koziel et al., *Biotechnology*, 11:194 (1993) (maize); Shimamoto et al., *Nature*, 338:274 (1989) (rice); Christou et al., *Biotechnology*, 2:957 (1991) (rice); European Patent Application EP 0 332 581 (orchardgrass and other Pooideae); Vasil et al., *Biotechnology*, 11:1553 (1993) (wheat); Weeks et al., *Plant Physiol.*, 102: 1077 (1993) (wheat). Methods in Molecular Biology, 82. *Arabidopsis* Protocols Ed. Martinez-Zapater and Salinas 1998 Humana Press (*Arabidopsis*).

Transformation of plants can be undertaken with a single DNA molecule or multiple DNA molecules (i.e., co-transformation), and both these techniques are suitable for use with the expression cassettes and constructs of the present invention. Numerous transformation vectors are available for plant transformation, and the expression cassettes of this invention can be used in conjunction with any such vectors. The selection of vector will depend upon the preferred transformation technique and the target species for transformation.

Ultimately, the most desirable DNA segments for introduction into a monocot genome may be homologous genes or gene families which encode a desired trait (e.g., hydrolysis of proteins, lipids or polysaccharides) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the targeting of a gene in a constitutive manner or in an inducible manner.

Examples of Suitable Transformation Vectors

Numerous transformation vectors available for plant transformation are known to those of ordinary skill in the plant transformation arts, and the genes pertinent to this invention can be used in conjunction with any such vectors known in the art. The selection of vector will depend upon the preferred transformation technique and the target species for transformation.

a. Vectors Suitable for *Agrobacterium* Transformation

Many vectors are available for transformation using *Agrobacterium tumefaciens*. These typically carry at least one T-DNA border sequence and include vectors such as pBIN19 (Bevan, *Nucl. Acids Res.* (1984)). Below, the construction of two typical vectors suitable for *Agrobacterium* transformation is described.

pCIB200 and pCIB2001

The binary vectors pcIB200 and pCIB2001 are used for the construction of recombinant vectors for use with *Agrobacterium* and are constructed in the following manner. pTJS75kan is created by NarI digestion of pTJS75 (Schmidhauser & Helinski, *J. Bacteriol.*, 164: 446 (1985)) allowing excision of the tetracycline-resistance gene, followed by insertion of an AccI fragment from pUC4K carrying an NPTII (Messing & Vierra, *Gene*, 19: 259 (1982): Bevan et al., *Nature*, 304: 184 (1983): McBride et al., *Plant Molecular Biology*, 14: 266 (1990)). XhoI linkers are ligated to the EcoRV fragment of PCIB7 which contains the left and right T-DNA borders, a plant selectable nos/nptII chimeric gene and the pUC polylinker (Rothstein et al., *Gene*, 53: 153 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

pCIB10 and Hygromycin Selection Derivatives Thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (*Gene,* 53: 153 (1987)). Various derivatives of pCIB10 are constructed which incorporate the gene for hygromycin B phosphotransferase described by Gritz et al. (*Gene,* 25: 179 (1983)). These derivatives enable selection of transgenic plant cells on hygromycin only (pCIB743), or hygromycin and kanamycin (pCIB715, pCIB717).

b. Vectors Suitable for Non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g., PEG and electroporation) and microinjection. The choice of vector depends largely on the preferred selection for the species being transformed. Non-limiting examples of the construction of typical vectors suitable for non-*Agrobacterium* transformation is further described.

pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 may be obtained from the John Innes Centre, Norwich and the a 400 bp SmaI fragment containing the bar gene from *Streptomyces viridochromogenes* is excised and inserted into the HpaI site of pCIB3060 (Thompson et al., *EMBO J,* 6: 2519 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

pSOG19 and pSOG35:

The plasmid pSOG35 is a transformation vector that utilizes the *E. coli* gene dihydrofolate reductase (DHFR) as a selectable marker conferring resistance to methotrexate. PCR is used to amplify the 35S promoter (−800 bp), intron 6 from the maize Adh1 gene (−550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

c. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Plant Hosts Subject to Transformation Methods

Any plant tissue capable of subsequent clonal propagation, whether by organogenesis or embryogenesis, may be transformed with a construct of the present invention. The term organogenesis means a process by which shoots and roots are developed sequentially from meristematic centers while the term embryogenesis means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include differentiated and undifferentiated tissues or plants, including but not limited to leaf disks, roots, stems, shoots, leaves, pollen, seeds, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem), tumor tissue, and various forms of cells and culture such as single cells, protoplast, embryos, and callus tissue. The plant tissue may be in plants or in organ, tissue or cell culture.

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

The present invention may be used for transformation of any plant species, including monocots or dicots, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, woody plants such as conifers and deciduous trees, squash, pumpkin, hemp, zucchini, apple, pear, quince, melon, plum, cherry, peach, nectarine, apricot, strawberry, grape, raspberry, blackberry, soybean, sorghum, sugarcane, rapeseed, clover, carrot, and *Arabidopsis thaliana*.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), cauliflower, broccoli, turnip, radish, spinach, asparagus, onion, garlic, pepper, celery, and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Leguminous plants include beans and peas. Beans include guar, locust bean, fenugreek, soybean, garden beans, cowpea, mungbean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, *Lotus*, e.g., trefoil, lens, e.g., lentil, and false indigo. Preferred forage and turf grass for use in the methods of the invention include alfalfa, orchard grass, tall fescue, perennial ryegrass, creeping bent grass, and redtop.

Preferably, plants of the present invention include crop plants, for example, corn, alfalfa, sunflower, *Brassica*, soybean, cotton, safflower, peanut, sorghum, wheat, millet, tobacco, barley, rice, tomato, potato, squash, melons, legume crops, etc. Other preferred plants include Liliopsida and Panicoideae.

Once a desired DNA sequence has been transformed into a particular plant species, it may be propagated in that species or moved into other varieties of the same species, particularly including commercial varieties, using traditional breeding techniques.

Below are descriptions of representative techniques for transforming both dicotyledonous and monocotyledonous plants, as well as a representative plastid transformation technique.

a. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J.* 3: 2717 (1984), Potrykus et al., *Mol. Gen. Genet.*, 199: 169 (1985), Reich et al., *Biotechnology*, 4: 1001 (1986), and Klein et al., *Nature*, 327: 70 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend on the complement of vir genes carried by the host *Agrobacterium* strain either on a co-resident Ti plasmid or chromosomally (e.g., strain CIB542 for pCIB200 and pCIB2001 (Uknes et al., *Plant Cell*, 5: 159 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, *Nucl. Acids Res.*, 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

The vectors may be introduced to plant cells in known ways. Preferred cells for transformation include *Agrobacterium*, monocot cells and dicots cells, including Liliopsida cells and Panicoideae cells. Preferred monocot cells are cereal cells, e.g., maize (corn), barley, and wheat, and starch accumulating dicot cells, e.g., potato.

Another approach to transforming a plant cell with a gene involves propelling inert or biologically active particles at plant tissues and cells. This technique is disclosed in U.S. Pat. Nos. 4,945,050, 5,036,006, and 5,100,792. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

b. Transformation of Monocotyledons

Transformation of most monocotyledon species has now also become routine. Preferred techniques include direct gene transfer into protoplasts using polyethylene glycol (PEG) or electroporation techniques, and particle bombardment into callus tissue. Transformations can be undertaken with a single DNA species or multiple DNA species (i.e., co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., *Biotechnology*, 4: 1093 1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (*Plant Cell*, 2: 603 (1990)) and Fromm et al. (*Biotechnology*, 8: 833 (1990)) have published techniques for transformation of A188-derived maize line using particle bombardment. Furthermore, WO 93/07278 and Koziel et al. (*Biotechnology*, 11: 194 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for *Japonica*-types and *Indica*-types (Zhang et al., *Plant Cell Rep*, 7: 379 (1988); Shimamoto et al., *Nature*, 338: 274 (1989); Datta et al., *Biotechnology*, 8: 736 (1990)). Both types are also routinely transformable using particle bombardment (Christou et al., *Biotechnology*, 9: 957 (1991)). Furthermore, WO 93/21335 describes techniques for the transformation of rice via electroporation. Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (*Biotechnology*, 10: 667 (1992)) using particle bombardment into cells of type C long-term regenerable callus, and also by Vasil et al. (*Biotechnology*, 11: 1553 (1993)) and Weeks et al. (*Plant Physiol.*, 102: 1077 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige & Skoog, *Physiologia Plantarum*, 15: 473 (1962)) and 3 mg/l 2,4-D for induction of somatic embryos, which is allowed to proceed in the dark. On the chosen day of bombardment, embryos are removed from the induction medium and placed onto the osmoticum (i.e., induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of about 1000 psi using a standard 80 mesh screen. After bombardment, the embryos are placed back into the dark to recover for about 24 hours (still on osmoticum). After 24 hours, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference.

c. Transformation of Plastids

Seeds of *Nicotiana tabacum* c.v. 'Xanthi nc' are germinated seven per plate in a 1" circular array on T agar medium and bombarded 12-14 days after sowing with 1 μm tungsten particles (M10, Biorad, Hercules, Calif.) coated with DNA from plasmids pPH143 and pPH145 essentially as described (Svab and Maliga, *PNAS* 90:913 (1993)). Bombarded seedlings are incubated on T medium for two days after which leaves are excised and placed abaxial side up in bright light (350-500 μmol photons/m$^2$/s) on plates of RMOP medium (Svab, Hajdukiewicz and Maliga, *PNAS*, 87:8526 (1990)) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., *Molecular Cloning: A Laboratory Manual*, Cold Spring Harbor Laboratory, Cold Spring Harbor (1989)). BamHI/EcoRI-digested total cellular DNA (Mettler, I. *J. Plant Mol Biol Reporter*, 5:346 (1987)) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride et al., *PNAS*, 91:7301 (1994)) and transferred to the greenhouse.

Production and Characterization of Stably Transformed Plants

Transformed plant cells are then placed in an appropriate selective medium for selection of transgenic cells, which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA which has been introduced. Components of DNA constructs, including transcription/expression cassettes of this invention, may be prepared from sequences, which are native (endogenous) or foreign (exogenous) to the host. By "foreign" it is meant that the sequence is not found in the wild-type host into which the construct is introduced. Heterologous constructs will contain at least one region, which is not native to the gene from which the transcription-initiation-region is derived.

To confirm the presence of the transgenes in transgenic cells and plants, a Southern blot analysis can be performed using methods known to those skilled in the art. Integration of a polynucleic acid segment into the genome can be detected and quantitated by Southern blot, since they can be readily distinguished from constructs containing the segments through use of appropriate restriction enzymes. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics.

The invention thus provides a transformed plant or plant part, such as an ear, seed, fruit, grain, stover, chaff, or bagasse comprising at least one polynucleotide, expression cassette or vector of the invention, methods of making such a plant and methods of using such a plant or a part thereof. The transformed plant or plant part expresses a processing enzyme, optionally localized in a particular cellular or subcellular compartment of a certain tissue or in developing grain. For instance, the invention provides a transformed plant part comprising at least one starch processing enzyme present in the cells of the plant, wherein the plant part is obtained from a transformed plant, the genome of which is augmented with an expression cassette encoding the at least one starch processing enzyme. The processing enzyme does not act on the target substrate unless activated by methods such as heating, grinding, or other methods, which allow the enzyme to contact the substrate under conditions where the enzyme is active Preferred Methods of the Present Invention The self-processing plants and plant parts of the present invention may be used in various methods employing the processing enzymes (mesophilic, thermophilic, or hyperthermophilic) expressed and activated therein. In accordance with the present invention, a transgenic plant part obtained from a transgenic plant the genome of which is augmented with at least one processing enzyme, is placed under conditions in which the processing enzyme is expressed and activated. Upon activation, the processing enzyme is activated and functions to act on the substrate in which it normally acts to obtained the desired result. For example, the starch-processing enzymes act upon starch to degrade, hydrolyze, isomerize, or otherwise modify to obtain the desired result upon activation. Non-starch processing enzymes may be used to disrupt the plant cell membrane in order to facilitate the extraction of starch, lipids, amino acids, or other products from the plants. Moreover, non-hyperthermophilic and hyperthermophilic enzymes may be used in combination in the self-processing plant or plant parts of the present invention. For example, a mesophilic non-starch degrading enzyme may be activated to disrupt the plant cell membrane for starch extraction, and subsequently, a hyperthermophilic starch-degrading enzyme may then be activated in the self-processing plant to degrade the starch.

Enzymes expressed in grain can be activated by placing the plant or plant part containing them in conditions in which their activity is promoted. For example, one or more of the following techniques may be used: The plant part may be contacted with water, which provides a substrate for a hydrolytic enzyme and thus will activate the enzyme. The plant part may be contacted with water which will allow enzyme to migrate from the compartment into which it was deposited during development of the plant part and thus to associate with its substrate. Movement of the enzyme is possible because compartmentalization is breached during maturation, drying of grain and re-hydration. The intact or cracked grain may be contacted with water which will allow enzyme to migrate from the compartment into which it was deposited during development of the plant part and thus to associate with its substrate. Enzymes can also be activated by addition of an activating compound. For example, a calcium-dependent enzyme can be activated by addition of calcium. Other activating compounds may determined by those skilled in the art. Enzymes can be activated by removal of an inactivator. For example, there are known peptide inhibitors of amylase enzymes, the amylase could be co-expressed with an amylase inhibitor and then activated by addition of a protease. Enzymes can be activated by alteration of pH to one at which the enzyme is most active. Enzymes can also be activated by increasing temperature. An enzyme generally increases in activity up to the maximal temperature for that enzyme. A mesophilic enzyme will increase in activity from the level of activity ambient temperature up to the temperature at which it loses activity which is typically less than or equal to 70° C. Similarly thermophilic and hyperthermophilic enzymes can also be activated by increasing temperature. Thermophilic enzymes can be activated by heating to temperatures up to the maximal temperature of activity or of stability. For a thermophilic enzyme the maximal temperatures of stability and activity will generally be between 70 and 85° C. Hyperthermophilic enzymes will have the even greater relative activation than mesophilic or thermophilic enzymes because of the greater potential change in temperature from 25° C. up to 85° C. to 95° C. or even 100° C. The increased temperature may be achieved by any method, for example by heating such as by baking, boiling, heating, steaming, electrical discharge or any combination thereof. Moreover, in plants expressing mesophilic or thermophilic enzyme(s), activation of the enzyme may be accomplished by grinding, thereby allowing the enzyme to contact the substrate.

The optimal conditions, e.g., temperature, hydration, pH, etc, may be determined by one having skill in the art and may depend upon the individual enzyme being employed and the desired application of the enzyme.

The present invention further provides for the use of exogenous enzymes that may assist in a particular process. For example, the use of a self-processing plant or plant part of the present invention may be used in combination with an exogenously provided enzyme to facilitate the reaction. As an example, transgenic α-amylase corn may be used in combination with other starch-processing enzymes, such as pullulanase, α-glucosidase, glucose isomerase, mannanases, hemicellulases, etc., to hydrolyze starch or produce ethanol. In fact, it has been found that combinations of the transgenic α-amylase corn with such enzymes has unexpectedly provided superior degrees of starch conversion relative to the use of transgenic α-amylase corn alone.

Example of suitable methods contemplated herein are provided.

a. Starch Extraction from Plants

The invention provides for a method of facilitating the extraction of starch from plants. In particular, at least one polynucleotide encoding a processing enzyme that disrupt the physically restraining matrix of the endosperm (cell walls, non-starch polysaccharide, and protein matrix) is introduced to a plant so that the enzyme is preferably in close physical proximity to starch granules in the plant. Preferably, in this embodiment of the invention, transformed plants express one or more protease, glucanase, xylanase, thioredoxin/thioredoxin reductase, esterase and the like, but not enzymes that have any starch degrading activity, so as to maintain the integrity of the starch granules. The expression of these enzymes in a plant part such as grain thus improves the process characteristics of grain. The processing enzyme may be mesophilic, thermophilic, or hyperthermophilic. In one example, grain from a transformed plant of the invention is heat dried, likely inactivating non-hyperthermophilic processing enzymes and improving seed integrity. Grain (or cracked grain) is steeped at low temperatures or high temperatures (where time is of the essence) with high or low moisture content or conditions (see Primary Cereal Processing, Gordon and Willm, eds., pp. 319-337 (1994), the disclosure of which is incorporated herein), with or without sulphur dioxide. Upon reaching elevated temperatures, optionally at certain moisture conditions, the integrity of the endosperm matrix is disrupted by activating the enzymes, e.g., proteases, xylanases, phytase or glucanases which degrade the proteins and non-starch polysaccharides present in the endosperm leaving the starch granule therein intact and more readily recoverable from the resulting material. Further, the proteins and non-starch polysaccharides in the effluent are at least partially degraded and highly concentrated, and so may be used for improved animal feed, food, or as media components for the fermentation of microorganisms. The effluent is considered a corn-steep liquor with improved composition.

Thus, the invention provides a method to prepare starch granules. The method comprises treating grain, for example cracked grain, which comprises at least one non-starch processing enzyme under conditions which activate the at least one enzyme, yielding a mixture comprising starch granules and non-starch degradation products, e.g., digested endosperm matrix products. The non-starch processing enzyme may be mesophilic, thermophilic, or hyperthermophilic. After activation of the enzyme, the starch granules are separated from the mixture. The grain is obtained from a transformed plant, the genome of which comprises (is augmented with) an expression cassette encoding the at least one processing enzyme. For example, the processing enzyme may be a protease, glucanase, xylanase, phytase, thiroredoxin/thioredoxin reductase, or esterase. Preferably, the processing enzyme is hyperthermophilic. The grain can be treated under low or high moisture conditions, in the presence or absence of sulfur dioxide. Depending on the activity and expression level of the processing enzyme in the grain from the transgenic plant, the transgenic grain may be mixed with commodity grain prior to or during processing. Also provided are products obtained by the method such as starch, non-starch products and improved steepwater comprising at least one additional component.

b. Starch-Processing Methods

Transformed plants or plant parts of the present invention may comprise starch-degrading enzymes as disclosed herein that degrade starch granules to dextrins, other modified starches, or hexoses (e.g., α-amylase, pullulanase, α-glucosidase, glucoamylase, amylopullulanase) or convert glucose into fructose (e.g., glucose isomerase). Preferably, the starch-degrading enzyme is selected from α-amylase, α-glucosidase, glucoamylase, pullulanase, neopullulanase, amylopullulanase, glucose isomerase, and combinations thereof is used to transform the grain. Moreover, preferably, the enzyme is operably linked to a promoter and to a signal sequence that targets the enzyme to the starch granule, an amyloplast, the apoplast, or the endoplasmic reticulum. Most preferably, the enzyme is expressed in the endosperm, and particularly, corn endosperm, and localized to one or more cellular compartments, or within the starch granule itself. The preferred plant part is grain. Preferred plant parts are those from corn, wheat, barley, rye, oat, sugar cane, or rice.

In accordance with one starch-degrading method of the present invention, the transformed grain accumulates the starch-degrading enzyme in starch granules, is steeped at conventional temperatures of 50° C.-60° C., and wet-milled as is known in the art. Preferably, the starch-degrading enzyme is hyperthermophilic. Because of sub-cellular targeting of the enzyme to the starch granule, or by virtue of the association of the enzyme with the starch granule, by contacting the enzyme and starch granule during the wet-milling process at the conventional temperatures, the processing enzyme is co-purified with the starch granules to obtain the starch granules/enzyme mixture. Subsequent to the recovery of the starch granules/enzyme mixture, the enzyme is then activated by providing favorable conditions for the activity of the enzyme. For example, the processing may be performed in various conditions of moisture and/or temperature to facilitate the partial (in order to make derivatized starches or dextrins) or complete hydrolysis of the starch into hexoses. Syrups containing high dextrose or fructose equivalents are obtained in this manner. This method effectively reduces the time, energy, and enzyme costs and the efficiency with which starch is converted to the corresponding hexose, and the efficiency of the production of products, like high sugar steepwater and higher dextrose equivalent syrups, are increased.

In another embodiment, a plant, or a product of the plant such as a fruit or grain, or flour made from the grain that expresses the enzyme is treated to activate the enzyme and convert polysaccharides expressed and contained within the plant into sugars. Preferably, the enzyme is fused to a signal sequence that targets the enzyme to a starch granule, an amyloplast, the apoplast or to the endoplasmic reticulum as disclosed herein. The sugar produced may then be isolated or recovered from the plant or the product of the plant. In another embodiment, a processing enzyme able to convert polysaccharides into sugars is placed under the control of an inducible promoter according to methods known in the art and disclosed herein. The processing enzyme may be mesophilic, thermophilic or hyperthermophilic. The plant is grown to a desired stage and the promoter is induced causing expression of the enzyme and conversion of the polysaccharides, within the plant or product of the plant, to sugars. Preferably the enzyme is operably linked to a signal sequence that targets the enzyme to a starch granule, an amyloplast, an apoplast or to the endoplasmic reticulum. In another embodiment, a transformed plant is produced that expresses a processing enzyme able to convert starch into sugar. The enzyme is fused to a signal sequence that targets the enzyme to a starch granule within the plant. Starch is then isolated from the transformed plant that contains the enzyme expressed by the transformed plant. The enzyme contained in the isolated starch may then be activated to convert the starch into sugar. The enzyme may be mesophilic, thermophilic, or hyperthermophilic. Examples of hyperthermophilic enzymes able to convert starch to sugar are provided herein. The methods may be used with any plant which produces a polysaccharide and that can express an enzyme able to convert a polysaccharide into sugars or hydrolyzed starch product such as dextrin, maltooligosaccharide, glucose and/or mixtures thereof.

The invention provides a method to produce dextrins and altered starches from a plant, or a product from a plant, that has been transformed with a processing enzyme which hydrolyses certain covalent bonds of a polysaccharide to form a polysaccharide derivative. In one embodiment, a plant, or a product of the plant such as a fruit or grain, or flour made from the grain that expresses the enzyme is placed under conditions sufficient to activate the enzyme and convert polysaccharides contained within the plant into polysaccharides of reduced molecular weight. Preferably, the enzyme is fused to a signal sequence that targets the enzyme to a starch granule, an amyloplast, the apoplast or to the endoplasmic reticulum as disclosed herein. The dextrin or derivative starch produced may then be isolated or recovered from the plant or the product of the plant. In another embodiment, a processing enzyme able to convert polysaccharides into dextrins or altered starches is placed under the control of an inducible promoter according to methods known in the art and disclosed herein. The plant is grown to a desired stage and the promoter is induced causing expression of the enzyme and conversion of the polysaccharides, within the plant or product of the plant, to dextrins or altered starches. Preferably the enzyme is α-amylase, pullulanase, iso or neo-pullulanase and is operably linked to a signal sequence that targets the enzyme to a starch granule, an amyloplast, the apoplast or to the endoplasmic reticulum. In one embodiment, the enzyme is targeted to the apoplast or to the endoreticulum. In yet another embodiment, a transformed plant is produced that expresses an enzyme able to convert starch into dextrins or altered starches. The enzyme is fused to a signal sequence that targets the enzyme to a starch granule within the plant. Starch is then isolated from the transformed plant that contains the enzyme expressed by the transformed plant. The enzyme contained in the isolated starch may then be activated under conditions sufficient for activation to convert the starch into dextrins or altered starches. Examples of hyperthermophilic enzymes, for example, able to convert starch to hydrolyzed starch products are provided herein. The methods may be used with any plant which produces a polysaccharide and that can express an enzyme able to convert a polysaccharide into sugar.

In another embodiment, grain from transformed plants of the invention that accumulate starch-degrading enzymes that degrade linkages in starch granules to dextrins, modified starches or hexose (e.g., α-amylase, pullulanase, α-glucosidase, glucoamylase, amylopullulanase) is steeped under conditions favoring the activity of the starch degrading enzyme for various periods of time. The resulting mixture may contain high levels of the starch-derived product. The use of such grain: 1) eliminates the need to mill the grain, or otherwise process the grain to first obtain starch granules, 2) makes the starch more accessible to enzymes by virtue of placing the enzymes directly within the endosperm tissue of the grain, and 3) eliminates the need for microbially produced starch-hydrolyzing enzymes. Thus, the entire process of wet-milling prior to hexose recovery is eliminated by simply heating grain, preferably corn grain, in the presence of water to allow the enzymes to act on the starch.

This process can also be employed for the production of ethanol, high fructose syrups, hexose (glucose) containing fermentation media, or any other use of starch that does not require the refinement of grain components.

The invention further provides a method of preparing dextrin, maltooligosaccharides, and/or sugar involving treating a plant part comprising starch granules and at least one starch processing enzyme under conditions so as to activate the at least one enzyme thereby digesting starch granules to form an aqueous solution comprising sugars. The plant part is obtained from a transformed plant, the genome of which is augmented with an expression cassette encoding the at least one processing enzyme. The aqueous solution comprising dextrins, maltooligosaccharides, and/or sugar is then collected. In one embodiment, the processing enzyme is α-amylase, α-glucosidase, pullulanase, glucoamylase, amylopullulanase, glucose isomerase, or any combination thereof. Preferably, the enzyme is hyperthermophilic. In another embodiment, the method further comprises isolating the dextrins, maltooligosaccharides, and/or sugar.

c. Improved Corn Varieties

The invention also provides for the production of improved corn varieties (and varieties of other crops) that have normal levels of starch accumulation, and accumulate sufficient levels of amylolytic enzyme(s) in their endosperm, or starch accumulating organ, such that upon activation of the enzyme contained therein, such as by boiling or heating the plant or a part thereof in the case of a hyperthermophilic enzyme, the enzyme(s) is activated and facilitates the rapid conversion of the starch into simple sugars. These simple sugars (primarily glucose) will provide sweetness to the treated corn. The resulting corn plant is an improved variety for dual use as a grain producing hybrid and as sweet corn. Thus, the invention provides a method to produce hyper-sweet corn, comprising treating transformed corn or a part thereof, the genome of which is augmented with and expresses in endosperm an expression cassette comprising a promoter operably linked to a first polynucleotide encoding at least one amylolytic enzyme, conditions which activate the at least one enzyme so as to convert polysaccharides in the corn into sugar, yielding hypersweet corn. The promoter may be a constitutive promoter, a seed-specific promoter, or an endosperm-specific promoter which is linked to a polynucleotide sequence which encodes a processing enzyme such as α-amylase, e.g., one comprising SEQ ID NO: 13, 14, or 16. Preferably, the enzyme is hyperthermophilic. In one embodiment, the expression cassette further comprises a second polynucleotide which encodes a signal sequence operably linked to the enzyme encoded by the first polynucleotide. Exemplary signal sequences in this embodiment of the invention direct the enzyme to apoplast, the endoplasmic reticulum, a starch granule, or to an amyloplast. The corn plant is grown such that the ears with kernels are formed and then the promoter is induced to cause the enzyme to be expressed and convert polysaccharide contained within the plant into sugar.

d. Self-Fermenting Plants

In another embodiment of the invention, plants, such as corn, rice, wheat, or sugar cane are engineered to accumulate large quantities of processing enzymes in their cell walls, e.g., xylanases, cellulases, hemicellulases, glucanases, pectinases and the like (non-starch polysaccharide degrading enzymes). Following the harvesting of the grain component (or sugar in the case of sugar cane), the stover, chaff, or bagasse is used as a source of the enzyme, which was targeted for expression and accumulation in the cell walls, and as a source of biomass. The stover (or other left-over tissue) is used as a feedstock in a process to recover fermentable sugars. The process of obtaining the fermentable sugars consists of activating the non-starch polysaccharide degrading enzyme. For example, activation may comprise heating the plant tissue in the presence of water for periods of time adequate for the hydrolysis of the non-starch polysaccharide into the resulting sugars. Thus, this self-processing stover produces the enzymes required for conversion of polysaccharides into monosaccharides, essentially at no incremental cost as they are a component of the feedstock. Further, the temperature-dependent enzymes have no detrimental effects on plant growth and development, and cell wall targeting, even targeting into polysaccharide microfibrils by virtue of cellulose/xylose binding domains fused to the protein, improves the accessibility of the substrate to the enzyme.

Thus, the invention also provides a method of using a transformed plant part comprising at least one non-starch polysaccharide processing enzyme in the cell wall of the cells of the plant part. The method comprises treating a transformed plant part comprising at least one non-starch polysaccharide processing enzyme under conditions which activate the at least one enzyme thereby digesting starch granules to form an aqueous solution comprising sugars, wherein the plant part is obtained from a transformed plant, the genome of which is augmented with an expression cassette encoding the at least one non-starch polysaccharide processing enzyme; and collecting the aqueous solution comprising the sugars. The invention also includes a transformed plant or plant part comprising at least one non-starch polysaccharide processing enzyme present in the cell or cell wall of the cells of the plant or plant part. The plant part is obtained from a transformed plant, the genome of which is augmented with an expression cassette encoding the at least one non-starch processing enzyme, e.g., a xylanase, a cellulase, a glucanase, a pectinase, or any combination thereof.

e. Aqueous Phase High in Protein and Sugar Content

In yet another embodiment, proteases and lipases are engineered to accumulate in seeds, e.g., soybean seeds. After activation of the protease or lipase, such as, for example, by heating, these enzymes in the seeds hydrolyze the lipid and storage proteins present in soybeans during processing. Soluble products comprising amino acids, which can be used as feed, food or fermentation media, and fatty acids, can thus be obtained. Polysaccharides are typically found in the insoluble fraction of processed grain. However, by combining polysaccharide degrading enzyme expression and accumulation in seeds, proteins and polysaccharides can be hydrolyzed and are found in the aqueous phase. For example, zeins from corn and storage protein and non-starch polysaccharides from soybean can be solubilized in this manner. Components of the aqueous and hydrophobic phases can be easily separated by extraction with organic solvent or supercritical carbon dioxide. Thus, what is provided is a method for producing an aqueous extract of grain that contains higher levels of protein, amino acids, sugars or saccharides.

f. Self-Processing Fermentation

The invention provides a method to produce ethanol, a fermented beverage, or other fermentation-derived product(s). The method involves obtaining a plant, or the product or part of a plant, or plant derivative such as grain flour, wherein a processing enzyme that converts polysaccharides into sugar is expressed. The plant, or product thereof, is treated such that sugar is produced by conversion of the polysaccharide as described above. The sugars and other components of the plant are then fermented to form ethanol or a fermented beverage, or other fermentation-derived products, according to methods known in the art. See, for example, U.S. Pat. No. 4,929,452. Briefly the sugar produced by conversion of polysaccharides is incubated with yeast under conditions that promote conversion of the sugar into ethanol. A suitable yeast includes high alcohol-tolerant and high-sugar tolerant strains of yeast, such as, for example, the yeast, *S. cerevisiae* ATCC No. 20867. This strain was deposited with the American Type Culture Collection, Rockville, Md., on Sep. 17, 1987 and assigned ATCC No. 20867. The fermented product or fermented beverage may then be distilled to isolate ethanol or a distilled beverage, or the fermentation product otherwise recovered. The plant used in this method may be any plant that contains a polysaccharide and is able to express an enzyme of the invention. Many such plants are disclosed herein. Preferably the plant is one that is grown commercially. More preferably the plant is one that is normally used to produce ethanol or fermented beverages, or fermented products, such as, for example, wheat, barley, corn, rye, potato, grapes or rice. Most preferably the plant is corn.

The method comprises treating a plant part comprising at least one polysaccharide processing enzyme under conditions to activate the at least one enzyme thereby digesting polysaccharide in the plant part to form fermentable sugar. The polysaccharide processing enzyme may be mesophilic, thermophilic, or hyperthermophilic. Preferably, the enzyme is hyperthermophilic. The plant part is obtained from a transformed plant, the genome of which is augmented with an expression cassette encoding the at least one polysaccharide processing enzyme. Plant parts for this embodiment of the invention include, but are not limited to, grain, fruit, seed, stalk, wood, vegetable or root. Preferred plants include but are not limited to oat, barley, wheat, berry, grape, rye, corn, rice, potato, sugar beet, sugar cane, pineapple, grass and tree. The plant part may be combined with commodity grain or other commercially available substrates; the source of the substrate for processing may be a source other than the self-processing plant. The fermentable sugar is then incubated under conditions that promote the conversion of the fermentable sugar into ethanol, e.g., with yeast and/or other microbes. In a preferred embodiment, the plant part is derived from corn transformed with α-amylase, which has been found to reduce the amount of time and cost of fermentation.

It has been found that the amount of residual starch is reduced when transgenic corn made in accordance with the present invention expressing a thermostable α-amylase, for example, is used in fermentation. This indicates that more starch is solubilized during fermentation. The reduced amount of residual starch results in the distillers' grains having higher protein content by weight and higher value. Moreover, the fermentation of the transgenic corn of the present invention allows the liquefaction process to be performed at a lower pH, resulting in savings in the cost of chemicals used to adjust the pH, at a higher temperature, e.g., greater than 85° C., preferably, greater than 90° C., more preferably, 95° C. or higher, resulting in shorter liquefaction times and more complete solubilization of starch, and reduction of liquefaction times, all resulting in efficient fermentation reactions with higher yields of ethanol.

Moreover, it has been found that contacting conventional plant parts with even a small portion of the transgenic plant made in accordance with the present invention may reduce the fermentation time and costs associated therewith. As such, the present invention relates to the reduction in the fermentation time for plants comprising subjecting a transgenic plant part from a plant comprising a polysaccharide processing enzyme that converts polysaccharides into sugar relative to the use of a plant part not comprising the polysaccharide processing enzyme.

g. Raw Starch Processing Enzymes and Polynucleotides Encoding them

A polynucleotide encoding a mesophilic processing enzyme(s) is introduced into a plant or plant part. In a preferred embodiment, the polynucleotide of the present invention is a maize-optimized polynucleotide such as provided in SEQ ID NOs: 48, 50, and 59, encoding a glucoamylase, such as provided in SEQ ID NOs: 47, and 49. In another preferred embodiment, the polynucleotide of the present invention is a maize-optimized polynucleotide such as provided in SEQ ID NO: 52, encoding an alpha-amylase, such as provided in SEQ ID NO: 51. Moreover, fusion products of processing enzymes is further contemplated. In one preferred embodiment, the polynucleotide of the present invention is a maize-optimized polynucleotide such as provided in SEQ ID NO: 46, encoding an alpha-amylase and glucoamylase fusion, such as provided in SEQ ID NO: 45. Combinations of processing enzymes are further envisioned by the present invention. For example, a combination of starch-processing enzymes and non-starch processing enzymes is contemplated herein. Such combinations of processing enzymes may be obtained by employing the use of multiple gene constructs encoding each of the enzymes. Alternatively, the individual transgenic plants stably transformed with the enzymes may be crossed by known methods to obtain a plant containing both enzymes. Another method includes the use of exogenous enzyme(s) with the transgenic plant.

The source of the starch-processing and non-starch processing enzymes may be isolated or derived from any source and the polynucleotides corresponding thereto may be ascertained by one having skill in the art. Preferably, the α-amylase is derived from *Aspergillus* (e.g., *Aspergillus shirousami* and *Aspergillus niger*), *Rhizopus* (eg., *Rhizopus oryzae*), and plants such as corn, barley, and rice. Preferably the glucoamylase is derived from *Aspergillus* (e.g., *Aspergillus shirousami* and *Aspergillus niger*), *Rhizopus* (eg., *Rhizopus oryzae*), and *Thermoanaerobacter* (eg., *Thermoanaerobacter thermosaccharolyticum*).

In another embodiment of the invention, the polynucleotide encodes a mesophilic starch-processing enzyme that is operably linked to a maize-optimized polynucleotide such as provided in SEQ ID NO: 54, encoding a raw starch binding domain, such as provided in SEQ ID NO: 53.

In another embodiment, a tissue-specific promoter includes the endosperm-specific promoters such as the maize γ-zein promoter (exemplified by SEQ ID NO:12) or the maize ADP-gpp promoter (exemplified by SEQ ID NO:11, which includes a 5' untranslated and an intron sequence). Thus, the present invention includes an isolated polynucleotide comprising a promoter comprising SEQ ID NO:11 or 12, a polynucleotide which hybridizes to the complement thereof under low stringency hybridization conditions, or a fragment thereof which has promoter activity, e.g., at least 10%, and preferably at least 50%, the activity of a promoter having SEQ ID NO:11 or 12.

In one embodiment, the product from a starch-hydrolysis gene, such as α-amylase, glucoamylase, or α-amylase/glucoamylase fusion may be targeted to a particular organelle or location such as the endoplasmic reticulum or apoplast, rather than to the cytoplasm. This is exemplified by the use of the maize γ-zein N-terminal signal sequence (SEQ ID NO:17), which confers apoplast-specific targeting of proteins, and the use of the γ-zein N-terminal signal sequence (SEQ ID NO:17) which is operably linked to the processing enzyme that is operably linked to the sequence SEKDEL for retention in the endoplasmic-reticulum. Directing the protein or enzyme to a specific compartment will allow the enzyme to be localized in a manner that it will not come into contact with the substrate. In this manner the enzymatic action of the enzyme will not occur until the enzyme contacts its substrate. The enzyme can be contacted with its substrate by the process of milling (physical disruption of the cell integrity) and hydrating. For example, a mesophilic starch-hydrolyzing enzyme can be targeted to the apoplast or to the endoplasmic reticulum and will therefore not come into contact with starch granules in the amyloplast. Milling of the grain will disrupt the integrity of the grain and the starch hydrolyzing enzyme will then contact the starch granules. In this manner the potential negative effects of co-localization of an enzyme and its substrate can be circumvented.

h. Food Products without Added Sweetener

Also provided is a method to produce a sweetened farinaceous food product without adding additional sweetener. Examples of farinaceous products include, but are not limited to, breakfast food, ready to eat food, baked food, pasta and cereal products such as breakfast cereal. The method comprises treating a plant part comprising at least one starch processing enzyme under conditions which activate the starch processing enzyme, thereby processing starch granules in the plant part to sugars so as to form a sweetened product, e.g., relative to the product produced by processing starch granules from a plant part which does not comprise the hyperthermophilic enzyme. Preferably, the starch processing enzyme is hyperthermophilic and is activated by heating, such as by baking, boiling, heating, steaming, electrical discharge, or any combination thereof. The plant part is obtained from a transformed plant, for instance from transformed soybean, rye, oat, barley, wheat, corn, rice or sugar cane, the genome of which is augmented with an expression cassette encoding the at least one hyperthermophilic starch processing enzyme, e.g., α-amylase, α-glucosidase, glucoamylase, pullulanase, glucose isomerase, or any combination thereof. The sweetened product is then processed into a farinaceous food product. The invention also provides a farinaceous food product, e.g., a cereal food, a breakfast food, a ready to eat food, or a baked food, produced by the method. The farinaceous food product may be formed from the sweetened product and water, and may contain malt, flavorings, vitamins, minerals, coloring agents or any combination thereof.

The enzyme may be activated to convert polysaccharides contained within the plant material into sugar prior to inclusion of the plant material into the cereal product or during the processing of the cereal product. Accordingly, polysaccharides contained within the plant material may be converted into sugar by activating the material, such as by heating in the case of a hyperthermophilic enzyme, prior to inclusion in the farinaceous product. The plant material containing sugar produced by conversion of the polysaccharides is then added to the product to produce a sweetened product. Alternatively, the polysaccharides may be converted into sugars by the enzyme during the processing of the farinaceous product. Examples of processes used to make cereal products are well known in the art and include heating, baking, boiling and the like as described in U.S. Pat. Nos. 6,183,788; 6,159,530; 6,149,965; 4,988,521 and 5,368,870.

Briefly, dough may be prepared by blending various dry ingredients together with water and cooking to gelatinize the starchy components and to develop a cooked flavor. The cooked material can then be mechanically worked to form a cooked dough, such as cereal dough. The dry ingredients may include various additives such as sugars, starch, salt, vitamins, minerals, colorings, flavorings, salt and the like. In addition to water, various liquid ingredients such as corn (maize) or malt syrup can be added. The farinaceous material may include cereal grains, cut grains, grits or flours from wheat, rice, corn, oats, barley, rye, or other cereal grains and mixtures thereof from that a transformed plant of the invention. The dough may then be processed into a desired shape through a process such as extrusion or stamping and further cooked using means such as a James cooker, an oven or an electrical discharge device.

Further provided is a method to sweeten a starch containing product without adding sweetener. The method comprises treating starch comprising at least one starch processing enzyme conditions to activate the at least one enzyme thereby digesting the starch to form a sugar thereby forming a treated (sweetened) starch, e.g., relative to the product produced by treating starch which does not comprise the hyperthermophilic enzyme. The starch of the invention is obtained from a transformed plant, the genome of which is augmented with an expression cassette encoding the at least one processing enzyme. Preferred enzymes include α-amylase, α-glucosidase, glucoamylase, pullulanase, glucose isomerase, or any combination thereof. Preferably, the enzyme is hyperthermophilic and is activated with heat. Preferred transformed plants include corn, soybean, rye, oat, barley, wheat, rice and sugar cane. The treated starch is then added to a product to produce a sweetened starch containing product, e.g., a farinaceous food product. Also provided is a sweetened starch containing product produced by the method.

The invention further provides a method to sweeten a polysaccharide containing fruit or vegetable comprising: treating a fruit or vegetable comprising at least one polysaccharide processing enzyme under conditions which activate the at least one enzyme, thereby processing the polysaccharide in the fruit or vegetable to form sugar, yielding a sweetened fruit or vegetable, e.g., relative to a fruit or vegetable from a plant which does not comprise the polysaccharide processing enzyme. The fruit or vegetable of the invention is obtained from a transformed plant, the genome of which is augmented with an expression cassette encoding the at least one polysaccharide processing enzyme. Preferred fruits and vegetables include potato, tomato, banana, squash, pea, and bean. Preferred enzymes include α-amylase, α-glucosidase, glucoamylase, pullulanase, glucose isomerase, or any combination thereof. Preferably, the enzyme is hyperthermophilic.

i. Sweetening a Polysaccharide Containing Plant or Plant Product

The method involves obtaining a plant that expresses a polysaccharide processing enzyme which converts a polysaccharide into a sugar as described above. Accordingly the enzyme is expressed in the plant and in the products of the plant, such as in a fruit or vegetable. In one embodiment, the enzyme is placed under the control of an inducible promoter such that expression of the enzyme may be induced by an external stimulus. Such inducible promoters and constructs are well known in the art and are described herein. Expression of the enzyme within the plant or product thereof causes polysaccharide contained within the plant or product thereof to be converted into sugar and to sweeten the plant or product thereof. In another embodiment, the polysaccharide processing enzyme is constitutively expressed. Thus, the plant or product thereof may be activated under conditions sufficient to activate the enzyme to convert the polysaccharides into sugar through the action of the enzyme to sweeten the plant or product thereof. As a result, this self-processing of the polysaccharide in the fruit or vegetable to form sugar yields a sweetened fruit or vegetable, e.g., relative to a fruit or vegetable from a plant which does not comprise the polysaccharide processing enzyme. The fruit or vegetable of the invention is obtained from a transformed plant, the genome of which is augmented with an expression cassette encoding the at least one polysaccharide processing enzyme. Preferred fruits and vegetables include potato, tomato, banana, squash, pea, and bean. Preferred enzymes include α-amylase, α-glucosidase, glucoamylase, pullulanase, glucose isomerase, or any combination thereof. Preferably, the polysaccharide processing enzyme is hyperthermophilic.

j. Isolation of Starch from Transformed Grain that Contains a Enzyme which Disrupts the Endosperm Matrix The invention provides a method to isolate starch from a transformed grain wherein an enzyme is expressed that disrupts the endosperm matrix. The method involves obtaining a plant that expresses an enzyme which disrupts the endosperm matrix by modification of, for example, cell walls, non-starch polysaccharides and/or proteins. Examples of such enzymes include, but are not limited to, proteases, glucanases, thioredoxin, thioredoxin reductase and esterase. Such enzymes do not include any enzyme that exhibits starch-degrading activity so as to maintain the integrity of the starch granules. Preferably the enzyme is fused to a signal sequence that targets the enzyme to the starch granule. In one embodiment the grain is heat dried to activate the enzyme and inactivate the endogenous enzymes contained within the grain. The heat treatment causes activation of the enzyme, which acts to disrupt the endosperm matrix which is then easily separated from the starch granules. In another embodiment, the grain is steeped at low or high temperature, with high or low moisture content, with or without sulfur dioxide. The grain is then heat treated to disrupt the endosperm matrix and allow for easy separation of the starch granules. In another embodiment, proper temperature and moisture conditions are created to allow proteases to enter into the starch granules and degrade proteins contained within the granules. Such treatment would produce starch granules with high yield and little contaminating protein.

k. Syrup Having a High Sugar Equivalent and Use of the Syrup to Produce Ethanol or a Fermented Beverage The method involves obtaining a plant that expresses a polysaccharide processing enzyme which converts a polysaccharide into a sugar as described above. The plant, or product thereof, is steeped in an aqueous stream under conditions where the expressed enzyme converts polysaccharide contained within the plant, or product thereof, into dextrin, maltooligosaccharide, and/or sugar. The aqueous stream containing the dextrin, maltooligosaccharide, and/or sugar produced through conversion of the polysaccharide is then separated to produce a syrup having a high sugar equivalent. The method may or may not include an additional step of wet-milling the plant or product thereof to obtain starch granules. Examples of enzymes that may be used within the method include, but are not limited to, α-amylase, glucoamylase, pullulanase and α-glucosidase. Preferably, the enzyme is hyperthermophilic. Sugars produced according to the method include, but are not limited to, hexose, glucose and fructose. Examples of plants that may be used with the method include, but are not limited to, corn, wheat or barley. Examples of products of a plant that may be used include, but are not limited to, fruit, grain and vegetables. In one embodiment, the polysaccharide processing enzyme is placed under the control of an inducible promoter. Accordingly, prior to or during the steeping process, the promoter is induced to cause expression of the enzyme, which then provides for the conversion of polysaccharide into sugar. Examples of inducible promoters and constructs containing them are well known in the art and are provided herein. Thus, where the polysaccharide processing is hyperthermophilic, the steeping is performed at a high temperature to activate the hyperthermophilic enzyme and inactivate endogenous enzymes found within the plant or product thereof. In another embodiment, a hyperthermophilic enzyme able to convert polysaccharide into sugar is constitutively expressed. This enzyme may or may not be targeted to a compartment within the plant through use of a signal sequence. The plant, or product thereof, is steeped under high temperature conditions to cause the conversion of polysaccharides contained within the plant into sugar.

Also provided is a method to produce ethanol or a fermented beverage from syrup having a high sugar equivalent. The method involves incubating the syrup with yeast under conditions that allow conversion of sugar contained within the syrup into ethanol or a fermented beverage. Examples of such fermented beverages include, but are not limited to, beer and wine. Fermentation conditions are well known in the art and are described in U.S. Pat. No. 4,929,452 and herein. Preferably the yeast is a high alcohol-tolerant and high-sugar tolerant strain of yeast such as *S. cerevisiae* ATCC No. 20867. The fermented product or fermented beverage may be distilled to isolate ethanol or a distilled beverage.

l. Accumulation of Hyperthermophilic Enzyme in the Cell Wall of a Plant

The invention provides a method to accumulate a hyperthermophilic enzyme in the cell wall of a plant. The method involves expressing within a plant a hyperthermophilic enzyme that is fused to a cell wall targeting signal such that the targeted enzyme accumulates in the cell wall. Preferably the enzyme is able to convert polysaccharides into monosaccharides. Examples of targeting sequences include, but are not limited to, a cellulose or xylose binding domain. Examples of hyperthermophilic enzymes include those listed in SEQ ID NO: 1, 3, 5, 10, 13, 14, 15 or 16. Plant material containing cell walls may be added as a source of desired enzymes in a process to recover sugars from the feedstock or as a source of enzymes for the conversion of polysaccharides originating from other sources to monosaccharides. Additionally, the cell walls may serve as a source from which enzymes may be purified. Methods to purify enzymes are well known in the art and include, but are not limited to, gel filtration, ion-exchange chromatography, chromatofocusing, isoelectric focusing, affinity chromatography, FPLC, HPLC, salt precipitation, dialysis, and the like. Accordingly, the invention also provides purified enzymes isolated from the cell walls of plants.

m. Method of Preparing and Isolating Processing Enzymes

In accordance with the present invention, recombinantly-produced processing enzymes of the present invention may be prepared by transforming plant tissue or plant cell comprising the processing enzyme of the present invention capable of being activated in the plant, selected for the transformed plant tissue or cell, growing the transformed plant tissue or cell into a transformed plant, and isolating the processing enzyme from the transformed plant or part thereof. Preferably, the recombinantly-produced enzyme is an α-amylase, glucoamylase, glucose isomerase, α-glucosidase, and pullulanase. Most preferably, the enzyme is encoded by the polynucleotide selected from any of SEQ ID NOS: 2, 4, 6, 9, 19, 21, 25, 37, 39, 41, 43, 46, 48, 50, 52, or 59.

The invention will be further described by the following examples, which are not intended to limit the scope of the invention in any manner.

EXAMPLES

Example 1

Construction of Maize-Optimized Genes for Hyperthermophilic Starch-Processing/Isomerization Enzymes The enzymes, α-amylase, pullulanase, α-glucosidase, and glucose isomerase, involved in starch degradation or glucose isomerization were selected for their desired activity profiles. These include, for example, minimal activity at ambient temperature, high temperature activity/stability, and activity at low pH. The corresponding genes were then designed by using maize preferred codons as described in U.S. Pat. No. 5,625,136 and synthesized by Integrated DNA Technologies, Inc. (Coralville, Iowa).

The 797GL3 α-amylase, having the amino acid sequence SEQ ID NO:1, was selected for its hyperthermophilic activity. This enzyme's nucleic acid sequence was deduced and maize-optimized as represented in SEQ ID NO:2. Similarly, the 6gp3 pullulanase was selected having the amino acid sequence set forth in SEQ ID NO:3. The nucleic acid sequence for the 6gp3 pullulanase was deduced and maize-optimized as represented in SEQ ID NO:4.

The amino acid sequence for malA α-glucosidase from *Sulfolobus solfataricus* was obtained from the literature, J. Bact. 177:482-485 (1995); J. Bact. 180:1287-1295 (1998). Based on the published amino acid sequence of the protein (SEQ ID NO:5), the maize-optimized synthetic gene (SEQ ID NO:6) encoding the malA α-glucosidase was designed.

Several glucose isomerase enzymes were selected. The amino acid sequence (SEQ ID NO:18) for glucose isomerase derived from *Themotoga maritima* was predicted based on the published DNA sequence having Accession No. NC_000853 and a maize-optimized synthetic gene was designed (SEQ ID NO: 19). Similarly the amino acid sequence (SEQ ID NO:20) for glucose isomerase derived from *Thermotoga neapolitana* was predicted based on the published DNA sequence from Appl. Envir. Microbiol. 61 (5):1867-1875 (1995), Accession No. L38994. A maize-optimized synthetic gene encoding the *Thermotoga neapolitana* glucose isomerase was designed (SEQ ID NO:21).

Example 2

Expression of Fusion of 797GL3 α-Amylase and Starch Encapsulating Region in *E. coli*

A construct encoding hyperthermophilic 797GL3 α-amylase fused to the starch encapsulating region (SER) from maize granule-bound starch synthase (waxy) was introduced and expressed in *E. coli*. The maize granule-bound starch synthase cDNA (SEQ ID NO:7) encoding the amino acid sequence (SEQ ID NO:8) (Klosgen R B, et al. 1986) was cloned as a source of a starch binding domain, or starch encapsulating region (SER). The full-length cDNA was amplified by RT-PCR from RNA prepared from maize seed using primers SV57 (5'AGCGAATTCATGGCGGCTCTG-GCCACGT 3') (SEQ ID NO: 22) and SV58 (5'AGCTAAGCTTCAGGGCGCGGCCACGTTCT 3') (SEQ ID NO: 23) designed from GenBank Accession No. X03935. The complete cDNA was cloned into pBluescript as an EcoRI/HindIII fragment and the plasmid designated pNOV4022.

The C-terminal portion (encoded by bp 919-1818) of the waxy cDNA, including the starch-binding domain, was amplified from pNOV4022 and fused in-frame to the 3' end of the full-length maize-optimized 797GL3 gene (SEQ ID NO:2). The fused gene product, 797GL3/Waxy, having the nucleic acid SEQ ID NO:9 and encoding the amino acid sequence, SEQ ID NO: 10, was cloned as an NcoI/XbaI fragment into pET28b (NOVAGEN, Madison, Wis.) that was cut with NcoI/NheI. The 797GL3 gene alone was also cloned into the pET28b vector as an NcoI/XbaI fragment.

The pET28/797GL3 and the pET28/797GL3/Waxy vectors were transformed into BL21/DE3 *E. coli* cells (NOVAGEN) and grown and induced according to the manufacturer's instruction. Analysis by PAGE/Coomassie staining revealed an induced protein in both extracts corresponding to the predicted sizes of the fused and unfused amylase, respectively.

Total cell extracts were analyzed for hyperthermophilic amylase activity as follows: 5 mg of starch was suspended in 20 μl of water then diluted with 25 μl of ethanol. The standard amylase positive control or the sample to be tested for amylase activity was added to the mixture and water was added to a final reaction volume of 500 μl. The reaction was carried out at 80° C. for 15-45 minutes. The reaction was then cooled down to room temperature, and 500 μl of o-dianisidine and glucose oxidase/peroxidase mixture (Sigma) was added. The mixture was incubated at 37° C. for 30 minutes. 500 μl of 12 N sulfuric acid was added to stop the reaction. Absorbance at 540 nm was measured to quantitate the amount of glucose released by the amylase/sample. Assay of both the fused and unfused amylase extracts gave similar levels of hyperthermophilic amylase activity, whereas control extracts were negative. This indicated that the 797GL3 amylase was still active (at high temperatures) when fused to the C-terminal portion of the waxy protein.

Example 3

Isolation of Promoter Fragments for Endosperm-Specific Expression in Maize

The promoter and 5' noncoding region I (including the first intron) from the large subunit of Zea mays ADP-gpp (ADP-glucose pyrophosphorylase) was amplified as a 1515 base pair fragment (SEQ ID NO:11) from maize genomic DNA using primers designed from Genbank accession M81603. The ADP-gpp promoter has been shown to be endosperm-specific (Shaw and Hannah, 1992).

The promoter from the Zea mays γ-zein gene was amplified as a 673 bp fragment (SEQ ID NO:12) from plasmid pGZ27.3 (obtained from Dr. Brian Larkins). The γ-zein promoter has been shown to be endosperm-specific (Torrent et al. 1997).

Example 4

Construction of Transformation Vectors for the 797GL3 Hyperthermophilic α-Amylase Expression cassettes were constructed to express the 797GL3 hyperthermophilic amylase in maize endosperm with various targeting signals as follows:

pNOV6200 (SEQ ID NO:13) comprises the maize γ-zein N-terminal signal sequence (MRVLLVALALLALAASATS) (SEQ ID NO:17) fused to the synthetic 797GL3 amylase as described above in Example 1 for targeting to the endoplasmic reticulum and secretion into the apoplast (Torrent et al. 1997). The fusion was cloned behind the maize ADP-gpp promoter for expression specifically in the endosperm.

pNOV6201 (SEQ ID NO:14) comprises the γ-zein N-terminal signal sequence fused to the synthetic 797GL3 amylase with a C-terminal addition of the sequence SEKDEL for targeting to and retention in the endoplasmic reticulum (ER) (Munro and Pelham, 1987). The fusion was cloned behind the maize ADP-gpp promoter for expression specifically in the endosperm.

pNOV7013 comprises the γ-zein N-terminal signal sequence fused to the synthetic 797GL3 amylase with a C-terminal addition of the sequence SEKDEL for targeting to and retention in the endoplasmic reticulum (ER). PNOV7013 is the same as pNOV6201, except that the maize γ-zein promoter (SEQ ID NO:12) was used instead of the maize ADP-spp promoter in order to express the fusion in the endosperm.

pNOV4029 (SEQ ID NO:15) comprises the waxy amyloplast targeting peptide (Klosgen et al., 1986) fused to the synthetic 797GL3 amylase for targeting to the amyloplast. The fusion was cloned behind the maize ADP-gpp promoter for expression specifically in the endosperm.

pNOV4031 (SEQ ID NO:16) comprises the waxy amyloplast targeting peptide fused to the synthetic 797GL3/waxy fusion protein for targeting to starch granules. The fusion was cloned behind the maize ADP-gpp promoter for expression specifically in the endosperm.

Additional constructs were made with these fusions cloned behind the maize γ-zein promoter to obtain higher levels of enzyme expression. All expression cassettes were moved into a binary vector for transformation into maize via Agrobacterium infection. The binary vector contained the phosphomannose isomerase (PMI) gene which allows for selection of transgenic cells with mannose. Transformed maize plants were either self-pollinated or outcrossed and seed was collected for analysis.

Additional constructs were made with the targeting signals described above fused to either 6gp3 pullulanase or to 340g12 α-glucosidase in precisely the same manner as described for the α-amylase. These fusions were cloned behind the maize ADP-gpp promoter and/or the γ-zein promoter and transformed into maize as described above. Transformed maize plants were either self-pollinated or outcrossed and seed was collected for analysis.

Combinations of the enzymes can be produced either by crossing plants expressing the individual enzymes or by cloning several expression cassettes into the same binary vector to enable cotransformation.

Example 5

Construction of Plant Transformation Vectors for the 6GP3 Thermophillic Pullulanase An expression cassette was constructed to express the 6GP3 thermophillic pullanase in the endoplasmic reticulum of maize endosperm as follows:

pNOV7005 (SEQ ID NOs:24 and 25) comprises the maize γ-zein N-terminal signal sequence fused to the synthetic 6GP3 pullulanase with a C-terminal addition of the sequence SEKDEL for targeting to and retention in the ER. The amino acid peptide SEKDEL was fused to the C-terminal end of the enzymes using PCR with primers designed to amplify the synthetic gene and simultaneously add the 6 amino acids at the C-terminal end of the protein. The fusion was cloned behind the maize γ-zein promoter for expression specifically in the endosperm.

Example 6

Construction of Plant Transformation Vectors for the malA Hyperthermophilic α-Glucosidase Expression cassettes were constructed to express the Sulfolobus solfataricus malA hyperthermophilic α-glucosidase in maize endosperm with various targeting signals as follows:

pNOV4831 (SEQ ID NO:26) comprises the maize γ-zein N-terminal signal sequence (MRVLLVALALLALAASATS) (SEQ ID NO:17) fused to the synthetic malA α-glucosidase with a C-terminal addition of the sequence SEKDEL for targeting to and retention in the endoplasmic reticulum (ER)

(Munro and Pelham, 1987). The fusion was cloned behind the maize γ-zein promoter for expression specifically in the endosperm.

pNOV4839 (SEQ ID NO:27) comprises the maize γ-zein N-terminal signal sequence (MRVLLVALALLALAASATS) (SEQ ID NO:17) fused to the synthetic malA α-glucosidase for targeting to the endoplasmic reticulum and secretion into the apoplast (Torrent et al. 1997). The fusion was cloned behind the maize γ-zein promoter for expression specifically in the endosperm.

pNOV4837 comprises the maize γ-zein N-terminal signal sequence (MRVLLVALALLALAASATS) (SEQ ID NO:17) fused to the synthetic malA α-glucosidase with a C-terminal addition of the sequence SEKDEL for targeting to and retention in the ER. The fusion was cloned behind the maize ADPgpp promoter for expression specifically in the endosperm. The amino acid sequence for this clone is identical to that of pNOV4831 (SEQ ID NO:26).

Example 7

Construction of Plant Transformation Vectors for the Hyperthermophillic *Thermotoga maritima* and *Thermotoga neapolitana* Glucose Isomerases Expression cassettes were constructed to express the *Thermotoga maritima* and *Thermotoga neapolitana* hyperthermophilic glucose isomerases in maize endosperm with various targeting signals as follows:

pNOV4832 (SEQ ID NO:28) comprises the maize γ-zein N-terminal signal sequence (MRVLLVALALLALAASATS) (SEQ ID NO:17) fused to the synthetic *Thermotoga maritima* glucose isomerase with a C-terminal addition of the sequence SEKDEL for targeting to and retention in the ER. The fusion was cloned behind the maize γ-zein promoter for expression specifically in the endosperm.

pNOV4833 (SEQ ID NO:29) comprises the maize γ-zein N-terminal signal sequence (MRVLLVALALLALAASATS) (SEQ ID NO: 17) fused to the synthetic *Thermotoga neapolitana* glucose isomerase with a C-terminal addition of the sequence SEKDEL for targeting to and retention in the ER. The fusion was cloned behind the maize γ-zein promoter for expression specifically in the endosperm.

pNOV4840 (SEQ ID NO:30) comprises the maize γ-zein N-terminal signal sequence (MRVLLVALALLALAASATS) (SEQ ID NO:17) fused to the synthetic *Thermotoga neapolitana* glucose isomerase for targeting to the endoplasmic reticulum and secretion into the apoplast (Torrent et al. 1997). The fusion was cloned behind the maize γ-zein promoter for expression specifically in the endosperm.

pNOV4838 comprises the maize γ-zein N-terminal signal sequence (MRVLLVALALLALAASATS) (SEQ ID NO:17) fused to the synthetic *Thermotoga neapolitana* glucose isomerase with a C-terminal addition of the sequence SEKDEL for targeting to and retention in the ER. The fusion was cloned behind the maize ADPgpp promoter for expression specifically in the endosperm. The amino acid sequence for this clone is identical to that of pNOV4833 (SEQ ID NO:29).

Example 8

Construction of Plant Transformation Vectors for the Expression of the Hyperthermophillic Glucanase EglA pNOV4800 (SEQ ID NO:58) comprises the barley alpha amylase AMY32b signal sequence (MGKNGNLCCFS-LLLLLLAGLASGHQ) (SEQ ID NO:31) fused with the EglA mature protein sequence for localization to the apoplast. The fusion was cloned behind the maize γ-zein promoter for expression specifically in the endosperm.

Example 9

Construction of Plant Transformation Vectors for the Expression of Multiple Hyperthermophillic Enzymes pNOV4841 comprises a double gene construct of a 797GL3 α-amylase fusion and a 6GP3 pullulanase fusion. Both 797GL3 fusion (SEQ ID NO:33) and 6GP3 fusion (SEQ ID NO:34) possessed the maize γ-zein N-terminal signal sequence and SEKDEL sequence for targeting to and retention in the ER. Each fusion was cloned behind a separate maize γ-zein promoter for expression specifically in the endosperm.

pNOV4842 comprises a double gene construct of a 797GL3 α-amylase fusion and a malA α-glucosidase fusion. Both the 797GL3 fusion polypeptide (SEQ ID NO:35) and malA α-glucosidase fusion polypeptide (SEQ ID NO:36) possess the maize γ-zein N-terminal signal sequence and SEKDEL sequence for targeting to and retention in the ER. Each fusion was cloned behind a separate maize γ-zein promoter for expression specifically in the endosperm.

pNOV4843 comprises a double gene construct of a 797GL3 α-amylase fusion and a malA α-glucosidase fusion. Both the 797GL3 fusion and malA α-glucosidase fusion possess the maize γ-zein N-terminal signal sequence and SEKDEL sequence for targeting to and retention in the ER. The 797GL3 fusion was cloned behind the maize γ-zein promoter and the malA fusion was cloned behind the maize ADPgpp promoter for expression specifically in the endosperm. The amino acid sequences of the 797GL3 fusion and the malA fusion are identical to those of pNOV4842 (SEQ ID Nos: 35 and 36, respectively).

pNOV4844 comprises a triple gene construct of a 797GL3 α-amylase fusion, a 6GP3 pullulanase fusion, and a malA α-glucosidase fusion. 797GL3, malA, and 6GP3 all possess the maize γ-zein N-terminal signal sequence and SEKDEL sequence for targeting to and retention in the ER. The 797GL3 and malA fusions were cloned behind 2 separate maize γ-zein promoters, and the 6GP3 fusion was cloned behind the maize ADPgpp promoter for expression specifically in the endosperm. The amino acid sequences for the 797GL3 and malA fusions are identical to those of pNOV4842 (SEQ ID Nos: 35 and 36, respectively). The amino acid sequence for the 6GP3 fusion is identical to that of the 6GP3 fusion in pNOV4841 (SEQ ID NO:34).

All expression cassettes were moved into the binary vector pNOV2117 for transformation into maize via *Agrobacterium* infection. pNOV2117 contains the phosphomannose isomerase (PMI) gene allowing for selection of transgenic cells with mannose. pNOV2117 is a binary vector with both the pVS1 and ColE1 origins of replication. This vector contains the constitutive VirG gene from pAD1289 (Hansen, G., et al., PNAS USA 91:7603-7607 (1994)) and a spectinomycin resistance gene from Tn7. Cloned into the polylinker between the right and left borders are the maize ubiquitin promoter, PMI coding region and nopaline synthase terminator of pNOV117 (Negrotto, D., et al., Plant Cell Reports 19:798-803 (2000)). Transformed maize plants will either be self-pollinated or outcrossed and seed collected for analysis. Combinations of the different enzymes can be produced either by crossing plants expressing the individual enzymes or by transforming a plant with one of the multi-gene cassettes.

Example 10

Construction of Bacterial and *Pichia* Expression Vectors

Expression cassettes were constructed to express the hyperthermophilic α-glucosidase and glucose isomerases in either *Pichia* or bacteria as follows:

pNOV4829 (SEQ ID NOS: 37 and 38) comprises a synthetic *Thermotoga maritima* glucose isomerase fusion with ER retention signal in the bacterial expression vector pET29a. The glucose isomerase fusion gene was cloned into the NcoI and SacI sites of pET29a, which results in the addition of an N-terminal S-tag for protein purification.

pNOV4830 (SEQ ID NOS: 39 and 40) comprises a synthetic *Thermotoga neapolitana* glucose isomerase fusion with ER retention signal in the bacterial expression vector pET29a. The glucose isomerase fusion gene was cloned into the NcoI and SacI sites of pET29a, which results in the addition of an N-terminal S-tag for protein purification.

pNOV4835 (SEQ ID NO: 41 and 42) comprises the synthetic *Thermotoga maritima* glucose isomerase gene cloned into the BamHI and EcoRI sites of the bacterial expression vector pET28C. This resulted in the fusion of a His-tag (for protein purification) to the N-terminal end of the glucose isomerase.

pNOV4836 (SEQ ID NO: 43 AND 44) comprises the synthetic *Thermotoga neapolitana* glucose isomerase gene cloned into the BamHI and EcoRI sites of the bacterial expression vector pET28C. This resulted in the fusion of a His-tag (for protein purification) to the N-terminal end of the glucose isomerase.

Example 11

Transformation of immature maize embryos was performed essentially as described in Negrotto et al., Plant Cell Reports 19: 798-803. For this example, all media constituents are as described in Negrotto et al., supra. However, various media constituents described in the literature may be substituted.

A. Transformation Plasmids and Selectable Marker

The genes used for transformation were cloned into a vector suitable for maize transformation. Vectors used in this example contained the phosphomannose isomerase (PMI) gene for selection of transgenic lines (Negrotto et al. (2000) Plant Cell Reports 19: 798-803).

B. Preparation of *Agrobacterium tumefaciens*

*Agrobacterium* strain LBA4404 (pSB1) containing the plant transformation plasmid was grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ *Agrobacterium* were suspended in LS-inf media supplemented with 100 µM As (Negrotto et al., (2000) Plant Cell Rep 19: 798-803). Bacteria were pre-induced in this medium for 30-60 minutes.

C. Inoculation

Immature embryos from A188 or other suitable genotype were excised from 8-12 day old ears into liquid LS-inf+100 µM As. Embryos were rinsed once with fresh infection medium. *Agrobacterium* solution was then added and embryos were vortexed for 30 seconds and allowed to settle with the bacteria for 5 minutes. The embryos were then transferred scutellum side up to LSAs medium and cultured in the dark for two to three days. Subsequently, between 20 and 25 embryos per petri plate were transferred to LSDc medium supplemented with cefotaxime (250 mg/l) and silver nitrate (1.6 mg/l) and cultured in the dark for 28° C. for 10 days.

D. Selection of Transformed Cells and Regeneration of Transformed Plants

Immature embryos producing embryogenic callus were transferred to LSD1M0.5S medium. The cultures were selected on this medium for 6 weeks with a subculture step at 3 weeks. Surviving calli were transferred to Reg1 medium supplemented with mannose. Following culturing in the light (16 hour light/8 hour dark regiment), green tissues were then transferred to Reg2 medium without growth regulators and incubated for 1-2 weeks. Plantlets are transferred to Magenta GA-7 boxes (Magenta Corp, Chicago Ill.) containing Reg3 medium and grown in the light. After 2-3 weeks, plants were tested for the presence of the PMI genes and other genes of interest by PCR. Positive plants from the PCR assay were transferred to the greenhouse.

Example 12

Analysis of T1 Seed from Maize Plants Expressing the α-Amylase Targeted to Apoplast or to the ER T1 seed from self-pollinated maize plants transformed with either pNOV6200 or pNOV6201 as described in Example 4 were obtained. Starch accumulation in these kernels appeared to be normal, based on visual inspection and on normal staining for starch with an iodine solution prior to any exposure to high temperature. Immature kernels were dissected and purified endosperms were placed individually in microfuge tubes and immersed in 200 µl of 50 mM $NaPO_4$ buffer. The tubes were placed in an 85° C. water bath for 20 minutes, then cooled on ice. Twenty microliters of a 1% iodine solution was added to each tube and mixed. Approximately 25% of the segregating kernels stained normally for starch. The remaining 75% failed to stain, indicating that the starch had been degraded into low molecular weight sugars that do not stain with iodine. It was found that the T1 kernels of pNOV6200 and pNOV6201 were self-hydrolyzing the corn starch. There was no detectable reduction in starch following incubation at 37° C.

Expression of the amylase was further analyzed by isolation of the hyperthermophilic protein fraction from the endosperm followed by PAGE/Coomassie staining. A segregating protein band of the appropriate molecular weight (50 kD) was observed. These samples are subjected to an α-amylase assay using commercially available dyed amylose (AMYLAZYME, from Megazyme, Ireland). High levels of hyperthermophilic amylase activity correlated with the presence of the 50 kD protein.

It was further found that starch in kernels from a majority of transgenic maize, which express hyperthermophilic α-amylase, targeted to the amyloplast, is sufficiently active at ambient temperature to hydrolyze most of the starch if the enzyme is allowed to be in direct contact with a starch granule. Of the eighty lines having hyperthermophilic α-amylase targeted to the amyloplast, four lines were identified that accumulate starch in the kernels. Three of these lines were analyzed for thermostable α-amylase activity using a colorimetric amylazyme assay (Megazyme). The amylase enzyme assay indicated that these three lines had low levels of thermostable amylase activity. When purified starch from these three lines was treated with appropriate conditions of moisture and heat, the starch was hydrolyzed indicating the presence of adequate levels of α-amylase to facilitate the autohydrolysis of the starch prepared from these lines.

Figure 1B:
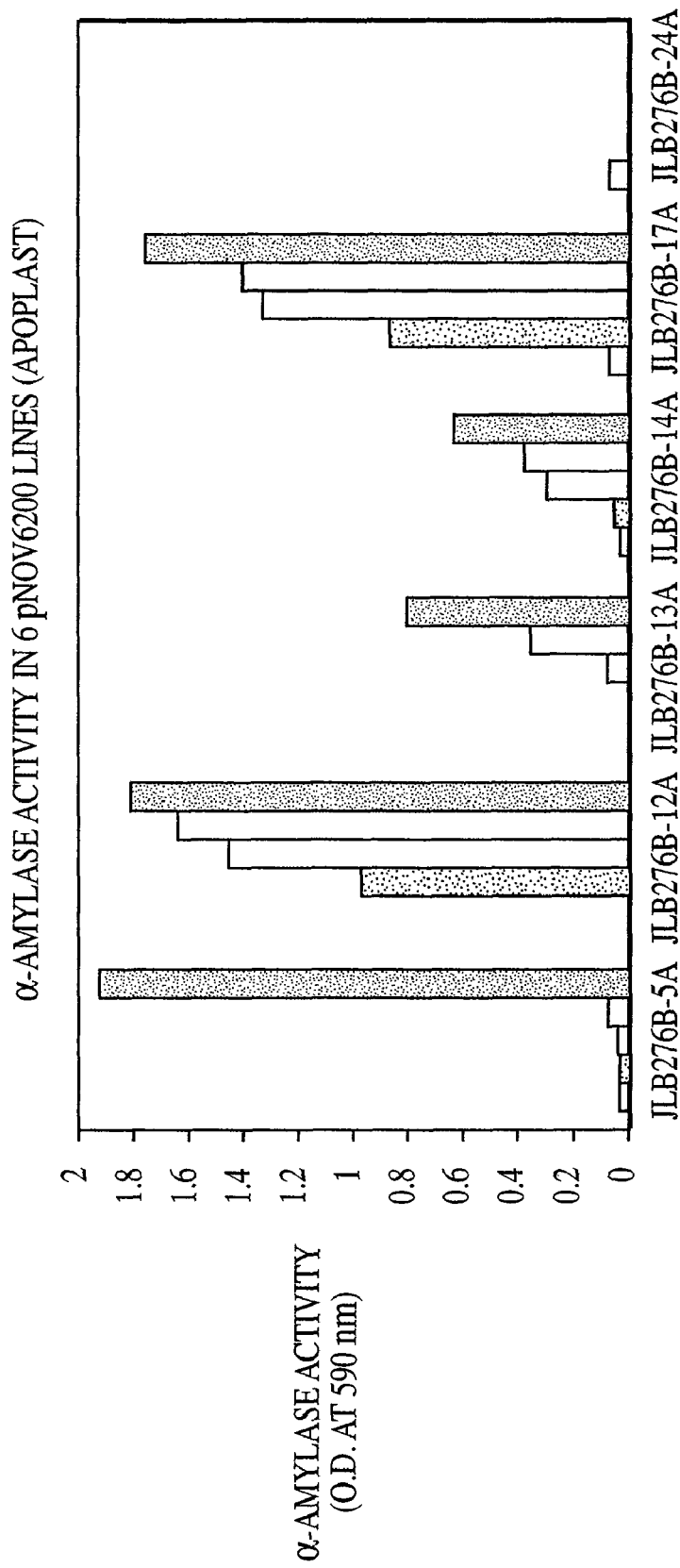
Figure 2:
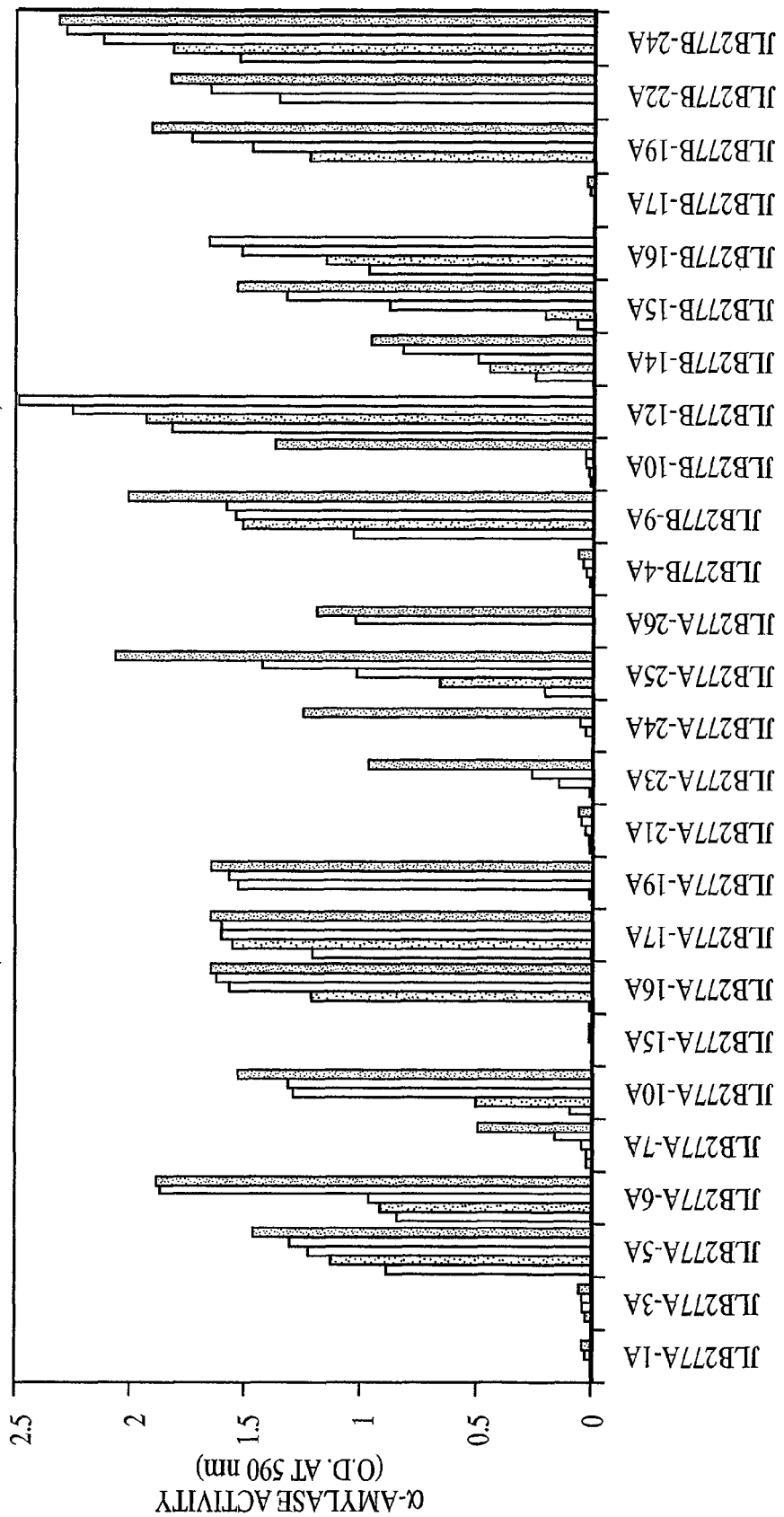
FIG. 2 illustrates the activity of α-amylase in segregating T1 kernels from pNOV6201 lines.

T1 seed from multiple independent lines of both pNOV6200 and pNOV6201 transformants was obtained. Individual kernels from each line were dissected and purified endosperms were homogenized individually in 300 µl of 50 mM $NaPO_4$ buffer. Aliquots of the endosperm suspensions were analyzed for α-amylase activity at 85° C. Approximately 80% of the lines segregate for hyperthermophilic activity (See FIGS. 1A, 1B, and 2).

Kernels from wild type plants or plants transformed with pNOV6201 were heated at 100° C. for 1, 2, 3, or 6 hours and then stained for starch with an iodine solution. Little or no starch was detected in mature kernels after 3 or 6 hours, respectively. Thus, starch in mature kernels from transgenic maize which express hyperthermophilic amylase that is targeted to the endoplasmic reticulum was hydrolyzed when incubated at high temperature.

In another experiment, partially purified starch from mature T1 kernels from pNOV6201 plants that were steeped at 50° C. for 16 hours was hydrolyzed after heating at 85° C. for 5 minutes. This illustrated that the α-amylase targeted to the endoplasmic reticulum binds to starch after grinding of the kernel, and is able to hydrolyze the starch upon heating. Iodine staining indicated that the starch remains intact in mature seeds after the 16 hour steep at 50° C.

In another experiment, segregating, mature kernels from plants transformed with pNOV6201 were heated at 95° C. for 16 hours and then dried. In seeds expressing the hyperthermophilic α-amylase, the hydrolysis of starch to sugar resulted in a wrinkled appearance following drying.

Example 13

Analysis of T1 Seed from Maize Plants Expressing the α-Amylase Targeted to the Amyloplast T1 seed from self-pollinated maize plants transformed with either pNOV4029 or pNOV4031 as described in Example 4 was obtained. Starch accumulation in kernels from these lines was clearly not normal. All lines segregated, with some variation in severity, for a very low or no starch phenotype. Endosperm purified from immature kernels stained only weakly with iodine prior to exposure to high temperatures. After 20 minutes at 85° C., there was no staining. When the ears were dried, the kernels shriveled up. This particular amylase clearly had sufficient activity at greenhouse temperatures to hydrolyze starch if allowed to be in direct contact with the granule Example 14

Fermentation of Grain from Maize Plants Expressing α-Amylase 100% Transgenic Grain 85° C. Vs. 95° C., Varied Liquefaction Time Transgenic corn (pNOV6201) that contains a thermostable α-amylase performs well in fermentation without addition of exogenous α-amylase, requires much less time for liquefaction and results in more complete solubilization of starch. Laboratory scale fermentations were performed by a protocol with the following steps (detailed below): 1) grinding, 2) moisture analysis, 3) preparation of a slurry containing ground corn, water, backset and α-amylase, 4) liquefaction and 5) simultaneous saccharification and fermentation (SSF). In this example the temperature and time of the liquefaction step were varied as described below. In addition the transgenic corn was liquefied with and without exogenous α-amylase and the performance in ethanol production compared to control corn treated with commercially available α-amylase.

The transgenic corn used in this example was made in accordance with the procedures set out in Example 4 using a vector comprising the α-amylase gene and the PMI selectable marker, namely pNOV6201. The transgenic corn was produced by pollinating a commercial hybrid (N3030BT) with pollen from a transgenic line expressing a high level of thermostable α-amylase. The corn was dried to 11% moisture and stored at room temperature. The α-amylase content of the transgenic corn flour was 95 units/g where 1 unit of enzyme generates 1 micromole reducing ends per min from corn flour at 85° C. in pH 6.0 MES buffer. The control corn that was used was a yellow dent corn known to perform well in ethanol production.

1) Grinding: Transgenic corn (1180 g) was ground in a Perten 3100 hammer mill equipped with a 2.0 mm screen thus generating transgenic corn flour. Control corn was ground in the same mill after thoroughly cleaning to prevent contamination by the transgenic corn.

2) Moisture analysis: Samples (20 g) of transgenic and control corn were weighed into aluminum weigh boats and heated at 100 C for 4 h. The samples were weighed again and the moisture content calculated from the weight loss. The moisture content of transgenic flour was 9.26%; that of the control flour was 12.54%.

3) Preparation of slurries: The composition of slurries was designed to yield a mash with 36% solids at the beginning of SSF. Control samples were prepared in 100 ml plastic bottles and contained 21.50 g of control corn flour, 23 ml of deionized water, 6.0 ml of backset (8% solids by weight), and 0.30 ml of a commercially available α-amylase diluted 1/50 with water. The α-amylase dose was chosen as representative of industrial usage. When assayed under the conditions described above for assay of the transgenic α-amylase, the control α-amylase dose was 2 U/g corn flour. pH was adjusted to 6.0 by addition of ammonium hydroxide. Transgenic samples were prepared in the same fashion but contained 20 g of corn flour because of the lower moisture content of transgenic flour. Slurries of transgenic flour were prepared either with α-amylase at the same dose as the control samples or without exogenous α-amylase.

4) Liquefaction: The bottles containing slurries of transgenic corn flour were immersed in water baths at either 85° C. or 95° C. for times of 5, 15, 30, 45 or 60 min. Control slurries were incubated for 60 min at 85° C. During the high temperature incubation the slurries were mixed vigorously by hand every 5 min. After the high temperature step the slurries were cooled on ice.

5) Simultaneous saccharification and fermentation: The mash produced by liquefaction was mixed with glucoamylase (0.65 ml of a 1/50 dilution of a commercially available L-400 glucoamylase), protease (0.60 ml of a 1,000-fold dilution of a commercially available protease), 0.2 mg Lactocide & urea (0.85 ml of a 10-fold dilution of 50% Urea Liquor). A hole was cut into the cap of the 100 ml bottle containing the mash to allow $CO_2$ to vent. The mash was then inoculated with yeast (1.44 ml) and incubated in a water bath set at 90 F. After 24 hours of fermentation the temperature was lowered to 86 F; at 48 hours it was set to 82 F.

Yeast for inoculation was propagated by preparing a mixture that contained yeast (0.12 g) with 70 grams maltodextrin, 230 ml water, 100 ml backset, glucoamylase (0.88 ml of a 10-fold dilution of a commercially available glucoamylase), protease (1.76 ml of a 100-fold dilution of a commercially available enzyme), urea (1.07 grams), penicillin (0.67 mg) and zinc sulfate (0.13 g). The propagation culture was initiated the day before it was needed and was incubated with mixing at 90° F.

At 24, 48 & 72 hour samples were taken from each fermentation vessel, filtered through 0.2 µm filters and analyzed by HPLC for ethanol & sugars. At 72 h samples were analyzed for total dissolved solids and for residual starch.

HPLC analysis was performed on a binary gradient system equipped with refractive index detector, column heater & Bio-Rad Aminex HPX-87H column. The system was equilibrated with 0.005 M $H_2SO_4$ in water at 1 ml/min. Column temperature was 50° C. Sample injection volume was 5 µl; elution was in the same solvent. The RI response was calibrated by injection of known standards. Ethanol and glucose were both measured in each injection.

Residual starch was measured as follows. Samples and standards were dried at 50° C. in an oven, then ground to a powder in a sample mill. The powder (0.2 g) was weighed into a 15 ml graduated centrifuge tube. The powder was washed 3 times with 10 ml aqueous ethanol (80% v/v) by vortexing followed by centrifugation and discarding of the supernatant. DMSO (2.0 ml) was added to the pellet followed by 3.0 ml of a thermostable alpha-amylase (300 units) in MOPS buffer. After vigorous mixing, the tubes were incubated in a water bath at 85° C. for 60 min. During the incubation, the tubes were mixed four times. The samples were cooled and 4.0 ml sodium acetate buffer (200 mM, pH 4.5) was added followed by 0.1 ml of glucoamylase (20 U). Samples were incubated at 50° C. for 2 hours, mixed, then centrifuged for 5 min at 3,500 rpm. The supernatant was filtered through a 0.2 um filter and analyzed for glucose by the HPLC method described above. An injection size of 50 µl was used for samples with low residual starch (<20% of solids).

Results Transgenic corn performed well in fermentation without added α-amylase. The yield of ethanol at 72 hours was essentially the same with or without exogenous α-amylase as shown in Table I. These data also show that a higher yield of ethanol is achieved when the liquefaction temperature is higher; the present enzyme expressed in the transgenic corn has activity at higher temperatures than other enzymes used commercially such as the *Bacillus* liquefaciens α-amylase.

TABLE I

| Liquefaction temp ° C. | Liquefaction time min. | Exogenous α-amylase | # replicates | Mean Ethanol % v/v | Std. Dev. % v/v |
|---|---|---|---|---|---|
| 85 | 60 | Yes | 4 | 17.53 | 0.18 |
| 85 | 60 | No | 4 | 17.78 | 0.27 |
| 95 | 60 | Yes | 2 | 18.22 | ND |
| 95 | 60 | No | 2 | 18.25 | ND |

Figure 3:
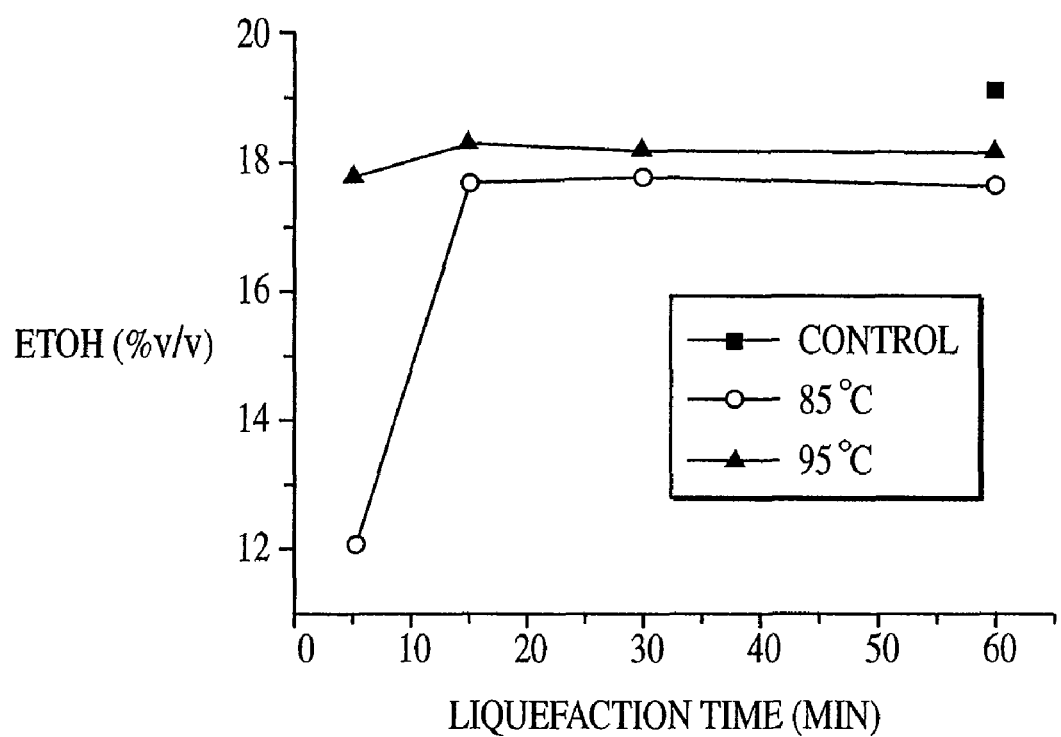
FIG. 3 depicts the amount of ethanol produced upon fermentation of mashes of transgenic corn containing thermostable 797GL3 alpha amylase that were subjected to liquefaction times of up to 60 minutes at 85° C. and 95° C. This figure illustrates that the ethanol yield at 72 hours of fermentation was almost unchanged from 15 minutes to 60 minutes of liquefaction. Moreover, it shows that mash produced by liquefaction at 95° C. produced more ethanol at each time point than mash produced by liquefaction at 85° C.

When the liquefaction time was varied, it was found that the liquefaction time required for efficient ethanol production was much less than the hour required by the conventional process. FIG. 3 shows that the ethanol yield at 72 hours fermentation was almost unchanged from 15 min to 60 min liquefaction. In addition liquefaction at 95° C. gave more ethanol at each time point than at the 85° C. liquefaction. This observation demonstrates the process improvement achieved by use of a hyperthermophilic enzyme.

The control corn gave a higher final ethanol yield than the transgenic corn, but the control was chosen because it performs very well in fermentation. In contrast the transgenic corn has a genetic background chosen to facilitate transformation. Introducing the α-amylase-trait into elite corn germplasm by well-known breeding techniques should eliminate this difference.

Figure 4:
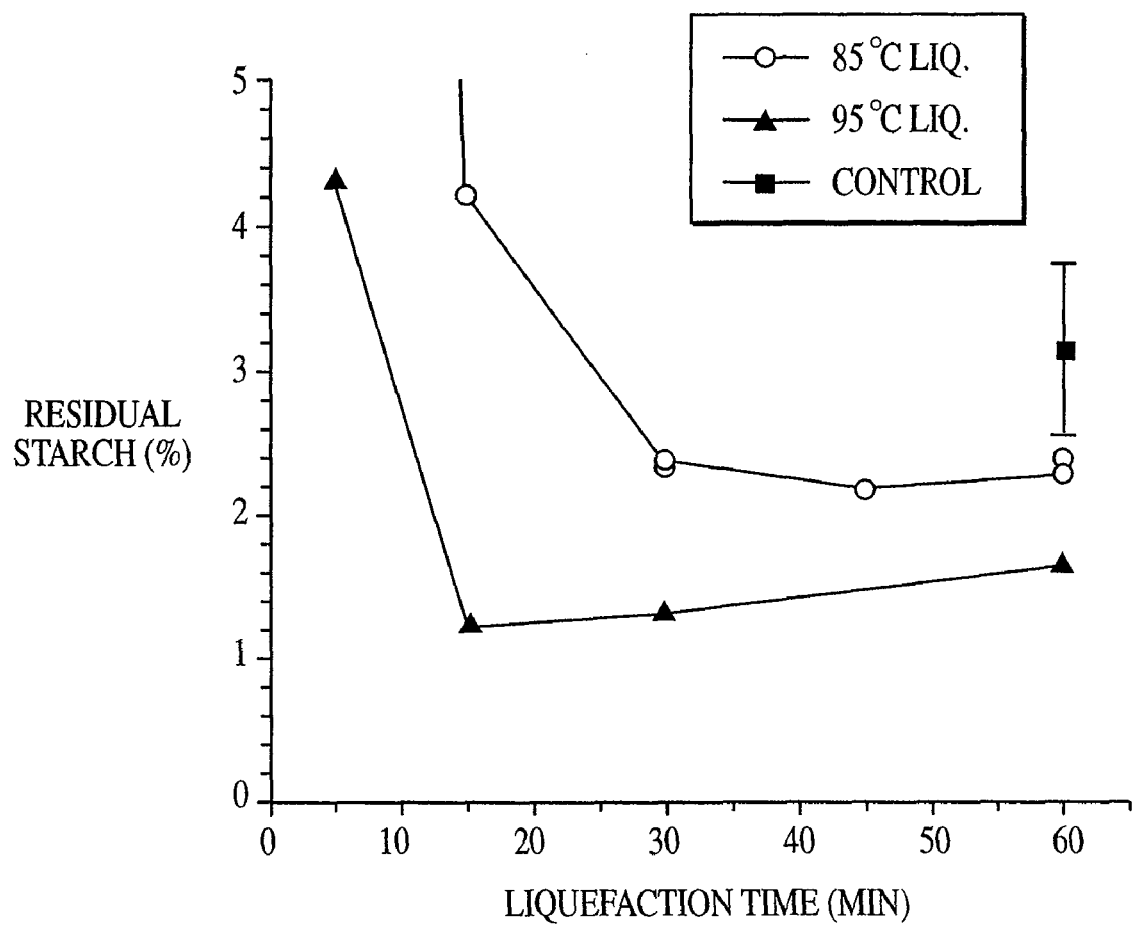
FIG. 4 depicts the amount of residual starch (%) remaining after fermentation of mashes of transgenic corn containing thermostable alpha amylase that were subjected to a liquefaction time of up to 60 minutes at 85° C. and 95° C. This figure illustrates that the ethanol yield at 72 hours of fermentation was almost unchanged from 15 minutes to 60 minutes of liquefaction. Moreover, it shows that mash produced by liquefaction at 95° C. produced more ethanol at each time point than mash produced by liquefaction at 85° C.

Examination of the residual starch levels of the beer produced at 72 hours (FIG. 4) shows that the transgenic α-amylase results in significant improvement in making starch available for fermentation; much less starch was left over after fermentation.

Using both ethanol levels and residual starch levels the optimal liquefaction times were 15 min at 95° C. and 30 min at 85° C. In the present experiments these times were the total time that the fermentation vessels were in the water bath and thus include a time period during which the temperature of the samples was increasing from room temperature to 85° C. or 95° C. Shorter liquefaction times may be optimal in large scale industrial processes that rapidly heat the mash by use of equipment such as jet cookers. Conventional industrial liquefaction processes require holding tanks to allow the mash to be incubated at high temperature for one or more hours. The present invention eliminates the need for such holding tanks and will increase the productivity of liquefaction equipment.

One important function of α-amylase in fermentation processes is to reduce the viscosity of the mash. At all time points the samples containing transgenic corn flour were markedly less viscous than the control sample. In addition the transgenic samples did not appear to go through the gelatinous phase observed with all control samples; gelatinization normally occurs when corn slurries are cooked. Thus having the α-amylase distributed throughout the fragments of the endosperm gives advantageous physical properties to the mash during cooking by preventing formation large gels that slow diffusion and increase the energy costs of mixing and pumping the mash.

The high dose of α-amylase in the transgenic corn may also contribute to the favorable properties of the transgenic mash. At 85° C., the α-amylase activity of the transgenic corn was many times greater activity than the of the dose of exogenous α-amylase used in controls. The latter was chosen as representative of commercial use rates.

Example 15

Effective Function of Transgenic Corn when Mixed with Control Corn

Transgenic corn flour was mixed with control corn flour in various levels from 5% to 100% transgenic corn flour. These were treated as described in Example 14. The mashes containing transgenically expressed α-amylase were liquefied at 85° C. for 30 min or at 95° C. for 15 min; control mashes were prepared as described in Example 14 and were liquefied at 85° C. for 30 or 60 min (one each) or at 95° C. for 15 or 60 min (one each).

Figure 5:
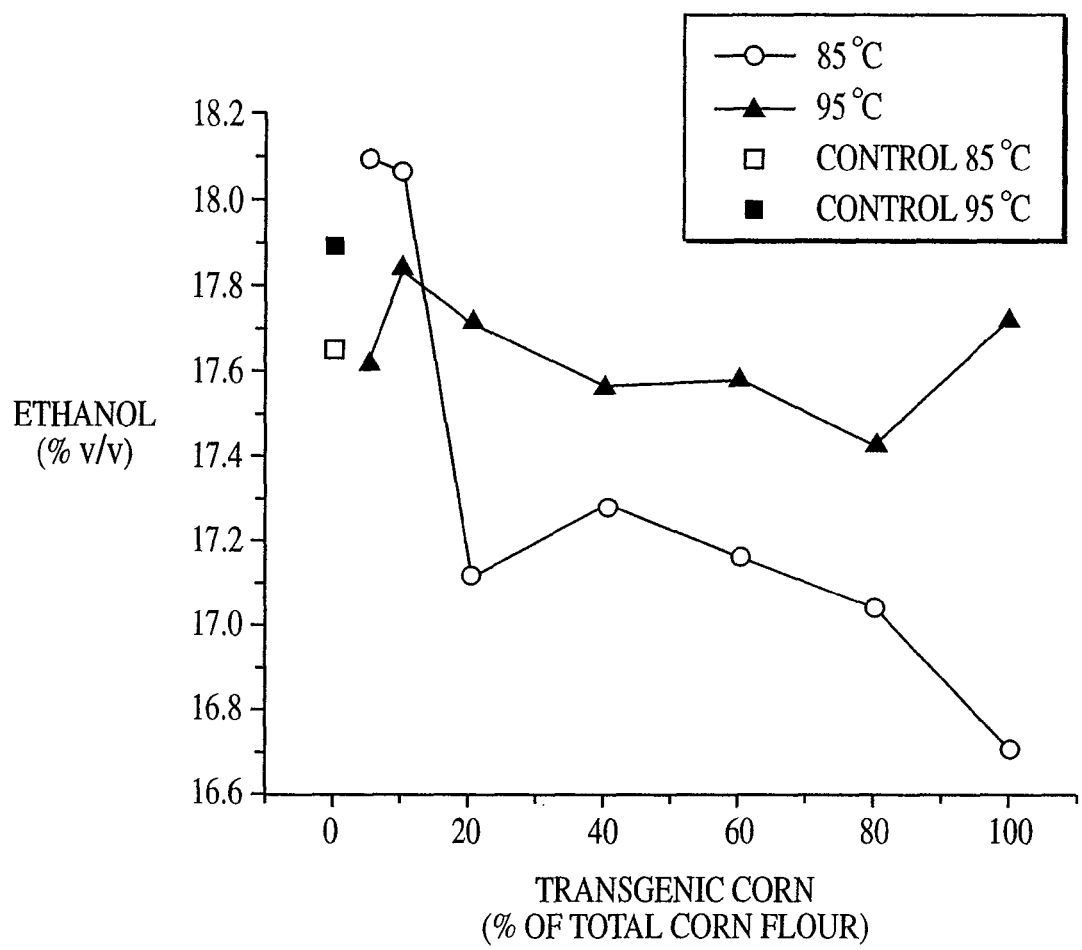
FIG. 5 depicts the ethanol yields for mashes of a transgenic corn, control corn, and various mixtures thereof prepared at 85° C. and 95° C. This figure illustrates that the transgenic corn comprising α-amylase results in significant improvement in making starch available for fermentation since there was a reduction of starch left over after fermentation.
Figure 6:
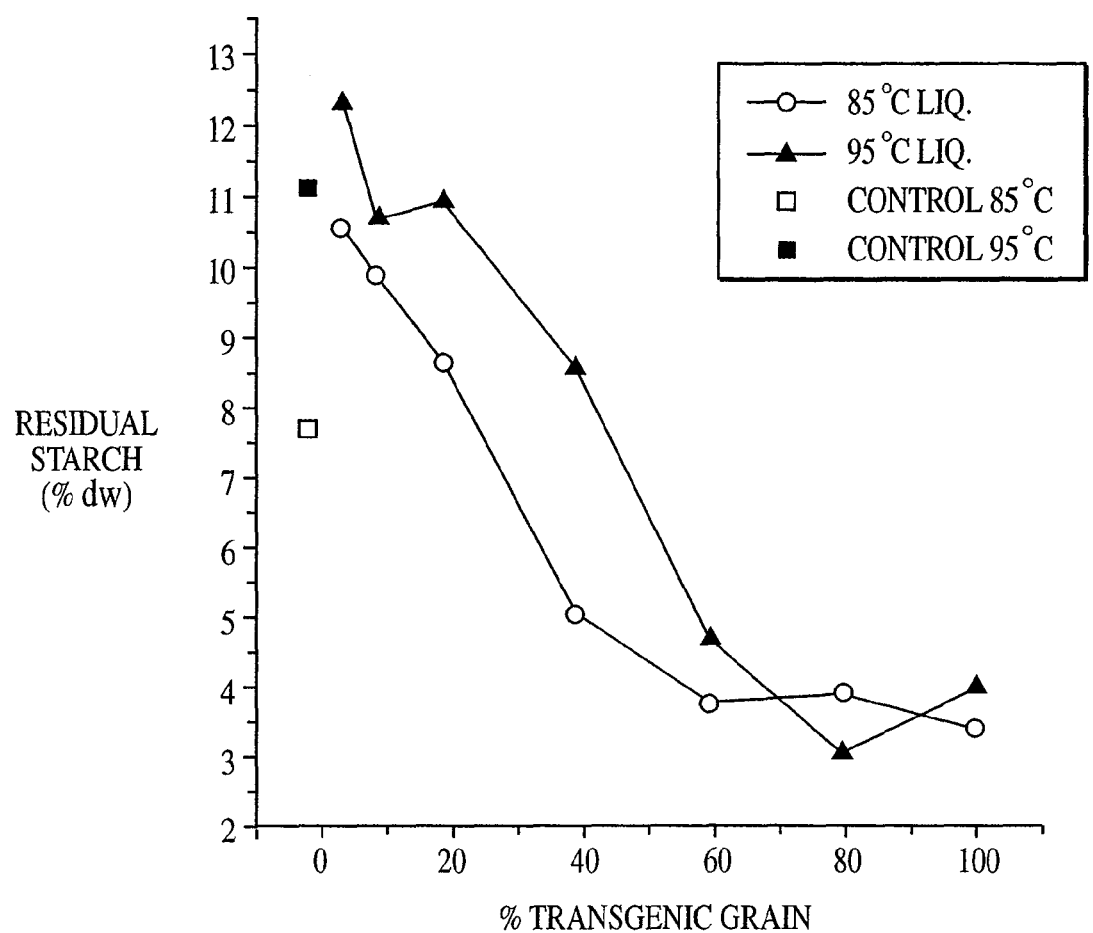
FIG. 6 depicts the amount of residual starch measured in dried stillage following fermentation for mashes of a transgenic grain, control corn, and various mixtures thereof at prepared at 85° C. and 95° C.

The data for ethanol at 48 and 72 hours and for residual starch are given in Table 2. The ethanol levels at 48 hours are graphed in FIG. 5; the residual starch determinations are shown in FIG. 6. These data show that transgenically expressed thermostable α-amylase gives very good performance in ethanol production even when the transgenic grain is only a small portion (as low as 5%) of the total grain in the mash. The data also show that residual starch is markedly lower than in control mash when the transgenic grain comprises at least 40% of the total grain.

TABLE 2

| Transgenic grain wt % | 85° C. Liquefaction | | | 95° C. Liquefaction | | |
|---|---|---|---|---|---|---|
| | Residual Starch | Ethanol 48 h | Ethanol % v/v 72 h | Residual Starch | Ethanol 48 h | Ethanol % v/v 72 h |
| 100 | 3.58 | 16.71 | 18.32 | 4.19 | 17.72 | 21.14 |
| 80 | 4.06 | 17.04 | 19.2 | 3.15 | 17.42 | 19.45 |
| 60 | 3.86 | 17.16 | 19.67 | 4.81 | 17.58 | 19.57 |
| 40 | 5.14 | 17.28 | 19.83 | 8.69 | 17.56 | 19.51 |
| 20 | 8.77 | 17.11 | 19.5 | 11.05 | 17.71 | 19.36 |
| 10 | 10.03 | 18.05 | 19.76 | 10.8 | 17.83 | 19.28 |
| 5 | 10.67 | 18.08 | 19.41 | 12.44 | 17.61 | 19.38 |
| 0* | 7.79 | 17.64 | 20.11 | 11.23 | 17.88 | 19.87 |

*Control samples. Values the average of 2 determinations

Example 16

Ethanol Production as a Function of Liquefaction pH Using Transgenic Corn at a Rate of 1.5 to 12% of Total Corn Because the transgenic corn performed well at a level of 5-10% of total corn in a fermentation, an additional series of fermentations in which the transgenic corn comprised 1.5 to 12% of the total corn was performed. The pH was varied from 6.4 to 5.2 and the α-amylase enzyme expressed in the transgenic corn was optimized for activity at lower pH than is conventionally used industrially.

The experiments were performed as described in Example 15 with the following exceptions:

1). Transgenic flour was mixed with control flour as a percent of total dry weight at the levels ranging from 1.5% to 12.0%.

2). Control corn was N3030BT which is more similar to the transgenic corn than the control used in examples 14 and 15.

3). No exogenous α-amylase was added to samples containing transgenic flour.

4). Samples were adjusted to pH 5.2, 5.6, 6.0 or 6.4 prior to liquefaction. At least 5 samples spanning the range from 0% transgenic corn flour to 12% transgenic corn flour were prepared for each pH.

5). Liquefaction for all samples was performed at 85° C. for 60 min.

Figure 7:
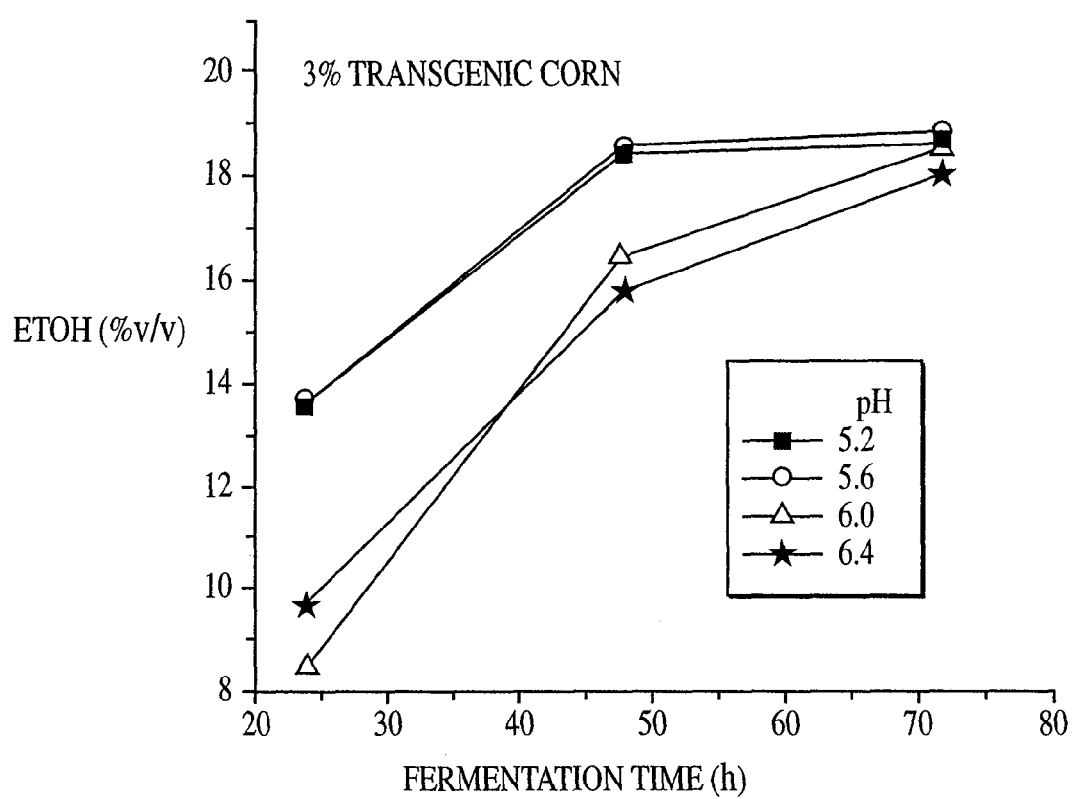
FIG. 7 depicts the ethanol yields as a function of fermentation time of a sample comprising 3% transgenic corn over a period of 20-80 hours at various pH ranges from 5.2-6.4. The figure illustrates that the fermentation conducted at a lower pH proceeds faster than at a pH of 6.0 or higher.

The change in ethanol content as a function of fermentation time are shown in FIG. 7. This figure shows the data obtained from samples that contained 3% transgenic corn. At the lower pH, the fermentation proceeds more quickly than at pH 6.0 and above; similar behavior was observed in samples with other doses of transgenic grain. The pH profile of activity of the transgenic enzyme combined with the high levels of expression will allow lower pH liquefactions resulting in more rapid fermentations and thus higher throughput than is possible at the conventional pH 6.0 process.

Figure 8:
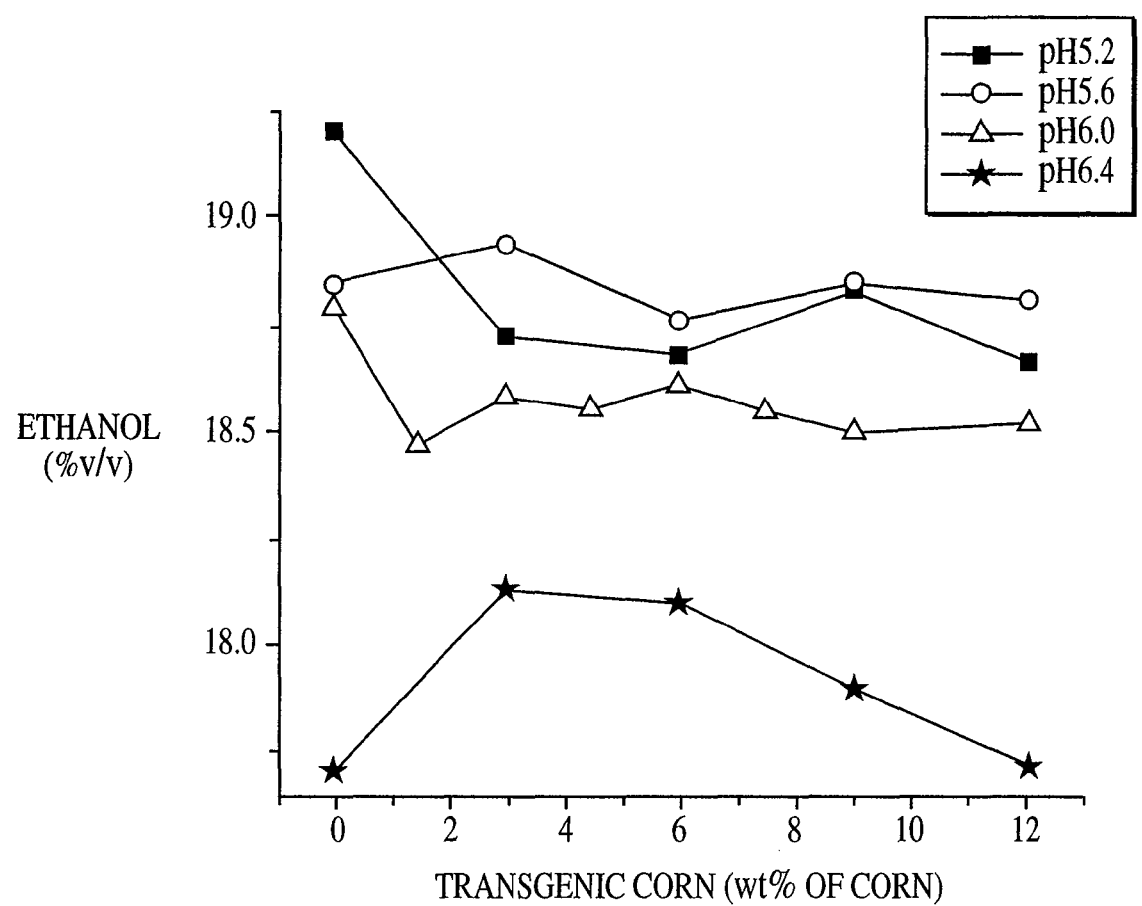
FIG. 8 depicts the ethanol yields during fermentation of a mash comprising various weight percentages of transgenic corn from 0-12 wt % at various pH ranges from 5.2-6.4. This figure illustrates that the ethanol yield was independent of the amount of transgenic grain included in the sample.

The ethanol yields at 72 hours are shown in FIG. 8. As can be seen, on the basis of ethanol yield, the results showed little dependence on the amount of transgenic grain included in the sample. Thus the grain contains abundant amylase to facilitate fermentative production of ethanol. It is also demonstrates that lower pH of liquefaction results in higher ethanol yield.

The viscosity of the samples after liquefaction was monitored and it was observed that at pH 6.0, 6% transgenic grain is sufficient for adequate reduction in viscosity. At pH 5.2 and 5.6, viscosity is equivalent to that of the control at 12% transgenic grain, but not at lower percentages of transgenic grain.

Example 17

Production of Fructose from Corn Flour Using Thermophilic Enzymes

Corn that expresses the hyperthermophilic α-amylase, 797GL3, was shown to facilitate production of fructose when mixed with an α-glucosidase (MalA) and a xylose isomerase (XylA).

Seed from pNOV6201 transgenic plants expressing 797GL3 were ground to a flour in a Kleco cell thus creating amylase flour. Non-transgenic corn kernels were ground in the same manner to generate control flour.

The α-glucosidase, MalA (from *S. solfataricus*), was expressed in *E. coli*. Harvested bacteria were suspended in 50 mM potassium phosphate buffer pH 7.0 containing 1 mM 4-(2-aminoethyl)benzenesulfonyl fluoride then lysed in a French pressure cell. The lysate was centrifuged at 23,000×g for 15 min at 4° C. The supernatant solution was removed, heated to 70° C. for 10 min, cooled on ice for 10 min, then centrifuged at 34,000×g for 30 min at 4° C. The supernatant solution was removed and the MalA concentrated two-fold in centricon 10 devices. The filtrate of the centricon 10 step was retained for use as a negative control for MalA.

Xylose (glucose) isomerase was prepared by expressing the xylA gene of *T. neapolitana* in *E. coli*. Bacteria were suspended in 100 mM sodium phosphate pH 7.0 and lysed by passage through a French pressure cell. After precipitation of cell debris, the extract was heated at 80° C. for 10 min then centrifuged. The supernatant solution contained the XylA enzymatic activity. An empty-vector control extract was prepared in parallel with the XylA extract.

Corn flour (60 mg per sample) was mixed with buffer and extracts from *E coli*. As indicated in Table 3, samples contained amylase corn flour (amylase) or control corn flour (control), 50 µl of either MalA extract (+) or filtrate (−), and 20 µl of either XylA extract (+) or empty vector control (−). All samples also contained 230 µl of 50 mM MOPS, 10 mM MgSO4, and 1 mM CoCl2; pH of the buffer was 7.0 at room temperature.

Samples were incubated at 85° C. for 18 hours. At the end of the incubation time, samples were diluted with 0.9 ml of 85° C. water and centrifuged to remove insoluble material. The supernatant fraction was then filtered through a Centricon3 ultrafiltration device and analyzed by HPLC with ELSD detection.

The gradient HPLC system was equipped with Astec Polymer Amino Column, 5 micron particle size, 250×4.6 mm and an Alltech ELSD 2000 detector. The system was pre-equilibrated with a 15:85 mixture of water:acetonitrile. The flow rate was 1 ml/min. The initial conditions were maintained for 5 min after injection followed by a 20 min gradient to 50:50 water:acetonitrile followed by 10 minutes of the same solvent. The system was washed with 20 min of 80:20 water: acetonitrile and then re-equilibrated with the starting solvent. Fructose was eluted at 5.8 min and glucose at 8.7 min.

TABLE 3

| Sample | Corn flour | MalA | XylA | fructose peak area × $10^{-6}$ | glucose peak area × $10^{-6}$ |
|---|---|---|---|---|---|
| 1 | amylase | + | + | 25.9 | 110.3 |
| 2 | amylase | − | + | 7.0 | 12.4 |
| 3 | amylase | + | − | 0.1 | 147.5 |
| 4 | amylase | − | − | 0 | 25.9 |
| 5 | control | + | + | 0.8 | 0.5 |
| 6 | control | − | + | 0.3 | 0.2 |
| 7 | control | + | − | 1.3 | 1.7 |
| 8 | control | − | − | 0.2 | 0.3 |

The HPLC results also indicated the presence of larger maltooligosaccharides in all samples containing the α-amylase. These results demonstrate that the three thermophilic enzymes can function together to produce fructose from corn flour at a high temperature.

Example 18

Amylase Flour with Isomerase

In another example, amylase flour was mixed with purified MalA and each of two bacterial xylose isomerases: XylA of *T. maritima*, and an enzyme designated BD8037 obtained from Diversa. Amylase flour was prepared as described in Example 18.

*S. solfataricus* MalA with a 6His purification tag was expressed in *E. coli*. Cell lysate was prepared as described in Example 18, then purified to apparent homogeneity using a nickel affinity resin (Probond, Invitrogen) and following the manufacturer's instructions for native protein purification.

*T. maritima* XylA with the addition of an S tag and an ER retention signal was expressed in *E. coli* and prepared in the same manner as the *T. neapolitana* XylA described in Example 18.

Xylose isomerase BD8037 was obtained as a lyophilized powder and resuspended in 0.4× the original volume of water.

Figure 15:
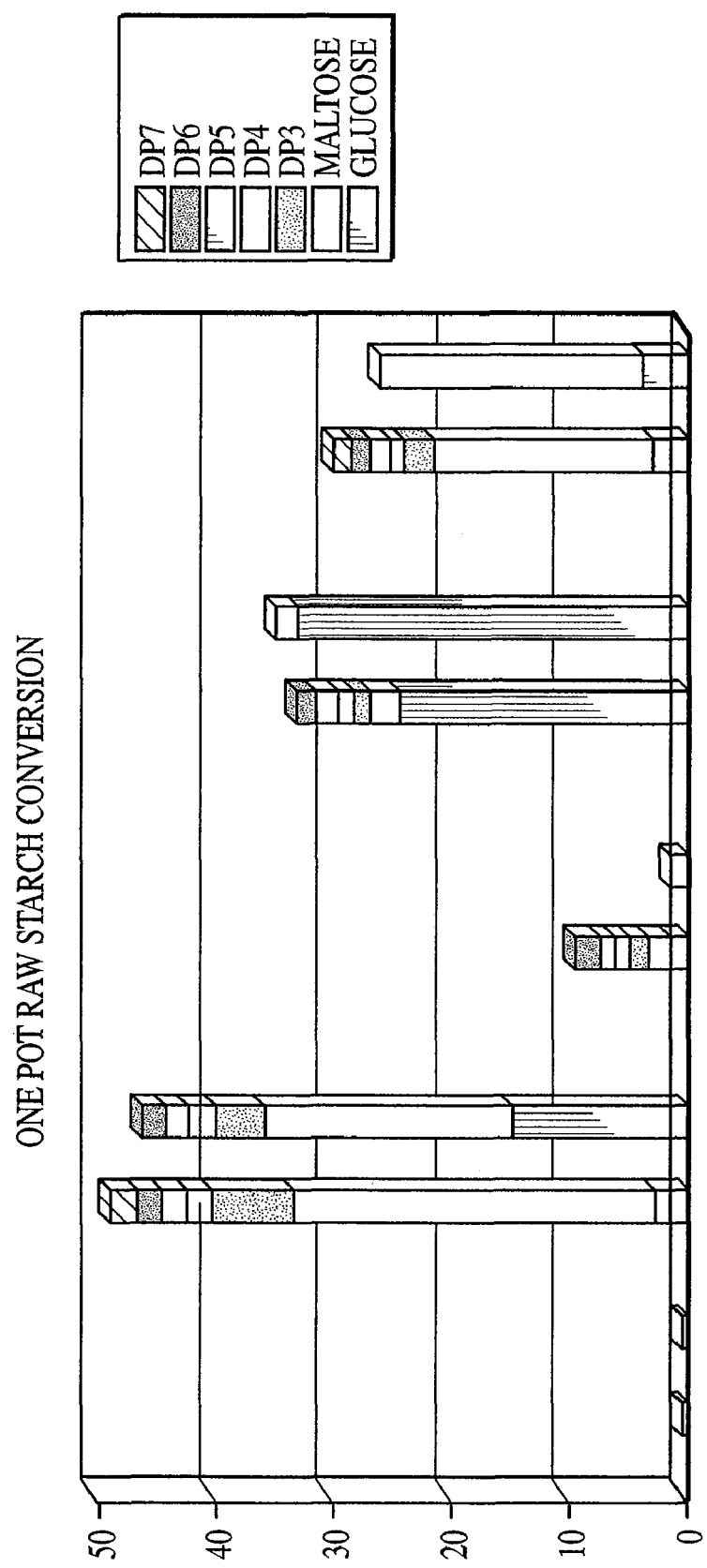
FIG. 15 depicts the conversion of raw starch at room temperature or 30° C. In this figure, the reaction mixtures 1 and 2 are a combination of water and starch at room temperature and 30° C., respectively. Reaction mixtures 3 and 4 are a combination of barley α-amylase and starch at room temperature and at 30° C., respectively. Reaction mixtures 5 and 6 are combinations of *Thermoanaerobacterium* glucoamylase and starch at room temperature and 30° C., respectively. Reactions mixtures 7 and 8 are combinations of barley α-amylase (sigma) and *Thermoanaerobacterium* glucoamylase and starch at room temperature and 30° C., respectively. Reaction mixtures 9 and 10 are combinations of Barley alpha-amylase (sigma) control, and starch at room temperature and 30° C., respectively. The degree of polymerization (DP) of the products of the *Thermoanaerobacterium* glucoamylase is indicated.
Figure 16:
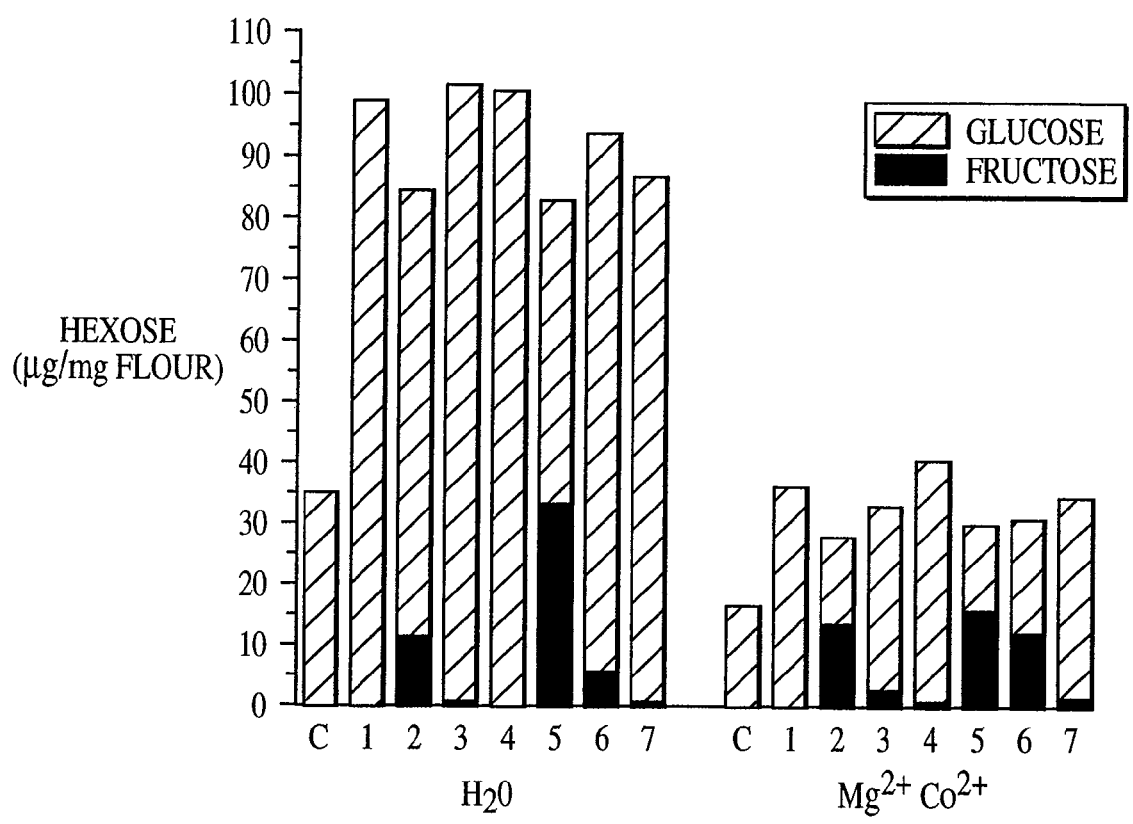
FIG. 16 depicts the production of fructose from amylase transgenic corn flour using a combination of alpha amylase, alpha glucosidase, and glucose isomerase as described in Example 19. Amylase corn flour was mixed with enzyme solutions plus water or buffer. All reactions contained 60 mg amylase flour and a total of 600 μl of liquid and were incubated for 2 hours at 90° C.

Amylase corn flour was mixed with enzyme solutions plus water or buffer. All reactions contained 60 mg amylase flour and a total of 600 µl of liquid. One set of reactions was buffered with 50 mM MOPS, pH 7.0 at room temperature, plus 10 nM MgSO4 and 1 mM CoCl2; in a second set of reactions the metal-containing buffer solution was replaced by water. Isomerase enzyme amounts were varied as indicated in Table 4. All reactions were incubated for 2 hours at 90° C. Reaction supernatant fractions were prepared by centrifugation. The pellets were washed with an additional 600 µl H₂O and recentrifuged. The supernatant fractions from each reaction were combined, filtered through a Centricon 10, and, analyzed by HPLC with ELSD detection as described in Example 17. The amounts of glucose and fructose observed are graphed in FIG. 15.

TABLE 4

| Sample | Amylase flour | Mal A | Isomerase |
|---|---|---|---|
| 1 | 60 mg | + | none |
| 2 | 60 mg | + | *T. maritima*, 100 µl |
| 3 | 60 mg | + | *T. maritima*, 10 µl |
| 4 | 60 mg | + | *T. maritima*, 2 µl |
| 5 | 60 mg | + | BD8037, 100 µl |
| 7 | 60 mg | + | BD8037, 2 µl |
| C | 60 mg | none | none |

With each of the isomerases, fructose was produced from corn flour in a dose-dependent manner when α-amylase and α-glucosidase were present in the reaction. These results demonstrate that the grain-expressed amylase 797GL3 can function with MalA and a variety of different thermophilic isomerases, with or without added metal ions, to produce fructose from corn flour at a high temperature. In the presence of added divalent metal ions, the isomerases can achieve the predicted fructose: glucose equilibrium at 90° C. of approximately 55% fructose. This would be an improvement over the current process using mesophilic isomerases, which requires a chromatographic separation to increase the fructose concentration.

Example 19

Expression of a Pullulanase in Corn

Transgenic plants that were homozygous for either pNOV7013 or pNOV7005 were crossed to generate transgenic corn seed expressing both the 797GL3 α-amylase and 6GP3 pullulanase.

T1 or T2 seed from self-pollinated maize plants transformed with either pNOV 7005 or pNOV 4093 were obtained. pNOV4093 is a fusion of the maize optimized synthetic gene for 6GP3 (SEQ ID: 3,4) with the amyloplast targeting sequence (SEQ ID NO: 7,8) for localization of the fusion protein to the amyloplast. This fusion protein is under the control of the ADPgpp promoter (SEQ ID NO:11) for expression specifically in the endosperm. The pNOV7005 construct targets the expression of the pullulanase in the endoplasmic reticulum of the endosperm. Localization of this enzyme in the ER allows normal accumulation of the starch in the kernels. Normal staining for starch with an iodine solution was also observed, prior to any exposure to high temperature.

As described in the case of α-amylase the expression of pullulanase targeted to the amyloplast (pNOV4093) resulted in abnormal starch accumulation in the kernels. When the corn-ears are dried, the kernels shriveled up. Apparently, this thermophilic pullulanase is sufficiently active at low temperatures and hydrolyzes starch if allowed to be in direct contact with the starch granules in the seed endosperm.

Enzyme preparation or extraction of the enzyme from corn-flour: The pullulanase enzyme was extracted from the transgenic seeds by grinding them in Kleco grinder, followed by incubation of the flour in 50 mM NaOAc pH 5.5 buffer for 1 hr at RT, with continuous shaking. The incubated mixture was then spun for 15 min. at 14000 rpm. The supernatant was used as enzyme source.

Pullulanase assay: The assay reaction was carried out in 96-well plate. The enzyme extracted from the corn flour (100 µl) was diluted 10 fold with 900 µl of 50 mM NaOAc pH5.5 buffer, containing 40 mM CaCl₂. The mixture was vortexed, 1 tablet of Limit-Dextrizyme (azurine-crosslinked-pullulan, from Megazyme) was added to each reaction mixture and incubated at 75° C. for 30 min (or as mentioned). At the end of the incubation the reaction mixtures were spun at 3500 rpm for 15 min. The supernatants were diluted 5 fold and transferred into 96-well flat bottom plate for absorbance measurement at 590 nm. Hydrolysis of azurine-crosslinked-pullulan substrate by the pullulanase produces water-soluble dye fragments and the rate of release of these (measured as the increase in absorbance at 590 nm) is related directly to enzyme activity.

Figure 9:
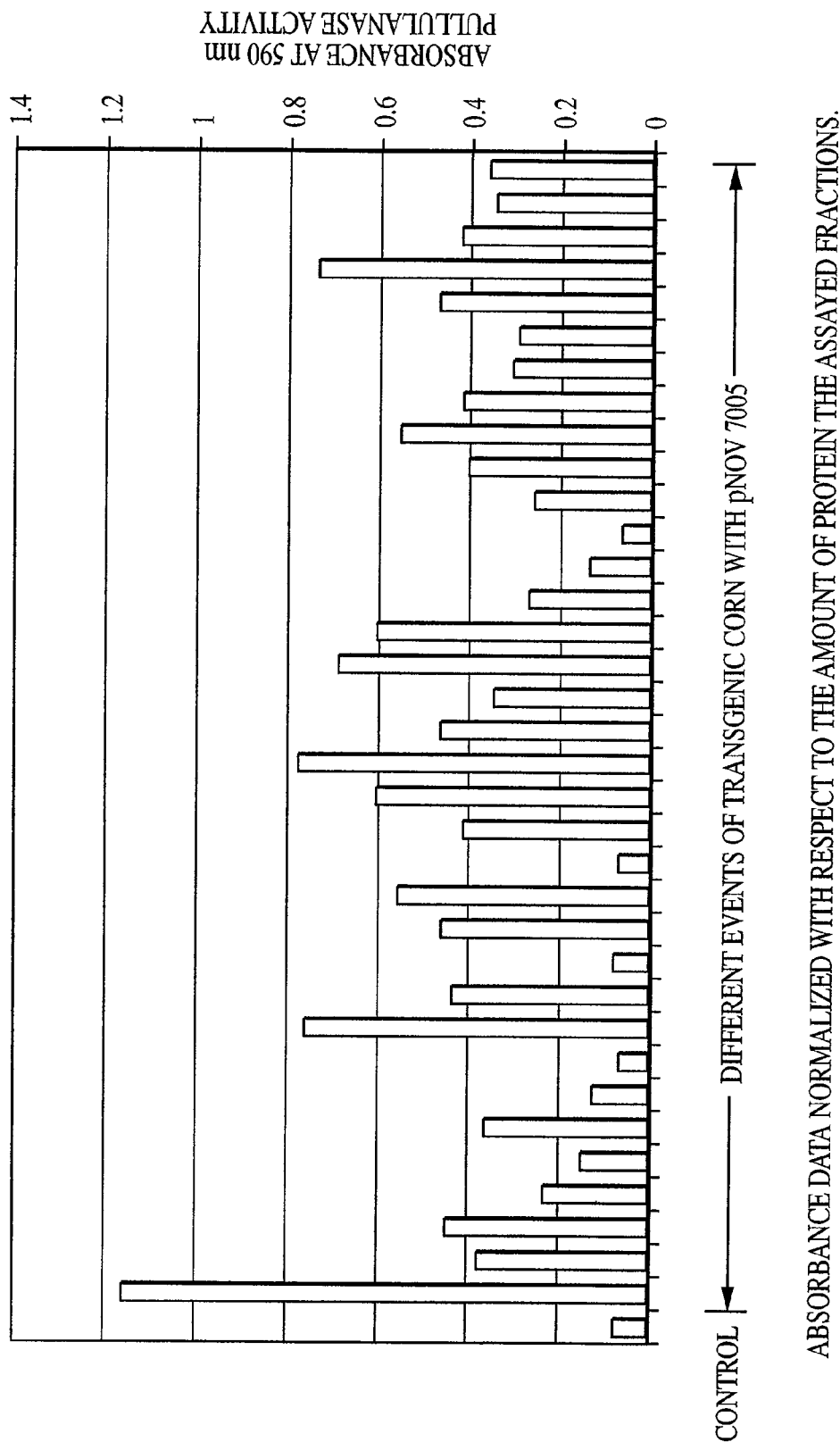
FIG. 9 shows the analysis of T2 seeds from different events transformed with pNOV 7005. High expression of pullulanase activity, compared to the non-transgenic control, can be detected in a number of events.

FIG. 9 shows the analysis of T2 seeds from different events transformed with pNOV 7005. High expression of pullulanase activity, compared to the non-transgenic control, can be detected in a number of events.

To a measured amount (~100 μg) of dry corn flour from transgenic (expressing pullulanase, or amylase or both the enzymes) and/or control (non-transgenic) 1000 μl of 50 mM NaOAc pH 5.5 buffer containing 40 mM $CaCl_2$ was added. The reaction mixtures were vortexed and incubated on a shaker for 1 hr. The enzymatic reaction was started by transferring the incubation mixtures to high temperature (75° C., the optimum reaction temperature for pullulanase or as mentioned in the figures) for a period of time as indicated in the figures. The reactions were stopped by cooling them down on ice. The reaction mixtures were then centrifuged for 10 min. at 14000 rpm. An aliquot (100 μl) of the supernatant was diluted three fold, filtered through 0.2-micron filter for HPLC analysis.

The samples were analyzed by HPLC using the following conditions:

Column: Alltech Prevail Carbohydrate ES 5 micron 250× 4.6 mm
Detector: Alltech ELSD 2000
Pump: Gilson 322
Injector: Gilson 215 injector/diluter
Solvents: HPLC grade Acetonitrile (Fisher Scientific) and Water (purified by Waters Millipore System)
Gradient used for oligosaccharides of low degree of polymerization (DP 1-15).

| Time | % Water | % Acetonitrile |
|---|---|---|
| 0 | 15 | 85 |
| 5 | 15 | 85 |
| 25 | 50 | 50 |
| 35 | 50 | 50 |
| 36 | 80 | 20 |
| 55 | 80 | 20 |
| 56 | 15 | 85 |
| 76 | 15 | 85 |

Gradient used for saccharides of high degree of polymerization (DP 20-100 and above).

| Time | % Water | % Acetonitrile |
|---|---|---|
| 0 | 35 | 65 |
| 60 | 85 | 15 |
| 70 | 85 | 15 |
| 85 | 35 | 65 |
| 100 | 35 | 65 |

System used for data analysis: Gilson Unipoint Software System Version 3.2

FIGS. 10A and 10B show the HPLC analysis of the hydrolytic products generated by expressed pullulanase from starch in the transgenic corn flour. Incubation of the flour of pullulanase expressing corn in reaction buffer at 75° C. for 30 minus results in production of medium chain oligosaccharides (DP ~10-30) and short amylose chains (DP ~100-200) from cornstarch. This figure also shows the dependence of pullulanase activity on presence of calcium ions.

Transgenic corn expressing pullulanase can be used to produce modified-starch/dextrin that is debranched (α1-6 linkages cleaved) and hence will have high level of amylose/straight chain dextrin. Also depending on the kind of starch (e.g. waxy, high amylose etc.) used the chain length distribution of the amylose/dextrin generated by the pullulanase will vary, and so will the property of the modified-starch/dextrin.

Hydrolysis of α1-6 linkage was also demonstrated using pullulan as the substrate. The pullulanase isolated from corn flour efficiently hydrolyzed pullulan. HPLC analysis (as described) of the product generated at the end of incubation showed production of maltotriose, as expected, due to the hydrolysis of the α1-6 linkages in the pullulan molecules by the enzyme from the corn.

Example 20

Expression of Pullulanase in Corn

Expression of the 6gp3 pullulanase was further analyzed by extraction from corn flour followed by PAGE and Coomassie staining. Corn-flour was made by grinding seeds, for 30 sec., in the Kleco grinder. The enzyme was extracted from about 150 mg of flour with 1 ml of 50 mM NaOAc pH 5.5 buffer. The mixture was vortexed and incubated on a shaker at RT for 1 hr, followed by another 15 min incubation at 70° C. The mixture was then spun down (14000 rpm for 15 min at RT) and the supernatant was used as SDS-PAGE analysis. A protein band of the appropriate molecular weight (95 kDal) was observed. These samples are subjected to a pullulanase assay using commercially available dye-conjugated limit-dextrins (LIMIT-DEXTRIZYME, from Megazyme, Ireland). High levels of thermophilic pullulanase activity correlated with the presence of the 95 kD protein.

The Western blot and ELISA analysis of the transgenic corn seed also demonstrated the expression of ~95 kD protein that reacted with antibody produced against the pullulanase (expressed in $E.\ coli$).

Example 21

Figure 11A:
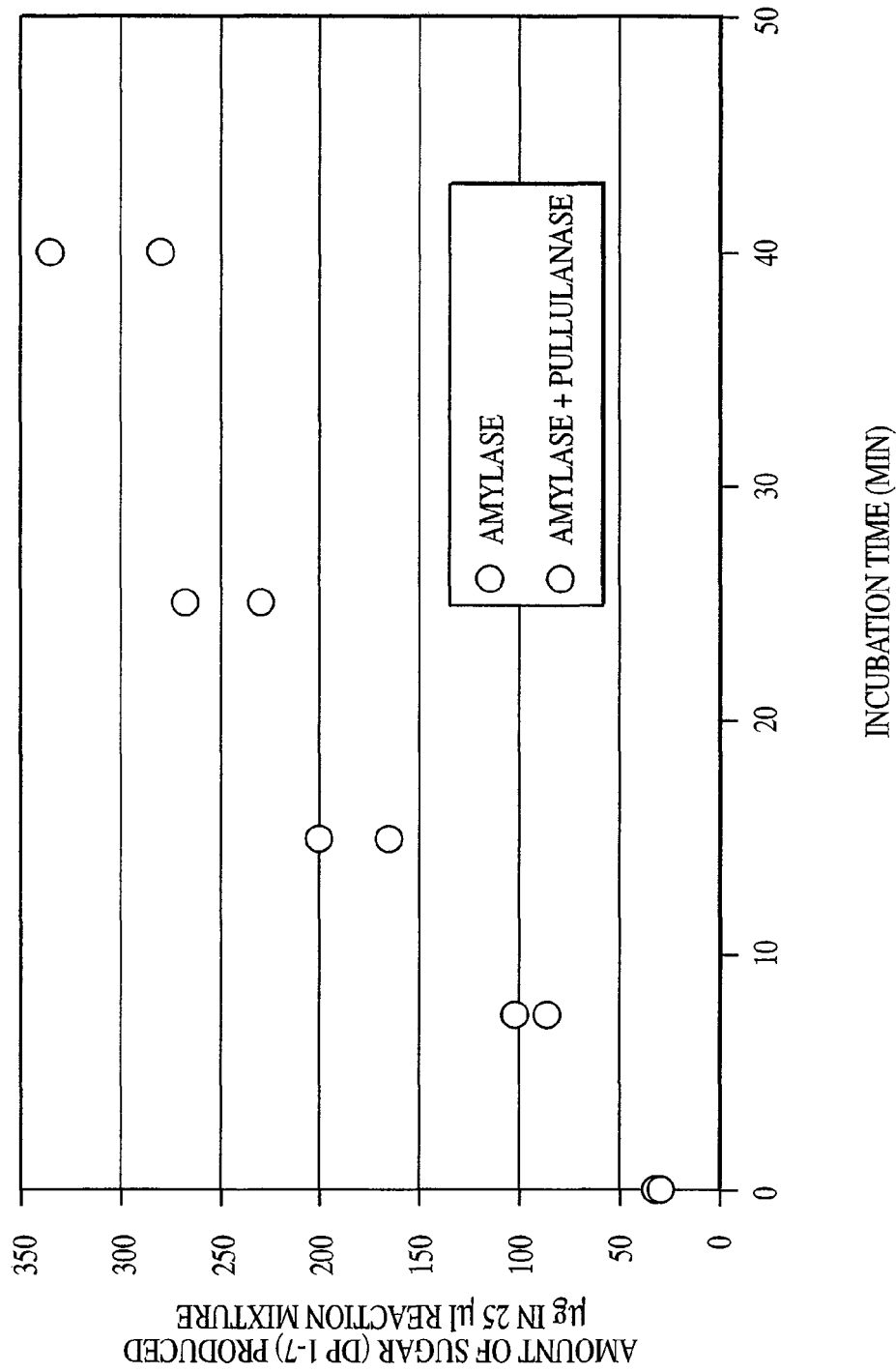
FIGS. 11A and 11B depict the data generated from HPLC analysis of the starch hydrolysis product from two reaction mixtures. The first reaction indicated as 'Amylase' contains a mixture [1:1 (w/w)] of corn flour samples of α-amylase expressing transgenic corn and non-transgenic corn A188; and the second reaction mixture 'Amylase+Pullulanase' contains a mixture [1:1 (w/w)] of corn flour samples of α-amylase expressing transgenic corn and pullulanase expressing transgenic corn.
Figure 11B:
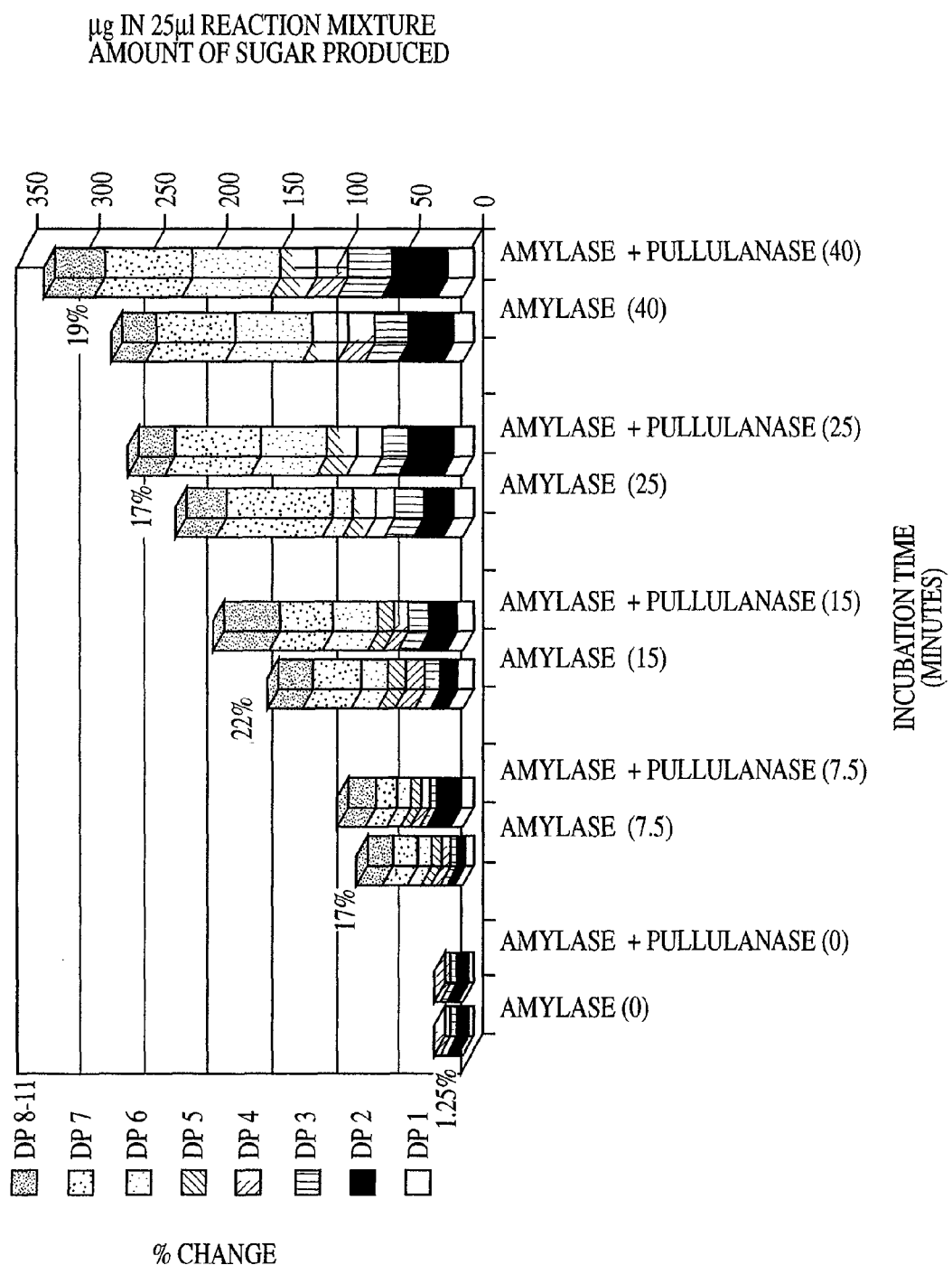

Increase in the Rate of Starch Hydrolysis and Improved Yield of Small Chain (Fermentable) Oligosaccharides by the Addition of Pullulanase Expressing Corn The data shown in FIGS. 11A and 11B was generated from HPLC analysis, as described above, of the starch hydrolysis products from two reaction mixtures. The first reaction indicated as 'Amylase' contains a mixture [1:1 (w/w)] of corn flour samples of α-amylase expressing transgenic corn made according to the method described in Example 4, for example, and non-transgenic corn A188; and the second reaction mixture 'Amylase+Pullulanase' contains a mixture [1:1 (w/w)] of corn flour samples of α-amylase expressing transgenic corn and pullulanase expressing transgenic corn made according to the method described in Example 19. The results obtained support the benefit of use of pullulanase in combination with α-amylase during the starch hydrolysis processes. The benefits are from the increased rate of starch hydrolysis (FIG. 11A) and increase yield of fermentable oligosaccharides with low DP (FIG. 11B).

It was found that α-amylase alone or α-amylase and pullulanase (or any other combination of starch hydrolytic enzymes) expressed in corn can be used to produce maltodextrin (straight or branched oligosaccharides) (FIGS. 11A, 11B, 12, and 13A). Depending on the reaction conditions, the type of hydrolytic enzymes and their combinations, the type of starch used the composition of the maltodextrins produced, and hence their properties, will vary.

Figure 12:
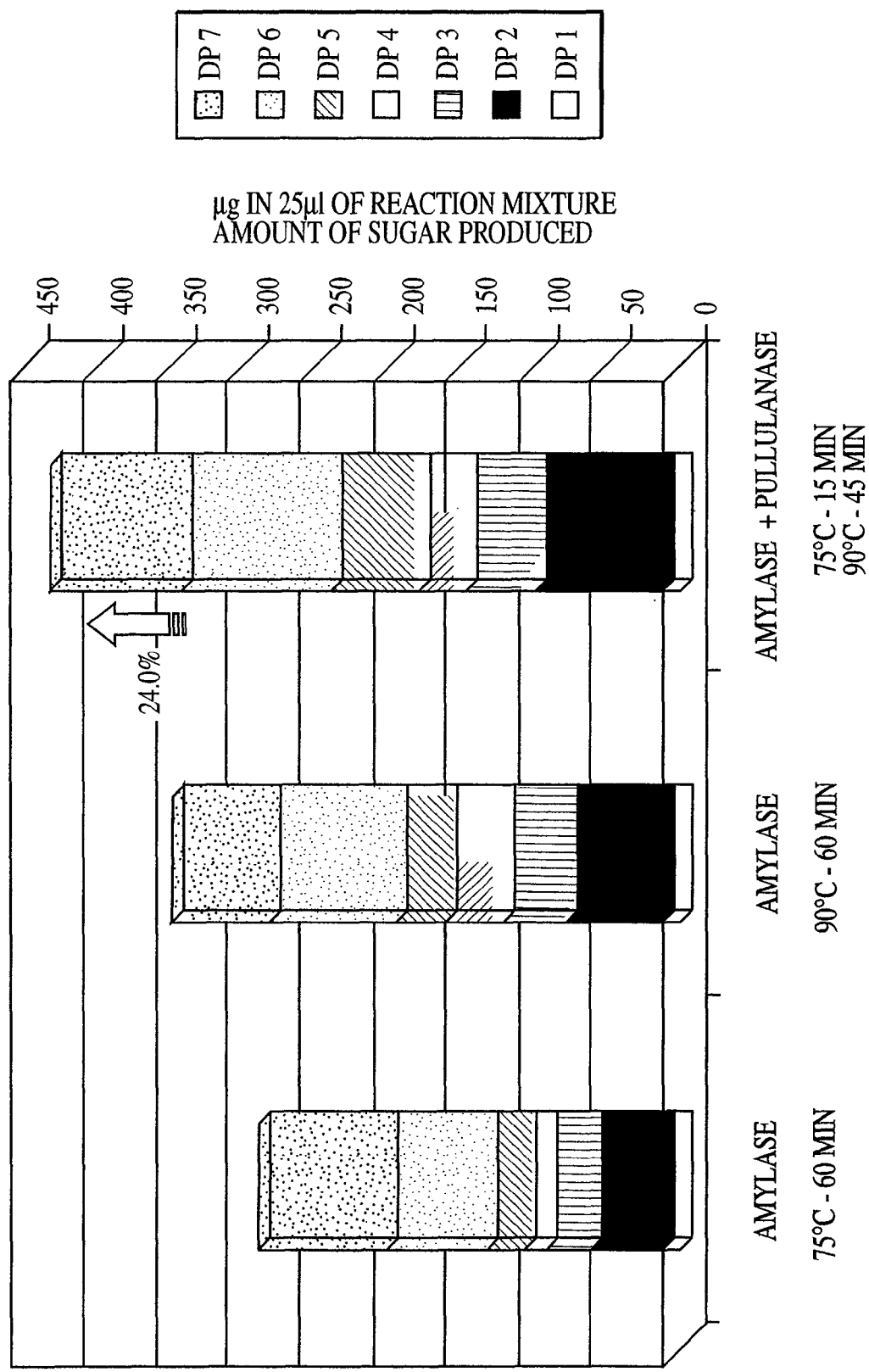
FIG. 12 depicts the amount of sugar product in μg in 25 μl of reaction mixture for two reaction mixtures. The first reaction indicated as 'Amylase' contains a mixture [1:1 (w/w)] of corn flour samples of α-amylase expressing transgenic corn and non-transgenic corn A188; and the second reaction mixture 'Amylase+Pullulanase' contains a mixture [1:1 (w/w)] of corn flour samples of α-amylase expressing transgenic corn and pullulanase expressing transgenic corn.

FIG. 12 depicts the results of an experiment carried out in a similar manner as described for FIG. 11. The different temperature and time schemes followed during incubation of the reactions are indicated in the figure. The optimum reaction temperature for pullulanase is 75° C. and for α-amylase it is >95° C. Hence, the indicated schemes were followed to provide scope to carry out catalysis by the pullulanase and/or the α-amylase at their respective optimum reaction temperature. It can be clearly deduced from the result shown that combination of α-amylase and pullulanase performed better in hydrolyzing cornstarch at the end of 60 min incubation period.

Figure 13A:
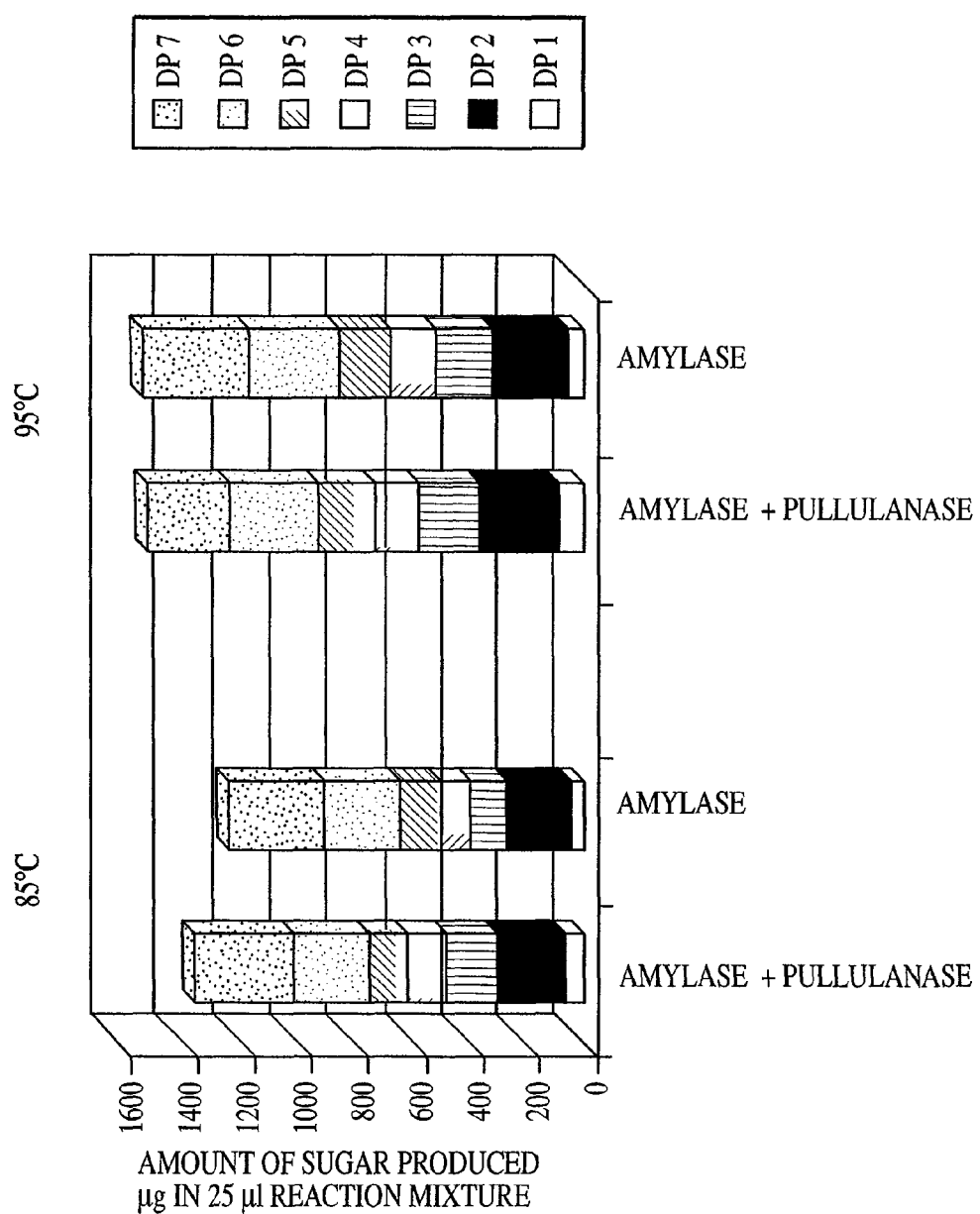
FIGS. 13A and 13B shows the starch hydrolysis product from two sets of reaction mixtures at the end of 30 minutes incubation at 85° C. and 95° C. For each set there are two reaction mixtures; the first reaction indicated as 'Amylase×Pullulanase' contains flour from transgenic corn (generated by cross pollination) expressing both the α-amylase and the pullulanase, and the second reaction indicated as 'Amylase' mixture of corn flour samples of α-amylase expressing transgenic corn and non-transgenic corn A188 in a ratio so as to obtain same amount of α-amylase activity as is observed in the cross (Amylase×Pullulanase).
Figure 13B:
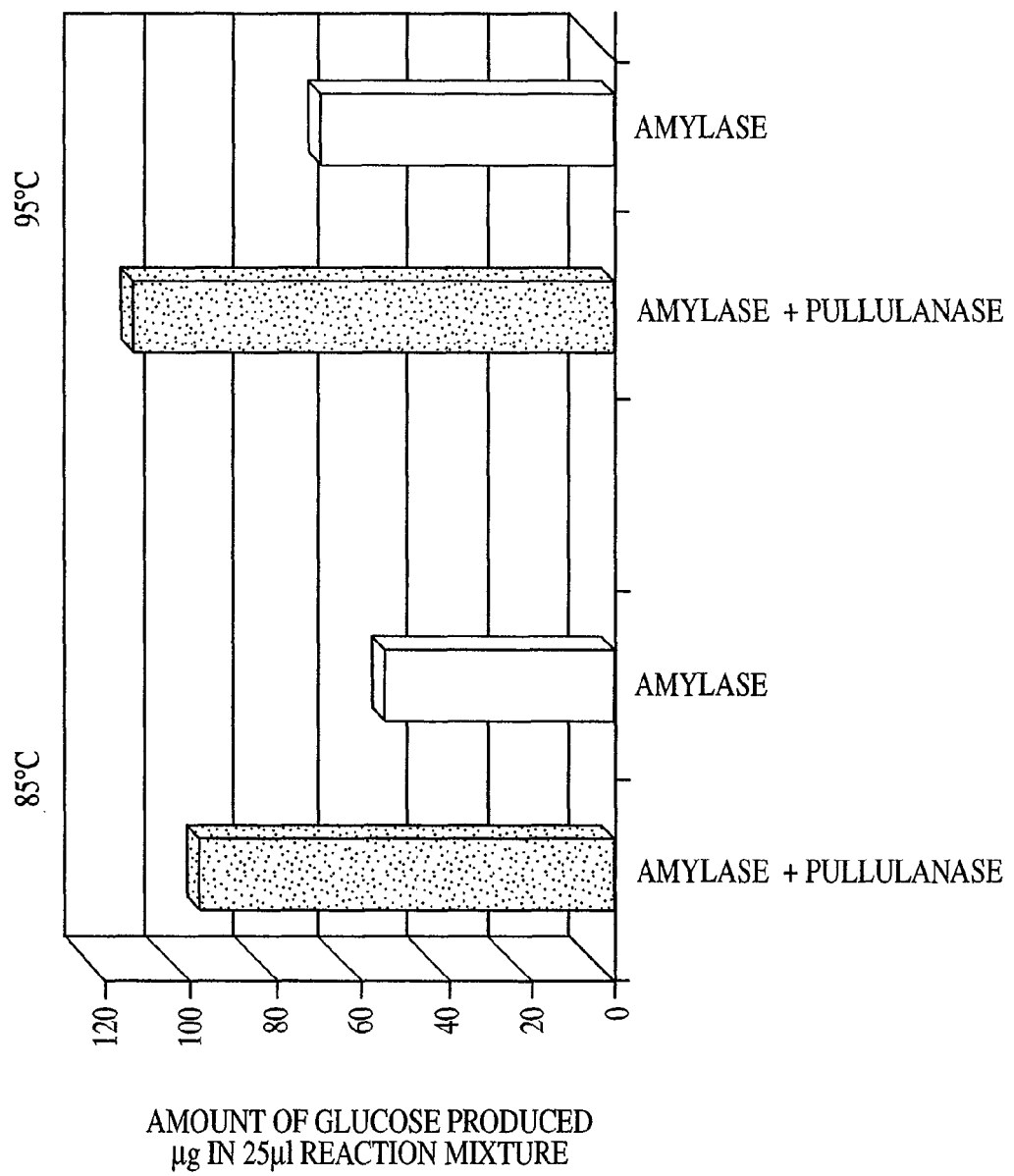

HPLC analysis, as described above (except ~150 mg of corn flour was used in these reactions), of the starch hydrolysis product from two sets of reaction mixtures at the end of 30 min incubation is shown in FIGS. 13A and 13B. The first set of reactions was incubated at 85° C. and the second one was incubated at 95° C. For each set there are two reaction mixtures; the first reaction indicated as 'Amylase×Pullulanase' contains flour from transgenic corn (generated by cross pollination) expressing both the α-amylase and the pullulanase, and the second reaction indicated as 'Amylase' mixture of corn flour samples of α-amylase expressing transgenic corn and non-transgenic corn A188 in a ratio so as to obtain same amount of α-amylase activity as is observed in the cross (Amylase×Pullulanase). The total yield of low DP oligosaccharides was more in case of α-amylase and pullulanase cross compared to corn expressing α-amylase alone, when the corn flour samples were incubated at 85° C. The incubation temperature of 95° C. inactivates (at least partially) the pullulanase enzyme, hence little difference can be observed between 'Amylase×Pullulanase' and 'Amylase'. However, the data for both the incubation temperatures shows significant improvement in the amount of glucose produced (FIG. 13B), at the end of the incubation period, when corn flour of α-amylase and pullulanase cross was used compared to corn expressing α-amylase alone. Hence use of corn expressing both α-amylase and pullulanase can be especially beneficial for the processes where complete hydrolysis of starch to glucose is important.

The above examples provide ample support that pullulanase expressed in corn seeds, when used in combination with α-amylase, improves the starch hydrolysis process. Pullulanase enzyme activity, being α1-6 linkage specific, debranches starch far more efficiently than α-amylase (an α-1-4 linkage specific enzyme) thereby reducing the amount of branched oligosaccharides (e.g. limit-dextrin, panose; these are usually non-fermentable) and increasing the amount of straight chain short oligosaccharides (easily fermentable to ethanol etc.). Secondly, fragmentation of starch molecules by pullulanase catalyzed debranching increases substrate accessibility for the α-amylase, hence an increase in the efficiency of the α-amylase catalyzed reaction results.

Example 22

Figure 14:
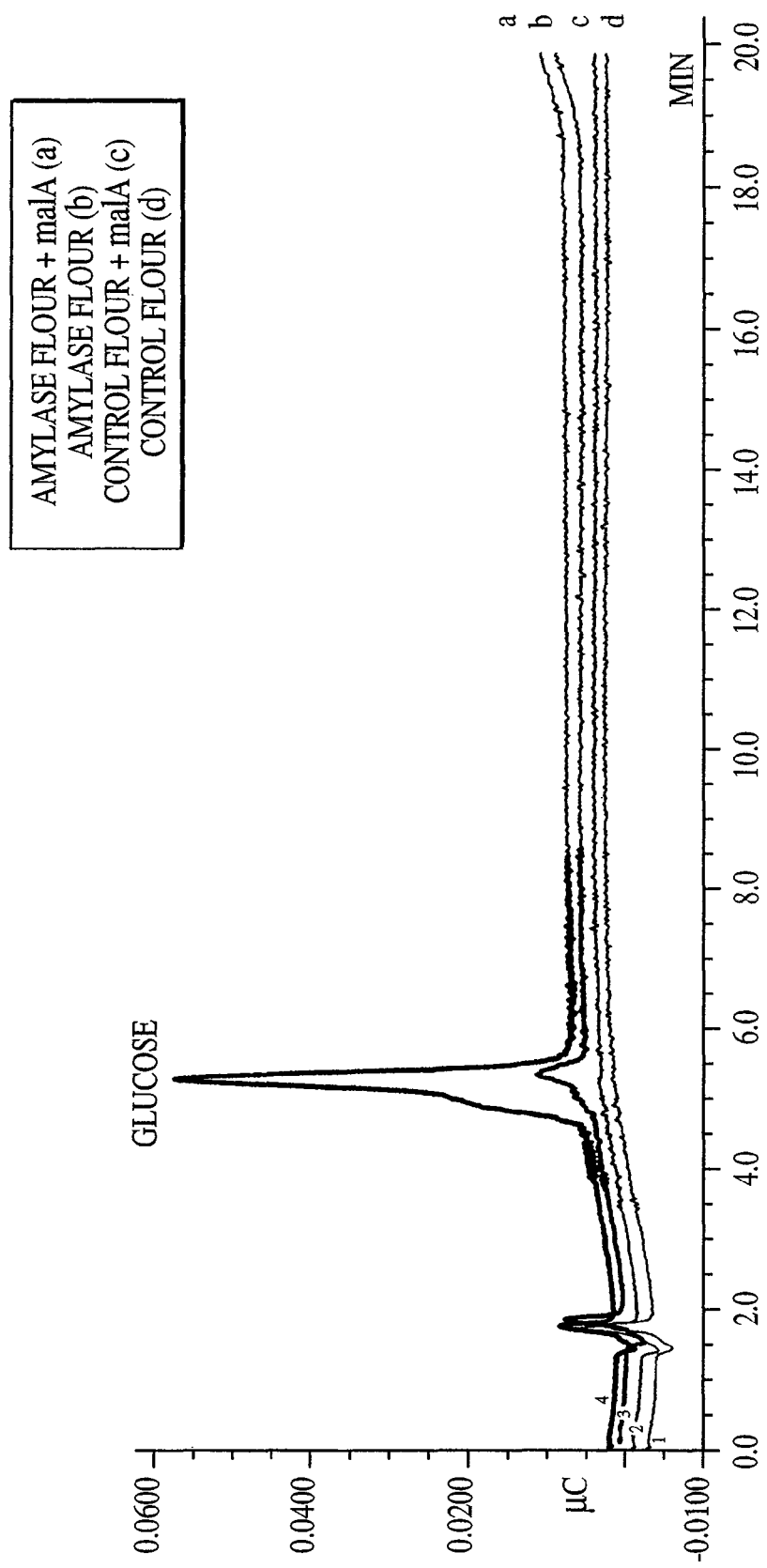
FIG. 14 depicts the degradation of starch to glucose using non-transgenic corn seed (control), transgenic corn seed comprising the 797GL3 α-amylase, and a combination of 797GL3 transgenic corn seed with Mal A α-glucosidase.

To determine whether the 797GL3 alpha amylase and malA alpha-glucosidase could function under similar pH and temperature conditions to generate an increased amount of glucose over that produced by either enzyme alone, approximately 0.35 ug of malA alpha glucosidase enzyme (produced in bacteria) was added to a solution containing 1% starch and starch purified from either non-transgenic corn seed (control) or 797GL3 transgenic corn seed (in 797GL3 corn seed the alpha amylase co-purifies with the starch). In addition, the purified starch from non-transgenic and 797GL3 transgenic corn seed was added to 1% corn starch in the absence of any malA enzyme. The mixtures were incubated at 90° C., pH 6.0 for 1 hour, spun down to remove any insoluble material, and the soluble fraction was analyzed by HPLC for glucose levels. As shown in FIG. 14, the 797GL3 alpha-amylase and malA alpha-glucosidase function at a similar pH and temperature to break down starch into glucose. The amount of glucose generated is significantly higher than that produced by either enzyme alone.

Example 23

The utility of the *Thermoanaerobacterium* glucoamylase for raw starch hydrolysis was determined. As set forth in FIG. 15, the hydrolysis conversion of raw starch was tested with water, barley α-amylase (commercial preparation from Sigma), *Thermoanaerobacterum* glucoamylase, and combinations thereof were ascertained at room temperature and at 30° C. As shown, the combination of the barley α-amylase with the *Thermoanaerobacterium* glucoamylase was able to hydrolyze raw starch into glucose. Moreover, the amount of glucose produced by the barley amylase and thermoanaerobacter GA is significantly higher than that produced by either enzyme alone.

Example 24

Maize-Optimized Genes and Sequences for Raw-Starch Hydrolysis and Vectors for Plant Transformation The enzymes were selected based on their ability to hydrolyze raw-starch at temperatures ranging from approximately 20°-50° C. The corresponding genes or gene fragments were then designed by using maize preferred codons for the construction of synthetic genes as set forth in Example 1.

*Aspergillus shirousami* α-amylase/glucoamylase fusion polypeptide (without signal sequence) was selected and has the amino acid sequence as set forth in SEQ ID NO: 45 as identified in Biosci. Biotech. Biochem., 56:884-889 (1992); Agric. Biol. Chem. 545:1905-14 (1990); Biosci. Biotechnol. Biochem. 56:174-79 (1992). The maize-optimized nucleic acid was designed and is represented in SEQ ID NO:46.

Similarly, *Thermoanaerobacterium thermosaccharolyticum* glucoamylase was selected, having the amino acid of SEQ ID NO:47 as published in Biosci. Biotech. Biochem., 62:302-308 (1998), was selected. The maize-optimized nucleic acid was designed (SEQ ID NO: 48).

*Rhizopus oryzae* glucoamylase was selected having the amino acid sequence (without signal sequence) (SEQ ID NO: 50), as described in the literature (Agric. Biol. Chem. (1986) 50, pg 957-964). The maize-optimized nucleic acid was designed and is represented in SEQ ID NO:51.

Moreover, the maize α-amylase was selected and the amino acid sequence (SEQ ID NO: 51) and nucleic acid sequence (SEQ ID NO:52) were obtained from the literature. See, e.g., Plant Physiol. 105:759-760 (1994).

Expression cassettes are constructed to express the *Aspergillus shirousami* α-amylase/glucoamylase fusion polypeptide from the maize-optimized nucleic acid was designed as represented in SEQ ID NO:46, the *Thermoanaerobacterium thermosaccharolyticum* glucoamylase from the maize-optimized nucleic acid was designed as represented in SEQ ID NO: 48, the *Rhizopus oryzae* glucoamylase was selected having the amino acid sequence (without signal sequence) (SEQ ID NO: 49) from the maize-optimized nucleic acid was designed and is represented in SEQ ID NO:50, and the maize α-amylase.

A plasmid comprising the maize γ-zein N-terminal signal sequence (MRVLLVALALLALAASATS) (SEQ ID NO:17)

is fused to the synthetic gene encoding the enzyme. Optionally, the sequence SEKDEL is fused to the C-terminal of the synthetic gene for targeting to and retention in the ER. The fusion is cloned behind the maize γ-zein promoter for expression specifically in the endosperm in a plant transformation plasmid. The fusion is delivered to the corn tissue via *Agrobacterium* transfection.

Example 25

Expression cassettes comprising the selected enzymes are constructed to express the enzymes. A plasmid comprising the sequence for a raw starch binding site is fused to the synthetic gene encoding the enzyme. The raw starch binding site allows the enzyme fusion to bind to non-gelatinized starch. The raw-starch binding site amino acid sequence (SEQ ID NO:53) was determined based on literature, and the nucleic acid sequence was maize-optimized to give SEQ ID NO:54. The maize-optimized nucleic acid sequence is fused to the synthetic gene encoding the enzyme in a plasmid for expression in a plant.

Example 26

Construction of Maize-Optimized Genes and Vectors for Plant Transformation

The genes or gene fragments were designed by using maize preferred codons for the construction of synthetic genes as set forth in Example 1.

*Pyrococcus furiosus* EGLA, hyperthermophilic endoglucanase amino acid sequence (without signal sequence) was selected and has the amino acid sequence as set forth in SEQ ID NO: 55, as identified in Journal of Bacteriology (1999) 181, pg 284-290). The maize-optimized nucleic acid was designed and is represented in SEQ ID NO:56.

*Thermus flavus* xylose isomerase was selected and has the amino acid sequence as set forth in SEQ ID NO:57, as described in Applied Biochemistry and Biotechnology 62:15-27 (1997).

Expression cassettes are constructed to express the *Pyrococcus furiosus* EGLA (endoglucanase) from the maize-optimized nucleic acid (SEQ ID NO:56) and the *Thermus flavus* xylose isomerase from a maize-optimized nucleic acid encoding amino acid sequence SEQ ID NO:57 A plasmid comprising the maize γ-zein N-terminal signal sequence (MRVLLVALALLALAASATS) (SEQ ID NO:17) is fused to the synthetic maize-optimized gene encoding the enzyme. Optionally, the sequence SEKDEL is fused to the C-terminal of the synthetic gene for targeting to and retention in the ER. The fusion is cloned behind the maize γ-zein promoter for expression specifically in the endosperm in a plant transformation plasmid. The fusion is delivered to the corn tissue via *Agrobacterium* transfection.

Example 27

Production of Glucose from Corn Flour Using Thermophilic Enzymes Expressed in Corn Expression of the hyperthermophilic α-amylase, 797GL3 and α-glucosidase (MalA) were shown to result in production of glucose when mixed with an aqueous solution and incubated at 90° C.

A transgenic corn line (line 168A10B, pNOV4831) expressing MalA enzyme was identified by measuring α-glucosidase activity as indicated by hydrolysis of p-nitrophenyl-α-glucoside.

Corn kernels from transgenic plants expressing 797GL3 were ground to a flour in a Kleco cell thus creating amylase flour. Corn kernels from transgenic plants expressing MalA were ground to a flour in a Kleco cell thus creating MalA flour Non-transgenic corn kernels were ground in the same manner to generate control flour.

Buffer was 50 mM MES buffer pH 6.0.

Corn flour hydrolysis reactions: Samples were prepared as indicated in Table 5 below. Corn flour (about 60 mg per sample) was mixed with 40 ml of 50 mM MES buffer, pH 6.0. Samples were incubated in a water bath set at 90° C. for 2.5 and 14 hours. At the indicated incubation times, samples were removed and analyzed for glucose content.

The samples were assayed for glucose by a glucose oxidase/horse radish peroxidase based assay. GOPOD reagent contained: 0.2 mg/ml o-dianisidine, 100 mM Tris pH 7.5, 100 U/ml glucose oxidase & 10 U/ml horse radish peroxidase. 20 µl of sample or diluted sample were arrayed in a 96 well plate along with glucose standards (which varied from 0 to 0.22 mg/ml). 100 µl of GOPOD reagent was added to each well with mixing and the plate incubated at 37° C. for 30 min. 100 µl of sulfuric acid (9M) was added and absorbance at 540 nm was read. The glucose concentration of the samples was determined by reference to the standard curve. The quantity of glucose observed in each sample is indicated in Table 5.

TABLE 5

| Sample | WT flour mg | amylase flour mg | MalA flour Mg | Buffer ml | Glucose 2.5 h mg | Glucose 14 h mg |
|---|---|---|---|---|---|---|
| 1 | 66 | 0 | 0 | 40 | 0 | 0 |
| 2 | 31 | 30 | 0 | 40 | 0.26 | 0.50 |
| 3 | 30 | 0 | 31.5 | 40 | 0 | 0.09 |
| 4 | 0 | 32.2 | 30.0 | 40 | 2.29 | 12.30 |
| 5 | 0 | 6.1 | 56.2 | 40 | 1.16 | 8.52 |

These data demonstrate that when expression of hyperthermophilic α-amylase and α-glucosidase in corn result in a corn product that will generate glucose when hydrated and heated under appropriate conditions.

Example 28

Production of Maltodextrins

Grain expressing thermophilic α-amylase was used to prepare maltodextrins. The exemplified process does not require prior isolation of the starch nor does it require addition of exogenous enzymes.

Corn kernels from transgenic plants expressing 797GL3 were ground to a flour in a Kleco cell to create "amylase flour". A mixture of 10% transgenic/90% non-transgenic kernels was ground in the same manner to create "10% amylase flour."

Amylase flour and 10% amylase flour (approximately 60 mg/sample) were mixed with water at a rate of 5 µl of water per mg of flour. The resulting slurries were incubated at 90° C. for up to 20 hours as indicated in Table 6. Reactions were stopped by addition of 0.9 ml of 50 mM EDTA at 85° C. and mixed by pipetting. Samples of 0.2 ml of slurry were removed, centrifuged to remove insoluble material and diluted 3× in water. The samples were analyzed by HPLC with ELSD detection for sugars and maltodextrins. The gradient HPLC system was equipped with Astec Polymer Amino Column, 5 micron particle size, 250×4.6 mm and an Alltech ELSD 2000 detector. The system was pre-equilibrated with a 15:85 mixture of water:acetonitrile. The flow rate was 1 ml/min. The initial conditions were maintained for 5 min after injection followed by a 20 min gradient to 50:50 water:acetonitrile followed by 10 minutes of the same solvent. The system was washed with 20 min of 80:20 water:acetonitrile and then re-equilibrated with the starting solvent.

The resulting peak areas were normalized for volume and weight of flour. The response factor of ELSD per µg of carbohydrate decreases with increasing DP, thus the higher DP maltodextrins represent a higher percentage of the total than indicated by peak area.

Figure 17:
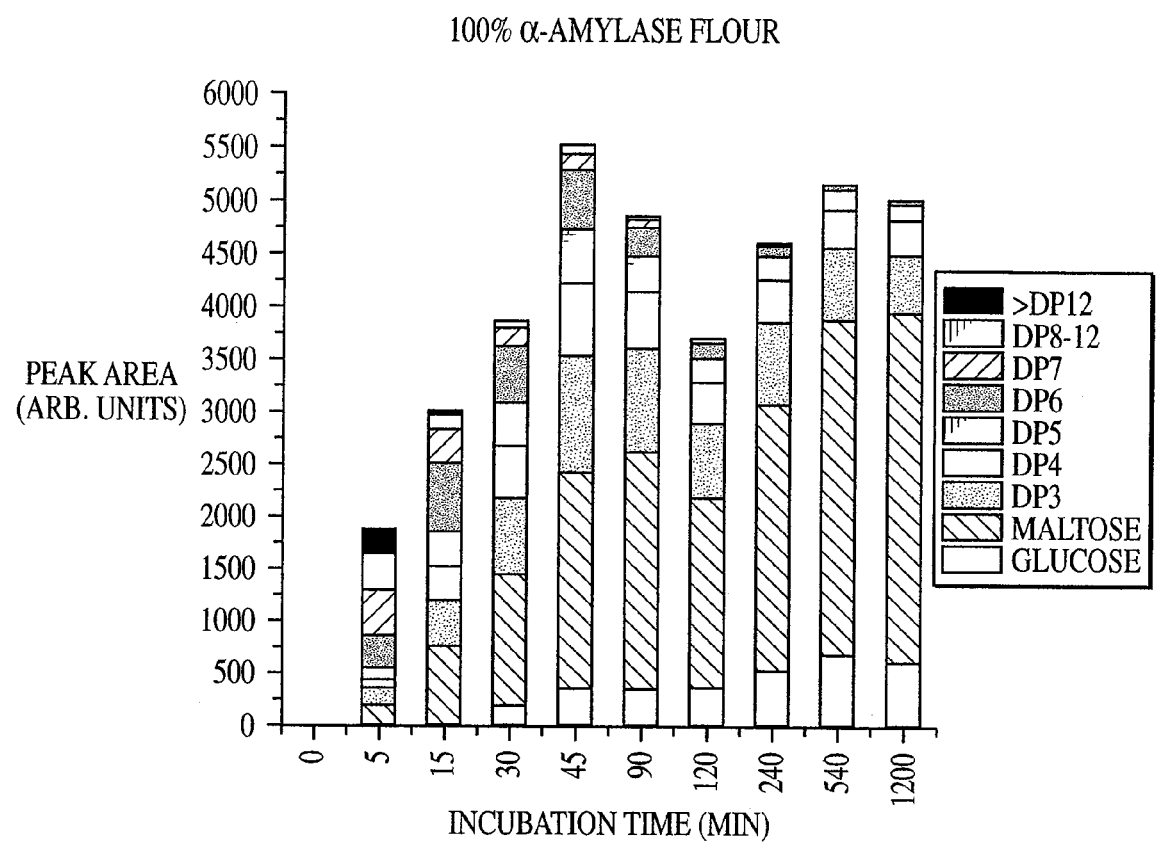
FIG. 17 depicts the peak areas of the products of reaction with 100% amylase flour from a self-processing kernel as a function of incubation time from 0-1200 minutes at 90° C.
Figure 18:
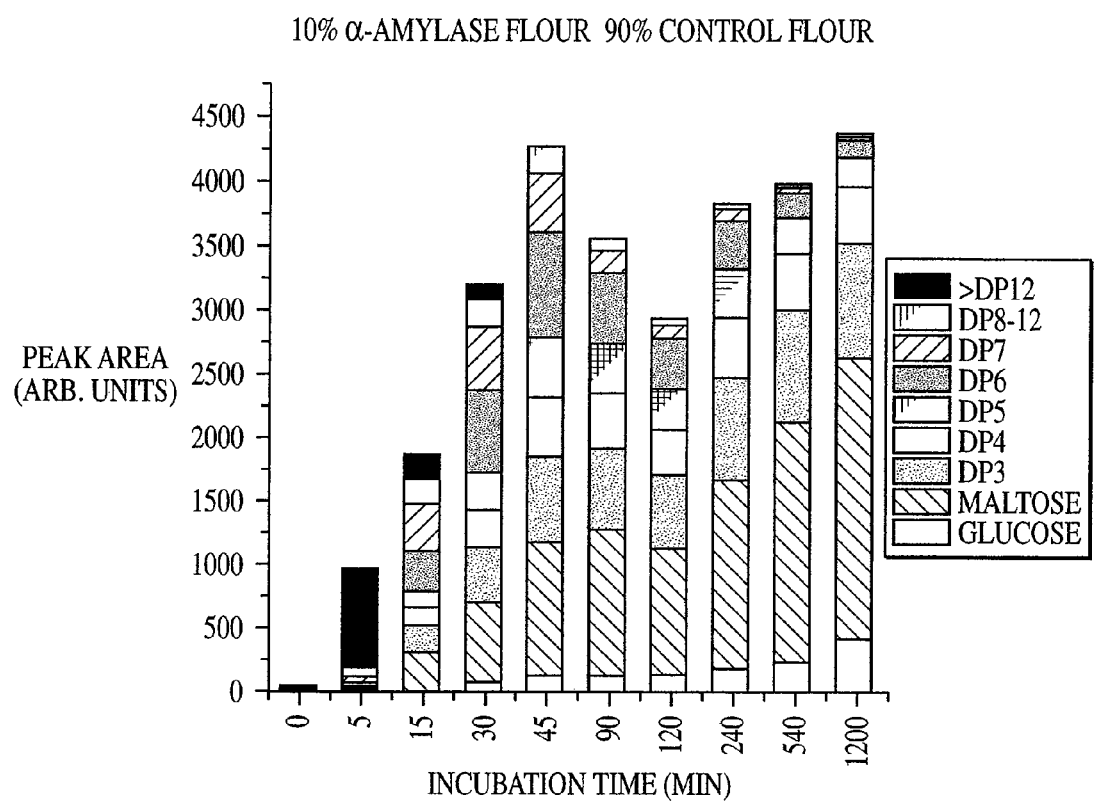
FIG. 18 depicts the peak areas of the products of reaction with 10% transgenic amylase flour from a self-processing kernel and 90% control corn flour as a function of incubation time from 0-1200 minutes at 90° C.

The relative peak areas of the products of reactions with 100% amylase flour are shown in FIG. 17. The relative peak areas of the products of reactions with 10% amylase flour are shown in FIG. 18.

These data demonstrate that a variety of maltodextrin mixtures can be produced by varying the time of heating. The level of α-amylase activity can be varied by mixing transgenic α-amylase-expressing corn with wild-type corn to alter the maltodextrin profile.

The products of the hydrolysis reactions described in this example can be concentrated and purified for food and other applications by use of a variety of well defined methods including: centrifugation, filtration, ion-exchange, gel permeation, ultrafiltration, nanofiltration, reverse osmosis, decolorizing with carbon particles, spray drying and other standard techniques known to the art.

Example 29

Effect of Time and Temperature on Maltodextrin Production

The composition of the maltodextrin products of autohydrolysis of grain containing thermophilic α-amylase may be altered by varying the time and temperature of the reaction.

In another experiment, amylase flour was produced as described in Example 28 above and mixed with water at a ratio of 300 µl water per 60 mg flour. Samples were incubated at 70°, 80°, 90°, or 100° C. for up to 90 minutes. Reactions were stopped by addition of 900 ml of 50 mM EDTA at 90° C., centrifuged to remove insoluble material and filtered through 0.45 µm nylon filters. Filtrates were analyzed by HPLC as described in Example 28.

Figure 19:
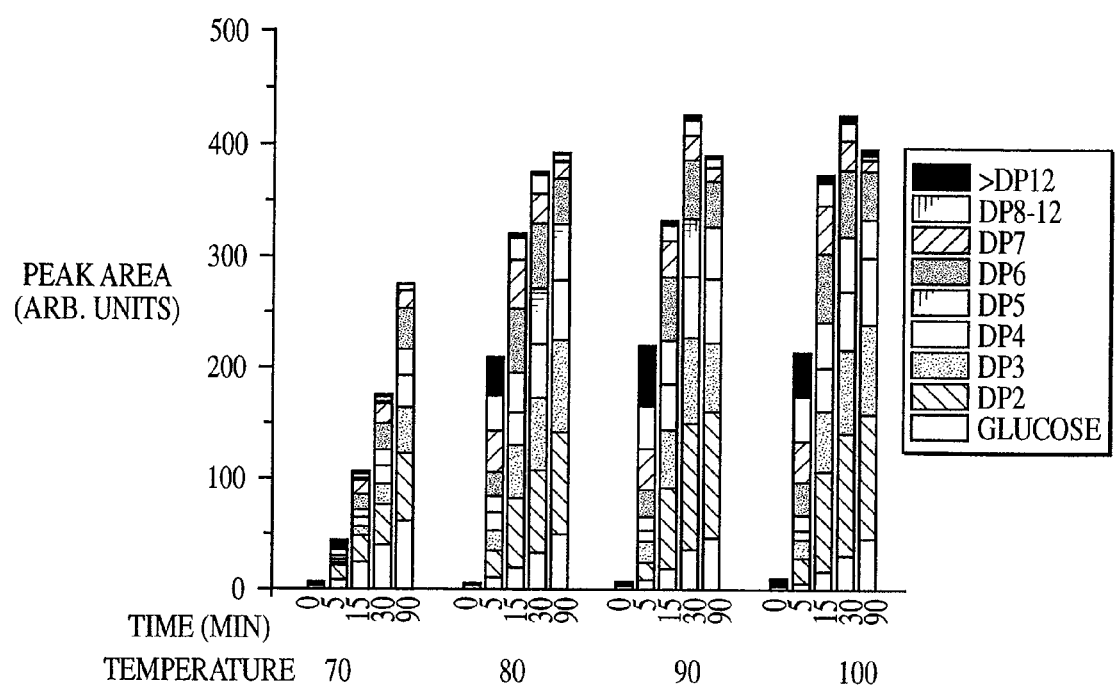
FIG. 19 provides the results of the HPLC analysis of transgenic amylase flour incubated at 70°, 80°, 90°, or 100° C. for up to 90 minutes to assess the effect of temperature on starch hydrolysis.

The result of this analysis is presented in FIG. 19. The DP number nomenclature refers to the degree of polymerization. DP2 is maltose; DP3 is maltotriose, etc. Larger DP maltodextrins eluted in a single peak near the end of the elution and are labeled ">DP12". This aggregate includes dextrins that passed through 0.45 µm filters and through the guard column and does not include any very large starch fragments trapped by the filter or guard column.

This experiment demonstrates that the maltodextrin composition of the product can be altered by varying both temperature and incubation time to obtain the desired maltooligosaccharide or maltodextrin product.

Example 30

Maltodextrin Production

The composition of maltodextrin products from transgenic maize containing thermophilic α-amylase can also be altered by the addition of other enzymes such as α-glucosidase and xylose isomerase as well as by including salts in the aqueous flour mixture prior to treating with heat.

In another, amylase flour, prepared as described above, was mixed with purified MalA and/or a bacterial xylose isomerase, designated BD8037. *S. sulfotaricus* MalA with a 6His purification tag was expressed in *E. coli*. Cell lysate was prepared as described in Example 28, then purified to apparent homogeneity using a nickel affinity resin (Probond, Invitrogen) and following the manufacturer's instructions for native protein purification. Xylose isomerase BD8037 was obtained as a lyophilized powder from Diversa and resuspended in 0.4× the original volume of water.

Amylase corn flour was mixed with enzyme solutions plus water or buffer. All reactions contained 60 mg amylase flour and a total of 600 µl of liquid. One set of reactions was buffered with 50 mM MOPS, pH 7.0 at room temperature, plus 10 mM MgSO4 and 1 mM $CoCl_2$; in a second set of reactions the metal-containing buffer solution was replaced by water. All reactions were incubated for 2 hours at 90° C. Reaction supernatant fractions were prepared by centrifugation. The pellets were washed with an additional 600 µl $H_2O$ and re-centrifuged. The supernatant fractions from each reaction were combined, filtered through a Centricon 10, and analyzed by HPLC with ELSD detection as described above.

Figure 20:
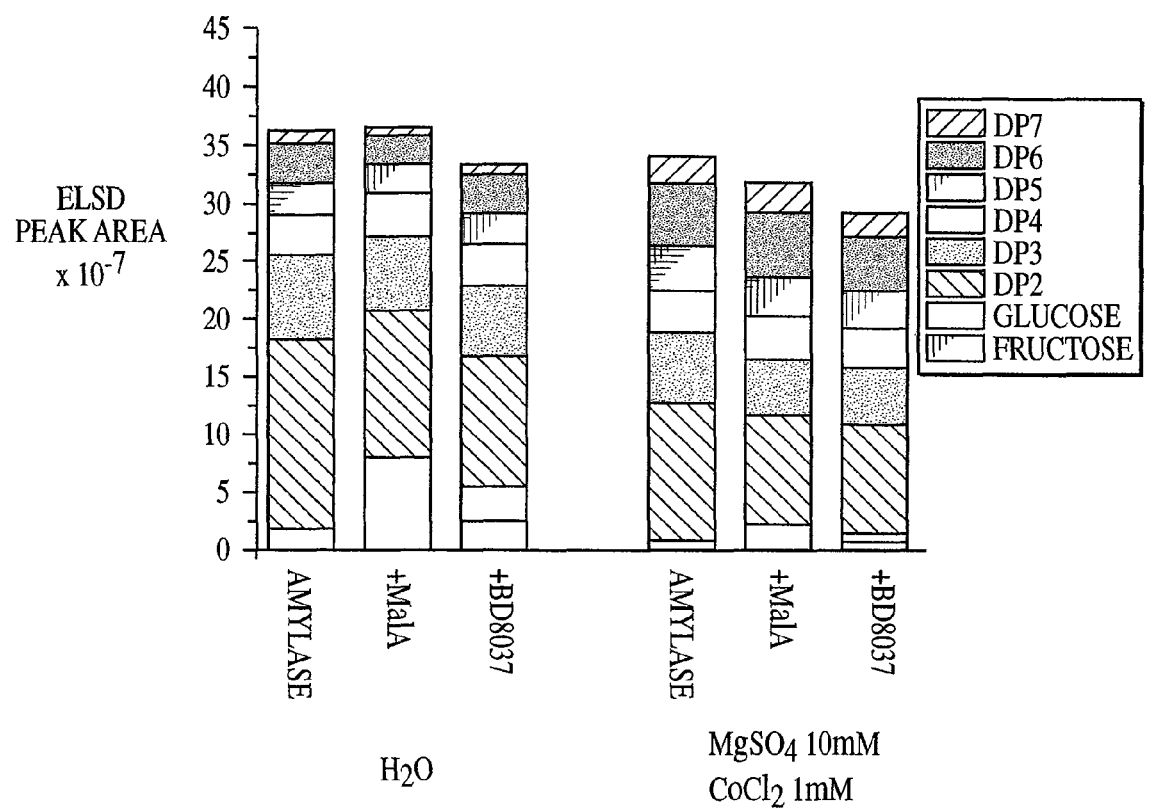
FIG. 20 depicts ELSD peak area for samples containing 60 mg transgenic amylase flour mixed with enzyme solutions plus water or buffer under various reaction conditions. One set of reactions was buffered with 50 mM MOPS, pH 7.0 at room temperature, plus 10 mM MgSO4 and 1 mM $CoCl_2$; in a second set of reactions the metal-containing buffer solution was replaced by water. All reactions were incubated for 2 hours at 90° C.

The results are graphed in FIG. 20. They demonstrate that the grain-expressed amylase 797GL3 can function with other thermophilic enzymes, with or without added metal ions, to produce a variety of maltodextrin mixtures from corn flour at a high temperature. In particular, the inclusion of a glucoamylase or α-glucosidase may result in a product with more glucose and other low DP products. Inclusion of an enzyme with glucose isomerase activity results in a product that has fructose and thus would be sweeter than that produced by amylase alone or amylase with α-glucosidase. In addition the data indicate that the proportion of DP5, DP6 and DP7 maltooligosaccharides can be increased by including divalent cationic salts, such as $CoCl_2$ and $MgSO_4$.

Other means of altering the maltodextrin composition produced by a reaction such as that described here include: varying the reaction pH, varying the starch type in the transgenic or non-transgenic grain, varying the solids ratio, or by addition of organic solvents.

Example 31

Preparing Dextrins, or Sugars from Grain without Mechanical Disruption of the Grain Prior to Recovery of Starch-Derived Products Sugars and maltodextrins were prepared by contacting the transgenic grain expressing the α-amylase, 797GL3, with water and heating to 90° C. overnight (>14 hours). Then the liquid was separated from the grain by filtration. The liquid product was analyzed by HPLC by the method described in Example 15. Table 6 presents the profile of products detected.

TABLE 6

| Molecular species | Concentration of Products µg/25 µl injection |
|---|---|
| Fructose | 0.4 |
| Glucose | 18.0 |
| Maltose | 56.0 |
| DP3* | 26.0 |
| DP4* | 15.9 |
| DP5* | 11.3 |

TABLE 6-continued

| Molecular species | Concentration of Products µg/25 µl injection |
|---|---|
| DP6* | 5.3 |
| DP7* | 1.5 |

*Quantification of DP3 includes maltotriose and may include isomers of maltotriose that have an α(1→6) bond in place of an α(1→4) bond. Similarly DP4 to DP7 quantification includes the linear maltooligosaccarides of a given chain length as well as isomers that have one or more α(1→6) bonds in place of one or more α(1→4) bonds These data demonstrate that sugars and maltodextrins can be prepared by contacting intact α-amylase-expressing grain with water and heating. The products can then be separated from the intact grain by filtration or centrifugation or by gravitational settling.

Example 32

Fermentation of Raw Starch in Corn Expressing *Rhizopus oryzae* Glucoamylase

Transgenic corn kernels are harvested from transgenic plants made as described in Example 29. The kernels are ground to a flour. The corn kernels express a protein that contains an active fragment of the glucoamylase of *Rhizopus oryzae* (Sequence ID NO: 49) targeted to the endoplasmic reticulum.

The corn kernels are ground to a flour as described in Example 15. Then a mash is prepared containing s 20 g of corn flour, 23 ml of de-ionized water, 6.0 ml of backset (8% solids by weight). pH is adjusted to 6.0 by addition of ammonium hydroxide. The following components are added to the mash: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mash is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

Example 33

Example of Fermentation of Raw Starch in Corn Expressing *Rhizopus oryzae* Glucoamylase Transgenic corn kernels are harvested from transgenic plants made as described in Example 28. The kernels are ground to a flour. The corn kernels express a protein that contains an active fragment of the glucoamylase of *Rhizopus oryzae* (Sequence ID NO: 49) targeted to the endoplasmic reticulum.

The corn kernels are ground to a flour as described in Example 15. Then a mash is prepared containing 20 g of corn flour, 23 ml of de-ionized water, 6.0 ml of backset (8% solids by weight). pH is adjusted to 6.0 by addition of ammonium hydroxide. The following components are added to the mash: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mash is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

Example 34

Example of Fermentation of Raw Starch in Whole Kernels of Corn Expressing *Rhizopus oryzae* Glucoamylase with Addition of Exogenous α-Amylase Transgenic corn kernels are harvested from transgenic plants made as described in Example 28. The corn kernels express a protein that contains an active fragment of the glucoamylase of *Rhizopus oryzae* (Sequence ID NO: 49) targeted to the endoplasmic reticulum.

The corn kernels are contacted with 20 g of corn flour, 23 ml of de-ionized water, 6.0 ml of backset (8% solids by weight). pH is adjusted to 6.0 by addition of ammonium hydroxide. The following components are added: barley α-amylase purchased from Sigma (2 mg), protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mixture in order to allow $CO_2$ to vent. The mixture is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

Example 35

Fermentation of Raw Starch in Corn Expressing *Rhizopus oryzae* Glucoamylase and *Zea mays* Amylase Transgenic corn kernels are harvested from transgenic plants made as described in Example 28. The corn kernels express a protein that contains an active fragment of the glucoamylase of *Rhizopus oryzae* (Sequence ID NO:49) targeted to the endoplasmic reticulum. The kernels also express the maize amylase with raw starch binding domain as described in Example 28.

The corn kernels are ground to a flour as described in Example 14. Then a mash is prepared containing 20 g of corn flour, 23 ml of de-ionized water, 6.0 ml of backset (8% solids by weight). pH is adjusted to 6.0 by addition of ammonium hydroxide. The following components are added to the mash: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mash is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

Example 36

Example of Fermentation of Raw Starch in Corn Expressing *Thermoanaerobacter thermosaccharolyticum* Glucoamylase Transgenic corn kernels are harvested from transgenic plants made as described in Example 28. The corn kernels express a protein that contains an active fragment of the glucoamylase of *Thermoanaerobacter thermosaccharolyticum* (Sequence ID NO: 47) targeted to the endoplasmic reticulum.

The corn kernels are ground to a flour as described in Example 15. Then a mash is prepared containing 20 g of corn flour, 23 ml of de-ionized water, 6.0 ml of backset (8% solids by weight). pH is adjusted to 6.0 by addition of ammonium hydroxide. The following components are added to the mash: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mash is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

Example 37

Example of Fermentation of Raw Starch in Corn Expressing *Aspergillus niger* Glucoamylase Transgenic corn kernels are harvested from transgenic plants made as described in Example 28. The corn kernels express a protein that contains an active fragment of the glucoamylase of *Aspergillus niger* (Fiil, N. P. "Glucoamylases G1 and G2 from *Aspergillus niger* are synthesized from two different but closely related mRNAs" EMBO J. 3 (5), 1097-1102 (1984), Accession number P04064). The maize-optimized nucleic acid encoding the glucoamylase has SEQ ID NO:59 and is targeted to the endoplasmic reticulum.

The corn kernels are ground to a flour as described in Example 14. Then a mash is prepared containing 20 g of corn flour, 23 ml of de-ionized water, 6.0 ml of backset (8% solids by weight). pH is adjusted to 6.0 by addition of ammonium hydroxide. The following components are added to the mash: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mash is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

Example 38

Example of Fermentation of Raw Starch in Corn Expressing *Aspergillus Niger* Glucoamylase and *Zea mays* Amylase Transgenic corn kernels are harvested from transgenic plants made as described in Example 28. The corn kernels express a protein that contains an active fragment of the glucoamylase of *Aspergillus niger* (Fiil, N. P. "Glucoamylases G1 and G2 from *Aspergillus niger* are synthesized from two different but closely related mRNAs" EMBO J. 3 (5), 1097-1102 (1984): Accession number P04064) (SEQ ID NO:59, maize-optimized nucleic acid) and is targeted to the endoplasmic reticulum. The kernels also express the maize amylase with raw starch binding domain as described in example 28.

The corn kernels are ground to a flour as described in Example 14. Then a mash is prepared containing 20 g of corn flour, 23 ml of de-ionized water, 6.0 ml of backset (8% solids by weight). pH is adjusted to 6.0 by addition of ammonium hydroxide. The following components are added to the mash: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mash is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

Example 39

Example of Fermentation of Raw Starch in Corn Expressing *Thermoanaerobacter thermosaccharolyticum* Glucoamylase and Barley Amylase Transgenic corn kernels are harvested from transgenic plants made as described in Example 28. The corn kernels express a protein that contains an active fragment of the glucoamylase of *Thermoanaerobacter thermosaccharolyticum* (Sequence ID NO: 47) targeted to the endoplasmic reticulum. The kernels also express the low pI barley amylase amy1 gene (Rogers, J. C. and Milliman, C. "Isolation and sequence analysis of a barley alpha-amylase cDNA clone" J. Biol. Chem. 258 (13), 8169-8174 (1983) modified to target expression of the protein to the endoplasmic reticulum.

The corn kernels are ground to a flour as described in Example 14. Then a mash is prepared containing 20 g of corn flour, 23 ml of de-ionized water, 6.0 ml of backset (8% solids by weight). pH is adjusted to 6.0 by addition of ammonium hydroxide. The following components are added to the mash: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mash is then inoculated with yeast (1.44 ml) and incubated in a water bath set at 90 F. After 24 hours of fermentation the temperature is lowered to 86 F; at 48 hours it is set to 82 F.

Example 40

Example of Fermentation of Raw Starch in Whole Kernels of Corn Expressing *Thermoanaerobacter thermosaccharolyticum* Glucoamylase and Barley Amylase Transgenic corn kernels are harvested from transgenic plants made as described in Example 28. The corn kernels express a protein that contains an active fragment of the glucoamylase of *Thermoanaerobacter thermosaccharolyticum* (Sequence ID NO: 47) targeted to the endoplasmic reticulum. The kernels also express the low pI barley amylase amyl gene (Rogers, J. C. and Milliman, C. "Isolation and sequence analysis of a barley alpha-amylase cDNA clone". J. Biol. Chem. 258 (13), 8169-8174 (1983) modified to target expression of the protein to the endoplasmic reticulum.

The corn kernels are contacted with 20 g of corn flour, 23 ml of de-ionized water, 6.0 ml of backset (8% solids by weight). pH is adjusted to 6.0 by addition of ammonium hydroxide. The following components are added to the mixture: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mixture is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

Example 41

Example of Fermentation of Raw Starch in Corn Expressing an Alpha-Amylase and Glucoamylase Fusion Transgenic corn kernels are harvested from transgenic plants made as described in Example 28. The corn kernels express a maize-optimized polynucleotide such as provided in SEQ ID NO: 46, encoding an alpha-amylase and glucoamylase fusion, such as provided in SEQ ID NO: 45, which are targeted to the endoplasmic reticulum.

The corn kernels are ground to a flour as described in Example 14. Then a mash is prepared containing 20 g of corn flour, 23 ml of de-ionized water, 6.0 ml of backset (8% solids by weight). pH is adjusted to 6.0 by addition of ammonium hydroxide. The following components are added to the mash: protease (0.60 ml of a 1,000-fold dilution of a commercially available protease), 0.2 mg Lactocide & urea (0.85 ml of a 10-fold dilution of 50% Urea Liquor). A hole is cut into the cap of the 100 ml bottle containing the mash to allow $CO_2$ to vent. The mash is then inoculated with yeast (1.44 ml) and incubated in a water bath set at 90 F. After 24 hours of fermentation the temperature is lowered to 86 F; at 48 hours it is set to 82 F.

Yeast for inoculation is propagated as described in Example 14.

Samples are removed as described in example 14 and then analyzed by the methods described in Example 14.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

---

The invention claimed is:

1. An expression cassette comprising a polynucleotide encoding an alpha-amylase operably linked to a promoter and a heterologous signal sequence, wherein the alpha-amylase is thermophilic, and wherein the heterologous signal sequence directs the alpha-amylase to a specific compartment allowing the alpha-amylase to be localized in a manner that it will not come into contact with its substrate.

2. The expression cassette of claim 1, wherein the expression cassette directs the alpha-amylase to a specific compartment wherein the alpha-amylase can be contacted with its substrate by the process of milling or heating.

3. The expression cassette of claim 1, wherein the polynucleotide comprises a polynucleotide which encodes a polypeptide comprising SEQ ID NO:10.

4. The expression cassette of claim 1, wherein the promoter is a seed-specific promoter.

5. The expression cassette of claim 4, wherein the seed-specific promoter is an endosperm-specific promoter.

6. The expression cassette of claim 5, wherein the endosperm-specific promoter is a maize gamma-zein promoter or a maize ADP-gpp promoter.

7. The expression cassette of claim 1, wherein the heterologous signal sequence targets the alpha-amylase enzyme to a vacuole, endoplasmic reticulum, seed or cell wall of a plant.

8. The expression cassette of claim 1, wherein the promoter is an endosperm-specific promoter and the heterologous signal sequence targets the alpha-amylase to the endoplasmic reticulum.

9. A cell comprising the expression cassette of claim 1.

10. A plant comprising the expression cassette of claim 1.

11. Seed, fruit, grain or plant part comprising the expression cassette of claim 1.

12. The cell of claim 9, which is selected from the group consisting of an *Agrobacterium* cell, a monocot cell, a dicot cell, a Liliopsida cell and a Panicoideae cell.

13. An expression cassette comprising a polynucleotide encoding an alpha-amylase operably linked to a promoter and a heterologous signal sequence, wherein the promoter is a seed-specific promoter, and wherein the heterologous signal sequence directs the alpha-amylase to a specific compartment allowing the alpha-amylase to be localized in a manner that it will not come into contact with its substrate.

14. The expression cassette of claim 13, wherein the expression cassette directs the alpha-amylase to a specific compartment wherein the alpha-amylase can be contacted with its substrate by the process of milling or heating.

15. The expression cassette of claim 13, wherein the alpha-amylase is thermophilic.

16. The expression cassette of claim 13, wherein the polynucleotide comprises a polynucleotide which encodes a polypeptide comprising SEQ ID NO:10.

17. The expression cassette of claim 13, wherein the seed-specific promoter is an endosperm-specific promoter.

18. The expression cassette of claim 17, wherein the endosperm-specific promoter is a maize gamma-zein promoter or a maize ADP-gpp promoter.

19. The expression cassette of claim 13, wherein the heterologous signal sequence targets the alpha-amylase enzyme to a vacuole, endoplasmic reticulum, seed or cell wall of a plant.

20. A cell comprising the expression cassette of claim 13.

21. A plant comprising the expression cassette of claim 13.

22. Seed, fruit, grain or plant part comprising the expression cassette of claim 13.

23. The cell of claim 20, which is selected from the group consisting of an *Agrobacterium* cell, a monocot cell, a dicot cell, a Liliopsida cell and a Panicoideae cell.

* * * * *